United States Patent
Hyde et al.

(10) Patent No.: US 10,127,361 B2
(45) Date of Patent: Nov. 13, 2018

(54) QUANTIFIED-SELF MACHINES AND CIRCUITS REFLEXIVELY RELATED TO KIOSK SYSTEMS AND ASSOCIATED FOOD-AND-NUTRITION MACHINES AND CIRCUITS

(71) Applicant: Elwha LLC, Bellevue, WA (US)

(72) Inventors: Roderick A. Hyde, Redmond, WA (US); Muriel Y. Ishikawa, Livermore, CA (US); Jordin T. Kare, Seattle, WA (US); Eric C. Leuthardt, St. Louis, MO (US); Royce A. Levien, Lexington, MA (US); Richard T. Lord, Gig Harbor, WA (US); Robert W. Lord, Seattle, WA (US); Mark A. Malamud, Seattle, WA (US); Clarence T. Tegreene, Mercer Island, WA (US); Charles Whitmer, North Bend, WA (US); Lowell L. Wood, Jr., Bellevue, WA (US); Victoria Y. H. Wood, Livermore, CA (US); Nathan P. Myhrvold, Medina, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 698 days.

(21) Appl. No.: 14/292,817

(22) Filed: May 30, 2014

(65) Prior Publication Data

US 2015/0278480 A1    Oct. 1, 2015

Related U.S. Application Data

(63) Continuation-in-part of application No. 14/230,625, filed on Mar. 31, 2014, now Pat. No. 9,364,151.

(51) Int. Cl.
*G06F 19/00* (2018.01)
*G16H 10/60* (2018.01)

(52) U.S. Cl.
CPC ......... *G06F 19/3475* (2013.01); *G16H 10/60* (2018.01); *Y02A 90/26* (2018.01)

(58) Field of Classification Search
CPC ........ G06C 50/22; G06C 50/24; G06Q 50/22; G06Q 50/24; G16H 10/00; G16H 10/20;
(Continued)

(56) References Cited

U.S. PATENT DOCUMENTS 3,628,004 A   12/1971   Claxton et al.
4,782,451 A   11/1988   Mazzarella et al.
(Continued)

FOREIGN PATENT DOCUMENTS

WO   WO 2010/136811 A1   12/2010
WO   WO 2015/153482      10/2015

OTHER PUBLICATIONS

Sun et al.; "eButton: A Wearable Computer for Health Monitoring and Personal Assistance"; DAC '14; bearing a date of Jun. 1-5, 2014; pp. 1-6; ACM.
(Continued)

*Primary Examiner* — Joseph D Burgess

(57) ABSTRACT

A computationally implemented system and method that is designed to, but is not limited to: electronically receiving user biological status information from electronically involved detection of one or more biological user conditions. In addition to the foregoing, other method aspects are described in the claims, drawings, and text forming a part of the present disclosure.

43 Claims, 136 Drawing Sheets

(58) Field of Classification Search
CPC ........ G16H 10/40; G16H 10/60; G16H 10/65;
G16H 15/00; G16H 20/00; G16H 20/10;
G16H 20/13; G16H 20/17; G16H 20/30;
G16H 20/40; G16H 20/60; G16H 20/70;
G16H 20/90; G16H 30/00; G16H 40/00;
G16H 40/20; G16H 40/40; G16H 40/60;
G16H 40/63; G16H 40/67; G16H 50/00;
G16H 70/00; G16H 70/20; G16H 70/40;
G16H 70/60; G16H 80/00
See application file for complete search history.

(56) References Cited

U.S. PATENT DOCUMENTS

| | | | |
|---|---|---|---|
| 4,818,707 A | 4/1989 | Breneman | |
| 4,951,197 A | 8/1990 | Mellinger | |
| 5,091,713 A | 2/1992 | Horne et al. | |
| 5,128,861 A | 7/1992 | Kagami et al. | |
| 5,154,314 A | 10/1992 | Van Wormer | |
| 5,168,445 A | 12/1992 | Kawashima et al. | |
| 5,412,564 A | 5/1995 | Ecer | |
| 5,577,410 A | 11/1996 | Willard et al. | |
| 5,673,691 A | 10/1997 | Abrams et al. | |
| 5,899,502 A | 5/1999 | Del Giorno | |
| 5,983,198 A | 11/1999 | Mowery et al. | |
| 6,230,150 B1 | 5/2001 | Walker et al. | |
| 6,280,409 B1 | 8/2001 | Stone et al. | |
| 6,370,341 B1 | 4/2002 | Haines | |
| 6,377,868 B1 | 4/2002 | Gardner, Jr. | |
| 6,397,126 B1 | 5/2002 | Nelson | |
| 6,513,024 B1 | 1/2003 | Li | |
| 6,513,532 B2 | 2/2003 | Mault et al. | |
| 6,609,101 B1 | 8/2003 | Landvater | |
| 6,618,692 B2 | 9/2003 | Takahashi et al. | |
| 6,629,003 B1 | 9/2003 | Frizzell et al. | |
| 6,715,514 B2 | 4/2004 | Parker, III et al. | |
| 6,726,947 B1 | 4/2004 | Gutwein et al. | |
| 6,772,096 B2 | 8/2004 | Murakami et al. | |
| 6,808,731 B1 | 10/2004 | Gutwein et al. | |
| 6,947,675 B2 | 9/2005 | Koyama et al. | |
| 6,978,182 B2 | 12/2005 | Mazar et al. | |
| 6,980,887 B2 | 12/2005 | Varga et al. | |
| 6,980,999 B1 | 12/2005 | Grana | |
| 7,065,409 B2 | 6/2006 | Mazar | |
| 7,103,407 B2 | 9/2006 | Hjelt et al. | |
| 7,115,297 B2 | 10/2006 | Stillman | |
| 7,177,699 B2 | 2/2007 | Fabian et al. | |
| 7,196,625 B1 | 3/2007 | Nguyen | |
| 7,244,231 B2 | 7/2007 | Dewing et al. | |
| 7,285,090 B2 | 10/2007 | Stivoric et al. | |
| 7,295,889 B2 | 11/2007 | Lahteenmaki | |
| 7,333,871 B2 | 2/2008 | Schwarm | |
| 7,359,894 B1 | 4/2008 | Liebman et al. | |
| 7,418,311 B1 | 8/2008 | Lagassey et al. | |
| 7,433,853 B2 | 10/2008 | Brockway et al. | |
| 7,468,032 B2 | 12/2008 | Stahmann et al. | |
| 7,502,643 B2 | 3/2009 | Farringdon et al. | |
| 7,601,509 B2 | 10/2009 | Power | |
| 7,680,690 B1 | 3/2010 | Catalano | |
| 7,762,181 B2 | 7/2010 | Boland et al. | |
| 7,776,372 B2 | 8/2010 | Hrudka | |
| 7,860,583 B2 | 12/2010 | Condurso et al. | |
| 7,899,713 B2 | 3/2011 | Rothschild | |
| 7,953,873 B1 | 5/2011 | Madurzak | |
| 7,970,550 B2 | 6/2011 | Arakelyan et al. | |
| 8,005,691 B2 | 8/2011 | Kumar et al. | |
| 8,175,917 B2 | 5/2012 | Flynn et al. | |
| 8,201,736 B2 | 6/2012 | Doglioni Majer | |
| 8,301,252 B2 | 10/2012 | Hatlestad et al. | |
| 8,398,546 B2 | 3/2013 | Pacione et al. | |
| 8,403,845 B2 | 3/2013 | Stivoric et al. | |
| 8,429,026 B1 | 4/2013 | Kolawa et al. | |
| 8,491,495 B1 | 7/2013 | Shuck | |
| 8,494,871 B2 | 7/2013 | Schaffer et al. | |
| 8,504,197 B2 | 8/2013 | Torres Farr | |
| 8,631,093 B2 | 1/2014 | Defosse | |
| 8,639,214 B1 | 1/2014 | Fujisaki | |
| 8,647,121 B1 | 2/2014 | Witlin et al. | |
| 8,666,672 B2 | 3/2014 | Winarski | |
| 8,747,312 B2 | 6/2014 | Yuen et al. | |
| 8,788,341 B1 | 7/2014 | Patel et al. | |
| 8,836,513 B2 | 9/2014 | Hafezi et al. | |
| 8,892,249 B2 | 11/2014 | Holman et al. | |
| 8,903,708 B2 | 12/2014 | Derks et al. | |
| 8,956,287 B2 | 2/2015 | Zdeblick et al. | |
| 8,961,413 B2 | 2/2015 | Teller et al. | |
| 8,977,517 B2 | 3/2015 | Reidelberger | |
| 8,990,274 B1 | 3/2015 | Hwang | |
| 9,037,478 B2 | 5/2015 | Holman et al. | |
| 9,047,746 B1 | 6/2015 | Euliano, II et al. | |
| 9,070,175 B2 | 6/2015 | Hurst | |
| 9,070,357 B1 * | 6/2015 | Kennedy ................ G10L 15/00 | |
| 9,075,909 B2 | 7/2015 | Almogy et al. | |
| 9,105,041 B2 | 8/2015 | Harman | |
| 9,111,256 B2 | 8/2015 | Holman et al. | |
| 9,183,498 B2 | 11/2015 | Landers | |
| 9,189,021 B2 | 11/2015 | Jerauld | |
| 9,334,150 B1 | 5/2016 | Ost et al. | |
| 9,364,106 B1 | 6/2016 | Ortiz | |
| 9,402,597 B1 | 8/2016 | Castellanos | |
| 9,415,010 B2 | 8/2016 | Hafezi et al. | |
| 9,424,495 B1 | 8/2016 | Trevino | |
| 9,499,385 B1 | 11/2016 | Studor | |
| 9,536,237 B2 | 1/2017 | Argue et al. | |
| 9,579,060 B1 | 2/2017 | Lisy et al. | |
| 9,702,858 B1 | 7/2017 | Minvielle | |
| 9,747,424 B2 | 8/2017 | Sablinski | |
| 9,786,281 B1 | 10/2017 | Adams et al. | |
| 2001/0025279 A1 | 9/2001 | Krulak et al. | |
| 2002/0004749 A1 | 1/2002 | Froseth et al. | |
| 2002/0013908 A1 | 1/2002 | Nishihata et al. | |
| 2002/0019586 A1 | 2/2002 | Teller et al. | |
| 2002/0032384 A1 | 3/2002 | Raymond et al. | |
| 2002/0032581 A1 | 3/2002 | Reitberg | |
| 2002/0161475 A1 * | 10/2002 | Varga ................... G06Q 10/087 |
| | | | 700/231 |
| 2002/0169583 A1 | 11/2002 | Gutta et al. | |
| 2003/0010791 A1 | 1/2003 | Gentiluomo et al. | |
| 2003/0033127 A1 | 2/2003 | Lett | |
| 2003/0036683 A1 | 2/2003 | Kehr et al. | |
| 2003/0059747 A1 | 3/2003 | Yoshida et al. | |
| 2003/0176989 A1 | 9/2003 | Matsuda | |
| 2003/0191558 A1 | 10/2003 | Arellano | |
| 2003/0208110 A1 | 11/2003 | Mault et al. | |
| 2003/0222905 A1 | 12/2003 | Wierenga et al. | |
| 2004/0103033 A1 | 5/2004 | Reade et al. | |
| 2004/0120985 A1 | 6/2004 | Geiss | |
| 2004/0137486 A1 | 7/2004 | Benson | |
| 2004/0138926 A1 | 7/2004 | Ishikawa et al. | |
| 2004/0162850 A1 | 8/2004 | Sanville et al. | |
| 2004/0169048 A1 | 9/2004 | Simmons | |
| 2004/0197424 A1 | 10/2004 | Zemel et al. | |
| 2004/0210459 A1 | 10/2004 | Kirchhoff et al. | |
| 2005/0010139 A1 | 1/2005 | Aminian et al. | |
| 2005/0048461 A1 * | 3/2005 | Lahteenmaki .......... A61J 3/002 |
| | | | 435/3 |
| 2005/0049942 A1 | 3/2005 | Richard et al. | |
| 2005/0058574 A1 | 3/2005 | Bysouth et al. | |
| 2005/0075934 A1 | 4/2005 | Knight et al. | |
| 2005/0144013 A1 | 6/2005 | Fujimoto et al. | |
| 2005/0153052 A1 | 7/2005 | Williams et al. | |
| 2005/0171627 A1 | 8/2005 | Funk et al. | |
| 2005/0171800 A1 | 8/2005 | Yamaguchi | |
| 2005/0250125 A1 | 11/2005 | Novakoff | |
| 2005/0288898 A1 | 12/2005 | Le | |
| 2006/0020483 A1 | 1/2006 | Hsu | |
| 2006/0081653 A1 | 4/2006 | Boland et al. | |
| 2006/0107331 A1 | 5/2006 | Kim et al. | |
| 2006/0122468 A1 | 6/2006 | Tavor | |
| 2006/0199155 A1 | 9/2006 | Mosher | |
| 2006/0247823 A1 | 11/2006 | Boucher | |
| 2006/0290885 A1 * | 12/2006 | Covannon ............... A61F 9/008 |
| | | | 351/212 |
| 2007/0027931 A1 | 2/2007 | Heckenbach | |

(56) References Cited

U.S. PATENT DOCUMENTS

| | | |
|---|---|---|
| 2007/0067189 A1 | 3/2007 | Boris et al. |
| 2007/0130287 A1* | 6/2007 | Kumar ............... A61N 1/08 709/217 |
| 2007/0235465 A1 | 10/2007 | Walker et al. |
| 2007/0271194 A1 | 11/2007 | Walker et al. |
| 2007/0276203 A1 | 11/2007 | Day |
| 2007/0281359 A1 | 12/2007 | Chait et al. |
| 2007/0299555 A1 | 12/2007 | Walker et al. |
| 2008/0007103 A1* | 1/2008 | Welles ............... A61B 5/11 297/330 |
| 2008/0025734 A1 | 1/2008 | Kehoe et al. |
| 2008/0033658 A1 | 2/2008 | Dalton et al. |
| 2008/0052175 A1 | 2/2008 | Walker et al. |
| 2008/0124434 A1 | 5/2008 | Hrudka |
| 2008/0133724 A1 | 6/2008 | Clark |
| 2008/0178749 A1 | 7/2008 | Stutman |
| 2008/0222553 A1 | 9/2008 | Benjamin-Lambert |
| 2008/0300993 A1 | 12/2008 | Rozenblatt |
| 2009/0037288 A1 | 2/2009 | Christensen |
| 2009/0095165 A1 | 4/2009 | Nosler et al. |
| 2009/0095813 A1 | 4/2009 | Chang et al. |
| 2009/0150181 A1 | 6/2009 | Gejdos et al. |
| 2009/0208917 A1 | 8/2009 | Vinch |
| 2009/0271342 A1 | 10/2009 | Eder |
| 2009/0281414 A1 | 11/2009 | Feldman et al. |
| 2009/0306979 A1 | 12/2009 | Jaiswal et al. |
| 2010/0028501 A1 | 2/2010 | Baxter et al. |
| 2010/0030355 A1 | 2/2010 | Insolia et al. |
| 2010/0041000 A1 | 2/2010 | Glass et al. |
| 2010/0045454 A1* | 2/2010 | Knight ............... G08B 21/0469 340/521 |
| 2010/0049095 A1* | 2/2010 | Bunn ............... A61B 5/1038 600/595 |
| 2010/0109876 A1 | 5/2010 | Schmid-Schonbein et al. |
| 2010/0136511 A1* | 6/2010 | Garner ............... G09B 5/00 434/307 R |
| 2010/0136540 A1 | 6/2010 | Hamet et al. |
| 2010/0161301 A1 | 6/2010 | Arakelyan et al. |
| 2010/0184565 A1 | 7/2010 | Avellino |
| 2010/0238180 A1 | 9/2010 | Kang et al. |
| 2010/0275625 A1 | 11/2010 | Lowenstein |
| 2010/0286490 A1* | 11/2010 | Koverzin ............ G06F 19/3418 600/301 |
| 2011/0038998 A1 | 2/2011 | Kohli |
| 2011/0054731 A1 | 3/2011 | DeRose et al. |
| 2011/0060233 A1 | 3/2011 | Spaulding et al. |
| 2011/0097807 A1 | 4/2011 | Monte et al. |
| 2011/0119130 A1 | 5/2011 | Agan et al. |
| 2011/0167100 A1 | 7/2011 | Brodowski |
| 2011/0208436 A1 | 8/2011 | Page |
| 2011/0276396 A1 | 11/2011 | Rathod |
| 2011/0289044 A1 | 11/2011 | Harrison |
| 2012/0072302 A1 | 3/2012 | Chen et al. |
| 2012/0089417 A1 | 4/2012 | Bardy et al. |
| 2012/0224021 A1 | 9/2012 | Begeja et al. |
| 2012/0285986 A1 | 11/2012 | Irvin |
| 2012/0322872 A1 | 12/2012 | Kraus et al. |
| 2012/0326873 A1 | 12/2012 | Utter, II |
| 2013/0006063 A1 | 1/2013 | Wang |
| 2013/0007063 A1 | 1/2013 | Kalra et al. |
| 2013/0013107 A1 | 1/2013 | Felique |
| 2013/0029906 A1 | 1/2013 | Simard et al. |
| 2013/0047864 A1 | 2/2013 | Holman et al. |
| 2013/0052616 A1 | 2/2013 | Silverstein et al. |
| 2013/0054010 A1 | 2/2013 | Holman et al. |
| 2013/0054011 A1* | 2/2013 | Holman ............... G06Q 10/10 700/232 |
| 2013/0054387 A1 | 2/2013 | Holman et al. |
| 2013/0110409 A1 | 5/2013 | Sakurada |
| 2013/0110582 A1 | 5/2013 | Starkman |
| 2013/0123976 A1 | 5/2013 | McClure et al. |
| 2013/0171304 A1 | 7/2013 | Huntley |
| 2013/0173339 A1 | 7/2013 | Briancon et al. |
| 2013/0183642 A1 | 7/2013 | Wan |
| 2013/0185646 A1 | 7/2013 | Wiggins et al. |
| 2013/0211814 A1 | 8/2013 | Derks et al. |
| 2013/0218586 A1 | 8/2013 | Huser |
| 2013/0218687 A1 | 8/2013 | Sohangir et al. |
| 2013/0265159 A1 | 10/2013 | Durian |
| 2013/0325404 A1 | 12/2013 | Yuen et al. |
| 2014/0004492 A1 | 1/2014 | O'Reilly et al. |
| 2014/0012117 A1 | 1/2014 | Mensinger et al. |
| 2014/0037158 A1 | 2/2014 | McNulty |
| 2014/0070957 A1 | 3/2014 | Longinotti-Buitoni et al. |
| 2014/0081777 A1 | 3/2014 | Mastrodonato et al. |
| 2014/0087336 A1 | 3/2014 | Wang |
| 2014/0095479 A1 | 4/2014 | Chang et al. |
| 2014/0101233 A1 | 4/2014 | Mina |
| 2014/0106312 A1 | 4/2014 | Klein |
| 2014/0114469 A1 | 4/2014 | Givens et al. |
| 2014/0127650 A1 | 5/2014 | Utter, II |
| 2014/0129243 A1 | 5/2014 | Utter, II |
| 2014/0141134 A1 | 5/2014 | Johnson et al. |
| 2014/0200460 A1 | 7/2014 | Johnson et al. |
| 2014/0236759 A1 | 8/2014 | Mirabile |
| 2014/0249966 A1 | 9/2014 | Zaragoza et al. |
| 2014/0295822 A1 | 10/2014 | Koo et al. |
| 2014/0316226 A1 | 10/2014 | Ferber et al. |
| 2014/0324447 A1 | 10/2014 | Dittus |
| 2014/0347265 A1 | 11/2014 | Aimone et al. |
| 2015/0005950 A1 | 1/2015 | Trench Roca et al. |
| 2015/0074259 A1 | 3/2015 | Ansari et al. |
| 2015/0087921 A1 | 3/2015 | Felix et al. |
| 2015/0120378 A1 | 4/2015 | Arden |
| 2015/0120506 A1 | 4/2015 | Dugan |
| 2015/0170543 A1 | 6/2015 | Shahar et al. |
| 2015/0182113 A1 | 7/2015 | Utter, II |
| 2015/0186971 A1 | 7/2015 | Holman et al. |
| 2015/0186981 A1 | 7/2015 | Holman et al. |
| 2015/0187026 A1 | 7/2015 | Holman et al. |
| 2015/0213232 A1 | 7/2015 | Walker, II |
| 2015/0216413 A1 | 8/2015 | Soyao et al. |
| 2015/0220883 A1 | 8/2015 | B 'Far et al. |
| 2015/0269848 A1 | 9/2015 | Yuen et al. |
| 2015/0317756 A1 | 11/2015 | Agiv et al. |
| 2015/0351688 A1 | 12/2015 | Just et al. |
| 2016/0027330 A1 | 1/2016 | Briancon et al. |
| 2016/0034663 A1 | 2/2016 | Nino et al. |
| 2016/0192620 A1 | 7/2016 | Hu et al. |
| 2017/0330481 A1 | 11/2017 | Sarbourian-Tarwe |

OTHER PUBLICATIONS

Bai et al.; "Designing a Wearable Computer for Lifestyle Evaluation"; Proc IEEE Annu Northeast Bioeng Conf.; 2012 (bearing a date of Jun. 11, 2014); pp. 1-6; IEEE.

Sazonov et al.; "A Sensor System for Automatic Detection of Food Intake Through Non-Invasive Monitoring of Chewing"; IEEE Sensors Journal; May 2012; pp. 1340-1348; vol. 12, No. 5; IEEE.

Dorman et al.; "Nutrition Monitor: A Food Purchase and Consumption Monitoring Mobile System"; MobiCASE 2009; 2010; pp. 1-11; vol. 35; Institute for Computer Sciences, Social-Informatics and Telecommunications Engineering.

Nishimura et al.; "Eating habits monitoring using wireless wearable in-ear microphone"; 2008; pp. 130-132; IEEE.

King, Ross D. et al.; "The Automation of Science"; Science; Apr. 3, 2009; pp. 85-89; vol. 324, No. 5923; American Association for the Advancement of Science; located at: http://www.jstor.org/stable/20493640.

Lo, Chris; "Robotic researchers: the next step in automated drug development"; Pharmaceutical Technology; Apr. 26, 2012; pp. 1-11; located at: http://www.pharmaceutical-technology.com/features/featurerobotic-research-pharmaceutical-robot-eve/.

Sparkes, Andrew et al.; "*AutoLabDB*: a substantial open source database schema to support a high-throughput *automated laboratory*"; Bioinformatics; Mar. 29, 2012; pp. 1-25; vol. 28, No. 10; Oxford Academic; located at: https://academic.oup.com/bioinformatics/article/28/10/1390/211917/AutoLabDB-a-substantial-open-source-database.

(56) References Cited

OTHER PUBLICATIONS

Sparkes, Andrew et al.; "Towards Robot Scientists for autonomous scientific discovery"; Automated Experimentation; 2010; pp. 1-11; vol. 2, No. 1; located at: http://www.aejournal.net/content/2/1/1.

McGee, Harold; "On Food and Cooking—The Science and Lore of the Kitchen"; 2004; pp. 442-447; ISBN 0-684-80001-2.

Bollini, M. et al; "Interpreting and Executing Recipes with a Cooking Robot"; International Symposium on Experimental Robotics, 2013; Springer Tracts in Advanced Robotics; pp. 1-15; vol. 88; Springer, Heidelberg, Germany.

Mikulak, Ron; "Personal chefs serve up tasty home cooking"; The Courier-Journal (Louisville, KY); Jan. 17, 2013; printed on Feb. 20, 2018; pp. 1-2 located at: https://www.usatoday.com/story/news/nation/2013/01/17/personal-chefs-home/1566412/.

Wilson, Mark; "Try the First Recipe Created by IBM's Supercomputer Chef"; Co.Design; Apr. 29, 2013; printed on Mar. 12, 2018; pp. 1-6 located at: https://www.fastscodesign.com/1672444/try-a-recipe-devised-by-ibms-supercomputer-chef.

Zyga, Lisa; "Two Robot Chefs Make Omelets"; Dec. 4, 2008; printed on Feb. 20, 2018; pp. 1-2 located at: httpsːphys.org/news/2008-12-robot-chefs-omelets.html.

Bernstein, Fred A.; "Trying Out Delivered Diet Meals", Suiting a Home Diet Meal Plan to My Tastes—The New York Times; May 4, 2010; created on Feb. 22, 2018; total of 5 pages; located at: http://www.nytimes.com/2010/05/05/dining/05diet.html.

Kummer, Corby; "Better Cooking through Technology"; MIT Technology Review; Jul./Aug. 2011; created on Feb. 20, 2018; total of 15 pages; located at: https://www.technologyreview.com/s/424410/better-cooking-through-technology/.

Wiggers, Pascal; "Modelling Context in Automatic Speech Recognition"; Delft University of Technology; Jun. 4, 2008; total of 203 pages.

\* cited by examiner

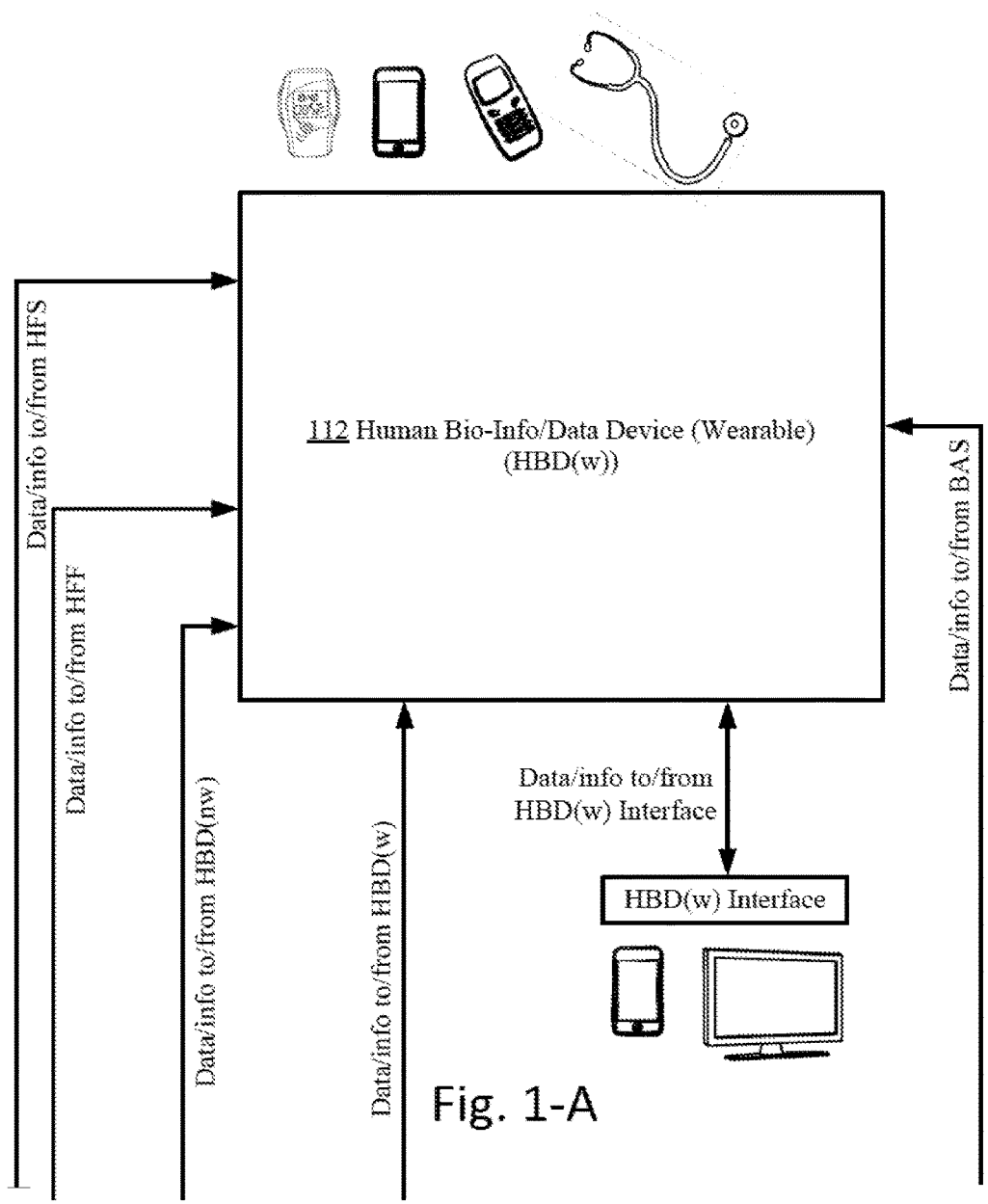
Fig. 1-A

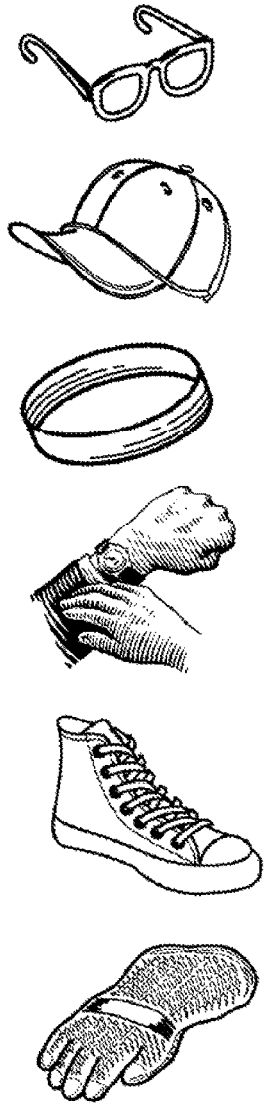
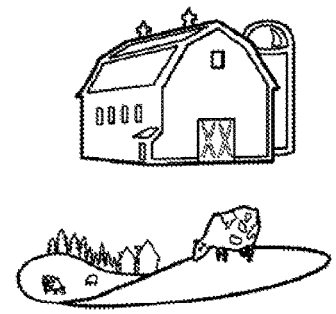
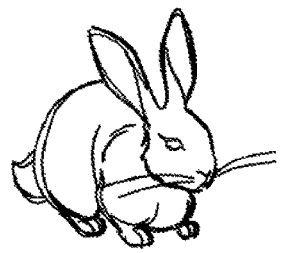
Fig. 1-B

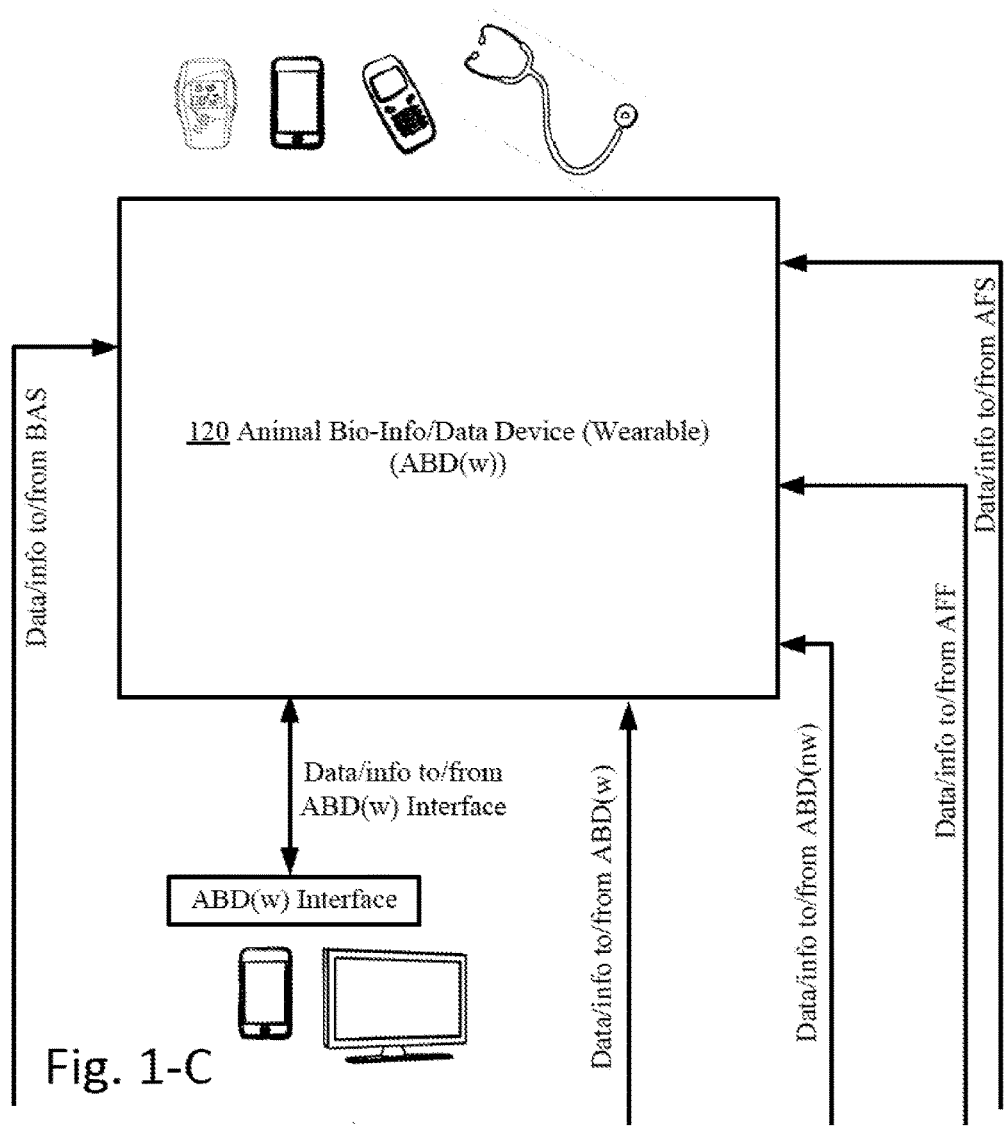
Fig. 1-C

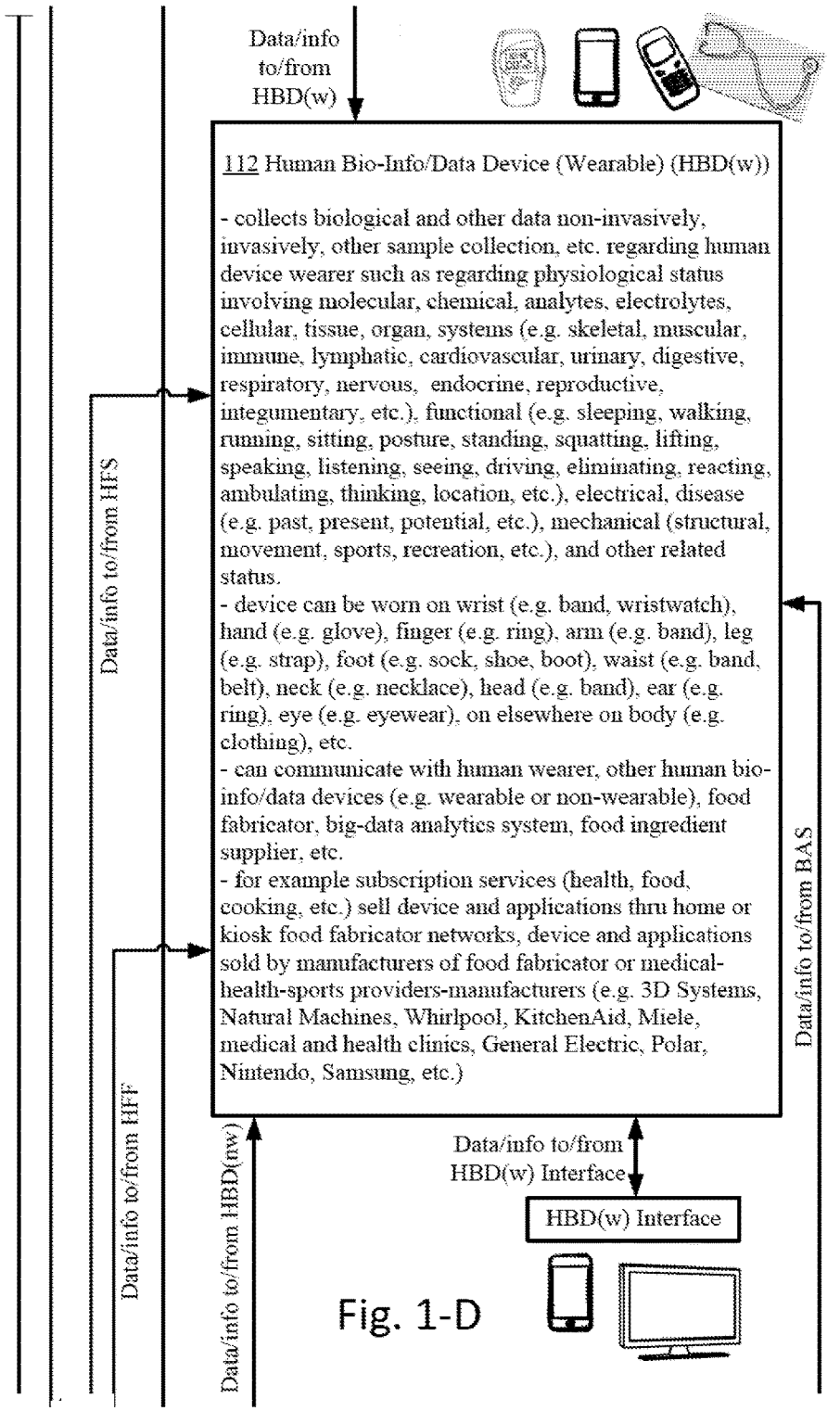
Fig. 1-D

Fig. 1-E

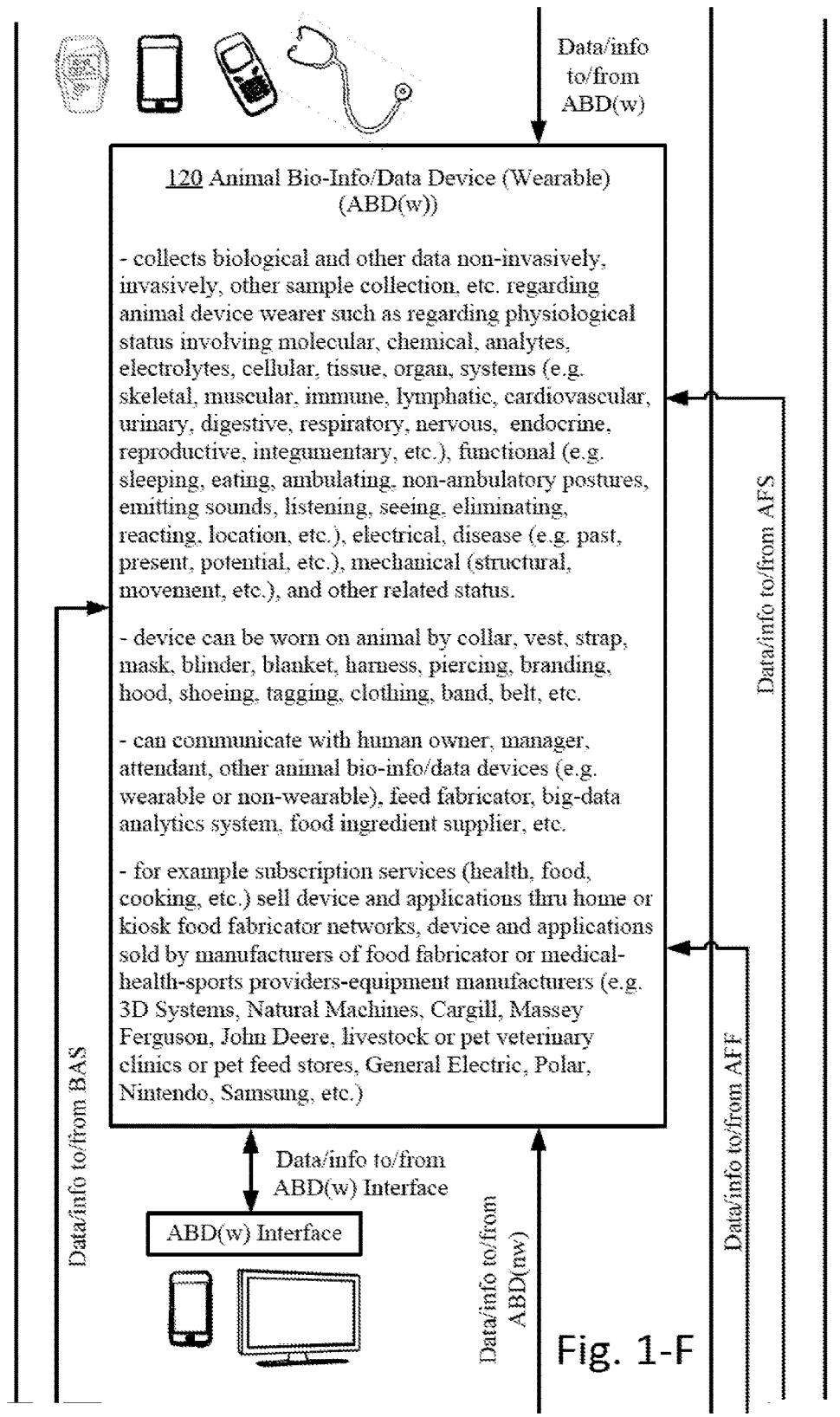
Fig. 1-F

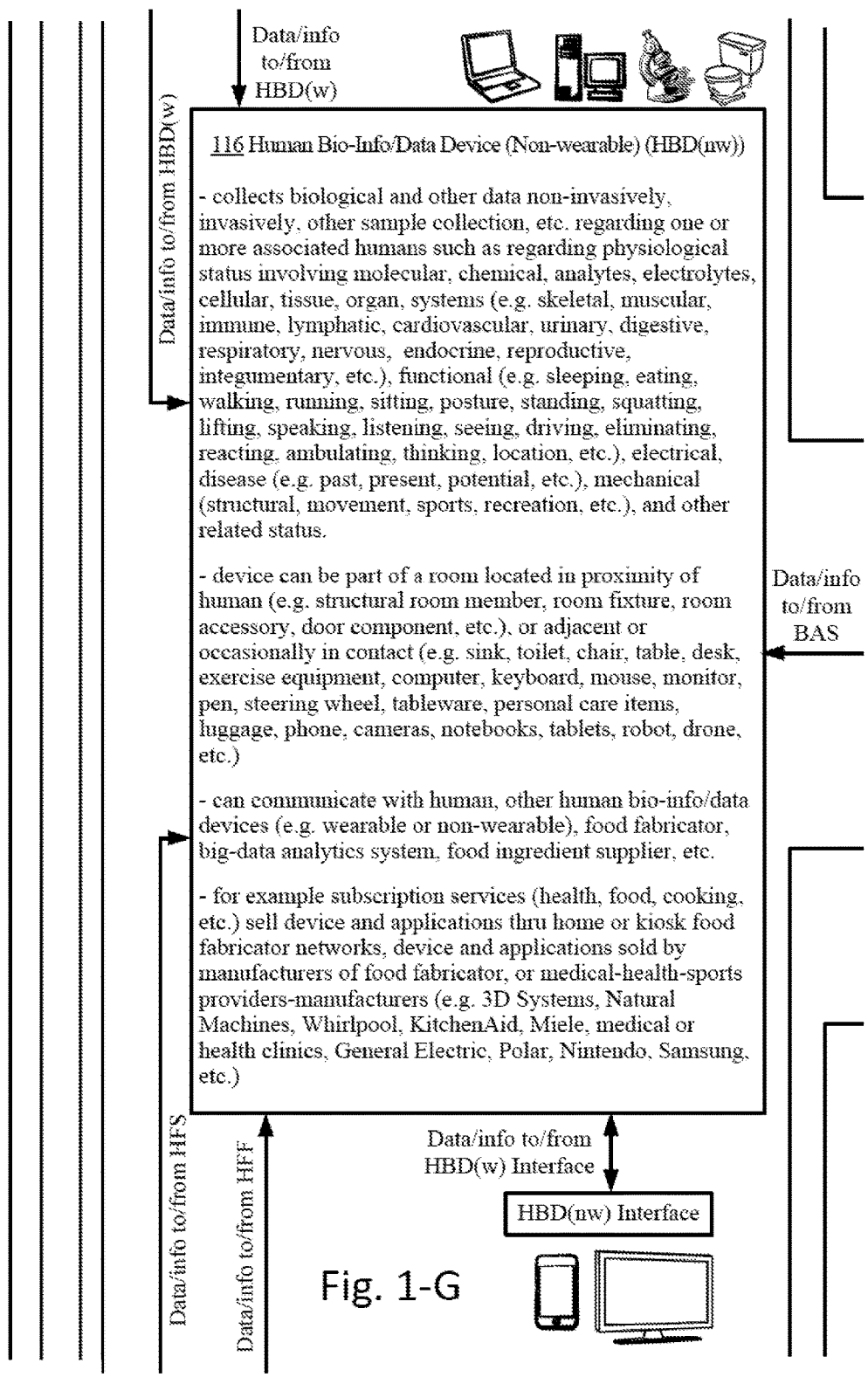
Fig. 1-G

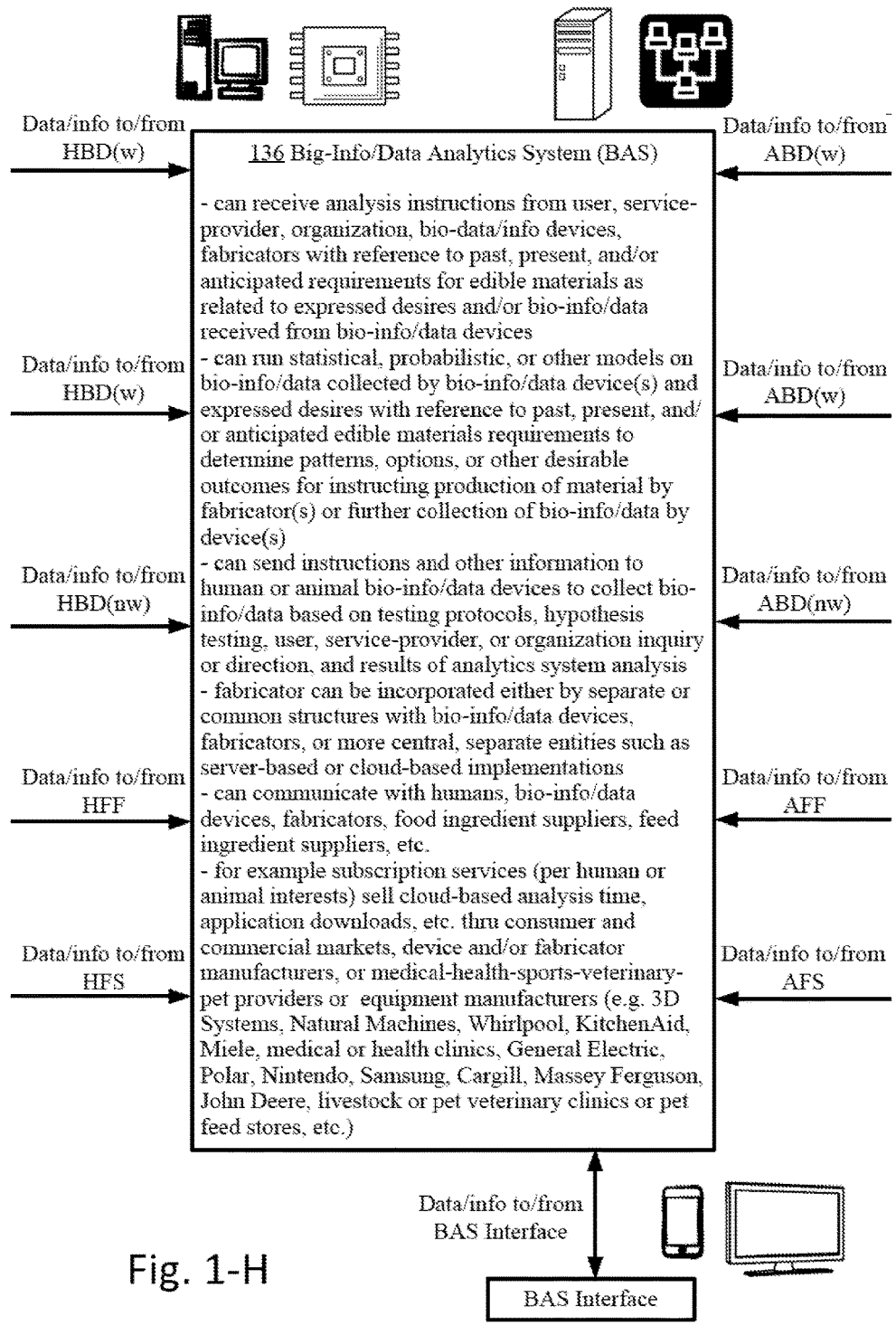
Fig. 1-H

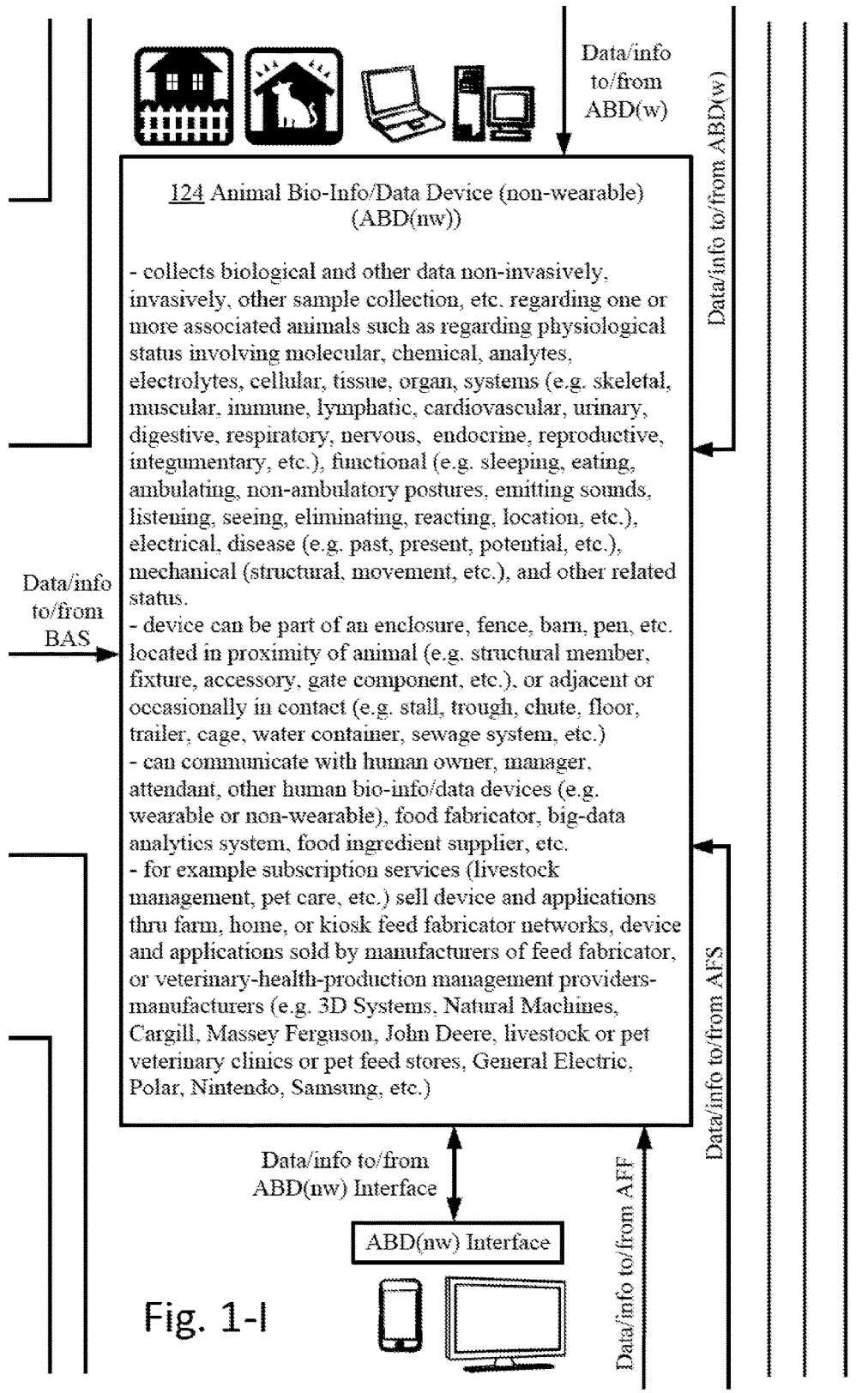
Fig. 1-I

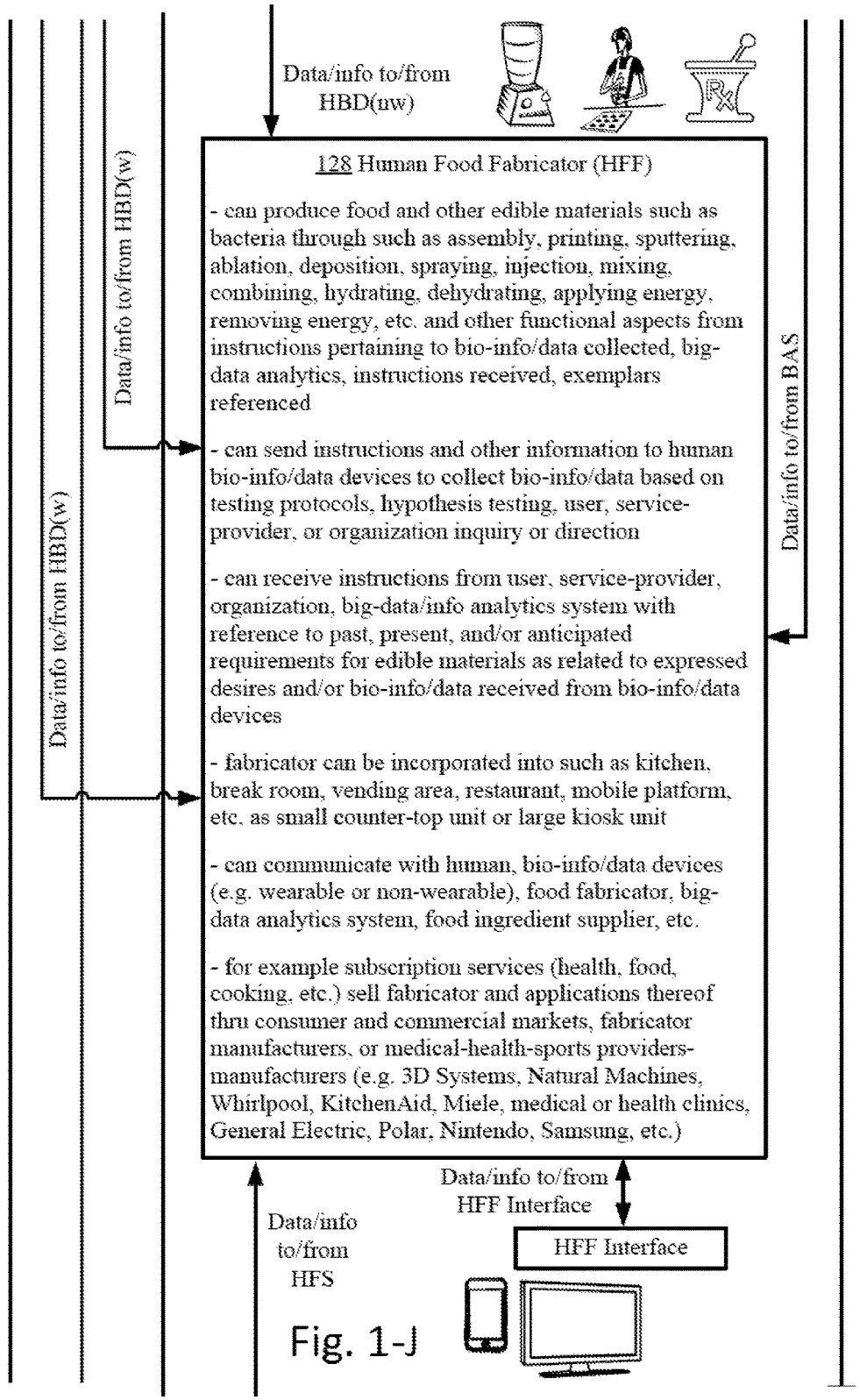
Fig. 1-J

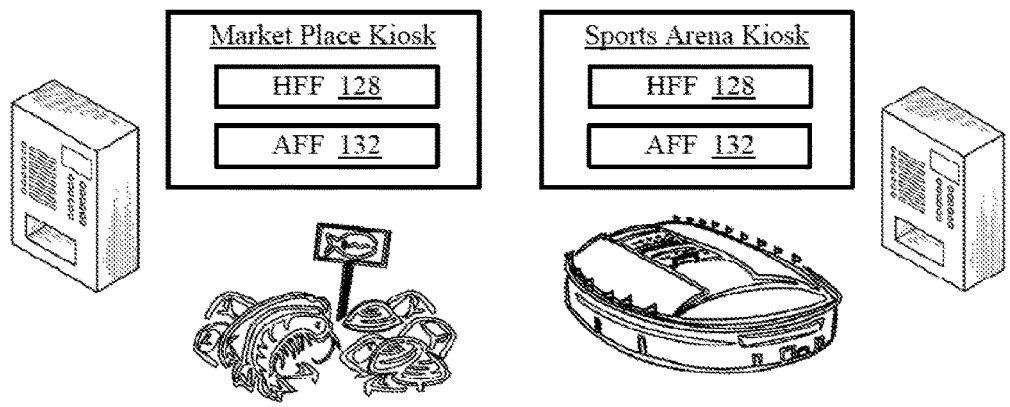
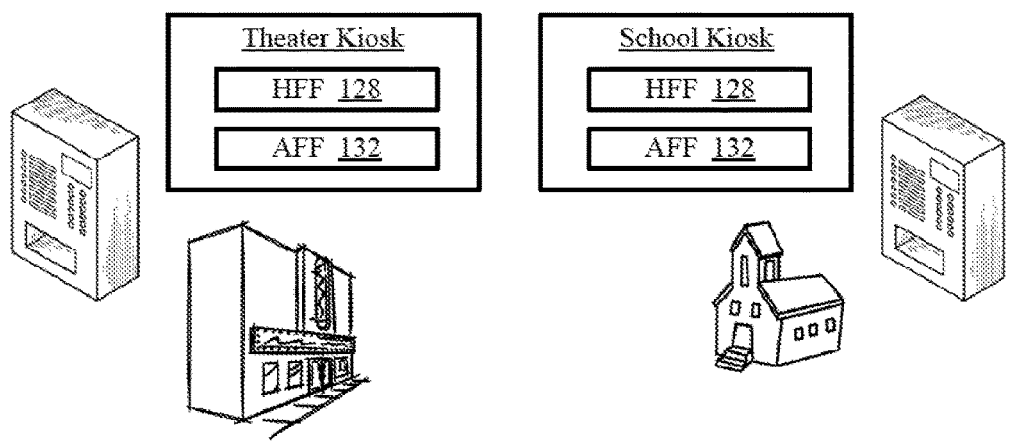
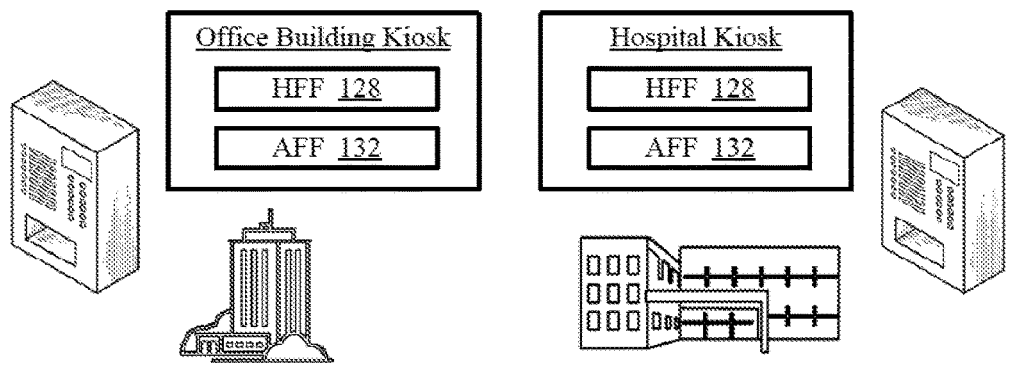
Fig. 1-K

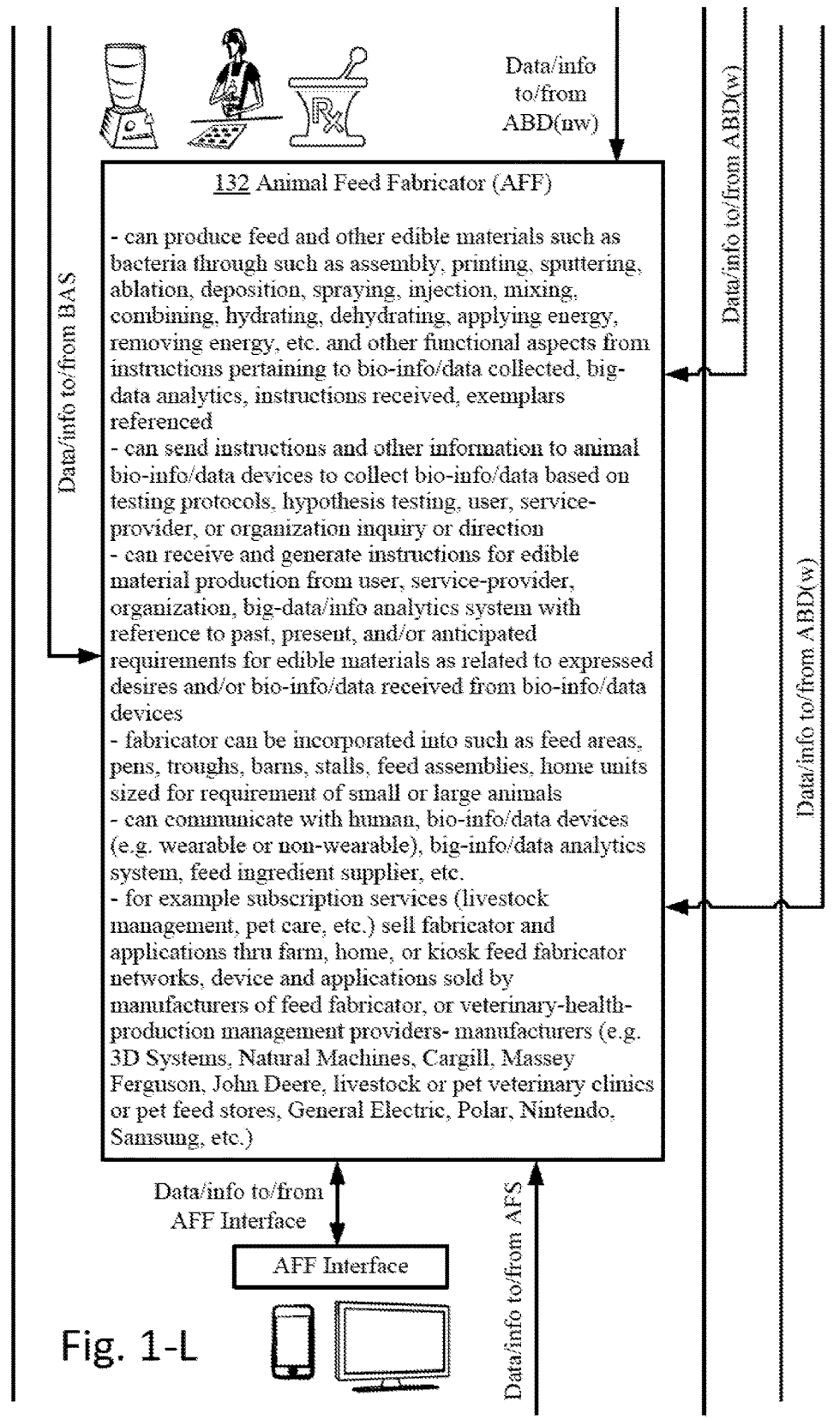
Fig. 1-L

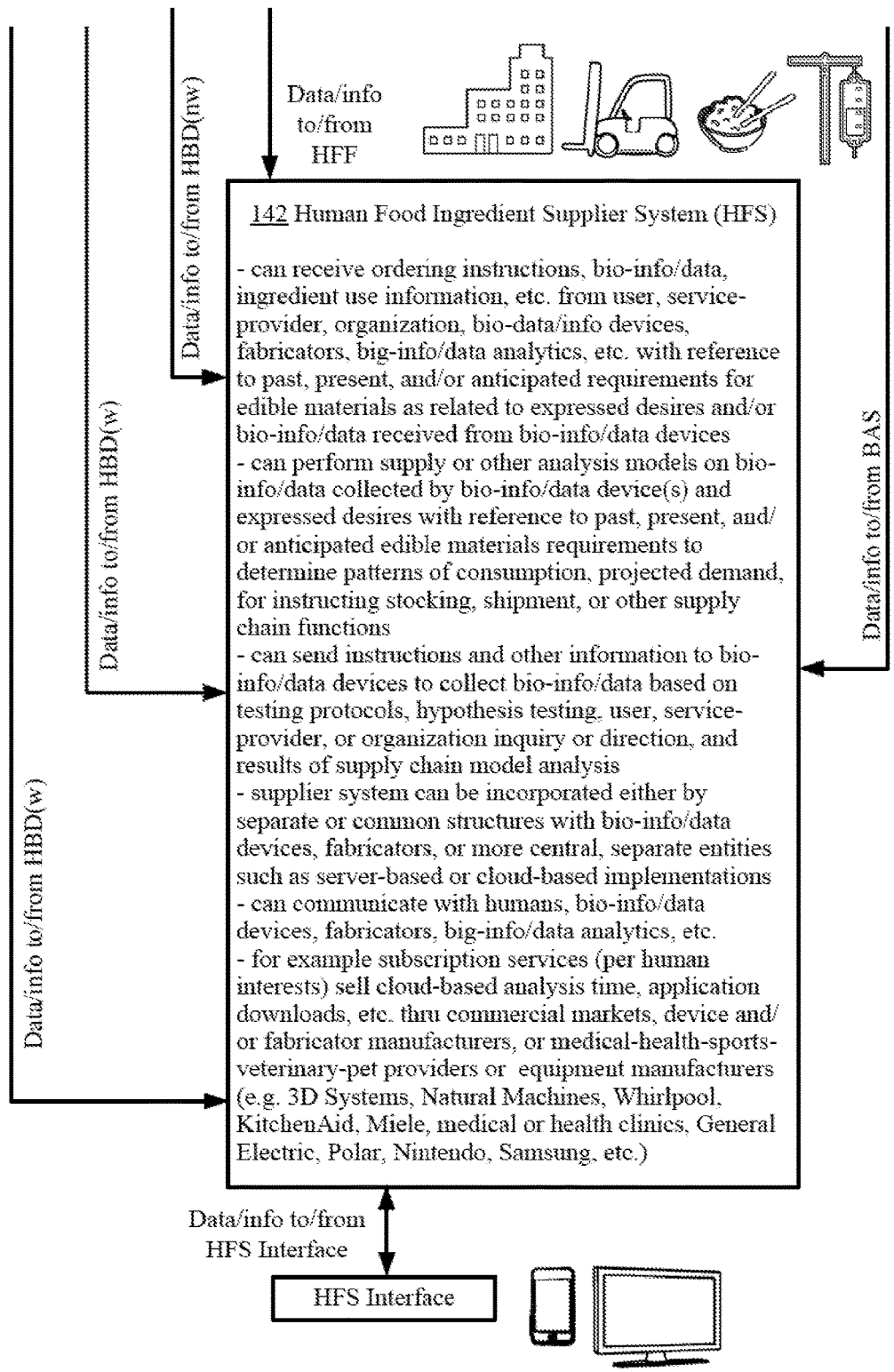
Fig. 1-M

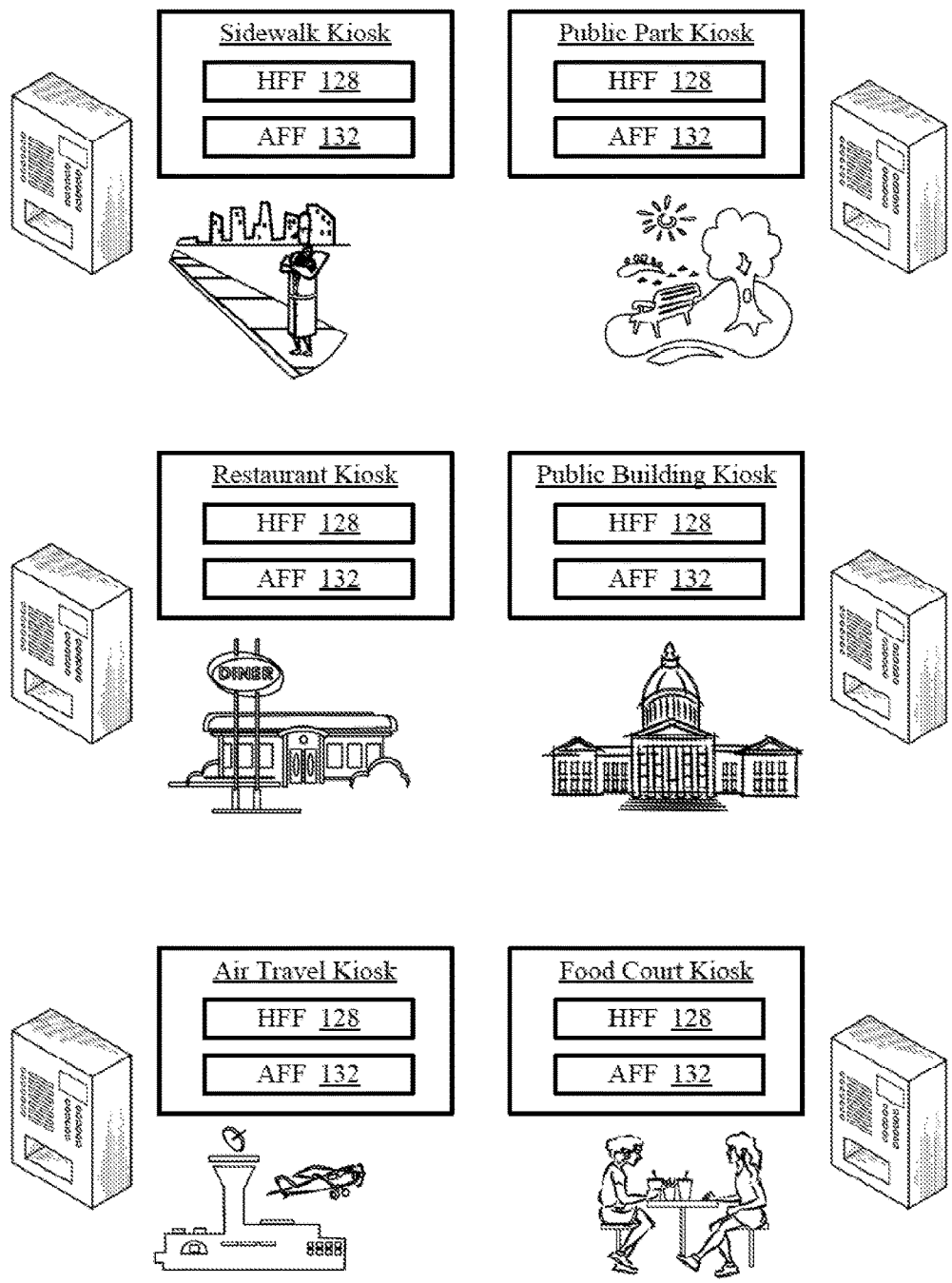
Fig. 1-N

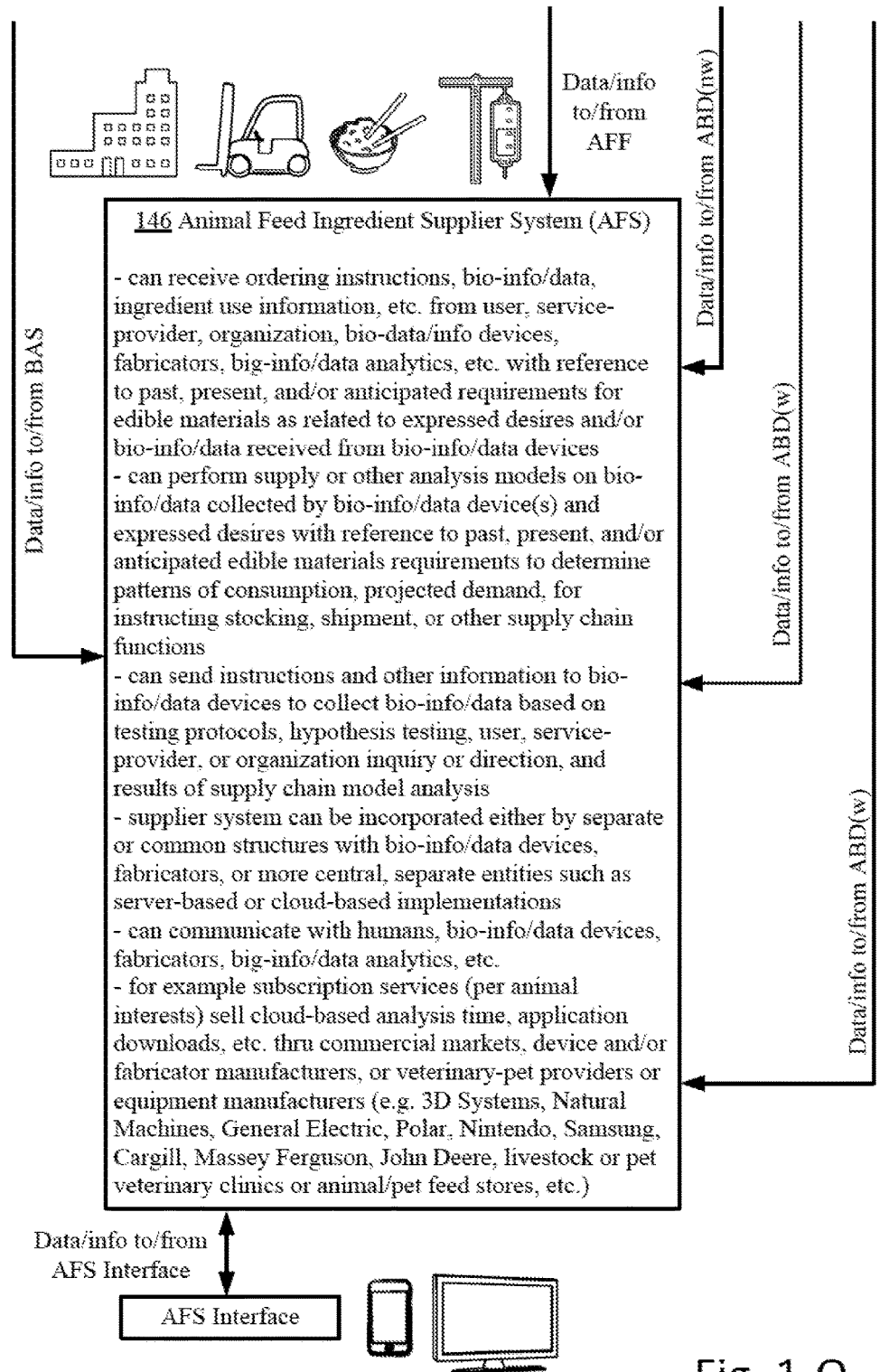
Fig. 1-O

QUANTIFIED-SELF MACHINES AND CIRCUITS REFLEXIVELY RELATED TO KIOSK SYSTEMS AND ASSOCIATED FOOD-AND-NUTRITION MACHINES AND CIRCUITS

CROSS-REFERENCE TO RELATED APPLICATIONS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 14/230,625, entitled Quantified-Self Machines and Circuits Reflexively Related to Food-and-Nutrition Machines and Circuits, naming Roderick A. Hyde, Muriel Y. Ishikawa, Jordin T. Kare, Eric C. Leuthardt, Royce A. Levien, Richard T. Lord, Robert W. Lord, Mark A. Malamud, Clarence T. Tegreene, Chuck Whitmer, Lowell L. Wood, Jr., and Victoria Y. H. Wood as inventors, filed 31, Mar. 2014, which is currently co-pending or is an application of which a currently co-pending application is entitled to the benefit of the filing date.

RELATED APPLICATIONS

None.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

BACKGROUND

This application is related to machines, machine states, etc. for data collection, communication, ingestible material fabrication or other dispensing, supply, etc., or analysis, etc.

SUMMARY

In one or more various aspects, a method includes, but is not limited to electronically receiving user biological status information from electronically involved detection of one or more biological user conditions; electronically obtaining one or more user ingestion preference indications; and electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein-referenced method aspects. The circuitry and/or programming may be virtually any combination of hardware, software (e.g. a high-level computer program serving as a hardware specification), and/or firmware configured to effect the herein-referenced method aspects depending upon the design choices of the system designer and limited to patentable subject matter under 35 USC 101.

In one aspect, a system includes, but is not limited to means for electronically receiving user biological status information from electronically involved detection of one or more biological user conditions; means for electronically obtaining one or more user ingestion preference indications; and means for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications. In addition to the foregoing, other system aspects are described in the claims, drawings, and text forming a part of the disclosure set forth herein.

In one aspect, a system includes, but is not limited to electrical circuitry arrangement for electronically-receiving-user-biological-status-information-from-electronically-involved-detection-of-biological-user-conditions; electrical circuitry arrangement for electronically-obtaining-user-ingestion-preference-indications; and electrical circuitry arrangement for electronically-providing-instruction-to-electronically-direct-factors-of-electronically-controlled-dispensing-of-manually-administrable-orally-ingestible-material-based-upon-the- electronically-receiving-user-biological-status-information-from-electronically-involved-detection-of-biological-user-conditions-and-based-upon-the-electronically-obtaining-user-ingestion-preference-indications. In addition to the foregoing, other system aspects are described in the claims, drawings, and text forming a part of the disclosure set forth herein.

In one aspect, a system includes, but is not limited to electronically-receiving-user-biological-status-information-from-electronically-involved-detection-of-biological-user-conditions module configured to operate in accordance with electronically receiving user biological status information from electronically involved detection of one or more biological user conditions; electronically-obtaining-user-ingestion-preference-indications module configured to operate in accordance with electronically obtaining one or more user ingestion preference indications; electronically-providing-instruction-to-electronically-direct-factors-of-electronically-controlled-dispensing-of-manually-administrable-orally-ingestible-material-based-upon-the- electronically-receiving-user-biological-status-information-from-electronically-involved-detection-of-biological-user-conditions-and-based-upon-the-electronically-obtaining-user-ingestion-preference-indications module configured to operate in accordance with electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications. In addition to the foregoing, other system aspects are described in the claims, drawings, and text forming a part of the disclosure set forth herein.

In one aspect, a computer program product may be expressed as an article of manufacture that bears instructions including, but not limited to one or more instructions for electronically receiving user biological status information from electronically involved detection of one or more biological user conditions; one or more instructions for electronically obtaining one or more user ingestion preference indications; and one or more instructions for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications. In addition to the foregoing, other computer program product aspects are described in the claims, drawings, and text forming a part of the disclosure set forth herein.

In one aspect, a system includes, but is not limited to one or more computing devices; and one or more instructions when executed on the one or more computing devices cause the one or more computing devices to perform electronically receiving user biological status information from electronically involved detection of one or more biological user conditions; electronically obtaining one or more user ingestion preference indications; and electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications. In addition to the foregoing, other computer program product aspects are described in the claims, drawings, and text forming a part of the disclosure set forth herein.

In addition to the foregoing, various other method and/or system and/or program product aspects are set forth and described in the text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the disclosures set forth herein.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise.

With reference now to the figures, shown are one or more examples of is an example of Quantified-Self Machines and Circuits Reflexively Related to Kiosk Systems and Associated Food-and-Nutrition Machines and Circuits that may provide context, for instance, in introducing one or more processes and/or devices described herein.

In accordance with 37 C.F.R. § 1.84(h)(2)

C.F.R. § 1.84(h)(2), and (ii) the partial view FIGS. 1-A through 1-O are ordered alphabetically, by increasing in columns from left to right, and increasing in rows top to bottom, as shown in the following table [with further orientation as indicated by assembly legends on the partial view figures]:

TABLE 1

Table showing alignment of enclosed drawings to form partial schematic of one or more environments.

| Pos. (0, 0) | X-Position 1 | X-Position 2 | X-Position 3 |
|---|---|---|---|
| Y-Pos. 1 | (1, 1): FIG. 1-A | (1, 2): FIG. 1-B | (1, 3): FIG. 1-C |
| Y-Pos. 2 | (2, 1): FIG. 1-D | (2, 2): FIG. 1-E | (2, 3): FIG. 1-F |
| Y-Pos. 3 | (3, 1): FIG. 1-G | (3, 2): FIG. 1-H | (3, 3): FIG. 1-I |
| Y-Pos. 4 | (4, 1): FIG. 1-J | (4, 2): FIG. 1-K | (4, 3): FIG. 1-L |
| Y-Pos. 5 | (5, 1): FIG. 1-M | (5, 2): FIG. 1-N | (5, 3): FIG. 1-O |

Figure 1:
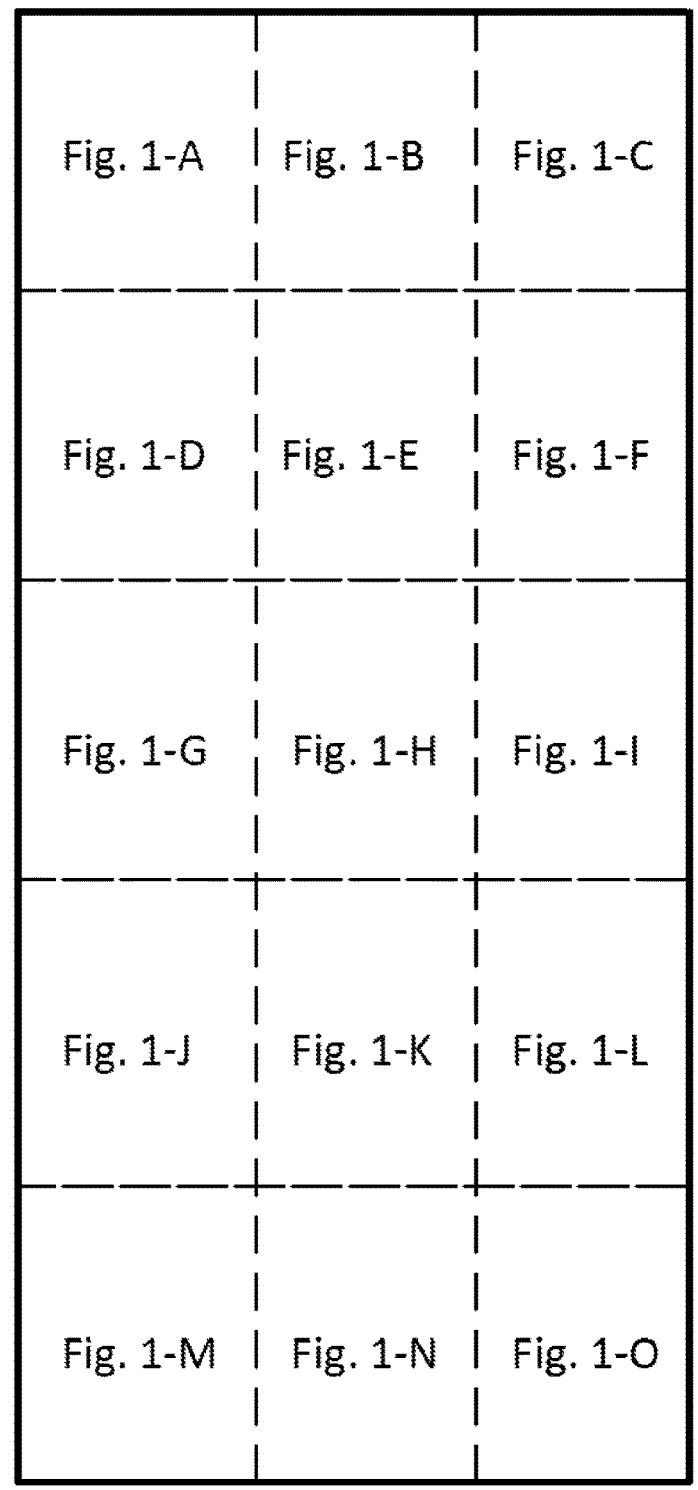
FIG. 1 shows "a view of a large machine or device in its entirety . . . broken into partial views . . . extended over several sheets" labeled FIG. 1-A through FIG. 1-O (Sheets 2-16). The "views on two or more sheets form, in effect, a single complete view, [and] the views on the several sheets . . . [are] so arranged that the complete figure can be assembled" from "partial views drawn on separate sheets . . . linked edge to edge. Thus, in FIG. 1, (i) a "smaller scale view" is "included, showing the whole formed by the partial views and indicating the positions of the parts shown," e.g., as described in 37

In accordance with 37 C.F.R. § 1.84(h)(2), FIG. 1 is " . . . a view of a large machine or device in its entirety . . . broken into partial views . . . extended over several sheets . . . [with] no loss in facility of understanding the view." [Assembly legends have been provided on one or more sheets where appropriate to assist in assembling the figures into a single view.] The partial views drawn on the several sheets indicated in the above table are capable of being linked edge to edge, so that no partial view contains parts of another partial view. [In addition, a smaller scale view has been included, showing the whole formed by the partial views and indicating the positions of the individual sheets in forming the complete view.] As here, "where views on two or more sheets form, in effect, a single complete view, the views on the several sheets are so arranged that the complete figure can be assembled without concealing any part of any of the views appearing on the various sheets." 37 C.F.R. § 1.84(h)(2).

It is noted that one or more of the partial views of the drawings may be blank, or may not contain substantive elements (e.g., may show only lines, connectors, and the like). These drawings are included in order to assist readers of the application in assembling the single complete view from the partial sheet format required for submission by the USPTO, and, while their inclusion is not required and may be omitted in this or other applications, their inclusion is proper, and should be considered intentional.

Figure 2:
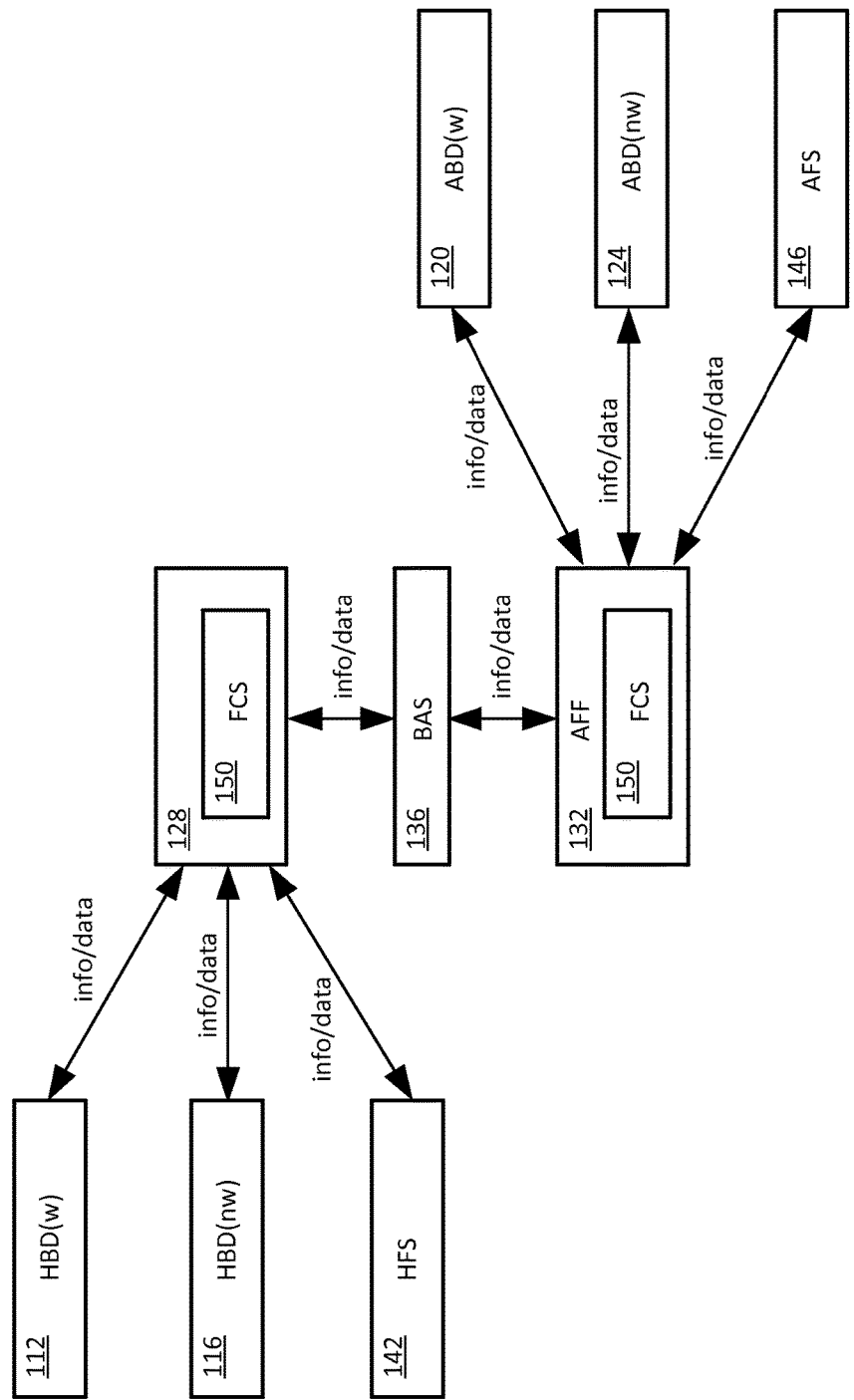

FIG. 2 shows a schematic diagram of implementation(s) of environment(s) and/or implementations(s) of one or more technologies described herein including food fabricator implementation(s) in communication with bio-info/data device implementation(s), with food supply implementation(s) and with big-data analytics implementation(s).

Figure 3:
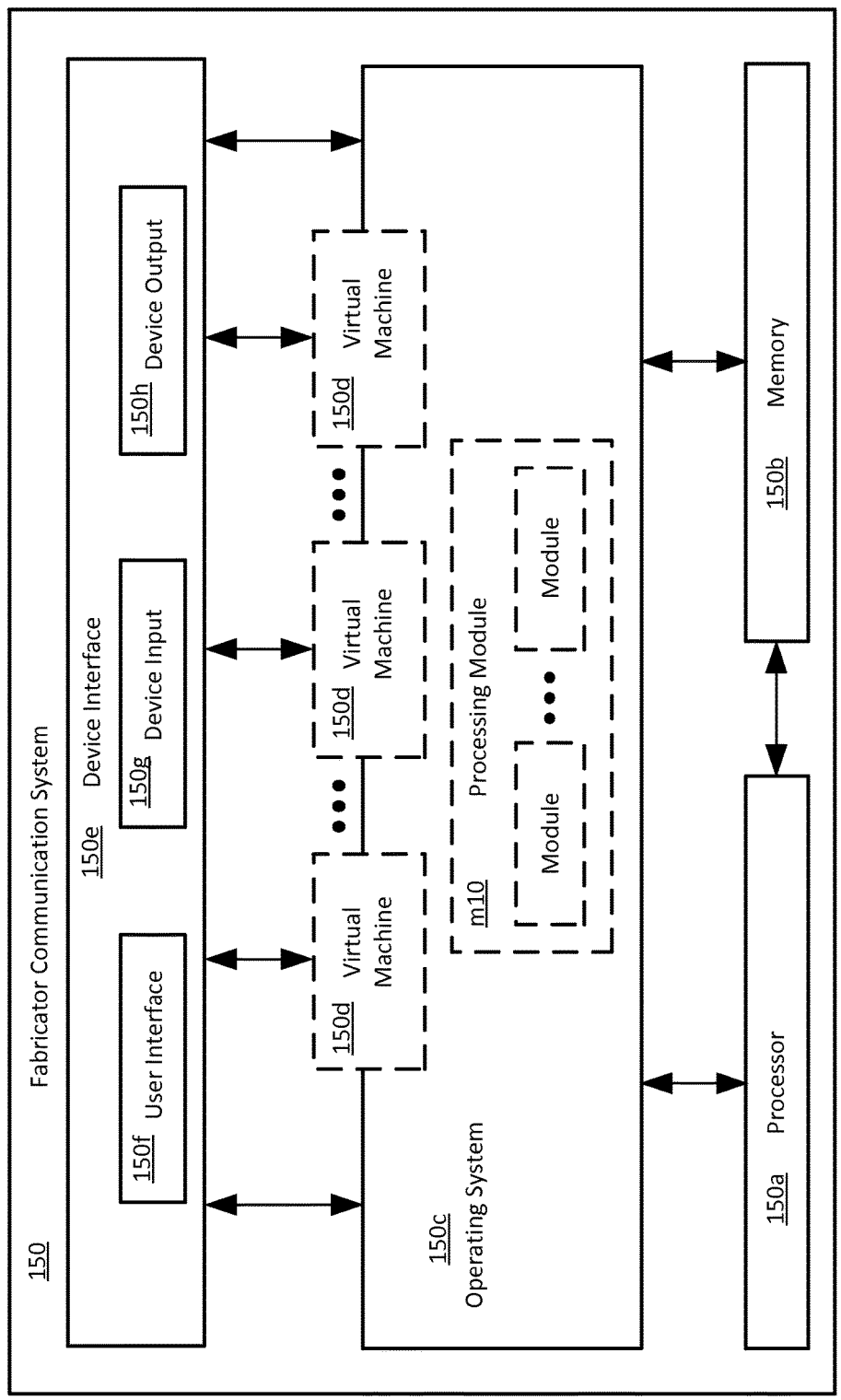

FIG. 3 shows a schematic diagram of implementation(s) of environment(s) and/or implementations(s) of one or more technologies described herein including fabricator communication system implementation(s).

Figure 4:
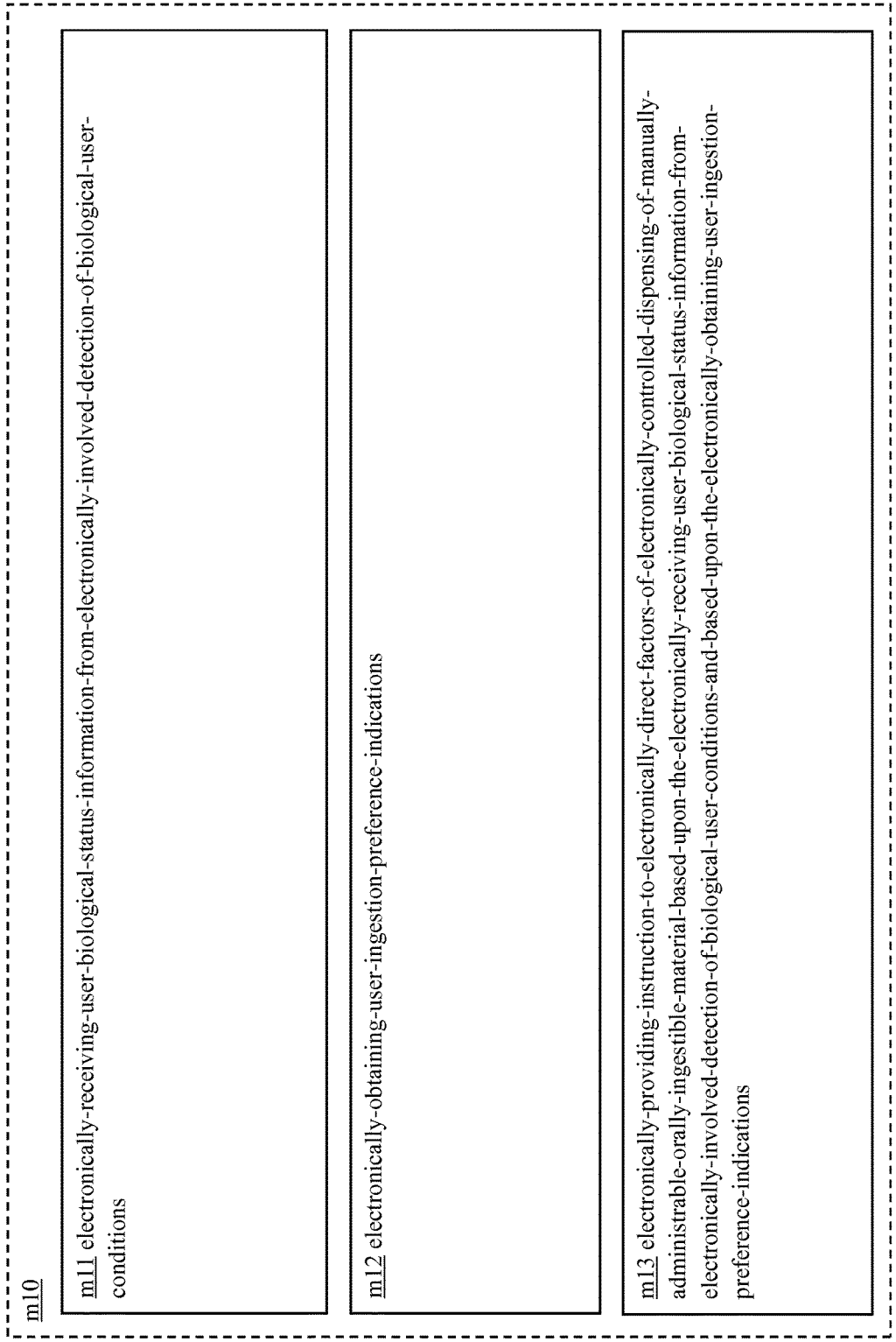

FIG. 4 shows a schematic diagram of implementation(s) of environment(s) and/or implementations(s) of one or more technologies described herein including processing module implementation(s).

FIG. 5 through FIG. 44 (sheets 20-59) show partially schematic diagrams of implementations of electronically-receiving-user-biological-status-information-from-electronically-involved-detection-of-biological-user-conditions modules.

FIG. 45 through FIG. 51 (sheets 60-66) show partially schematic diagrams of implementation(s) of electronically-obtaining-user-ingestion-preference-indications modules.

FIG. 52 through FIG. 62 (sheets 67-77) show partially schematic diagrams of an implementations of electronically-providing-instruction-to-electronically-direct-factors-of-electronically-controlled-dispensing-of-manually-administrable-orally-ingestible-material-based-upon-the-electronically-receiving- user-biological-status-information-from-electronically-involved-detection-of-biological-user-conditions-and-based-upon-the-electronically-obtaining-user-ingestion-preference-indications modules.

Figure 63:
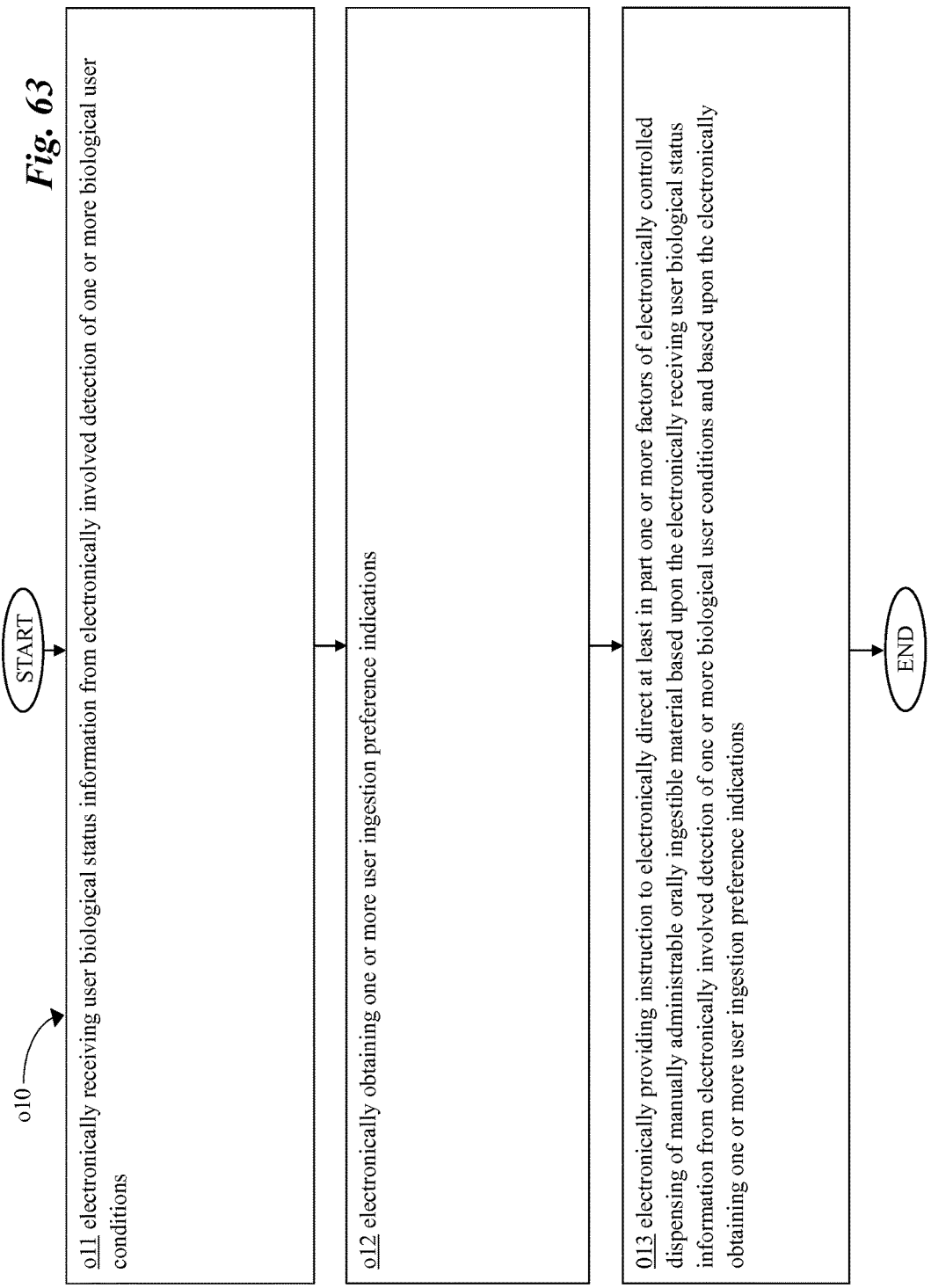

FIG. 63 shows a high-level flowchart illustrating an operational flow o10 representing exemplary operations related to operation o11, operation o12, and operation o13.

Figure 8:
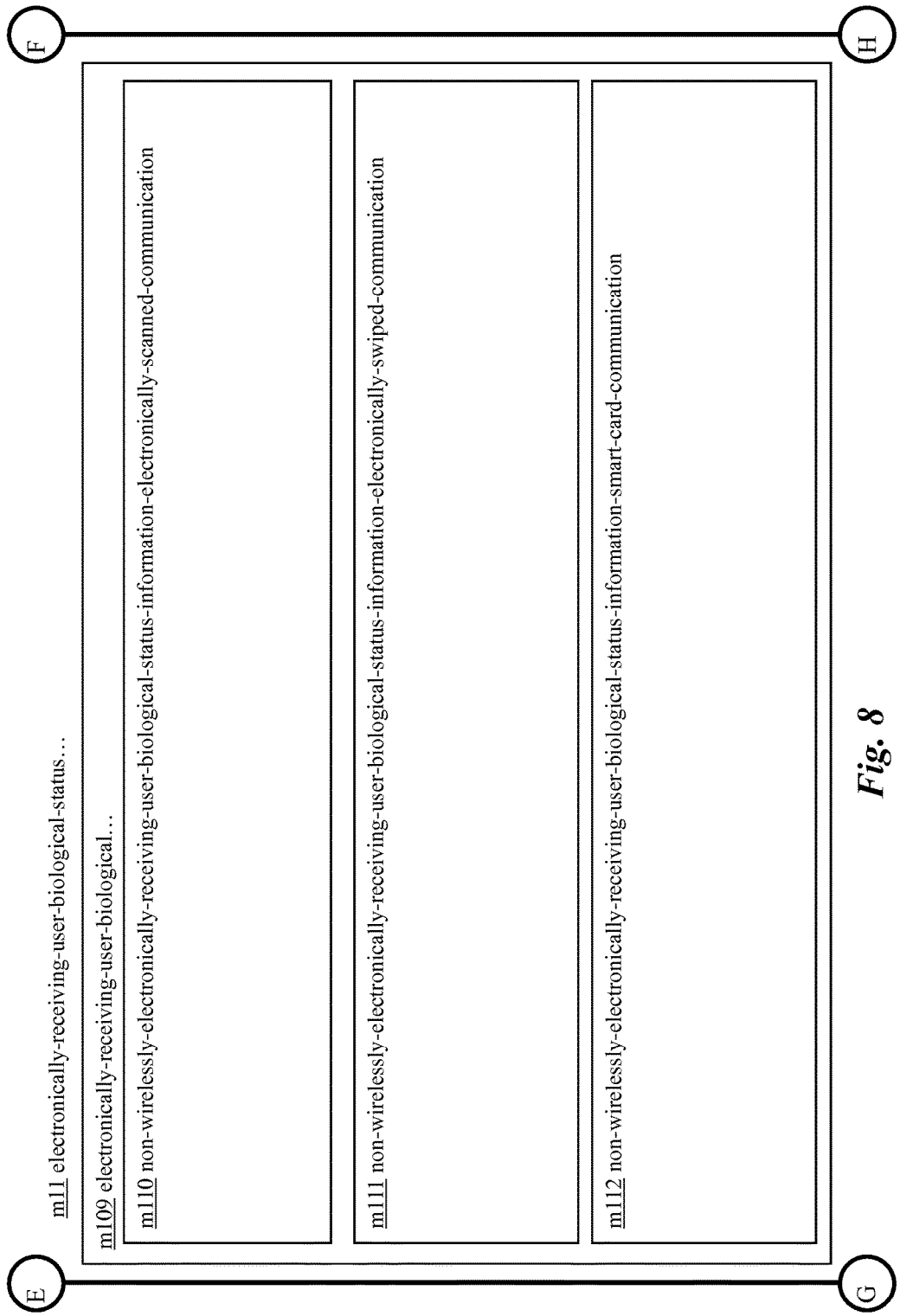

FIG. 64 through FIG. 103 (Sheets 79-118) show high-level flowcharts including exemplary implementations of operation o11 of FIG. 8.

FIG. 104 through FIG. 110 (Sheets 119-125) show high-level flowcharts including exemplary implementations of operation o12 of FIG. 8.

FIG. 111 through FIG. 121 (Sheets 126-136) show high-level flowcharts including exemplary implementations of operation o13 of FIG. 8.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software (e.g., a high-level computer program serving as a hardware specification)).

Importantly, although the operational/functional descriptions described herein are understandable by the human mind, they are not abstract ideas of the operations/functions divorced from computational implementation of those operations/functions. Rather, the operations/functions represent a specification for massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to a human reader. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail herein, these logical operations/functions are not representations of abstract ideas, but rather are representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct" (e.g., that "software"—a computer program or computer programming—is somehow an ineffable mental construct, because at a high level of abstraction, it can be conceived and understood by a human reader). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of logic, such as Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configurations, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT). Thus, programs written in machine language—which may be tens of millions of machine language instructions long—are incomprehensible to most humans. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that useful, tangible, and concrete work is done. For example, as indicated above, such machine language—the compiled version of the higher-level language—functions as a technical specification which selects out hardware logic gates, specifies voltage levels, voltage transition timings, etc., such that the useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality of logic(s), or (d) virtually any combination of the foregoing. Indeed, any physical object which has a stable, measurable, and changeable state may be used to construct a machine based on the above technical description. Charles Babbage, for example, constructed the first mechanized computational apparatus out of wood, with the apparatus powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language should not be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

Those having skill in the art will recognize that the state of the art has progressed to the point where there is little distinction left between hardware, software (e.g., a high-level computer program serving as a hardware specification), and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software (e.g., a high-level computer program serving as a hardware specification), and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software (e.g., a high-level computer program serving as a hardware specification) implementation; or, yet again alternatively, the implementer may opt for some combination of hardware, software (e.g., a high-level computer program serving as a hardware specification), and/or firmware in one or more machines, compositions of matter, and articles of manufacture, limited to patentable subject matter under 35 U.S.C. § 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software (e.g., a high-level computer program serving as a hardware specification), and or firmware.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software (e.g., a high-level computer program serving as a hardware specification) or firmware, or of gate arrays or programmable hardware, such as by performing a reception of or a transmission of one or more instructions in relation to one or more operations described herein. Alternatively or additionally, in some variants, an implementation may include special-purpose hardware, software (e.g., a high-level computer program serving as a hardware specification), firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software (e.g., a high-level computer program serving as a hardware specification), firmware, or virtually any combination thereof, limited to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software (e.g., a high-level computer program serving as a hardware specification) and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The term module, as used in the foregoing/following disclosure, may refer to a collection of one or more components that are arranged in a particular manner, or a collection of one or more general-purpose components that may be configured to operate in a particular manner at one or more particular points in time, and/or also configured to operate in one or more further manners at one or more further times. For example, the same hardware, or same portions of hardware, may be configured/reconfigured in sequential/parallel time(s) as a first type of module (e.g., at a first time), as a second type of module (e.g., at a second time, which may in some instances coincide with, overlap, or follow a first time), and/or as a third type of module (e.g., at a third time which may, in some instances, coincide with, overlap, or follow a first time and/or a second time), etc. Reconfigurable and/or controllable components (e.g., general purpose processors, digital signal processors, field programmable gate arrays, etc.) are capable of being configured as a first module that has a first purpose, then a second module that has a second purpose and then, a third module that has a third purpose, and so on. The transition of a reconfigurable and/or controllable component may occur in as little as a few nanoseconds, or may occur over a period of minutes, hours, or days.

In some such examples, at the time the component is configured to carry out the second purpose, the component may no longer be capable of carrying out that first purpose until it is reconfigured. A component may switch between configurations as different modules in as little as a few nanoseconds. A component may reconfigure on-the-fly, e.g., the reconfiguration of a component from a first module into a second module may occur just as the second module is needed. A component may reconfigure in stages, e.g., portions of a first module that are no longer needed may reconfigure into the second module even before the first module has finished its operation. Such reconfigurations may occur automatically, or may occur through prompting by an external source, whether that source is another component, an instruction, a signal, a condition, an external stimulus, or similar.

For example, a central processing unit of a personal computer may, at various times, operate as a module for displaying graphics on a screen, a module for writing data to a storage medium, a module for receiving user input, and a module for multiplying two large prime numbers, by configuring its logical gates in accordance with its instructions. Such reconfiguration may be invisible to the naked eye, and in some embodiments may include activation, deactivation, and/or re-routing of various portions of the component, e.g., switches, logic gates, inputs, and/or outputs. Thus, in the examples found in the foregoing/following disclosure, if an example includes or recites multiple modules, the example includes the possibility that the same hardware may implement more than one of the recited modules, either contemporaneously or at discrete times or timings. The implementation of multiple modules, whether using more components, fewer components, or the same number of components as the number of modules, is merely an implementation choice and does not generally affect the operation of the modules themselves. Accordingly, it should be understood that any recitation of multiple discrete modules in this disclosure includes implementations of those modules as any number of underlying components, including, but not limited to, a single component that reconfigures itself over time to carry out the functions of multiple modules, and/or multiple components that similarly reconfigure, and/or special purpose reconfigurable components.

In a general sense, those skilled in the art will recognize that the various embodiments described herein can be implemented, individually and/or collectively, by various types of electro-mechanical systems having a wide range of electrical components such as hardware, software (e.g., a high-level computer program serving as a hardware specification), firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software (e.g., a high-level computer program serving as a hardware specification), firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software (e.g., a high-level computer program serving as a hardware specification), and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, Verizon, AT&T, etc.), or (g) a wired/wireless services entity (e.g., Sprint, AT&T, Verizon, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, including but not limited to [insert list], are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user XXX is shown/described herein as a single illustrated figure, those skilled in the art will appreciate that user XXX may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

For the purposes of this application, "cloud" computing may be understood as described in the cloud computing literature. For example, cloud computing may be methods and/or systems for the delivery of computational capacity and/or storage capacity as a service. The "cloud" may refer to one or more hardware and/or software (e.g., a high-level computer program serving as a hardware specification) components that deliver or assist in the delivery of computational and/or storage capacity, including, but not limited to, one or more of a client, an application, a platform, an infrastructure, and/or a server The cloud may refer to any of the hardware and/or software (e.g., a high-level computer program serving as a hardware specification) associated with a client, an application, a platform, an infrastructure, and/or a server. For example, cloud and cloud computing may refer to one or more of a computer, a processor, a storage medium, a router, a switch, a modem, a virtual machine (e.g., a virtual server), a data center, an operating system, a middleware, a firmware, a hardware back-end, an application back-end, and/or a programmed application. A cloud may refer to a private cloud, a public cloud, a hybrid cloud, and/or a community cloud. A cloud may be a shared pool of configurable computing resources, which may be public, private, semi-private, distributable, scaleable, flexible, temporary, virtual, and/or physical. A cloud or cloud service may be delivered over one or more types of network, e.g., a mobile communication network, and the Internet.

As used in this application, a cloud or a cloud service may include one or more of infrastructure-as-a-service ("IaaS"), platform-as-a-service ("PaaS"), software-as-a-service ("SaaS"), and/or desktop-as-a-service ("DaaS"). As a non-exclusive example, IaaS may include, e.g., one or more virtual server instantiations that may start, stop, access, and/or configure virtual servers and/or storage centers (e.g., providing one or more processors, storage space, and/or network resources on-demand, e.g., EMC and Rackspace). PaaS may include, e.g., one or more program, module, and/or development tools hosted on an infrastructure (e.g., a computing platform and/or a solution stack from which the client can create software-based interfaces and applications, e.g., Microsoft Azure). SaaS may include, e.g., software hosted by a service provider and accessible over a network (e.g., the software for the application and/or the data associated with that software application may be kept on the network, e.g., Google Apps, SalesForce). DaaS may include, e.g., providing desktop, applications, data, and/or services for the user over a network (e.g., providing a multi-application framework, the applications in the framework, the data associated with the applications, and/or services related to the applications and/or the data over the network, e.g., Citrix). The foregoing is intended to be exemplary of the types of systems and/or methods referred to in this application as "cloud" or "cloud computing" and should not be considered complete or exhaustive.

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

As depicted in FIG. 1, a quantified-self information system regarding quantified-self information and data such as human bio-info/data and animal bio-info/data includes human bio-info/data devices (wearable) 112, human bio-info/data devices (non-wearable) 116, animal bio-info/data devices (wearable) 120, animal bio-info/data (non-wearable) 124, human food fabricators 128, animal feed fabricators 132, big-info/data analytics system 136, human food ingredient supplier systems 142, and animal feed ingredient supplier systems 146 electronically communicatively linked together for information and data collection, analysis and operational guidance thereby, and other interrelated functionality therebetween.

The human bio-info/data device (wearable) 112 can include the following. The human bio-info/data device (wearable) 112 can collect biological and other data non-invasively, invasively, other sample collection, etc. regarding human device wearer such as regarding physiological status involving molecular, chemical, analytes, electrolytes, cellular, tissue, organ, systems (e.g. skeletal, muscular, immune, lymphatic, cardiovascular, urinary, digestive, respiratory, nervous, endocrine, reproductive, integumentary, etc.), functional (e.g. sleeping, walking, running, sitting, posture, standing, squatting, lifting, speaking, listening, seeing, driving, eliminating, reacting, ambulating, thinking, location, etc.), electrical, disease (e.g. past, present, potential, etc.), mechanical (structural, movement, sports, recreation, etc.), and other related status.

The human bio-info/data device (wearable) 112 can be worn on wrist (e.g. band, wristwatch), hand (e.g. glove), finger (e.g. ring), arm (e.g. band), leg (e.g. strap), foot (e.g. sock, shoe, boot), waist (e.g. band, belt), neck (e.g. necklace), head (e.g. band), ear (e.g. ring), eye (e.g. eyewear), on elsewhere on body (e.g. clothing), etc. The human bio-info/data device (wearable) 112 can communicate with human wearer, other human bio-info/data devices (e.g. wearable or non-wearable), food fabricator, big-data analytics system, food ingredient supplier, etc.

The human bio-info/data device (wearable) 112 can include for example subscription services (health, food, cooking, etc.) sell device and applications thru home or kiosk food fabricator networks, device and applications sold by manufacturers of food fabricator or medical-health-sports providers-manufacturers (e.g. 3D Systems, Natural Machines, Whirlpool, KitchenAid, Miele, medical and health clinics, General Electric, Polar, Nintendo, Samsung, etc.).

The human bio-info/data device (non-wearable) 116 can include the following. The human bio-info/data device (non-wearable) 116 can collect biological and other data non-invasively, invasively, other sample collection, etc. regarding one or more associated humans such as regarding physiological status involving molecular, chemical, analytes, electrolytes, cellular, tissue, organ, systems (e.g. skeletal, muscular, immune, lymphatic, cardiovascular, urinary, digestive, respiratory, nervous, endocrine, reproductive, integumentary, etc.), functional (e.g. sleeping, eating, walking, running, sitting, posture, standing, squatting, lifting, speaking, listening, seeing, driving, eliminating, reacting, ambulating, thinking, location, etc.), electrical, disease (e.g. past, present, potential, etc.), mechanical (structural, movement, sports, recreation, etc.), and other related status.

The human bio-info/data device (non-wearable) 116 can be part of a room located in proximity of human (e.g. structural room member, room fixture, room accessory, door component, etc.), or adjacent or occasionally in contact (e.g. sink, toilet, chair, table, desk, exercise equipment, computer, keyboard, mouse, monitor, pen, steering wheel, tableware, personal care items, luggage, phone, cameras, notebooks, tablets, robot, drone, etc.). The human bio-info/data device (non-wearable) 116 can communicate with human, other human bio-info/data devices (e.g. wearable or non-wearable), food fabricator, big-data analytics system, food ingredient supplier, etc.

The human bio-info/data device (non-wearable) 116 for example subscription services (health, food, cooking, etc.) sell device and applications thru home or kiosk food fabricator networks, device and applications sold by manufacturers of food fabricator, or medical-health-sports providers-manufacturers (e.g. 3D Systems, Natural Machines, Whirlpool, KitchenAid, Miele, medical or health clinics, General Electric, Polar, Nintendo, Samsung, etc.).

Further aspects regarding the wearable and non-wearable human bio-info/data devices can include collecting information or data related to food preferences such as texture, color, or taste such as sweet, sour, salty, or other taste sensations. Such collected information or data can in a sense profile a particular individual as far as how the individual reacts to various foods and other indigestible materials from a psychological, physiological, sensory, or other aspects. This type of profiling can then be used in order to tailor the various food and other indigestible materials for the individual. For instance, the profiling information can be used to tune macronutrient, micronutrient, bacterial or other content of food in real time regarding various activity levels of the individual. These activity levels can be related to environmental conditions such as weather conditions, location in various architectures or other locations, or various activity goals. Such activities can involve educational pursuits, vocational activities, sports events, or other varied activities.

The human bio-info/data can also include other aspects besides that which is physiologically related such as location data. Location data can be matched with location of other humans or location of various occurrences of activity in which performance or habit patterns of an individual can be assessed. For instance, performance or habit patterns related to parenting can be determined such as how much time is spent with a child regarding certain activities. These activities can include eating, educational events, sports or entertainment events, etc. This human-bio info/data can then be analyzed statistically or otherwise to determine rankings or other assessments related to parenting.

Other human bio-info/data can include recorded observations by one or more individual humans regarding preferences or dislikes associated with activities, habits, food choices, associations, better aspects associated with one or more individual humans etc. For instance, an individual may express a desire to be like another individual in terms of physical fitness, general overall appearance, mental acuity, or other such admirable traits. The human bio-info/data as recorded observations can be used real-time or later on to assist in food selection for the individual. These recorded observations can be also incorporated into other goals such as having diet constraints, physiological requirements, etc. These observations can also be directed to other humans such as a parent desiring their child to eat in a certain manner or to have certain food items or to avoid other food items. These observations can then be used for determining what food to provide to the child in certain instances such as at school or a sporting event. Observations obtained from the child as to likes and dislikes and observations obtained from the parent as to health, physiological, illness management, and other parental goals can then be combined to determine or optimize various choices available. This approach can allow for implementation of desires and goals of both parent and child in a peaceable manner.

Other human bio-info/data can include activity parameters involving measurement of quality or quality of various activities performed. For instance, these activities could include instructional activities at school having to do with concentration levels, amount of involvement, degree of insight and expression, work capacity, interest level, level a distraction, ingenuity, leadership, and other factors related to a learning environment. These sorts of factors can also be measured or otherwise observed as human bio-info/data in other environments such as a workplace, a home environment, an entertainment environment, or other such environments or locations. For instance in a home environment, bio-info/data could be related to communication levels, cooperation levels, interest levels, selfishness levels, etc. of one or more household members either individually or collectively. Information or data content can be extracted from visual, audio, location, or other data to various recognition schemes, statistical analysis, etc. Behavioral profiles can be then establish their individual members or collection of members and compared with normative standards. These sorts of determinations can also be applicable to other environments such as workplace, entertainment, etc.

Various human bio-info/data devices can be set up in a local or wide area network anywhere within a particular architectural structure or across the Internet. By networking the human bio-info/data devices together they can be working in a synergistic approach in which human bio-info/data collected by one device can be shared with other devices so that complementary human bio-info/data can be collected by the various device members of the networked team of devices. This arrangement can be conducive for such desires is testing hypotheses in which human bio-info/data collected by a set of one or more first devices can then be fed and with other bio-info/data collected by us set of one or more second devices. For instance, human bio-info/data devices could be located in refrigerators, food fabricators or printers, stoves, microwave ovens, conventional ovens, convection ovens, cook tops, sinks, dishwashers, wearable devices, food utensils, eating area furniture, kitchen sinks, bathroom equipment including sinks, showers, bathtubs, and toilets, and other structures, equipment, etc. related to an individual's living environments such as office furniture, bedroom furniture, etc.

Human bio-info/data devices can include Google glasses, smart watches, mobile devices such as iPhone, smart phones, handsets, Android phones, tablets, phablets, laptops, personal devices, smart earpieces, electronically enabled clothing, made by Apple, Samsung, Google, etc. Human-info/data devices can be formed as non-reconfigurable hardware devices or can be programmable devices to receive programming related to human bio-info/data functionality. Functionality can also be incorporated into operating systems such as Android OS or the Apple OS. Other form factors can include sports equipment and other such athletic gear. For instance, skis with various sensors to determine quantity and quality of athletic output by a skier over a course of a day or season could be used as another sort of bio-info/data device. Another example could include sensors integrated with bicycles, hiking gear, sports balls, and other athletic equipment. What are more of these human bio-info/databases can be branded under various corporate marketing or other programs which furnish one or more portions of generic or hardware specific programming or other instruction sets related to functionality in collecting or analyzing bio-info/data such as through food suppliers, big-data analytics, food fabricator system providers, or device makers. Branding can include subscription services to information such as updated recipes, lifestyle adjustment, or other aspects related to quantified life interests, etc.

Human bio-info/data devices can include sophisticated data collection instruments such as nuclear magnetic resonance equipment including NMR rings to determine such as molecular markers. Human bio-info/data devices can be used to collect other quantified-self information and data to be used in turn by human food fabricators, big-data analytics, and human food supply systems. For instance, human bio-info/data can be collected regarding home life including dialogue between spouses, parents and children, siblings, other relatives, visitors, guests, etc. Dialogue can be analyzed for emotional, intellectual, psychological, physiological, behavioral, normative, aberrant, and other content, etc., assessing performance relative to peers, normative behavior, outside of normative behavior, spouse, other norms, children relative to other children, relative to other parents, etc. Scenarios can include percentage of emotionally heated dialogue to train parents and children relative to norms or other statistical patterns, whether homework atmosphere is conducive for substantive production, accounting and other financial data associated with household expenditures, stress levels, health levels, etc., driving habits as recorded by vehicle instrumentation, quantity, quality, scheduling, etc. of exercise regimens, etc. Quantified-self or human bio-info/data measurements and information can also be used to identify interests, desires, or dislikes regarding activities, environments are other aspects mentioned herein using quantified scoring or other reporting techniques. Other scenarios can include assessing reading level and suggesting appropriate materials to be read. Other reading data could include number of words read to children on a daily, weekly, monthly, annual, etc. basis.

Human bio-info/data or quantified-self data can tie performance levels with ingestion of food and other materials. For instance, ingestion of various sugars such as fructose, dextrose, sucrose, or other combinations thereof can affect ability to lose adipose tissue, maintain energy and endurance levels, and other factors of performance including intellectual performance and work-product production. Types of fats included in the diet such as amount of omega-three, omega-six, and the ratios thereof and also including DHA, EPA, trans-fats, or arachadonic acid, saturated fats, polyunsaturated fats, monounsaturated fats, or other fats can also affect performance levels including intellectual ability. Various contaminants such as lectins, and phytic acid as found in grains, beans, seeds, nuts, tubers, etc. can detrimentally affect mineral absorption along with other biochemical activities further impacting performance and health levels. Protein quality including issues related to denaturation of amino acids can affect absorbability and digestion efficacy. These and other factors can be tracked as bio-info/data and integrated into systems using bio-info/data devices, food fabricators, egg-data analytics, and food supplier systems to assist users with optimizing goals and performance levels.

Human bio-info/data regarding educational environments can include how many times did a child speak to a teacher, activity levels for various endeavors such as athletics, classroom participation, extracurricular activities, study hall, etc. Bio-info/data regarding educational environments can include other quantified-self info/data such as amount of bullying experienced, amount of positive social interaction with other students during a school week, amount and type of food eaten during lunchtime, and comparisons of this and other data with statistical groupings such as averages, means, etc. such as locally, regionally, nationally, etc.

Quantified-self info/data as human bio-info/data can include that involving self-improvement, efficiency, or other measurements in various environments requiring performance such as workplace, home, athletics, education, etc. Quantity and quality of work-product through use of text-based, speech-based, pattern recognition, brainwave pattern tracking, measurement sensors attached to equipment, and other instruments such as musical instruments, etc. or other sorts of analysis can be implemented. Efficiency measures can be used to track duration, time on task, output level profiles, rest break profiles, etc. For instance, measures such as time using twitter, typing, talking on phone, etc. can be compared with other activities. These efficiency measures and other data can be related to degree of difficulty of the task at hand. Other bio-info/data can include measurements related to habits or traits targeted for acquisition, improvement, decrease, or elimination. Such habits or traits can relate to diet, physical exercise, skill practice sessions including intellectual, physical, musical, artistic, athletic, social, communication, educational, governmental, and other skills. Objective measures related to work and include time spent consuming recreational media, time spent on social networks, time spent on personal phone, etc. and can be compared to coworkers or expectation by company managers and graphical display of comparisons or issues flagged about level of engagement with work compared with thresholds. Other quantified-self or bio-info/data can include other objective measures of activities related to life including trips outside the home, meal and snack patterns, social contacts, activity patterns, etc. as compared to specified others or standardized norms. Results can be displayed changes can be recommended based on goals, therapies, norms, etc., such as for instance, recommendations of more trips for depressed individuals, less eating for the abuse, more social contacts for those with few social contacts, alerts regarding activity levels indicating possible individual addiction, etc.

Quantified-self info/data or otherwise human bio-info/data can be linked with systems such as big-data analytics or personal analytics in various user interfaces including visual, audio, tactile, and other such user interfaces to provide feedback, incentives, and further encouragement in behavioral modification on an individual, group, corporate, or other basis. Users or others can identify which types of information or data should be tracked, assessed, or otherwise processed. For instance, users may specify desires to be more effective in interacting with others, gaining experiences, skills, production goals, etc. Such systems can be directed for manipulation of behavior associated with diet such as increasing or decreasing intake of various foods, adopting habit patterns involving exercise duration, quantity, quality, type, etc., associating with other individuals or groups with common goals or desires, etc. adopting or shunning various mannerisms and expression such as volume level, word choice, content of speech, signals of irritation, abrasive content, or other methods of expression. Computer use can be tracked as well regarding type of use, duration, rest breaks, etc. Quality of family life such as time spent together in various activities. Personality traits of individuals and groups can also be identified through statistical and other analysis of such data to be used for planning and other purposes.

Human bio-info/data or otherwise quantified-self info/data can include shopping activities related to food acquisition, exposure to toxins, dietary goals such as amount of desired food items to be ingested over a period of time, recording itinerary or other travel routes taken between or within stores such as grocery stores, department stores, discount stores, etc., or shopping through other means such as Internet-based purchasing on various websites. Collection of such information can also be further encouraged through discounting cost of various items or other incentives.

Human bio-info/data or quantified-self info/data can be used to acquire objective measurements and other assessments related to the various activities of parenting. For instance, regarding tummy time, theories include that infants should be spending a certain amount of time every day on their stomach for instance 30 minutes a day or as recommended by a physician. A system integrated with such human bio-info data could provide three user interfaces various alerts and other parenting information for instance, if tummy time is below recommended thresholds. Measurements regarding the spoken word from parents can be used to alert, train, or otherwise inform parents of their performance levels. Infants or small children could be assigned target words that parents are to speak to a child at certain times or throughout the day. Such performance can be them monitored such as through daily, local, national averages are other statistical measures to assess relative performance levels.

Quantified-self bio-info/data for parenting and other activities can also include measurements related to book reading such as particular types, subject areas, quantity, quality, amount of time spent on a daily, weekly, monthly, etc. basis, reading level for grade or age with comparisons regarding such measures statistically or otherwise on various local to national, etc. levels. Another measurement can include amount of eye contact through neurotypical metrics or neurotypical eye contacts. Such human bio-info/databases as Google glasses, or other glasses that can measure eye contact can be used, or other devices such as facial analyzers can be used as human bio-info/data devices. Feedback can be provided to users with a variety of intelligence levels to increase cooperation among themselves or for other training purposes.

Other parenting applications for quantified-self info/data or otherwise human bio-info/data can involve monitor, screen, television, movie, or other media displays. For instance, parental goals could include limiting amounts at which their children spend such time. Various parental controls can also involve content monitoring, encrypted logging of activity, content ratings for objectionable material including levels, degrees, intensity, etc. of violence, pornography, vulgarity, wantonness, shock effect, social aberration, instilling of fear, etc. Other factors can include viewing location in relation to proximity of display, etc.

Human bio-info/data can also include metrics related to sleep quantity, quality, etc. These measurements can be compared with various norms to ascertain, classify, etc. sleep patterns for children. For instance, a child starts to get sleepy at 7 PM and has a period of light sleep around 11 PM. Through use of a system integrated such as with big-data analytics and human bio-info data this and other behavior can be compared or classified to inform parents of any concerns to be noted. Insights derived from this analysis can also be used to tailor calendars or otherwise schedule activities of the children based on their particular sleep-wake patterns occur throughout the day and night rather than merely relying on expected norms of behavior. This tailoring approach could also be applied directly with educational institutions such as advanced or progressive grade school or higher levels schools.

Parental use of human bio-info data can also include potty training where parents can track toileting successes of their children over a period of time. Such success training can be used for motivational purposes for the children or to provide feedback to the parents regarding their skills in training their children. Objective measures of success can include amount of accidents over a period of time with a trend toward gradual reduction indicating success. Comparison with training profiles of other children can help parents determine if there are concerns to be had.

Analysis of parenting performance can further include comparison of objective measures involving other parents similarly situated regarding location such as city, state, nation, etc., parental lifestyle including whether both spouses work outside the home, amount and type of social network friends, rankings regarding top ten percent or top quartile, etc. Further comparisons include objective measurements those of others same school, citywide, statewide, nationwide, worldwide, social network-wide with analysis or other outcomes reported to parents, teachers, others in authority, etc. and can include such as recommendations for suitable responses.

The animal bio-info/data device (wearable) 120 can include the following. The animal bio-info/data device (wearable) 120 can collect biological and other data non-invasively, invasively, other sample collection, etc. regarding animal device wearer such as regarding physiological status involving molecular, chemical, analytes, electrolytes, cellular, tissue, organ, systems (e.g. skeletal, muscular, immune, lymphatic, cardiovascular, urinary, digestive, respiratory, nervous, endocrine, reproductive, integumentary, etc.), functional (e.g. sleeping, eating, ambulating, non-ambulatory postures, emitting sounds, listening, seeing, eliminating, reacting, location, etc.), electrical, disease (e.g. past, present, potential, etc.), mechanical (structural, movement, etc.), and other related status.

The animal bio-info/data device (wearable) 120 can be worn on animal by collar, vest, strap, mask, blinder, blanket, harness, piercing, branding, hood, shoeing, tagging, clothing, band, belt, etc. The animal bio-info/data device (wearable) 120 can communicate with human owner, manager, attendant, other animal bio-info/data devices (e.g. wearable or non-wearable), feed fabricator, big-data analytics system, food ingredient supplier, etc.

The animal bio-info/data device (wearable) 120 can include for example subscription services (health, food, cooking, etc.) sell device and applications thru home or kiosk food fabricator networks, device and applications sold by manufacturers of food fabricator or medical-health-sports providers-equipment manufacturers (e.g. 3D Systems, Natural Machines, Cargill, Massey Ferguson, John Deere, livestock or pet veterinary clinics or pet feed stores, General Electric, Polar, Nintendo, Samsung, etc.).

The animal bio-info/data device (non-wearable) 124 can include the following. The animal bio-info/data device (non-wearable) 124 can collect biological and other data non-invasively, invasively, other sample collection, etc. regarding one or more associated animals such as regarding physiological status involving molecular, chemical, analytes, electrolytes, cellular, tissue, organ, systems (e.g. skeletal, muscular, immune, lymphatic, cardiovascular, urinary, digestive, respiratory, nervous, endocrine, reproductive, integumentary, etc.), functional (e.g. sleeping, eating, ambulating, non-ambulatory postures, emitting sounds, listening, seeing, eliminating, reacting, location, etc.), electrical, disease (e.g. past, present, potential, etc.), mechanical (structural, movement, etc.), and other related status.

The animal bio-info/data device (non-wearable) 124 can be part of an enclosure, fence, barn, pen, etc. located in proximity of animal (e.g. structural member, fixture, accessory, gate component, etc.), or adjacent or occasionally in contact (e.g. stall, trough, chute, floor, trailer, cage, water container, sewage system, etc.). The animal bio-info/data device (non-wearable) 124 can communicate with human owner, manager, attendant, other human bio-info/data devices (e.g. wearable or non-wearable), food fabricator, big-data analytics system, food ingredient supplier, etc.

The animal bio-info/data device (non-wearable) 124 can for example subscription services (livestock management, pet care, etc.) sell device and applications thru farm, home, or kiosk feed fabricator networks, device and applications sold by manufacturers of feed fabricator, or veterinary-health-production management providers-manufacturers (e.g. 3D Systems, Natural Machines, Cargill, Massey Ferguson, John Deere, livestock or pet veterinary clinics or pet feed stores, General Electric, Polar, Nintendo, Samsung, etc.).

Further aspects regarding the wearable and non-wearable animal bio-info/data devices can include collecting information or data related to feed preferences of the animals such as texture, color, or taste such as sweet, sour, salty, or other taste sensations. Such collected information or data can in a sense profile a particular individual animal as far as how the individual animal reacts to various foods and other indigestible materials from a psychological, physiological, sensory, or other aspects. This type of profiling can then be used in order to tailor the various food and other indigestible materials for the individual animal. For instance, the profiling information can be used to tune macronutrient, micronutrient, bacterial or other content of feed in real time regarding various activity levels of the individual animal. These activity levels can be related to environmental conditions such as weather conditions, location in various architectures, such as barns or pens, or other locations, or various activity goals. Such activities can involve grazing in pasture, being controlled in pens, involving slaughter time regarding the fat or protein content, or other activities requiring more or less energy levels of the individual animal.

The bio-info/data can also include other aspects besides that which is physiologically related such as location data. Location data can be matched with location of other humans or location of various occurrences of activity in which performance or habit patterns of an individual can be assessed. For instance, performance or habit patterns related to parenting can be determined such as how much time is spent with a child regarding certain activities. These activities can include eating, educational events, sports or entertainment events, etc.

The human food fabricator 128 can include the following. The human food fabricator 128 can produce food and other edible materials such as bacteria through such as assembly, printing, sputtering, ablation, deposition, spraying, injection, mixing, combining, hydrating, dehydrating, applying energy, removing energy, etc. and other functional aspects from instructions pertaining to bio-info/data collected, big-data analytics, instructions received, exemplars referenced.

The human food fabricator 128 can send instructions and other information to human bio-info/data devices to collect bio-info/data based on testing protocols, hypothesis testing, user, service-provider, or organization inquiry or direction. The human food fabricator 128 can receive instructions from user, service-provider, organization, big-data/info analytics system with reference to past, present, and/or anticipated requirements for edible materials as related to expressed desires and/or bio-info/data received from bio-info/data devices. The human food fabricator 128 can be incorporated into such as kitchen, break room, vending area, restaurant, mobile platform, etc. as small counter-top unit or large kiosk unit.

The human food fabricator 128 can communicate with human, bio-info/data devices (e.g. wearable or non-wearable), food fabricator, big-data analytics system, food ingredient supplier, etc. The human food fabricator 128 can include for example subscription services (health, food, cooking, etc.) sell fabricator and applications thereof thru consumer and commercial markets, fabricator manufacturers, or medical-health-sports providers-manufacturers (e.g. 3D Systems, Natural Machines, Whirlpool, KitchenAid, Miele, medical or health clinics, General Electric, Polar, Nintendo, Samsung, etc.).

Human food fabricator can be used independently or in combination with communicating with human bio-info/data devices, big-data analytics, or human food supply systems to test hypotheses regarding combination of ingredients that may solve a problem, induce a condition, relieve a symptom, or otherwise achieve an expressed or unexpressed goal. Hypotheses testing can be achieved through adjustment of various ingredient levels of food or other ingested materials over a period of time sufficient to produce a variety of samples having different combinations of the varying ingredients.

Human food fabricator can be used to determine what food or other ingested material to provide to the user based upon received human bio-info/data, direction or information from big-data analytics, or information or data from human food supply system. By doing so, it may be possible for the human food fabricator to provide desired materials to the user without the user having to input much or any explicit information to the human food fabricator. Human food fabricator can be formed to include non-reconfigurable hardware or can be programmable to receive programming related to human food fabrication functionality. Such functionality can also be incorporated into operating systems such as Android OS or Apple OS.

Human food fabricators can be communicatively linked to human bio-info/data devices to collect status from humans before they human food fabricators are used for instance as utilized in pre-production staging. As an example, as a user approaches a human food fabricator, one or more human bio-info/data devices worn by the user can communicate to the human food fabricator various bio-info/data status such as blood sugar levels, last time food or beverage was consumed, past or planned activity levels, hormone levels, etc. to provide additional context in determining optimal production of food and other ingested materials to provide to the user.

Kiosk-style dispensing machines having relatively small footprint ranging in size such as countertop units to larger floor model vending machines can incorporate human food fabricators and other communication systems linked to human bio-info/data devices, big-data analytics, and human food supply systems. Kiosk-style dispensing machines can include aspects of the human food fabricators as well as further communication and bio-info/data functionality to provide fuller service regarding selection and purchasing options for users. Kiosk-style dispensing machines as network together can provide overall bio-info/data collection for a user or group of users for such functions as tracking participation in various activities and events. For instance, as further described below kiosk-style dispensing machines can be located at educational, business, entertainment, shopping, institutional, and other locations for activities in advance such that use of the kiosk-dispensing machines will indicate participation by the users in certain activities and events related to these locations. Food chains such as McDonald's or Burger King, or other food distribution chains, or vending chains such as Red Box or Coinstar could locate kiosk-style dispensing machines in numerous varied locations some of which are depicted in FIG. 1-K to include location such as marketplaces, sports arenas, theaters, schools, office buildings, and hospitals. Other locations are depicted in FIG. 1-N to include sidewalks, public parks, restaurants, public buildings, air-travel facilities, and food courts. These locations are exemplary so or not limiting as far as other possibilities for positioning kiosk-style dispensing machines.

For instance, on aircraft of an airline, passengers may send quantified-self bio-info/data to communication system located on the plane integrated with one or more kiosk-style dispensing machines containing food fabricators. Such quantified-self bio-info/data can then be used by the fabricators on the aircraft to be Incorporated in production or otherwise dispensing of food and other ingested materials as tailored to the passenger requirements and desires. For instance, passengers would particular health requirements such as levels of salt, sugar, mineral, fat, protein, carbohydrate, micronutrients, macronutrients, etc. can receive tailored food and other ingested materials accordingly. Status of other passengers such as stress levels, hunger levels, past, present, or future activities, etc. can also be used to formulate tailored food and other ingested materials for the passengers. In certain circumstances enough information and data can be collected by fabricator systems on the plane so that it may be possible for the passengers to receive food or other ingested materials without having to directly communicate with airline attendants yet the passengers can receive what they require or desire.

Travel facilities could include airports, train stations, bus stations, ocean liner ports, transit stations, and other facilities. Kiosk-style dispensing machines could also be located on the vehicles themselves including airplanes, trains, buses, ocean liners, transit vehicles, and other vehicles, etc.

Kiosk-style dispensing machines can combine fabricator aspects with being a waypoint for big-data analytics, food supplier systems, and bio-info/data quantified-self data acquisition in order to receive quantified-self bio-info/data, analytics, and supply information to assist in determining various food and other ingested materials to produce, arrange or otherwise furnish. Kiosk-style dispensing machines can also provide production or other use data to human bio-info/data devices, big-data analytics, or food supply systems for their use and analysis. For instance, kiosk-style dispensing machines having received bio-info/data indicating that the user has a certain health condition may note in the user's record that the kiosk-style dispensing machine provided food or other ingested materials in compliance with were not in compliance with recommendations for such health condition.

For instance, large food chains such as McDonald's or Burger King could use kiosk-style dispensing machines to collect quantified-self bio-info/data in the process of fabricating or otherwise providing food and ingested materials through the branded kiosk-style dispensing machines. The quantified-self bio-info/data could involve health, physiology, lifestyle, family life, occupational data, educational data, etc. of the one or more users. Such information and data can then be fed into the food chain network, big-data analytics, supply chain systems, information vendors, health systems, etc. Analytics could be analyzing such information and data, for instance, such as frequency of visits, amount of time spent with others such as children and parents in locations of kiosk-style dispensing machines, participation in activities and events such as sports, movies, recreational parks, educational center such as libraries, etc. Kiosk-style dispensing machines in this and other approaches can then be viewed as related to family lifestyle, occupational pursuits, entertainment and recreational interests, and other areas. Kiosk-style dispensing machines located in educational institutions such as schools could afford students a wide variety of selection of food and other ingested materials as provided with constraints and other factors related to interests of the students and those related such as parents, health providers, educators, school board members, etc. Kiosk-style dispensing machines could be integrated with other facilities, locations, event centers, activity areas, etc. to help track user or customer activity. For instance, kiosk-style dispensing machines could be tied in with social networks or other social networking systems as related to comments of others such as friends, relatives, observers, and others accessing the social networks or other social networking systems. With this and other approaches kiosk-style dispensing machines and their networks thereof and other systems and networks can be used in a universe of overlapping functionality and collection of data and information through word analysis, comment recognition. For instance comments from friends can be quantified as quantified-self bio-info/data, for instance, on how well a person is doing in a particular area of pursuit such as improvement in health, sociability, educational pursuits, social presence, occupational goals, etc. including positive improvement or setbacks.

The animal feed fabricator 132 can include the following. The animal feed fabricator 132 can produce feed and other edible materials such as bacteria through such as assembly, printing, sputtering, ablation, deposition, spraying, injection, mixing, combining, hydrating, dehydrating, applying energy, removing energy, etc. and other functional aspects from instructions pertaining to bio-info/data collected, big-data analytics, instructions received, exemplars referenced.

The animal feed fabricator 132 can send instructions and other information to animal bio-info/data devices to collect bio-info/data based on testing protocols, hypothesis testing, user, service-provider, or organization inquiry or direction. The animal feed fabricator 132 can receive and generate instructions for edible material production from user, service-provider, organization, big-data/info analytics system with reference to past, present, and/or anticipated requirements for edible materials as related to expressed desires and/or bio-info/data received from bio-info/data devices.

The animal feed fabricator 132 can be incorporated into such as feed areas, pens, troughs, barns, stalls, feed assemblies, home units sized for requirement of small or large animals. The animal feed fabricator 132 can communicate with human, bio-info/data devices (e.g. wearable or non-wearable), big-info/data analytics system, feed ingredient supplier, etc.

The animal feed fabricator 132 can include for example subscription services (livestock management, pet care, etc.) sell fabricator and applications thru farm, home, or kiosk feed fabricator networks, device and applications sold by manufacturers of feed fabricator, or veterinary-health-production management providers-manufacturers (e.g. 3D Systems, Natural Machines, Cargill, Massey Ferguson, John Deere, livestock or pet veterinary clinics or pet feed stores, General Electric, Polar, Nintendo, Samsung, etc.).

Animal feed fabricator can be used independently or in combination with communicating with animal bio-info/data devices, big-data analytics, or animal feed supply systems to test hypotheses regarding combination of ingredients that may solve a problem, induce a condition, relieve a symptom, or otherwise achieve an expressed or unexpressed goal. Hypotheses testing can be achieved through adjustment of various ingredient levels of feed or other ingested materials over a period of time sufficient to produce a variety of samples having different combinations of the varying ingredients.

Animal feed fabricator can be used to determine what feed or other ingested material to provide to an animal based upon received animal bio-info/data, direction or information from big-data analytics, or information or data from animal food supply system. By doing so, it may be possible for the animal food fabricator to provide desired materials to the animal with little or no intervention required by human. Animal feed fabricators can take the form of feed printers or can take other forms such as assemblers, combiners, mixers, etc. Feed furnished by animal feed fabricators can be tailored toward either pet markets such as PetSmart or livestock involved with agribusiness industries such as ConAgra. In either case, the feed can be tailored by the animal feed fabricator regarding micronutrients, macronutrients, bacterial content, and other ingredients for goals such as activity levels in which the animal is to his stay in a stationary position for lengthy periods of time, or is to be fully animated, for instance, in order to transport itself from one location to another.

The big-info/data analytics system 136 can include the following. The big-info/data analytics system 136 can receive analysis instructions from user, service-provider, organization, bio-data/info devices, fabricators with reference to past, present, and/or anticipated requirements for edible materials as related to expressed desires and/or bio-info/data received from bio-info/data devices.

The big-info/data analytics system 136 can run statistical, probabilistic, or other models on bio-info/data collected by bio-info/data device(s) and expressed desires with reference to past, present, and/or anticipated edible materials requirements to determine patterns, options, or other desirable outcomes for instructing production of material by fabricator(s) or further collection of bio-info/data by device(s). The big-info/data analytics system 136 can send instructions and other information to human or animal bio-info/data devices to collect bio-info/data based on testing protocols, hypothesis testing, user, service-provider, or organization inquiry or direction, and results of analytics system analysis.

The big-info/data analytics system 136 can communicate with humans, bio-info/data devices, fabricators, food ingredient suppliers, feed ingredient suppliers, etc. The big-info/data analytics system 136 can include for example subscription services (per human or animal interests) sell cloud-based analysis time, application downloads, etc. thru consumer and commercial markets, device and/or fabricator manufacturers, or medical-health-sports-veterinary-pet providers or equipment manufacturers (e.g. 3D Systems, Natural Machines, Whirlpool, KitchenAid, Miele, medical or health clinics, General Electric, Polar, Nintendo, Samsung, Cargill, Massey Ferguson, John Deere, livestock or pet veterinary clinics or pet feed stores, etc.).

Big-data analytics such as for special-purpose as provided by such companies as IBM, Microsoft, Amazon, SAP, Oracle, cloud services, Apple, Google, Accenture, Twitter, Facebook, etc. can be used to drive communication with human or animal bio-info/data devices, human or animal food or feed fabricators, human or animal food or feed supply systems, etc. to test hypotheses regarding combination of ingredients that may solve a problem, induce a condition, relieve a symptom, or otherwise achieve an expressed or unexpressed goal. Hypotheses testing can be achieved through adjustment of various ingredient levels of food, feed or other ingested materials over a period of time sufficient to produce a variety of samples having different combinations of the varying ingredients.

Big-data analytics can be used to conduct experiments to see the effects of various food or other ingested materials or combinations thereof upon users. For instance, direction can be sent from big-data analytics to a human food fabricator or an animal food fabricator to dispense particular kinds of food or feed materials based upon a subjects behavioral profile such as including the extent of exercise, sleep quality, plan performance levels, etc. Parameters regarding materials to be dispensed can be varied in order for big-data analytics to assess statistically significant correlations, spikes in probability distributions, etc. Studies on various populations can also be performed to identify similarities or differences related to lifestyle factors found with impacts on health, workplace performance, education levels, economic output, social integrity, and other outcomes. Big-data analytics can be tied in with social networks for further analysis and distribution of outcomes.

Statistical and other analysis can be performed on other aspects including parenting such as duration of time spent with children in relation to eating, teaching, playing, overseeing, chauffeuring, taking trips, etc. Proximity data based on location can be used for some of this analysis. Big-data analytics can also be directly tied through communication links to human food supply systems or animal feed supply systems to send information and data backup the supply chain. For instance, big-data analytics through various analysis could determine trends in health or sickness and possibly identify sources for such. This analysis could then be fed back up through the various supply chains to alert those in positions of responsibility.

Human food ingredient supplier system 142 can include the following. Human food ingredient supplier system 142 can receive ordering instructions, bio-info/data, ingredient use information, etc. from user, service-provider, organization, bio-data/info devices, fabricators, big-info/data analytics, etc. with reference to past, present, and/or anticipated requirements for edible materials as related to expressed desires and/or bio-info/data received from bio-info/data devices. Human food ingredient supplier system 142 can perform supply or other analysis models on bio-info/data collected by bio-info/data device(s) and expressed desires with reference to past, present, and/or anticipated edible materials requirements to determine patterns of consumption, projected demand, for instructing stocking, shipment, or other supply chain functions.

Human food ingredient supplier system 142 can send instructions and other information to bio-info/data devices to collect bio-info/data based on testing protocols, hypothesis testing, user, service-provider, or organization inquiry or direction, and results of supply chain model analysis. Human food ingredient supplier system 142 can be incorporated either by separate or common structures with bio-info/data devices, fabricators, or more central, separate entities such as server-based or cloud-based implementations.

Human food ingredient supplier system 142 can communicate with humans, bio-info/data devices, fabricators, big-info/data analytics, etc. Human food ingredient supplier system 142 can include for example subscription services (per human interests) sell cloud-based analysis time, application downloads, etc. thru commercial markets, device and/or fabricator manufacturers, or medical-health-sports-veterinary-pet providers or equipment manufacturers (e.g.

3D Systems, Natural Machines, Whirlpool, KitchenAid, Miele, medical or health clinics, General Electric, Polar, Nintendo, Samsung, etc.).

Human food supply systems can be communicatively linked to big-data analytics to receive information and instruction related to analysis performed on human food and other materials thereby supplied. Sending information and instruction based upon this analysis up the supply chain can be beneficial to those in positions of responsibility for instance, in cases where outbreaks of illness have occurred. Other sorts of analysis can include information related to improvement in health in various subjects using food or other ingested materials. Trends in shopping or preferences in selection can also be identified and supplied to the human food supply systems. The human food supply systems cannot only provide food ingredients and other materials to the human food fabricators but can also furnish ready-made food items to be delivered through commercial channels such as UPS, FedEx, U.S. Postal Service, etc. Such human food supply systems could include Amazon, Amazon Fresh, Walmart outlets, Costco outlets, or other such conglomerates with various other distribution channels such as Nestlé, Unilever, General Mills, McDonald's, Coca-Cola, PepsiCo, or other big-food conglomerates, etc. see having broad families of food and other ingested materials, etc. such as possibly to institutions as hospitals, schools, prisons, etc.

Human bio-info/data, fabricator information, big-data analytics, and human food supply system information can be used by human food supply systems for delivery analysis, planning, execution, etc., providing recommendation to users, assessing information to collect from customers, determination of advertising targeting, etc.

Animal feed ingredient supplier system 146 can include the following. Animal feed ingredient supplier system 146 can receive ordering instructions, bio-info/data, ingredient use information, etc. from user, service-provider, organization, bio-data/info devices, fabricators, big-info/data analytics, etc. with reference to past, present, and/or anticipated requirements for edible materials as related to expressed desires and/or bio-info/data received from bio-info/data devices.

Animal feed ingredient supplier system 146 can perform supply or other analysis models on bio-info/data collected by bio-info/data device(s) and expressed desires with reference to past, present, and/or anticipated edible materials requirements to determine patterns of consumption, projected demand, for instructing stocking, shipment, or other supply chain functions. Animal feed ingredient supplier system 146 can send instructions and other information to bio-info/data devices to collect bio-info/data based on testing protocols, hypothesis testing, user, service-provider, or organization inquiry or direction, and results of supply chain model analysis.

Animal feed ingredient supplier system 146 can be incorporated either by separate or common structures with bio-info/data devices, fabricators, or more central, separate entities such as server-based or cloud-based implementations. Animal feed ingredient supplier system 146 can communicate with humans, bio-info/data devices, fabricators, big-info/data analytics, etc. Animal feed ingredient supplier system 146 can include for example subscription services (per animal interests) sell cloud-based analysis time, application downloads, etc. thru commercial markets, device and/or fabricator manufacturers, or veterinary-pet providers or equipment manufacturers (e.g. 3D Systems, Natural Machines, General Electric, Polar, Nintendo, Samsung, Cargill, Massey Ferguson, John Deere, ConAgra, livestock or pet veterinary clinics or animal/pet feed stores, etc.).

Turning now to FIG. 2, FIG. 2 depicts some aspects also depicted in FIGS. 1A-1O and discussed above and also below regarding communication between human bio-info/data device (wearable) (HBD (w)) 112, human bio-info/data device (non-wearable) (HBD (nw)) 116, animal bio-info/data device (wearable) (ABD (w)) 120, animal bio-info/data device (non-wearable) (ABD (nw)) 124, human food fabricator (HFF) 128, animal feed fabricator (AFF) 132, big-info/data analytics system (BAS) 136, human food ingredient supplier system (HFS) 142, and animal feed ingredient supplier system (AFS) 146.

Turning now to FIG. 3, human food fabricator 128 and animal feed fabricator 132 are depicted as both including fabricator communication system 150, which is depicted to include processor 150*a*, memory 150*b*, operating system 150*c*, and device interface 150*e*.

Processor 150*a* may include one or more microprocessors, central processing units ("cpu"), a graphics processing units ("gpu"), physics processing units, digital signal processors, network processors, floating point processors, and the other processors. In implementation(s), processor 150*a* may be a server. In implementation(s), processor 150*a* may be a distributed-core processor. Although processor 150*a* can be understood in one sense as depicted as a single processor that is part of a single employment information center communication system 150, processor 150*a* may be multiple processors distributed over one or many employment information center communication systems 150, which may or may not be configured to operate together. Processor 150*a* is illustrated as being configured to execute computer readable instructions in order to execute one or more operations described above.

Further shown in FIG. 3, employment information center communication system 150 includes memory 150*b*, which may include memory, cache memory such as random access memory (RAM), flash memory, synchronous random access memory (SRAM), dynamic random access memory (DRAM), or other types of memory such as read only memory ("ROM"), programmable read only memory ("PROM"), flash memory, hard drives, erasable programmable read-only memory (EPROM), disk-based media, disc-based media, magnetic storage, optical storage, volatile memory, nonvolatile memory, mass storage devices, and any combination thereof. In implementation(s), memory 150*b* may be at single network site(s) or separated from the communication system 150, e.g., available on different system(s) on a network, wired or wirelessly. For example, in a networked system, there may be many communication systems 150 having memory 150*b* as located at central server(s) that may be a few feet away or located across an ocean. In implementation(s) memory 150*b* may be located at multiple network sites, including sites that are distant from each other.

Referring again to FIG. 3, employment information center communication system 150 includes operating system 150*c*, some versions thereof being mobile or otherwise, and may include processing module m10, which may further include modules (some of which are described below), and may further include virtual machines 150*d* (such as process virtual machines, virtual machines of hardware, virtual machines of virtual machines, Java virtual machines, Dalvik virtual machines, virtual machines for use with Android operating systems such as Samsung or Google mobile devices or for use with other mobile operating systems such as Apple iOS on Microsoft Windows based mobile operating systems, etc.).

As shown also in FIG. 3, employment information center communication system 150 can include device interface 150e, which can include user interface 150f, device input 150g, and device output 150h.

In implementation(s), device interface 150e can include any component that allows interaction with its environment. For example, in implementation(s) device interface 150e can include one or more sensors, e.g., a camera, a microphone, an accelerometer, a thermometer, a satellite positioning system (SPS) sensor, a barometer, a humidity sensor, a compass, a gyroscope, a magnetometer, a pressure sensor, an oscillation detector, a light sensor, an inertial measurement unit (IMU), a tactile sensor, a touch sensor, a flexibility sensor, a microelectromechanical system (MEMS), a radio, including a wireless radio, a transmitter, a receiver, an emitter, a broadcaster, etc.

In implementation(s), device interface 150e also may include one or more user interface components, e.g., user interface 150f (e.g., although they are drawn separately, in implementation(s), user interface 150f is a type of device interface 150e)), and in implementation(s) including one or more device inputs 150g and one or more device outputs 150h. User interface 150f may include any hardware, software, firmware, and combination thereof that allows one or more users to interact with employment information center communication system 150, and for vice versa. In implementation(s), user interface 150f may include a monitor, screen, touchscreen, liquid crystal display ("LCD") screen, light emitting diode ("LED") screen, speaker, handset, earpiece, keyboard, keypad, touchpad, mouse, trackball, remote control, button set, microphone, video camera, still camera, a charge-coupled device ("CCD") element, a photovoltaic element, etc.

Referring again to FIG. 3, implementation(s) of device interface 150e may include one or more components in addition to or integrated with user interface 150f to provide ways that communication system 150 can input and output information with its environment(s) and/or user(s). These components of device interface 150e for user interface 150f, device input 150g, and/or device output 150h may include one or more sensors, e.g., a camera, a microphone, an accelerometer, a thermometer, a satellite positioning system (SPS) sensor, a barometer, a humidity sensor, a compass, a gyroscope, a magnetometer, a pressure sensor, an oscillation detector, a light sensor, an inertial measurement unit (IMU), a tactile sensor, a touch sensor, a flexibility sensor, a microelectromechanical system (MEMS), a radio, including a wireless radio, a transmitter, a receiver, an emitter, a broadcaster, etc., and other components as well to serve user interface, input and/or output function(s) for device interface 150e such as for user interface 150f, device input 150g and device output 150h.

Further examples of user interface 150f, device input 150g, and/or device output 150h may include any hardware, software, firmware, and combination thereof, to provide capability for a user thereof to interact with employment information center communication system 150. Implementation(s) of user interface 150f, device input 150g, and/or device output 150h can include monitor(s), screen(s), touchscreen(s), liquid crystal display ("LCD") screen(s), light emitting diode ("LED") screen(s), speaker(s), handset(s), earpiece(s), keyboard(s), keypad(s), touchpad(s), mouse(s), trackball(s), remote control(s), button set(s), microphone(s), video camera(s), still camera(s), a charge-coupled device ("CCD") element(s), a photovoltaic element(s), etc.

As other examples, implementation(s) of device interface 150e can include including portions for outputting information, inputting information, and/or controlling aspects thereof. Various arrangements such as display window(s), audio emitter(s), tactile interface(s), button(s), slider(s), gesture interface(s), articulation(s), knob(s), icon(s), desktop(s), ribbon(s), bar(s), tool(s), stylus area(s), keypad(s), keyboard(s), and other audio, video, graphic, tactile, etc. input, output, or control aspects can be used. For instance, graphical user interface presentations can be presented upon display surfaces while other input and/or output aspects can be utilized.

Implementations of modules can involve different combinations (limited to patentable subject matter under 35 U.S.C. 101) of one or more aspects from one or more electrical circuitry arrangements and/or one or more aspects from one or more instructions.

In one or more implementations, as shown in FIG. 4, the processing module m10 may include electronically-receiving-user-biological-status-information-from-electronically-involved-detection-of-biological-user-conditions module m11.

In one or more implementations, as shown in FIG. 4, the processing module m10 may include electronically-obtaining-user-ingestion-preference-indications module m12.

In one or more implementations, as shown in FIG. 4, the processing module m10 may include electronically-providing-instruction-to-electronically-direct-factors-of-electronically-controlled-dispensing-of-manually-administrable-orally-ingestible-material-based-upon-the-electronically-receiving-user- biological-status-information-from-electronically-involved-detection-of-biological-user-conditions-and-based-upon-the-electronically-obtaining-user-ingestion-preference-indications module m13.

Figure 5:
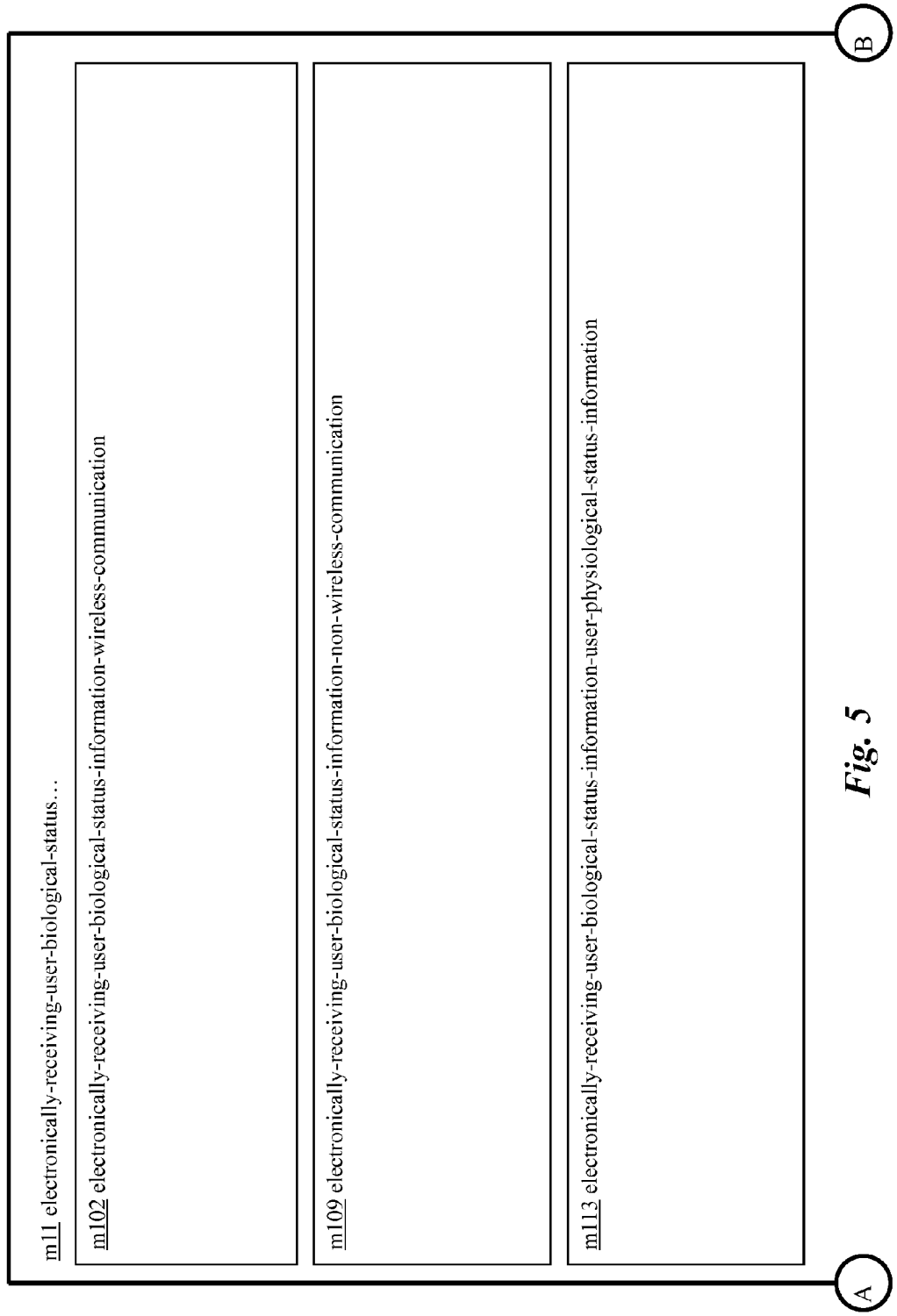

In one or more implementations, as shown in FIG. 5, module m11 may include electronically-receiving-user-biological-status-information-wireless-communication module m102.

Figure 6:
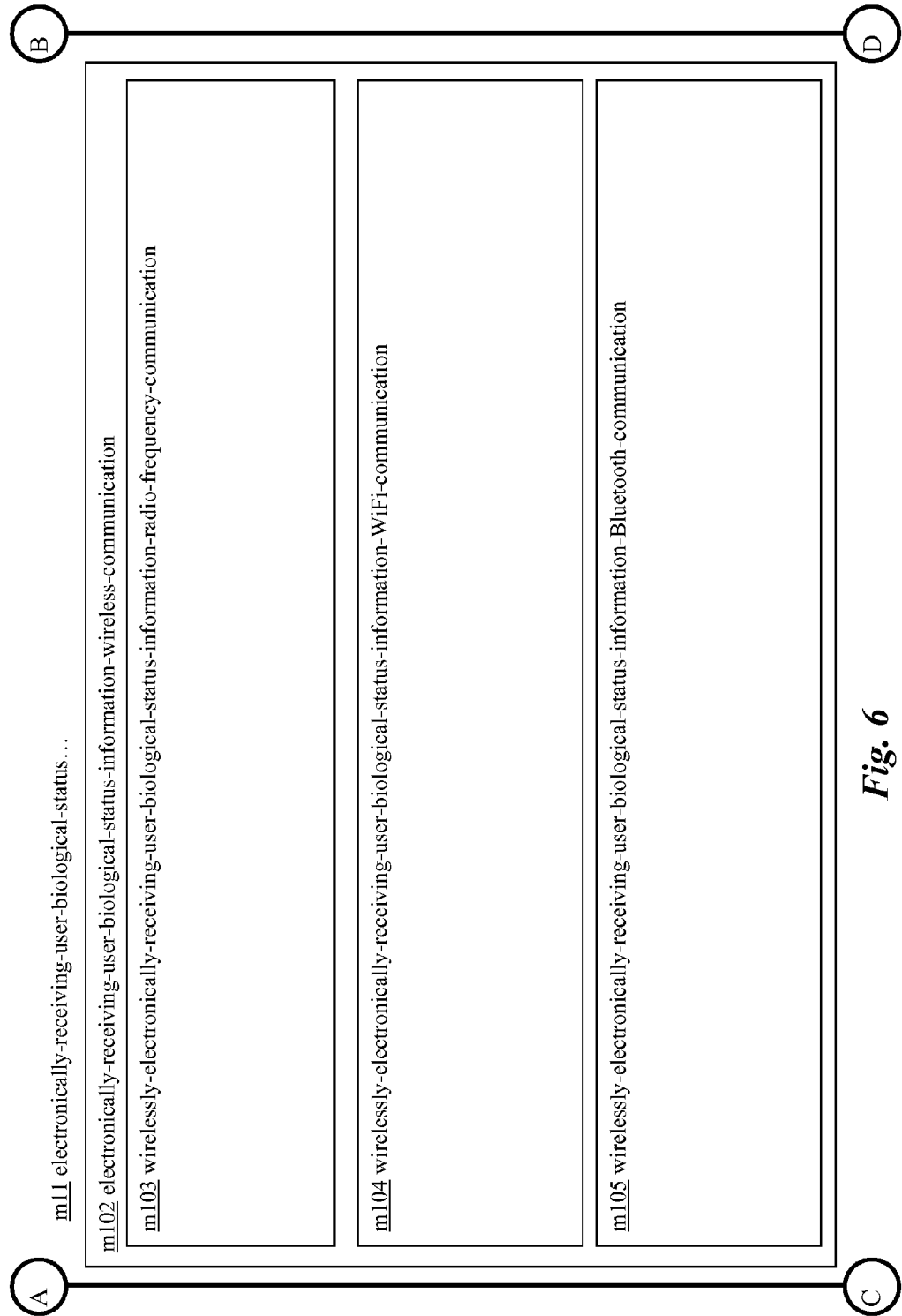

In one or more implementations, as shown in FIG. 6, module m102 may include wirelessly-electronically-receiving-user-biological-status-information-radio-frequency-communication module m103.

In one or more implementations, as shown in FIG. 6, module m102 may include wirelessly-electronically-receiving-user-biological-status-information-WiFi-communication module m104.

In one or more implementations, as shown in FIG. 6, module m102 may include wirelessly-electronically-receiving-user-biological-status-information-Bluetooth-communication module m105.

Figure 7:
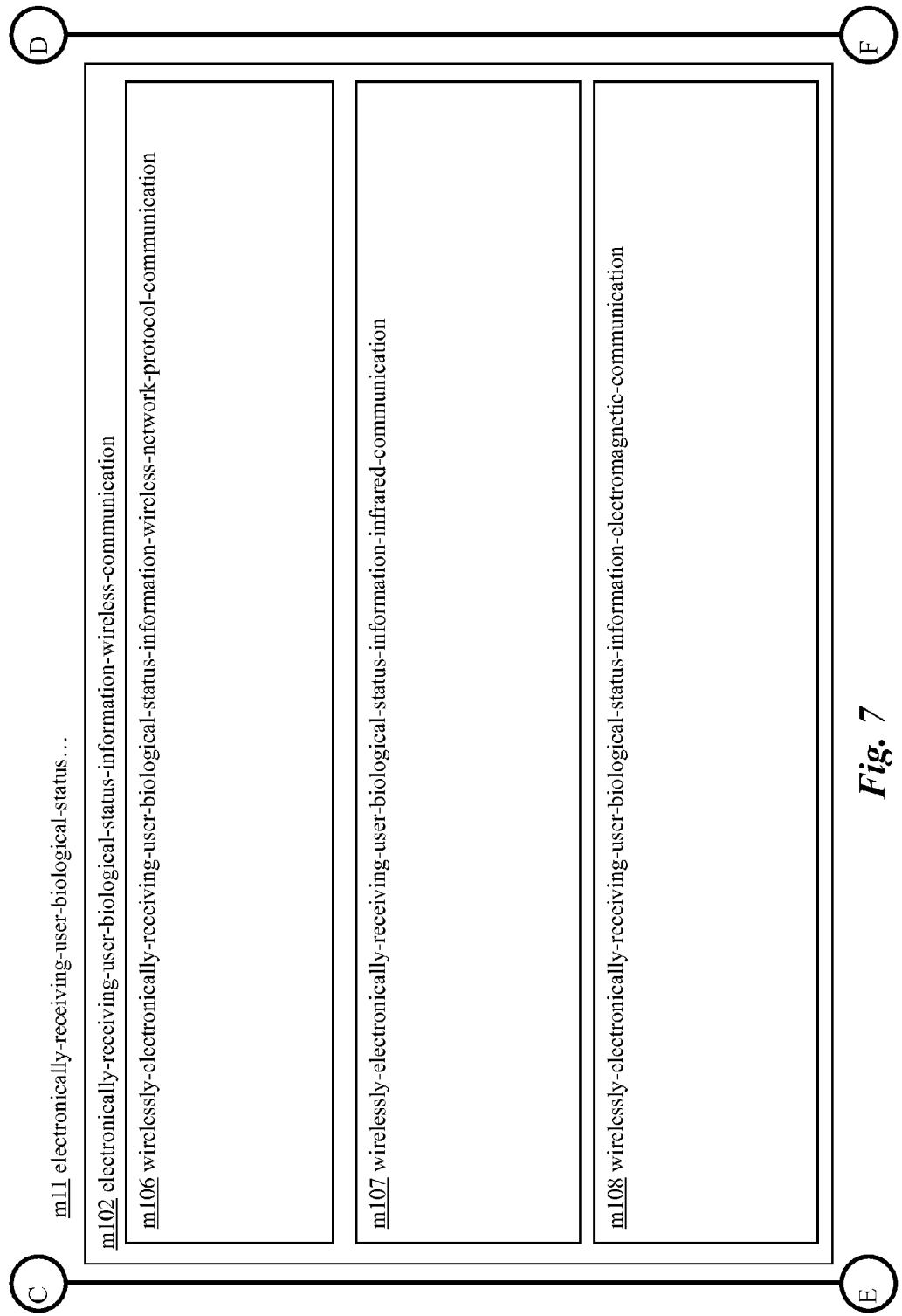

In one or more implementations, as shown in FIG. 7, module m102 may include wirelessly-electronically-receiving-user-biological-status-information-wireless-network-protocol-communication module m106.

In one or more implementations, as shown in FIG. 7, module m102 may include wirelessly-electronically-receiving-user-biological-status-information-infrared-communication module m107.

In one or more implementations, as shown in FIG. 7, module m102 may include wirelessly-electronically-receiving-user-biological-status-information-electromagnetic-communication module m108.

In one or more implementations, as shown in FIG. 5, module m11 may include electronically-receiving-user-biological-status-information-non-wireless-communication module m109.

In one or more implementations, as shown in FIG. 8, module m109 may include non-wirelessly-electronically-receiving-user-biological-status-information-electronically-scanned-communication module m110.

In one or more implementations, as shown in FIG. 8, module m109 may include non-wirelessly-electronically-receiving-user-biological-status-information-electronically-swiped-communication module m111.

In one or more implementations, as shown in FIG. 8, module m109 may include non-wirelessly-electronically-receiving-user-biological-status-information-smart-card-communication module m112.

In one or more implementations, as shown in FIG. 5, module m11 may include electronically-receiving-user-biological-status-information-user-physiological-status-information module m113.

Figure 9:
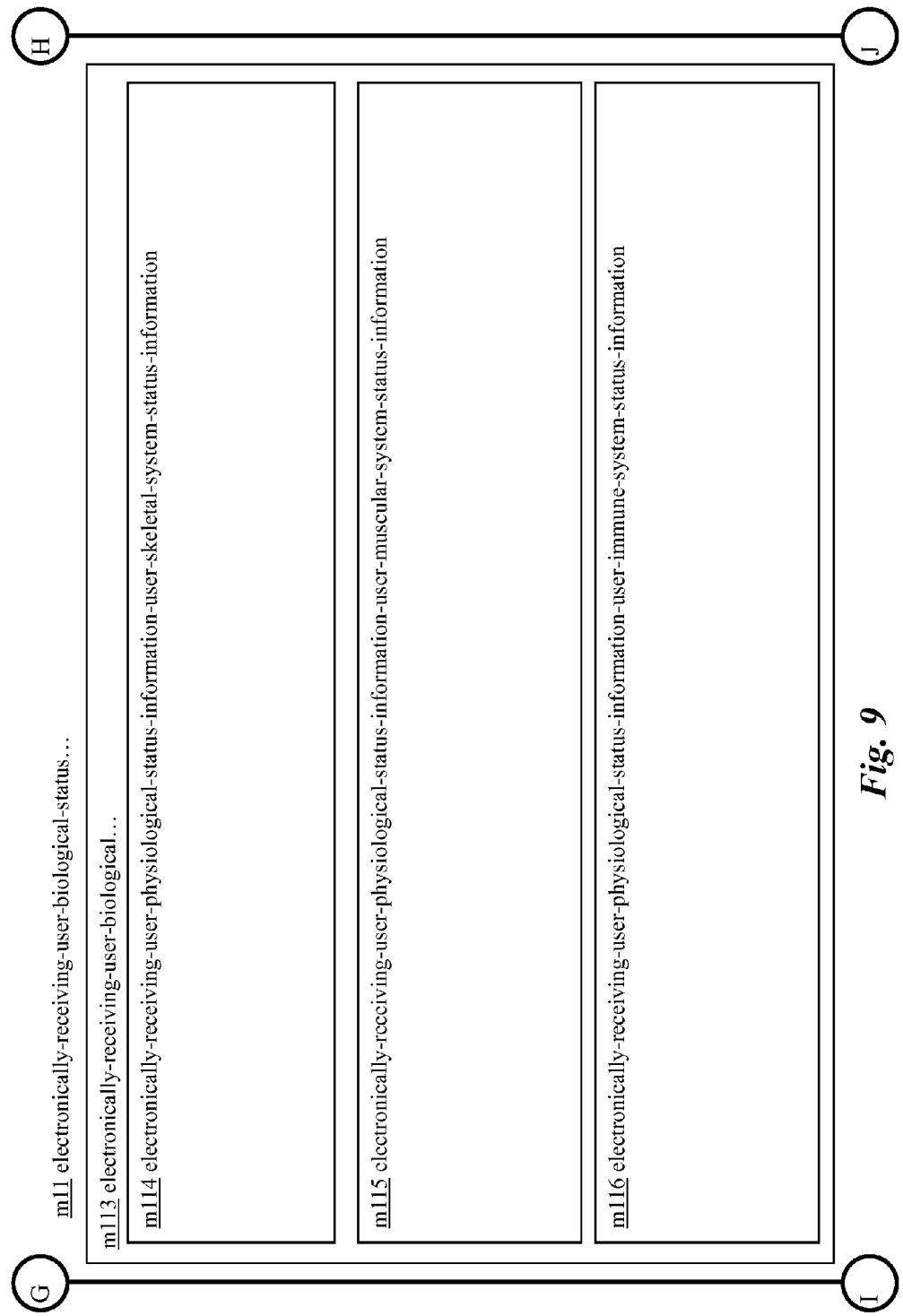

In one or more implementations, as shown in FIG. 9, module m113 may include electronically-receiving-user-physiological-status-information-user-skeletal-system-status-information module m114.

In one or more implementations, as shown in FIG. 9, module m113 may include electronically-receiving-user-physiological-status-information-user-muscular-system-status-information module m115.

In one or more implementations, as shown in FIG. 9, module m113 may include electronically-receiving-user-physiological-status-information-user-immune-system-status-information module m116.

Figure 10:
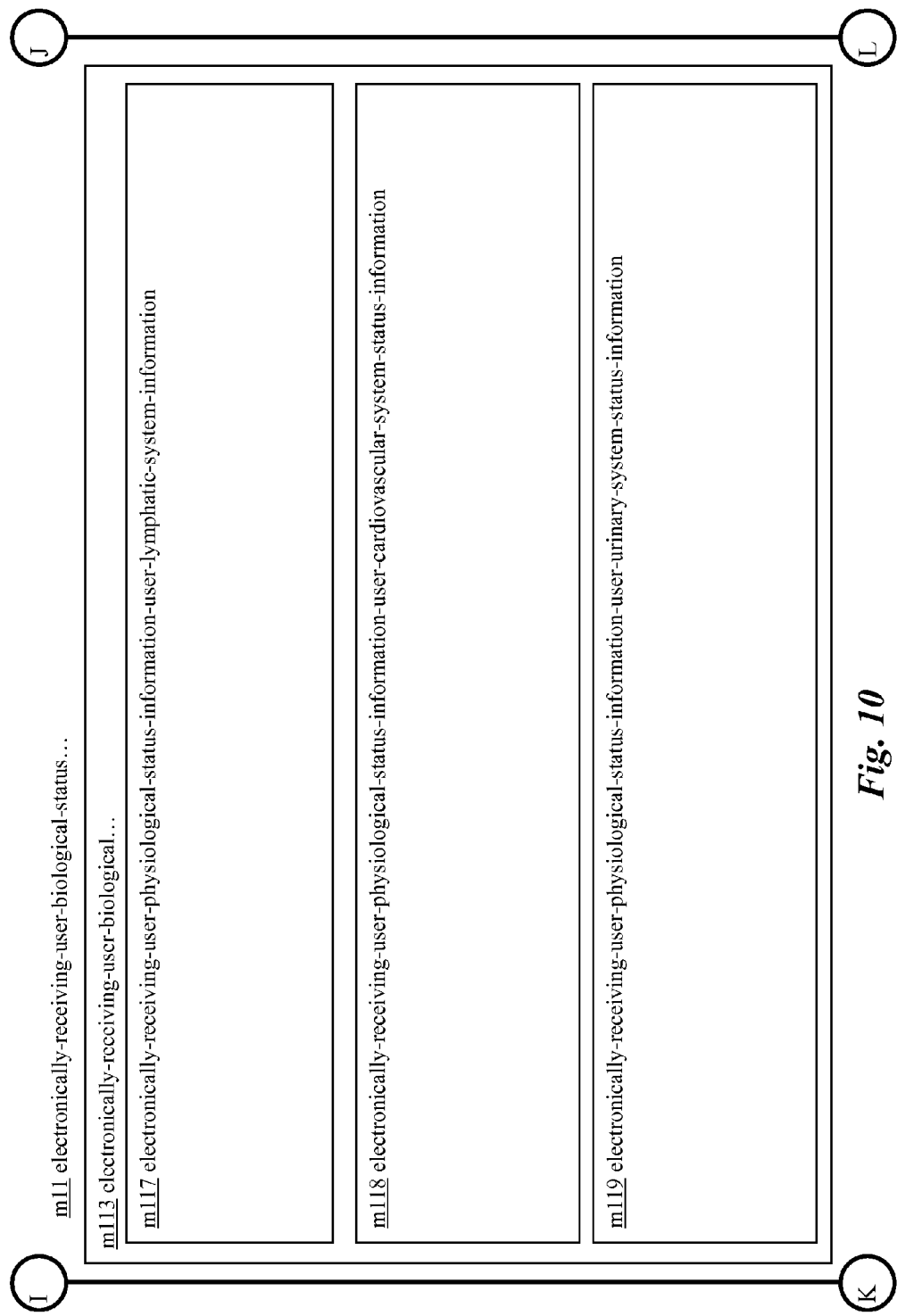

In one or more implementations, as shown in FIG. 10, module m113 may include electronically-receiving-user-physiological-status-information-user-lymphatic-system-information module m117.

In one or more implementations, as shown in FIG. 10, module m113 may include electronically-receiving-user-physiological-status-information-user-cardiovascular-system-status-information module m118.

In one or more implementations, as shown in FIG. 10, module m113 may include electronically-receiving-user-physiological-status-information-user-urinary-system-status-information module m119.

Figure 11:
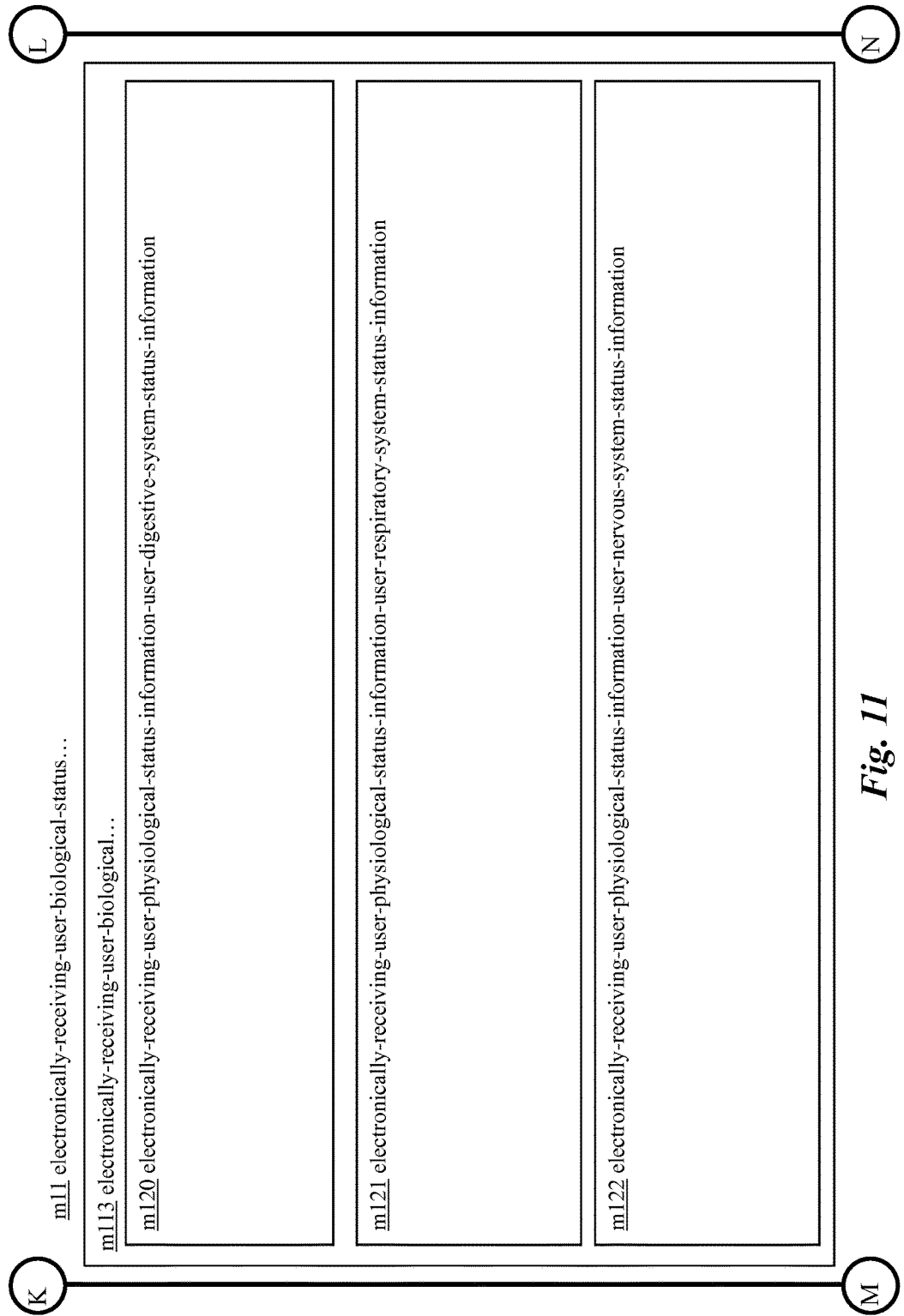

In one or more implementations, as shown in FIG. 11, module m113 may include electronically-receiving-user-physiological-status-information-user-digestive-system-status-information module m120.

In one or more implementations, as shown in FIG. 11, module m113 may include electronically-receiving-user-physiological-status-information-user-respiratory-system-status-information module m121.

In one or more implementations, as shown in FIG. 11, module m113 may include electronically-receiving-user-physiological-status-information-user-nervous-system-status-information module m122.

Figure 12:
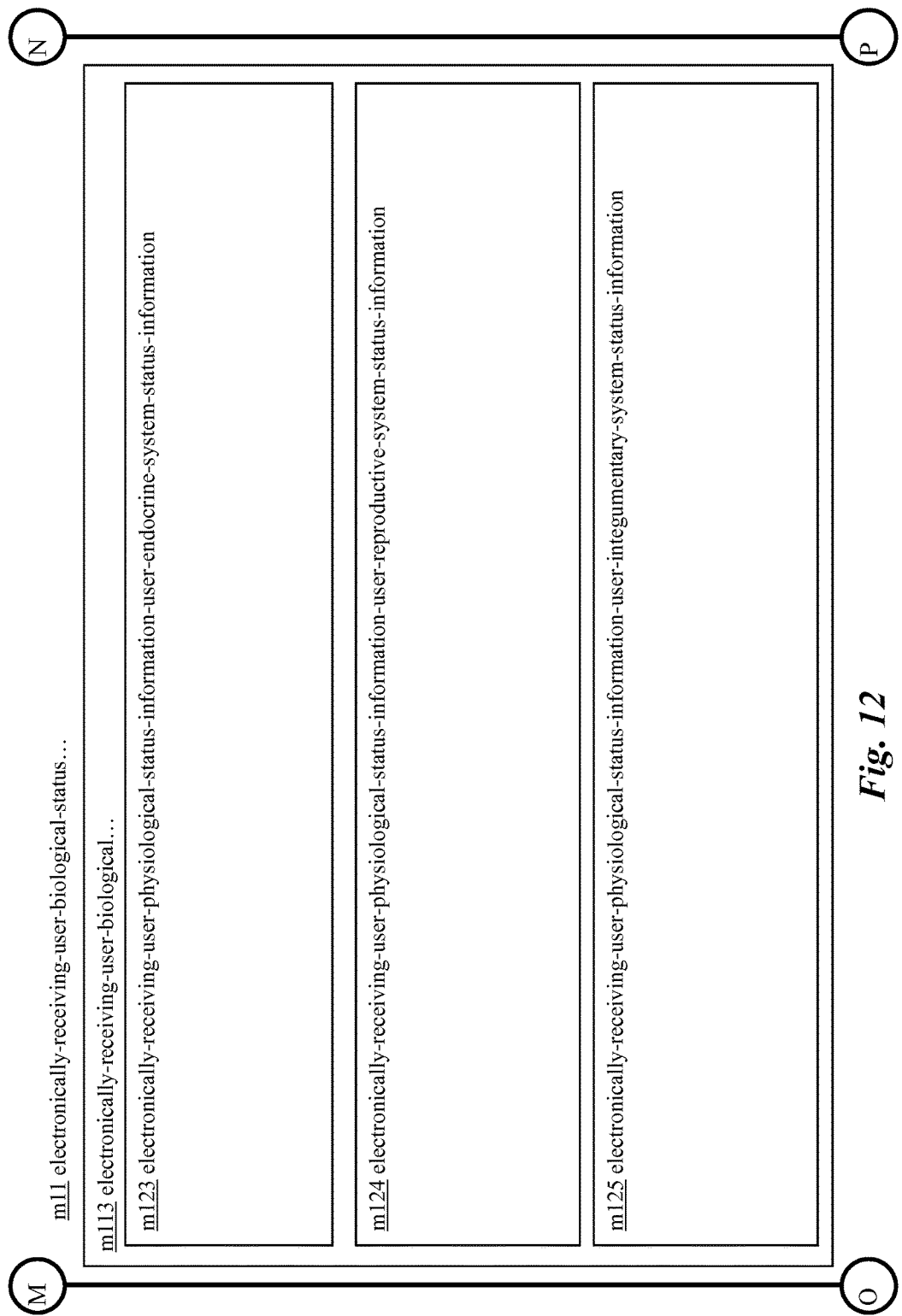

In one or more implementations, as shown in FIG. 12, module m113 may include electronically-receiving-user-physiological-status-information-user-endocrine-system-status-information module m123.

In one or more implementations, as shown in FIG. 12, module m113 may include electronically-receiving-user-physiological-status-information-user-reproductive-system-status-information module m124.

In one or more implementations, as shown in FIG. 12, module m113 may include electronically-receiving-user-physiological-status-information-user-integumentary-system-status-information module m125.

Figure 13:
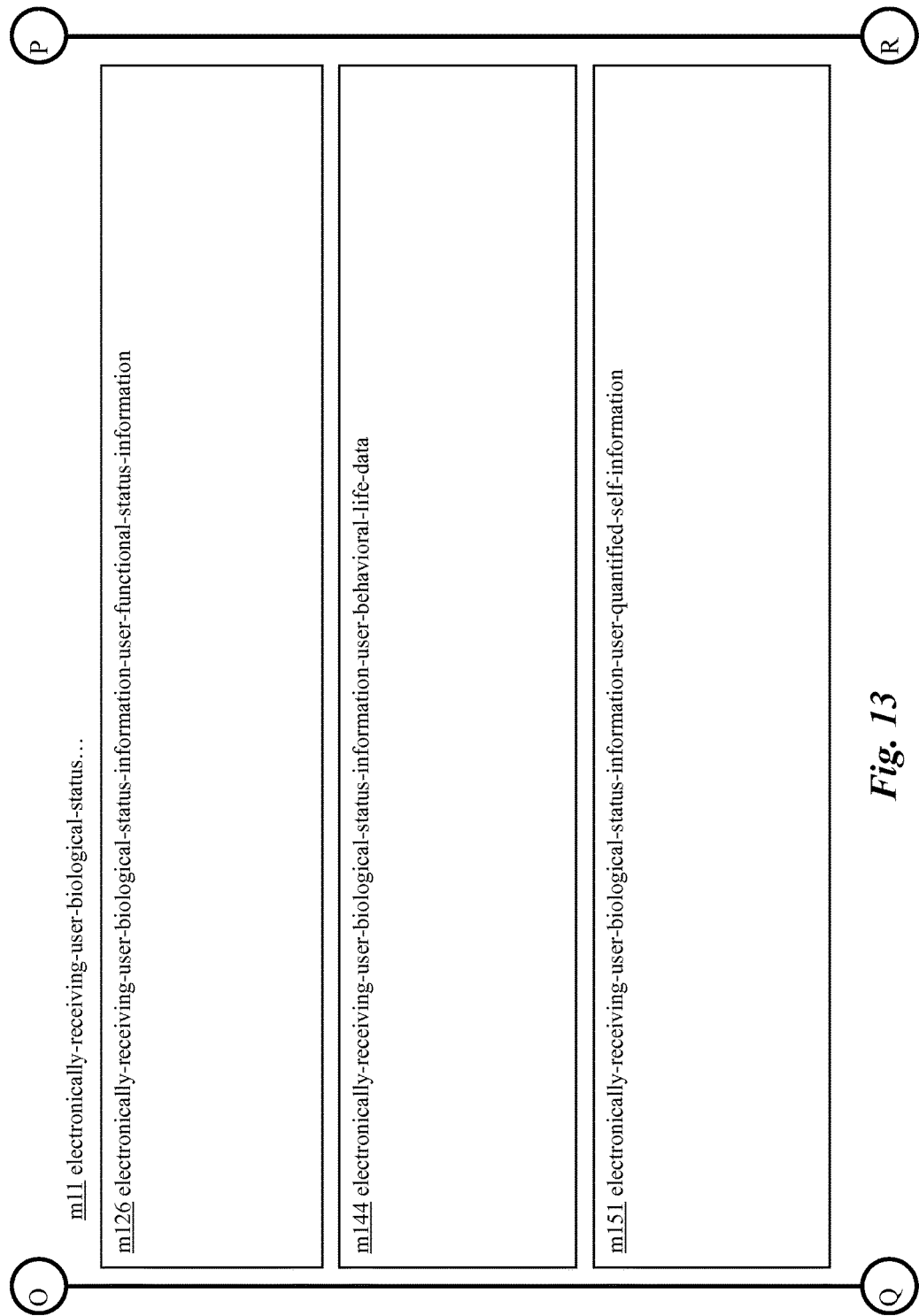

In one or more implementations, as shown in FIG. 13, module m11 may include electronically-receiving-user-biological-status-information-user-functional-status-information module m126.

Figure 14:
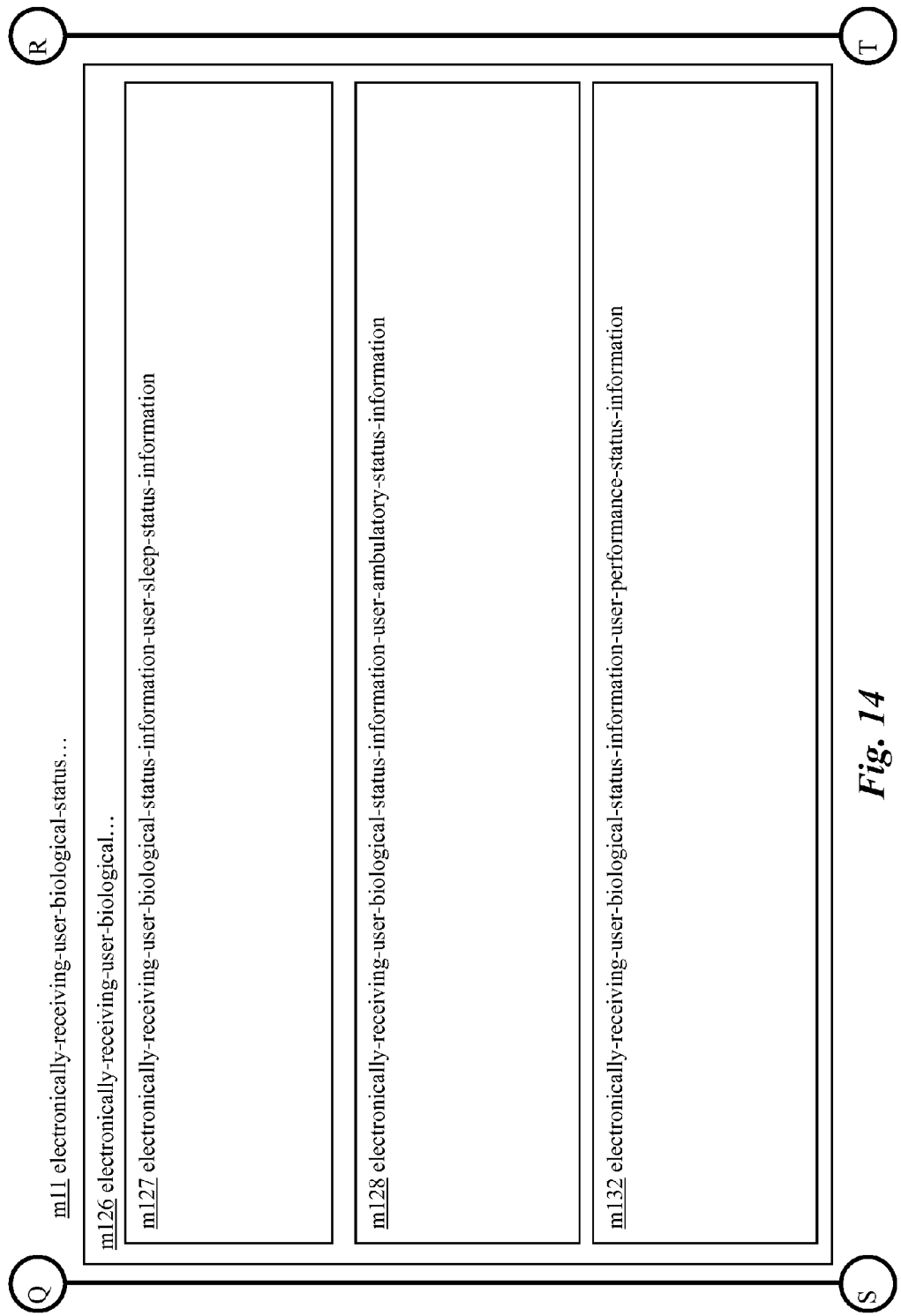

In one or more implementations, as shown in FIG. 14, module m126 may include electronically-receiving-user-biological-status-information-user-sleep-status-information module m127.

In one or more implementations, as shown in FIG. 14, module m126 may include electronically-receiving-user-biological-status-information-user-ambulatory-status-information module m128.

Figure 15:
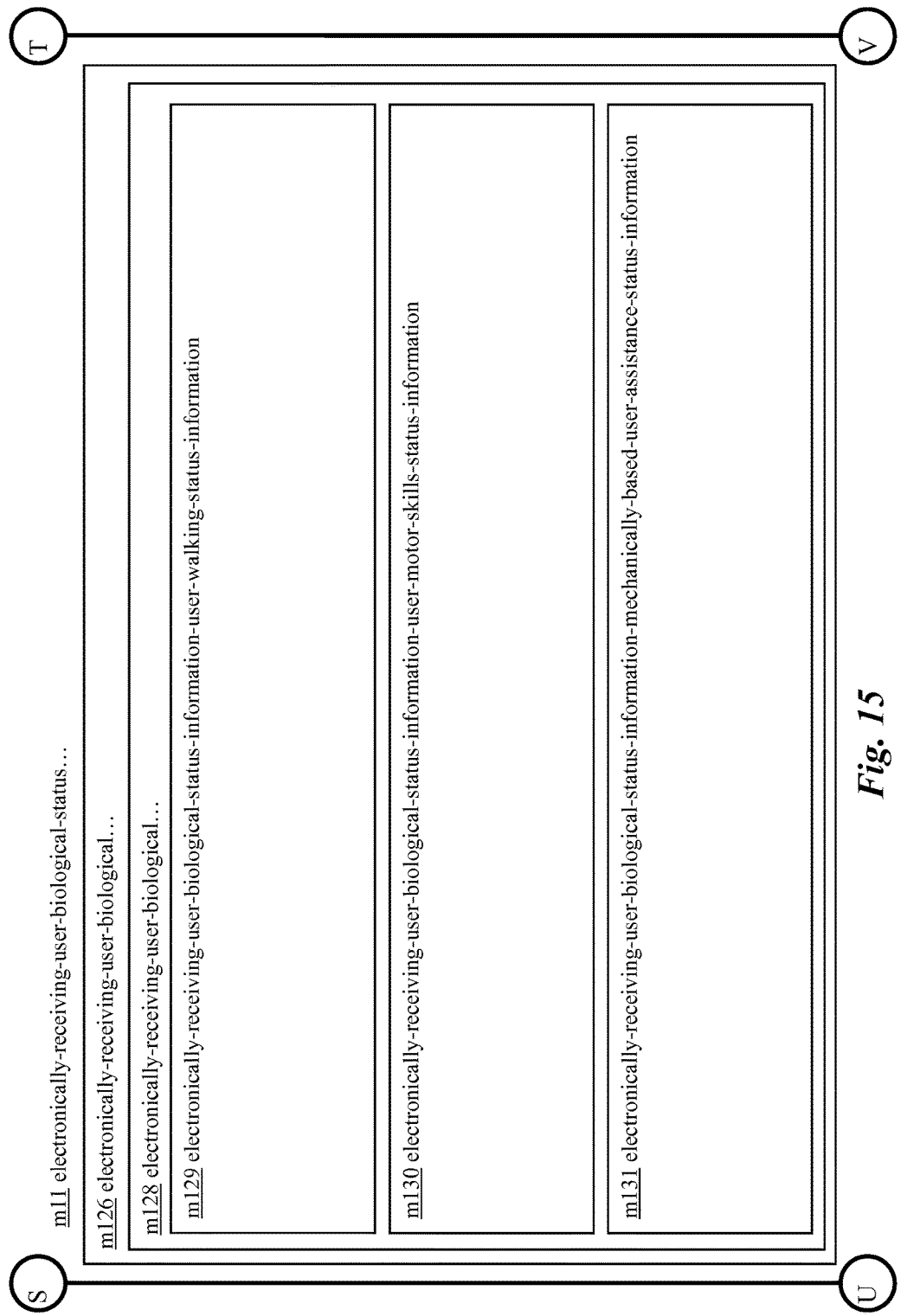

In one or more implementations, as shown in FIG. 15, module m128 may include electronically-receiving-user-biological-status-information-user-walking-status-information module m129.

In one or more implementations, as shown in FIG. 15, module m128 may include electronically-receiving-user-biological-status-information-user-motor-skills-status-information module m130.

In one or more implementations, as shown in FIG. 15, module m128 may include electronically-receiving-user-biological-status-information-mechanically-based-user-assistance-status-information module m131.

In one or more implementations, as shown in FIG. 14, module m126 may include electronically-receiving-user-biological-status-information-user-performance-status-information module m132.

Figure 16:
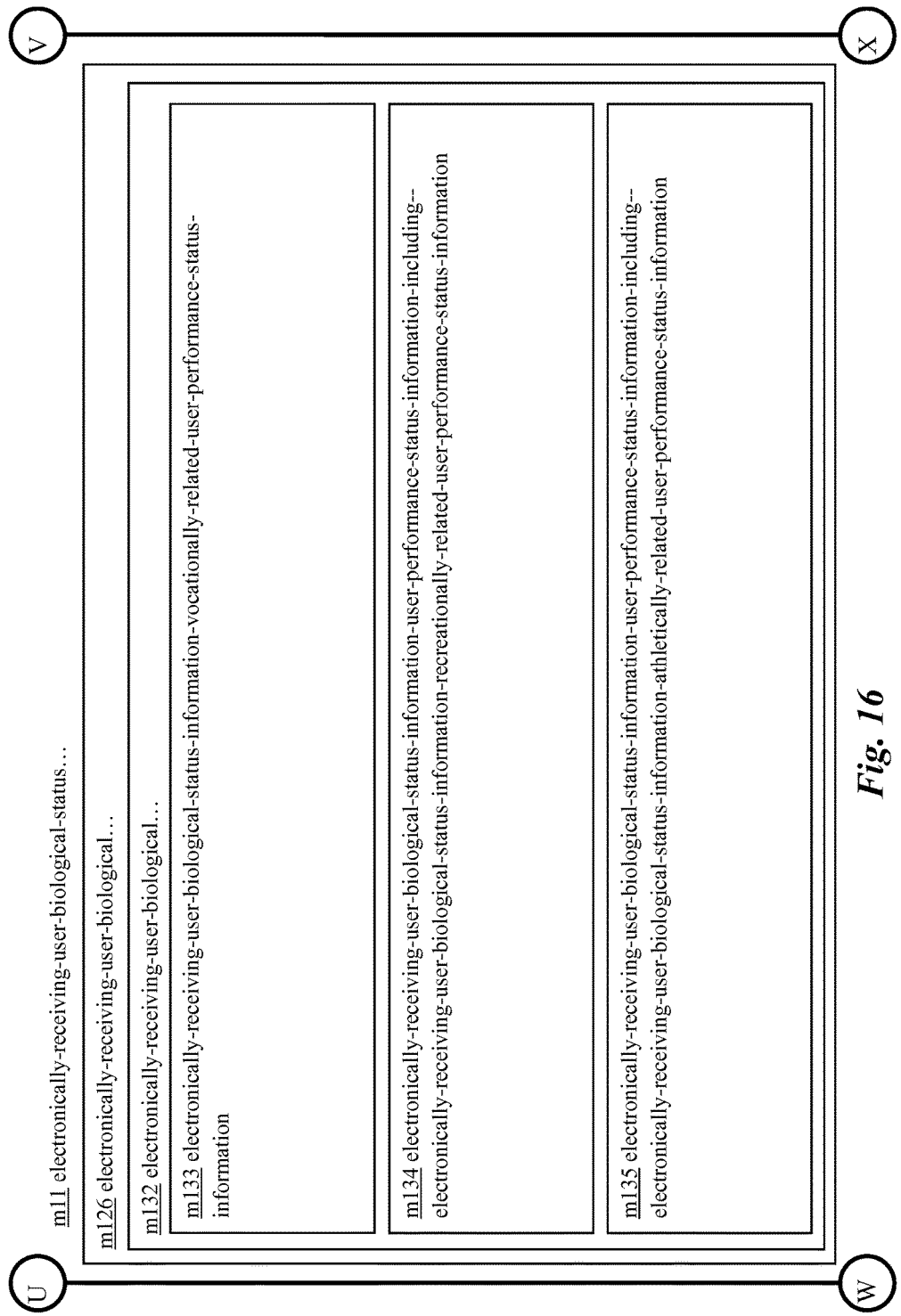

In one or more implementations, as shown in FIG. 16, module m132 may include electronically-receiving-user-biological-status-information-vocationally-related-user-performance-status-information module m133.

In one or more implementations, as shown in FIG. 16, module m132 may include electronically-receiving-user-biological-status-information-user-performance-status-information-including-electronically-receiving-user-biological-status-information-recreationally-related-user-performance-status- information module m134.

In one or more implementations, as shown in FIG. 16, module m132 may include electronically-receiving-user-biological-status-information-user-performance-status-information-including-electronically-receiving-user-biological-status-information-athletically-related-user-performance-status- information module m135.

Figure 17:
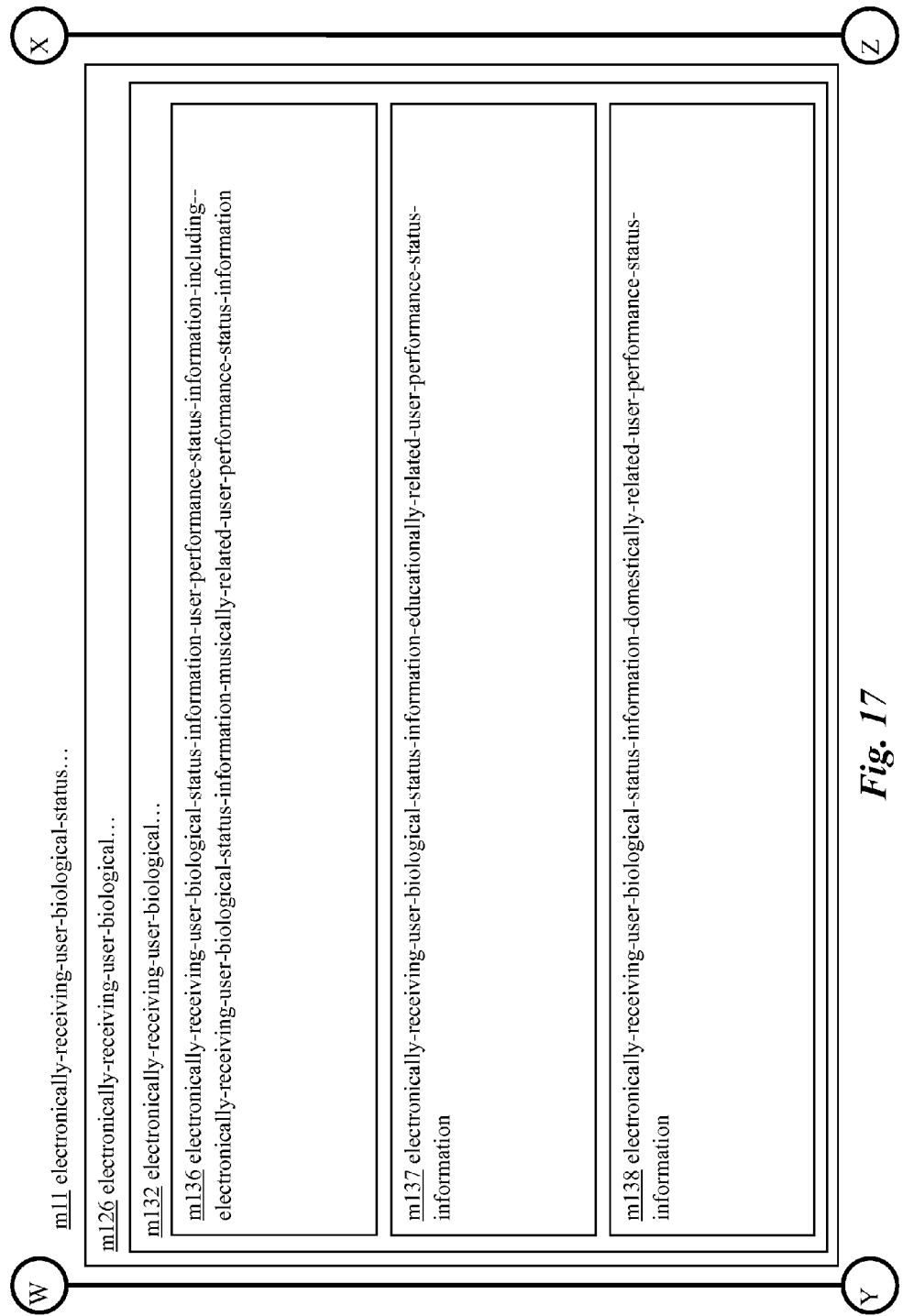

In one or more implementations, as shown in FIG. 17, module m132 may include electronically-receiving-user-biological-status-information-user-performance-status-information-including-electronically-receiving-user-biological-status-information-musically-related-user-performance-status-information module m136.

In one or more implementations, as shown in FIG. 17, module m132 may include electronically-receiving-user-biological-status-information-educationally-related-user-performance-status-information module m137.

In one or more implementations, as shown in FIG. 17, module m132 may include electronically-receiving-user-biological-status-information-domestically-related-user-performance-status-information module m138.

Figure 18:
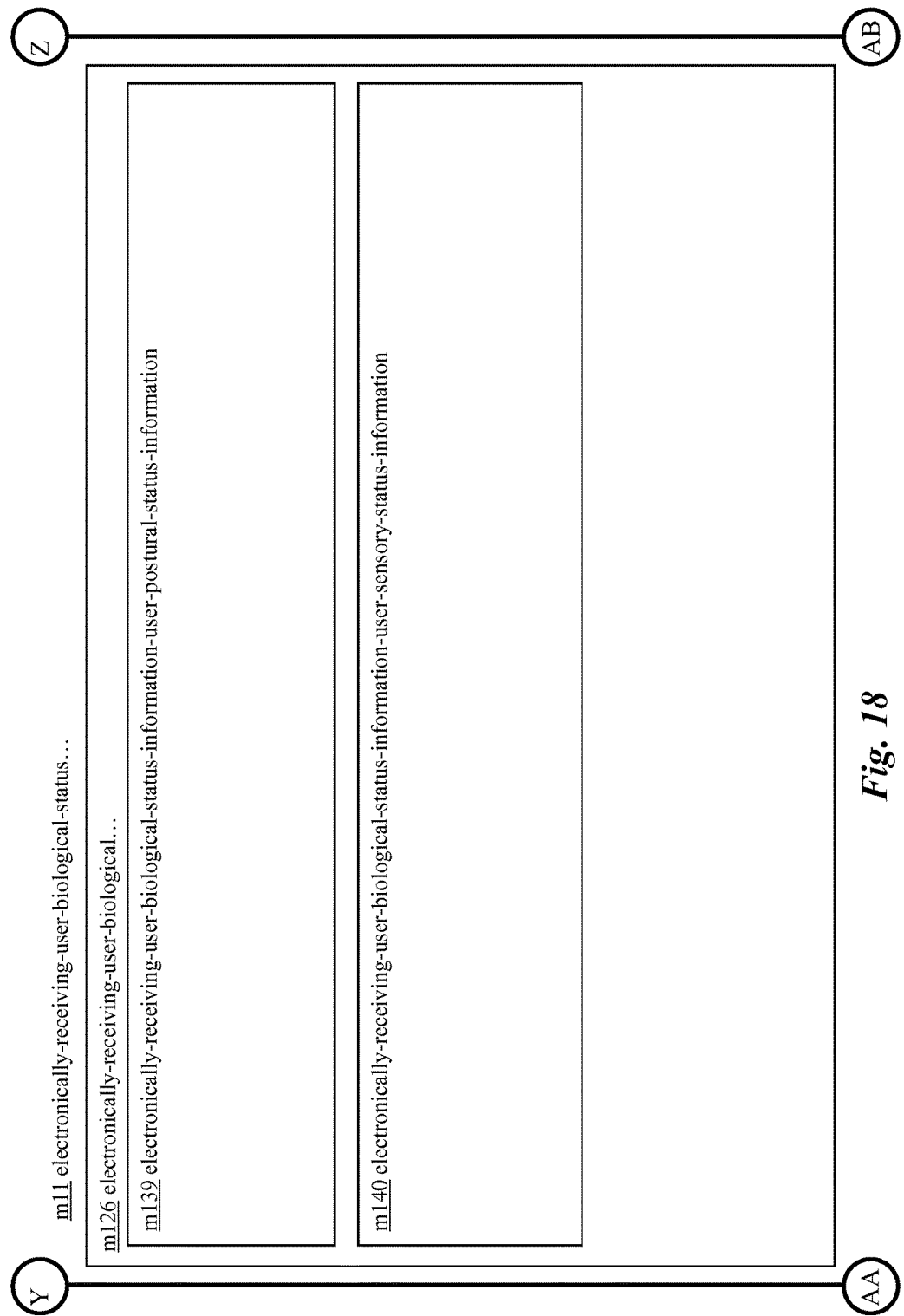

In one or more implementations, as shown in FIG. 18, module m126 may include electronically-receiving-user-biological-status-information-user-postural-status-information module m139.

In one or more implementations, as shown in FIG. 18, module m126 may include electronically-receiving-user-biological-status-information-user-sensory-status-information module m140.

Figure 19:
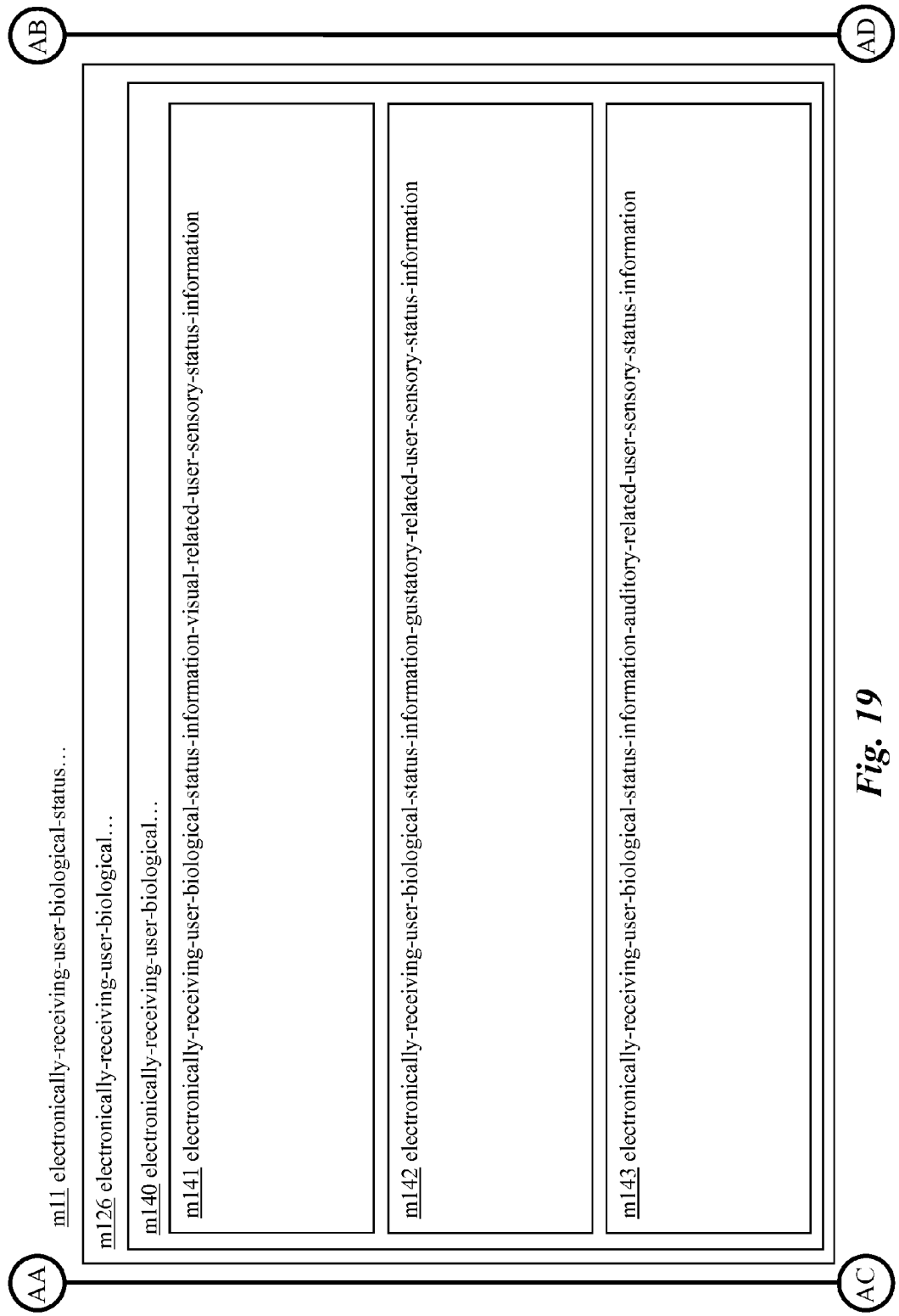

In one or more implementations, as shown in FIG. 19, module m140 may include electronically-receiving-user-biological-status-information-visual-related-user-sensory-status-information module m141.

In one or more implementations, as shown in FIG. 19, module m140 may include electronically-receiving-user-biological-status-information-gustatory-related-user-sensory-status-information module m142.

In one or more implementations, as shown in FIG. 19, module m140 may include electronically-receiving-user-biological-status-information-auditory-related-user-sensory-status-information module m143.

In one or more implementations, as shown in FIG. 13, module m11 may include electronically-receiving-user-biological-status-information-user-behavioral-life-data module m144.

Figure 20:
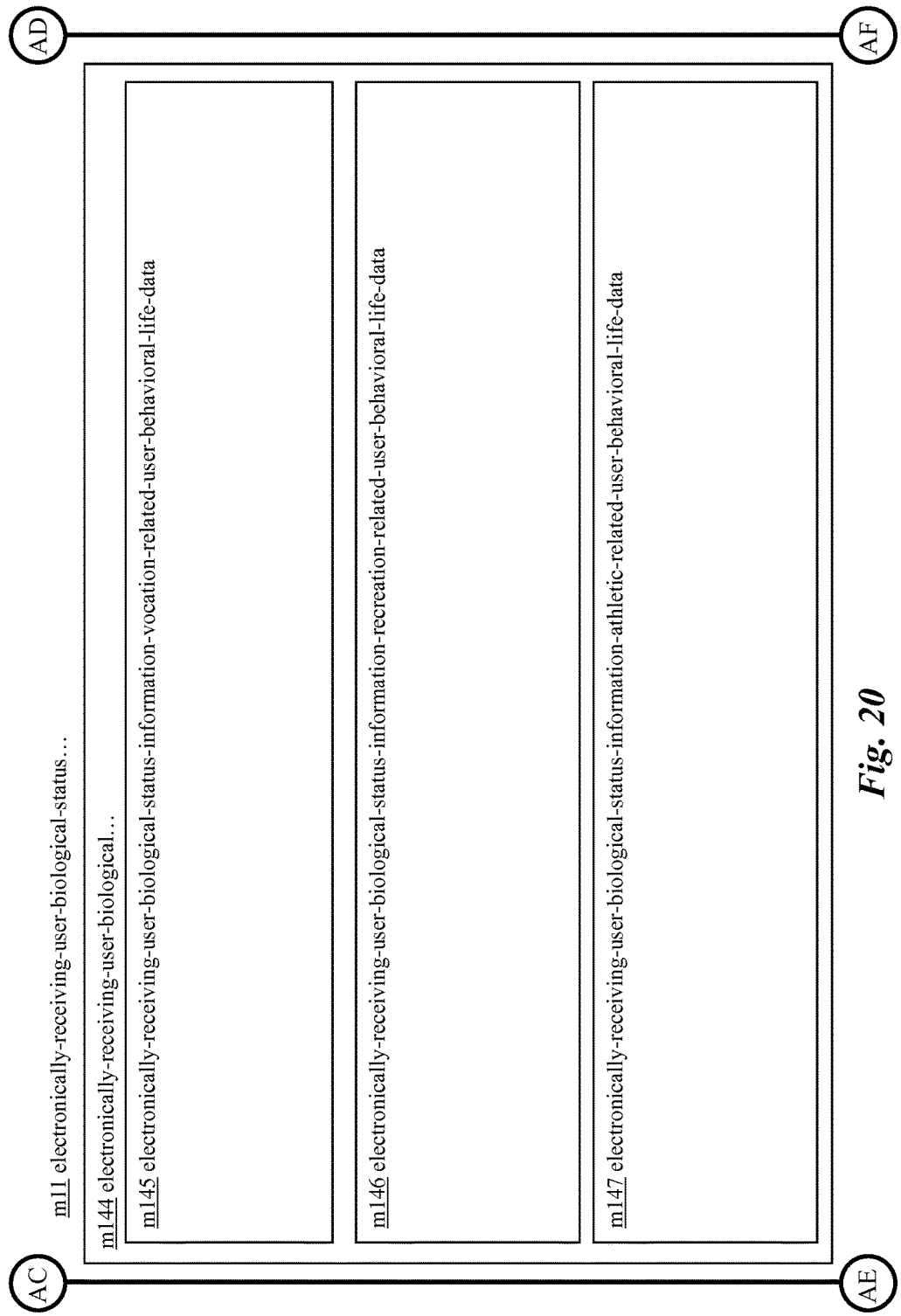

In one or more implementations, as shown in FIG. 20, module m144 may include electronically-receiving-user-biological-status-information-vocation-related-user-behavioral-life-data module m145.

In one or more implementations, as shown in FIG. 20, module m144 may include electronically-receiving-user-biological-status-information-recreation-related-user-behavioral-life-data module m146.

In one or more implementations, as shown in FIG. 20, module m144 may include electronically-receiving-user-biological-status-information-athletic-related-user-behavioral-life-data module m147.

Figure 21:
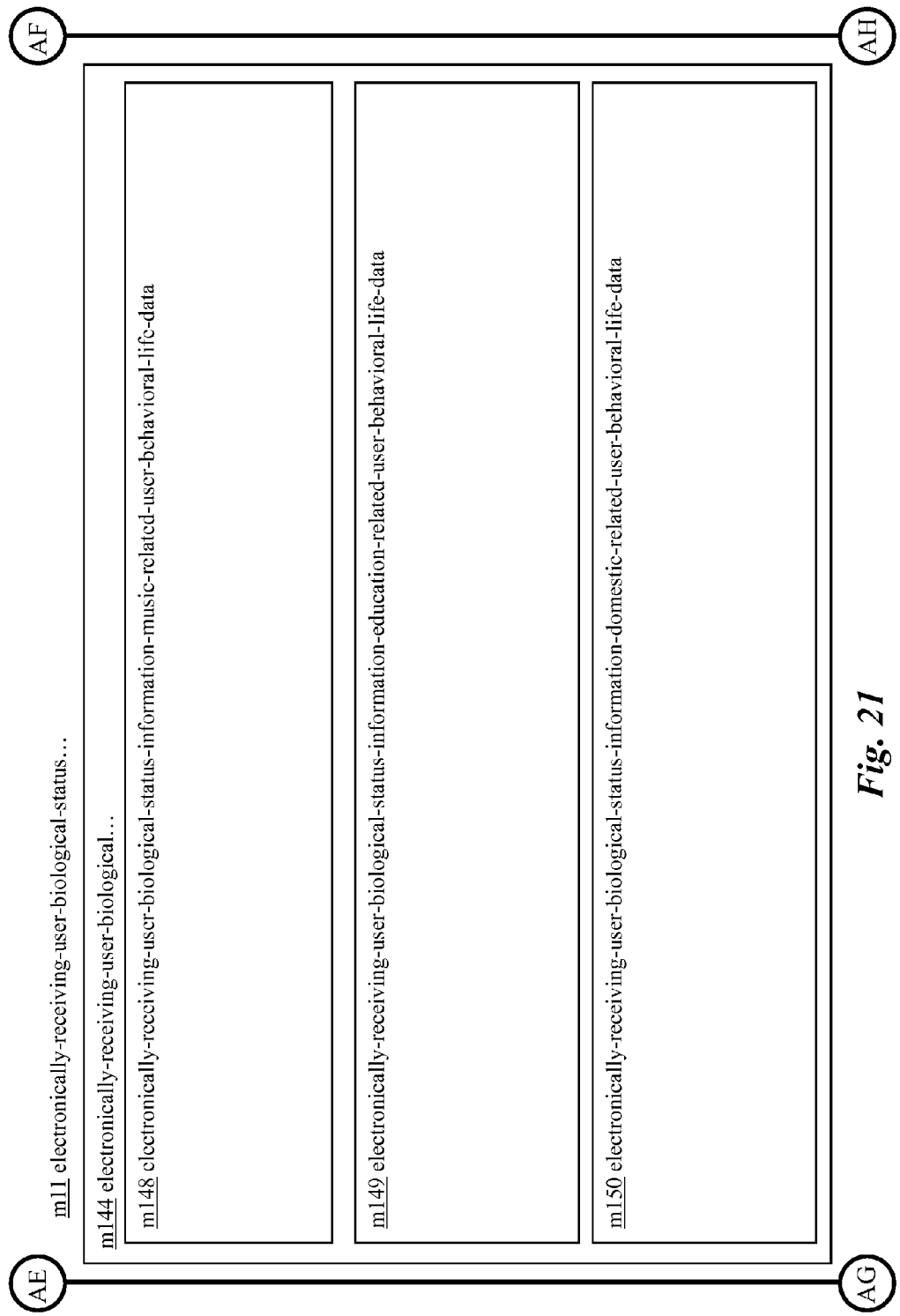

In one or more implementations, as shown in FIG. 21, module m144 may include electronically-receiving-user-biological-status-information-music-related-user-behavioral-life-data module m148.

In one or more implementations, as shown in FIG. 21, module m144 may include electronically-receiving-user-biological-status-information-education-related-user-behavioral-life-data module m149.

In one or more implementations, as shown in FIG. 21, module m144 may include electronically-receiving-user-biological-status-information-domestic-related-user-behavioral-life-data module m150.

In one or more implementations, as shown in FIG. 13, module m11 may include electronically-receiving-user-biological-status-information-user-quantified-self-information module m151.

Figure 22:
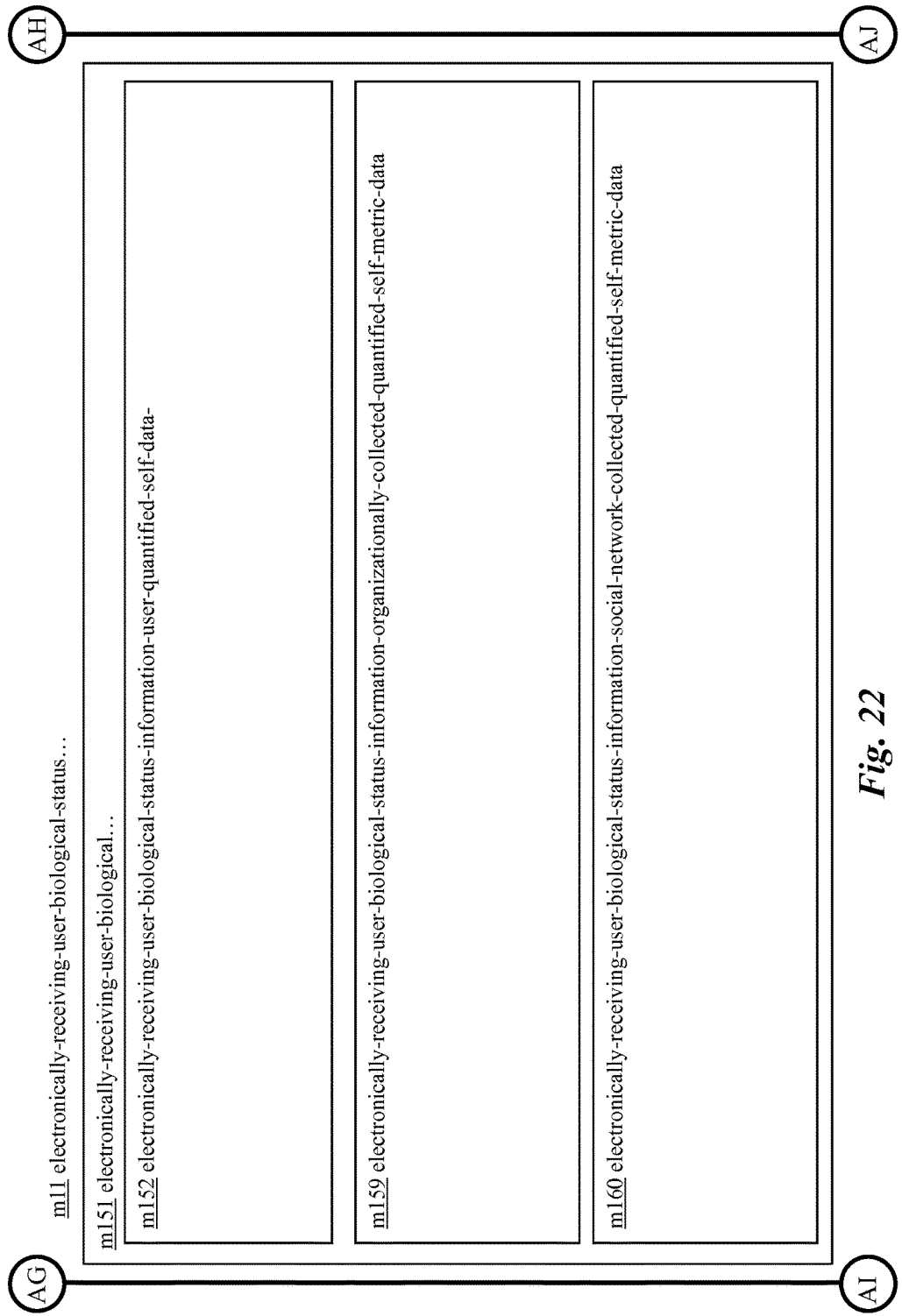

In one or more implementations, as shown in FIG. 22, module m151 may include electronically-receiving-user-biological-status-information-user-quantified-self-data-module m152.

Figure 23:
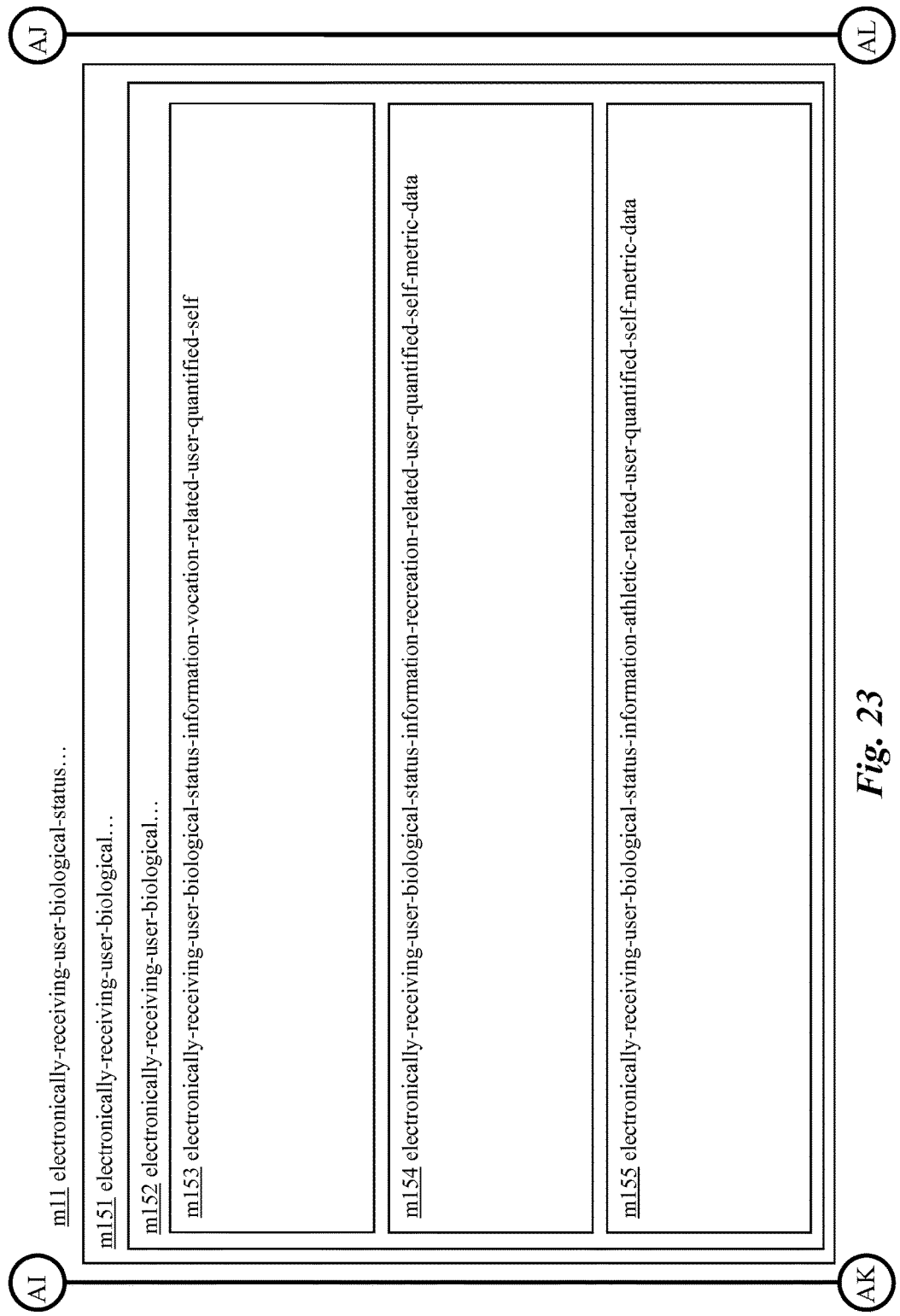

In one or more implementations, as shown in FIG. 23, module m152 may include electronically-receiving-user-biological-status-information-vocation-related-user-quantified-self module m153.

In one or more implementations, as shown in FIG. 23, module m152 may include electronically-receiving-user-biological-status-information-recreation-related-user-quantified-self-metric-data module m154.

In one or more implementations, as shown in FIG. 23, module m152 may include electronically-receiving-user-biological-status-information-athletic-related-user-quantified-self-metric-data module m155.

Figure 24:
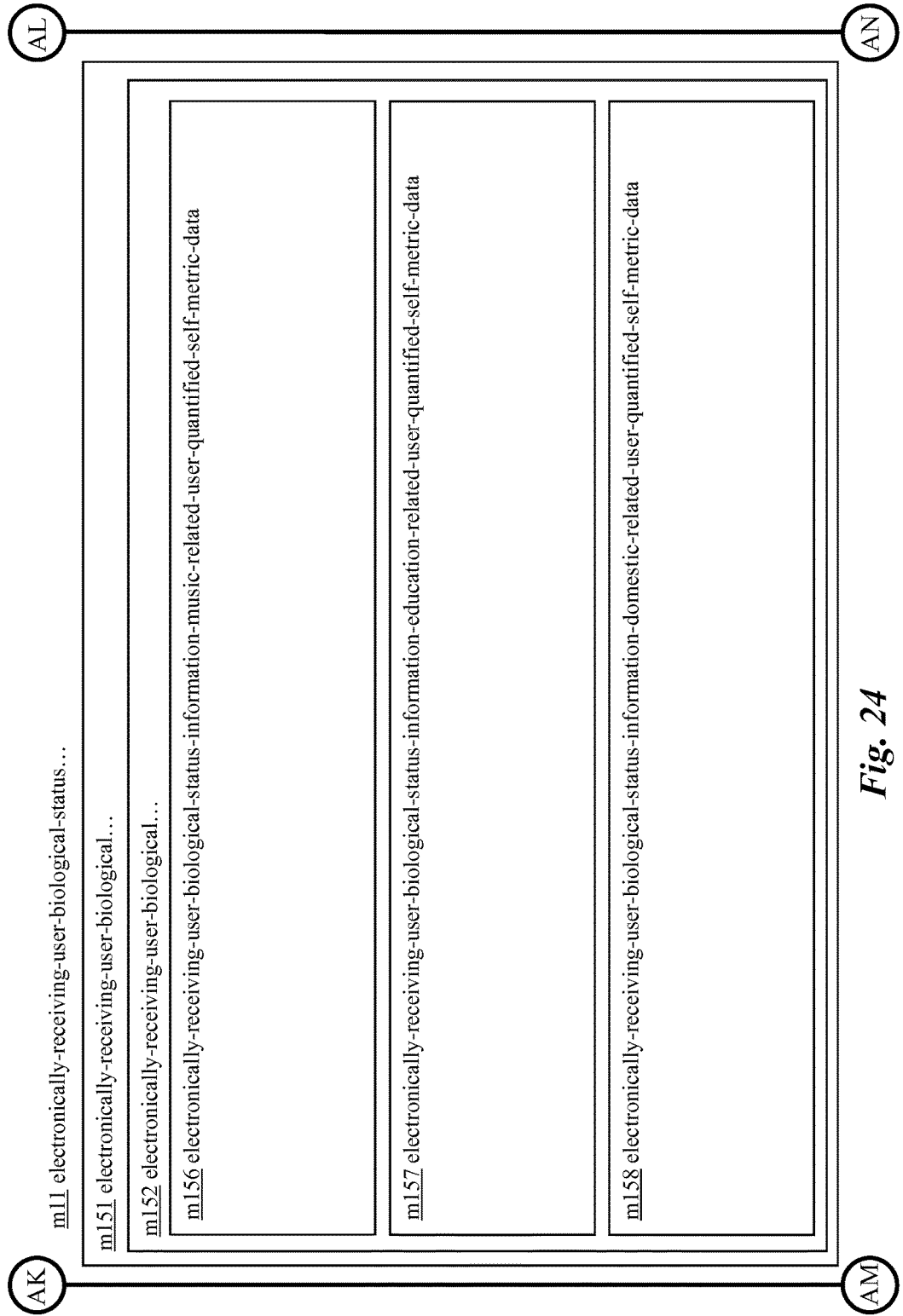

In one or more implementations, as shown in FIG. 24, module m152 may include electronically-receiving-user-biological-status-information-music-related-user-quantified-self-metric-data module m156.

In one or more implementations, as shown in FIG. 24, module m152 may include electronically-receiving-user-biological-status-information-education-related-user-quantified-self-metric-data module m157.

In one or more implementations, as shown in FIG. 24, module m152 may include electronically-receiving-user-biological-status-information-domestic-related-user-quantified-self-metric-data module m158.

In one or more implementations, as shown in FIG. 22, module m151 may include electronically-receiving-user-biological-status-information-organizationally-collected-quantified-self-metric-data module m159.

In one or more implementations, as shown in FIG. 22, module m151 may include electronically-receiving-user-biological-status-information-social-network-collected-quantified-self-metric-data module m160.

Figure 25:
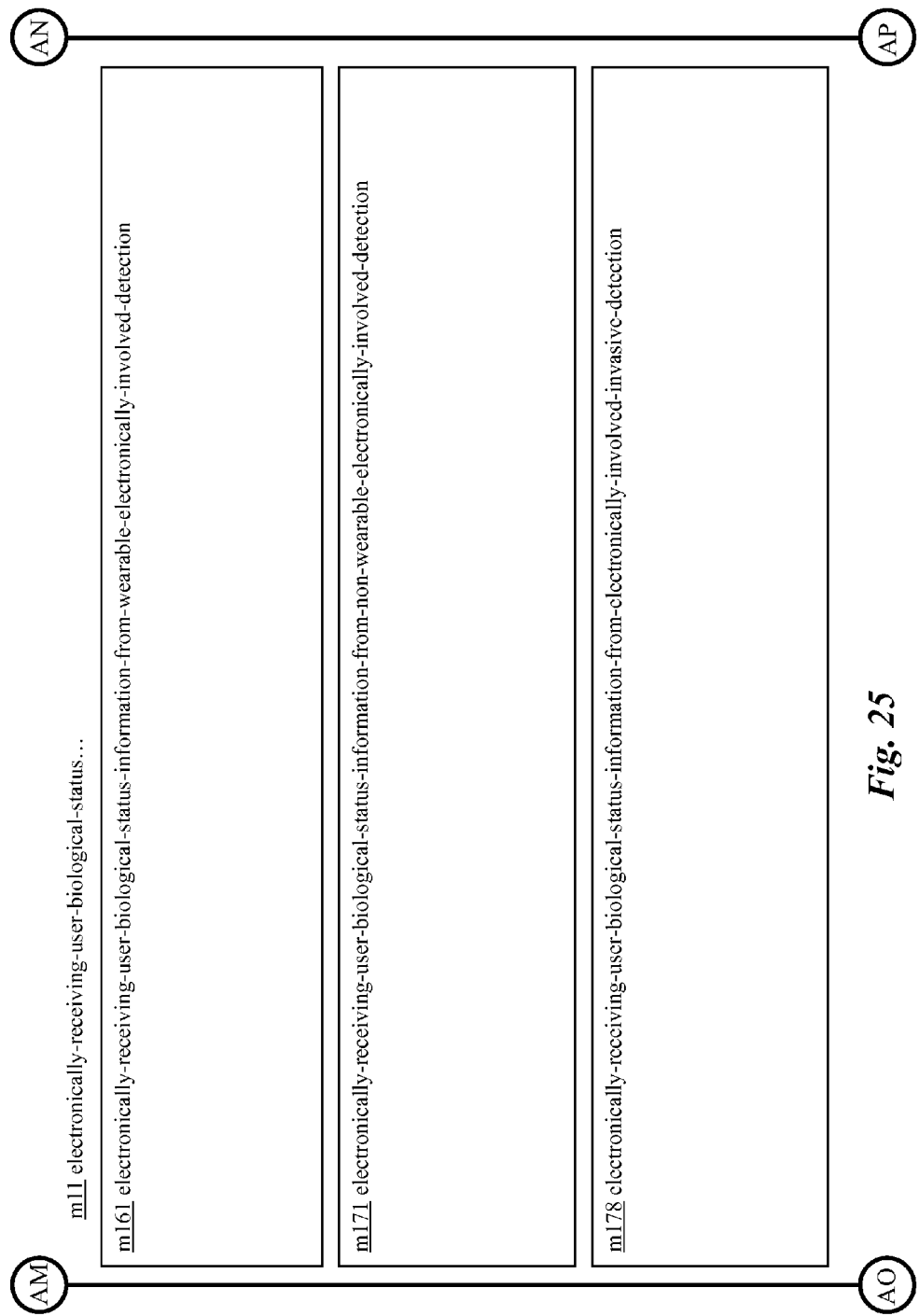

In one or more implementations, as shown in FIG. 25, module m11 may include electronically-receiving-user-biological-status-information-from-wearable-electronically-involved-detection module m161.

Figure 26:
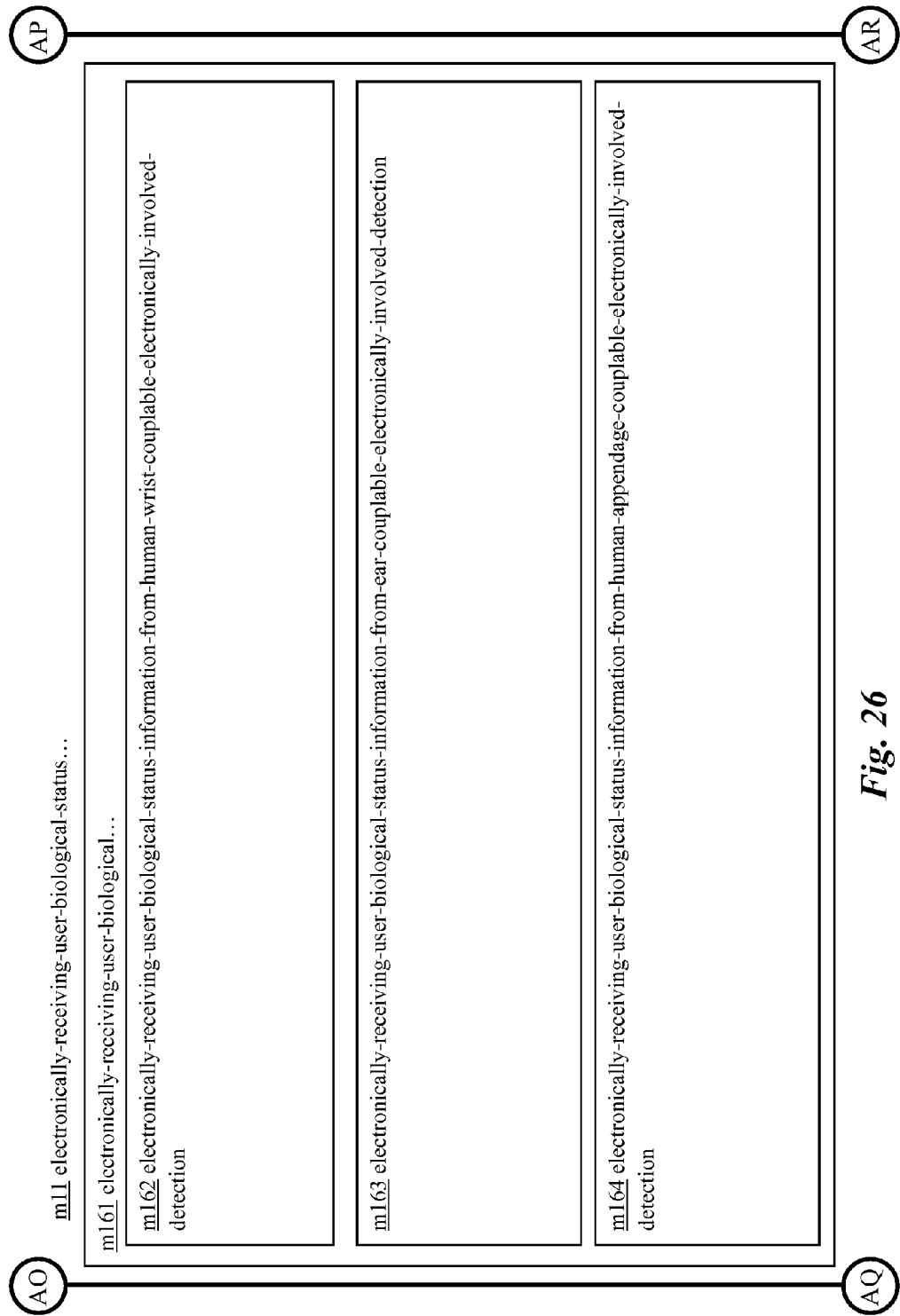

In one or more implementations, as shown in FIG. 26, module m161 may include electronically-receiving-user-biological-status-information-from-human-wrist-couplable-electronically-involved-detection module m162.

In one or more implementations, as shown in FIG. 26, module m161 may include electronically-receiving-user-biological-status-information-from-ear-couplable-electronically-involved-detection module m163.

In one or more implementations, as shown in FIG. 26, module m161 may include electronically-receiving-user-biological-status-information-from-human-appendage-couplable-electronically-involved-detection module m164.

Figure 27:
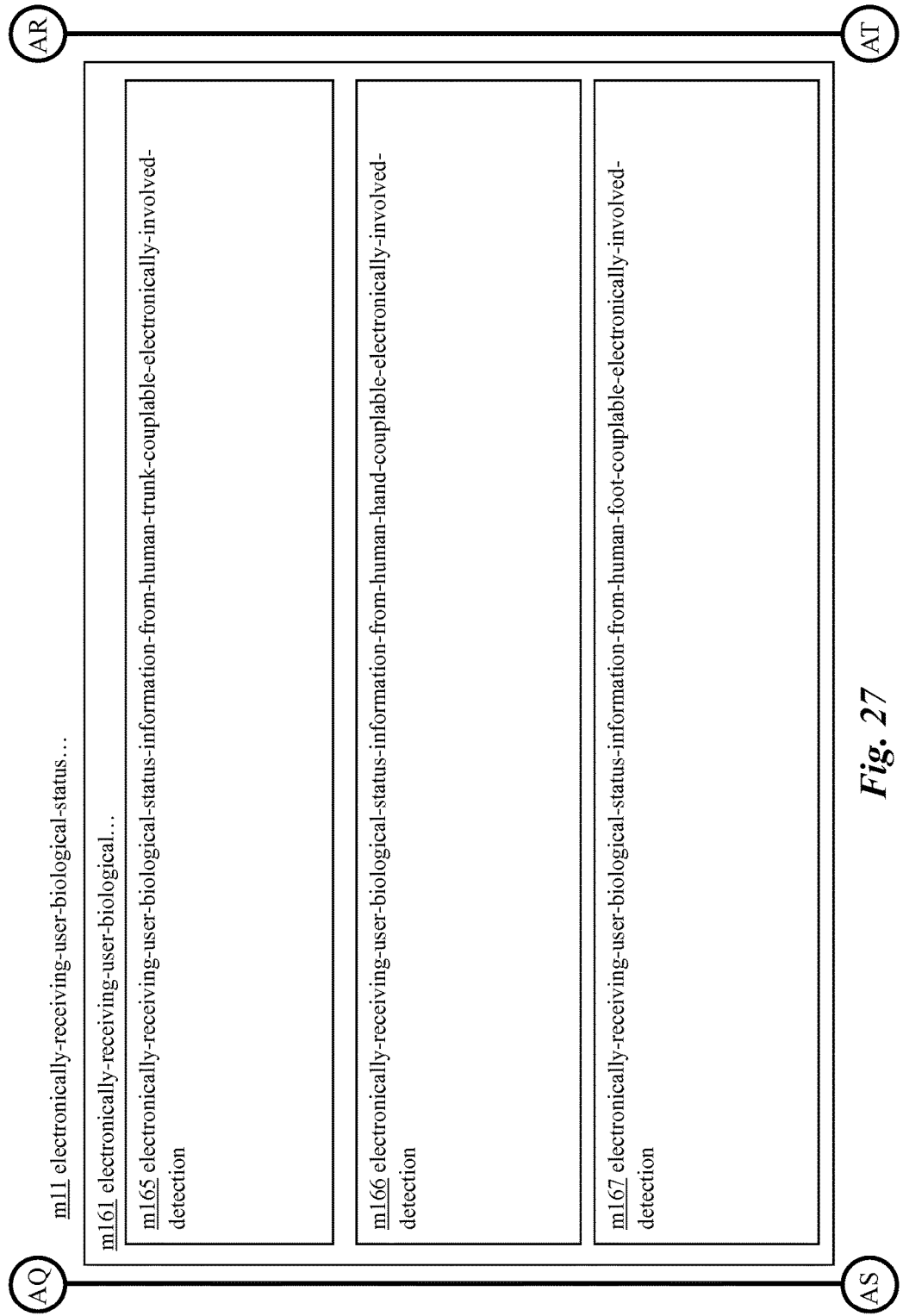

In one or more implementations, as shown in FIG. 27, module m161 may include electronically-receiving-user-biological-status-information-from-human-trunk-couplable-electronically-involved-detection module m165.

In one or more implementations, as shown in FIG. 27, module m161 may include electronically-receiving-user-biological-status-information-from-human-hand-couplable-electronically-involved-detection module m166.

In one or more implementations, as shown in FIG. 27, module m161 may include electronically-receiving-user-biological-status-information-from-human-foot-couplable-electronically-involved-detection module m167.

Figure 28:
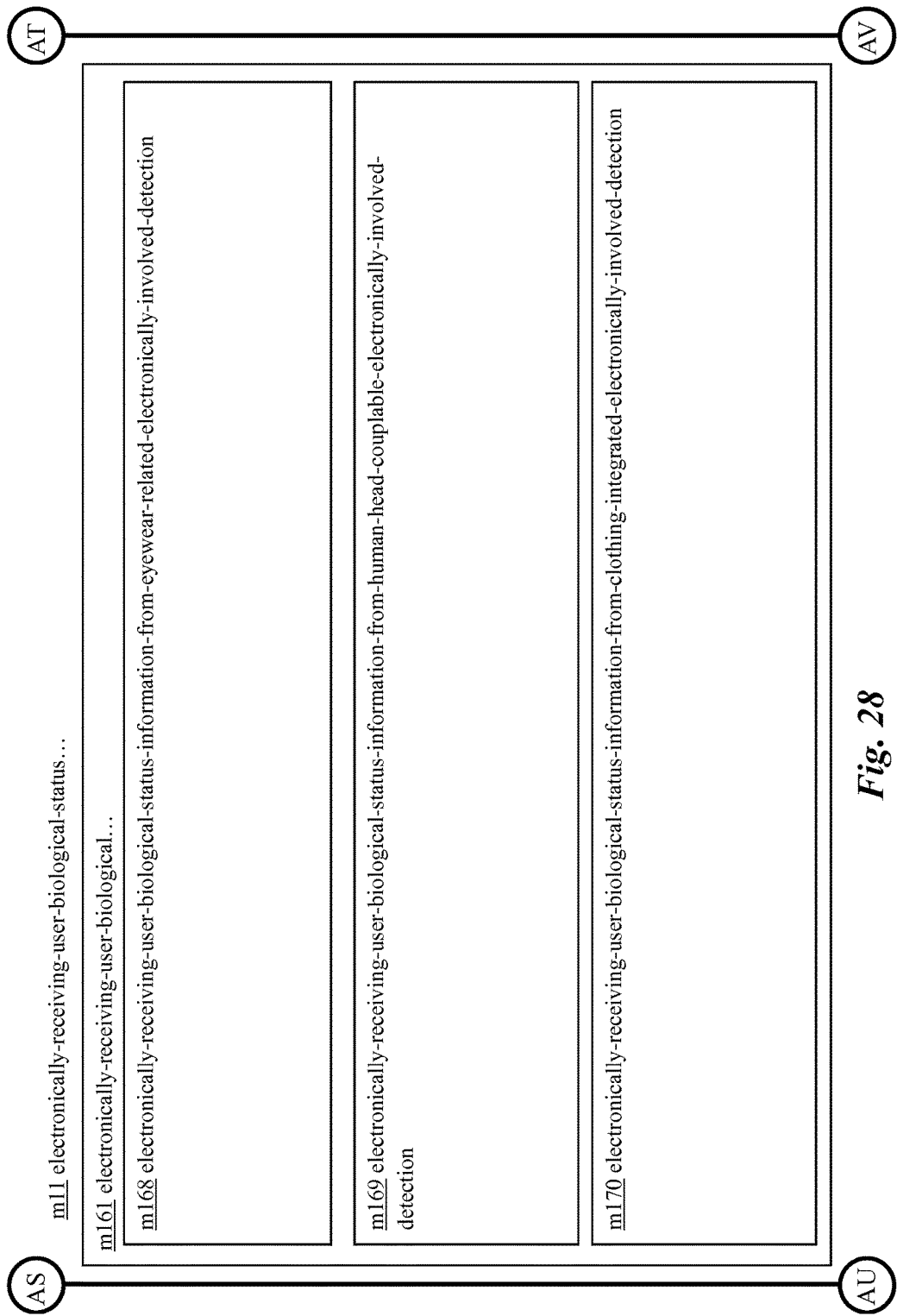

In one or more implementations, as shown in FIG. 28, module m161 may include electronically-receiving-user-biological-status-information-from-eyewear-related-electronically-involved-detection module m168.

In one or more implementations, as shown in FIG. 28, module m161 may include electronically-receiving-user-biological-status-information-from-human-head-couplable-electronically-involved-detection module m169.

In one or more implementations, as shown in FIG. 28, module m161 may include electronically-receiving-user-biological-status-information-from-clothing-integrated-electronically-involved-detection module m170.

In one or more implementations, as shown in FIG. 25, module m11 may include electronically-receiving-user-biological-status-information-from-non-wearable-electronically-involved-detection module m171.

Figure 29:
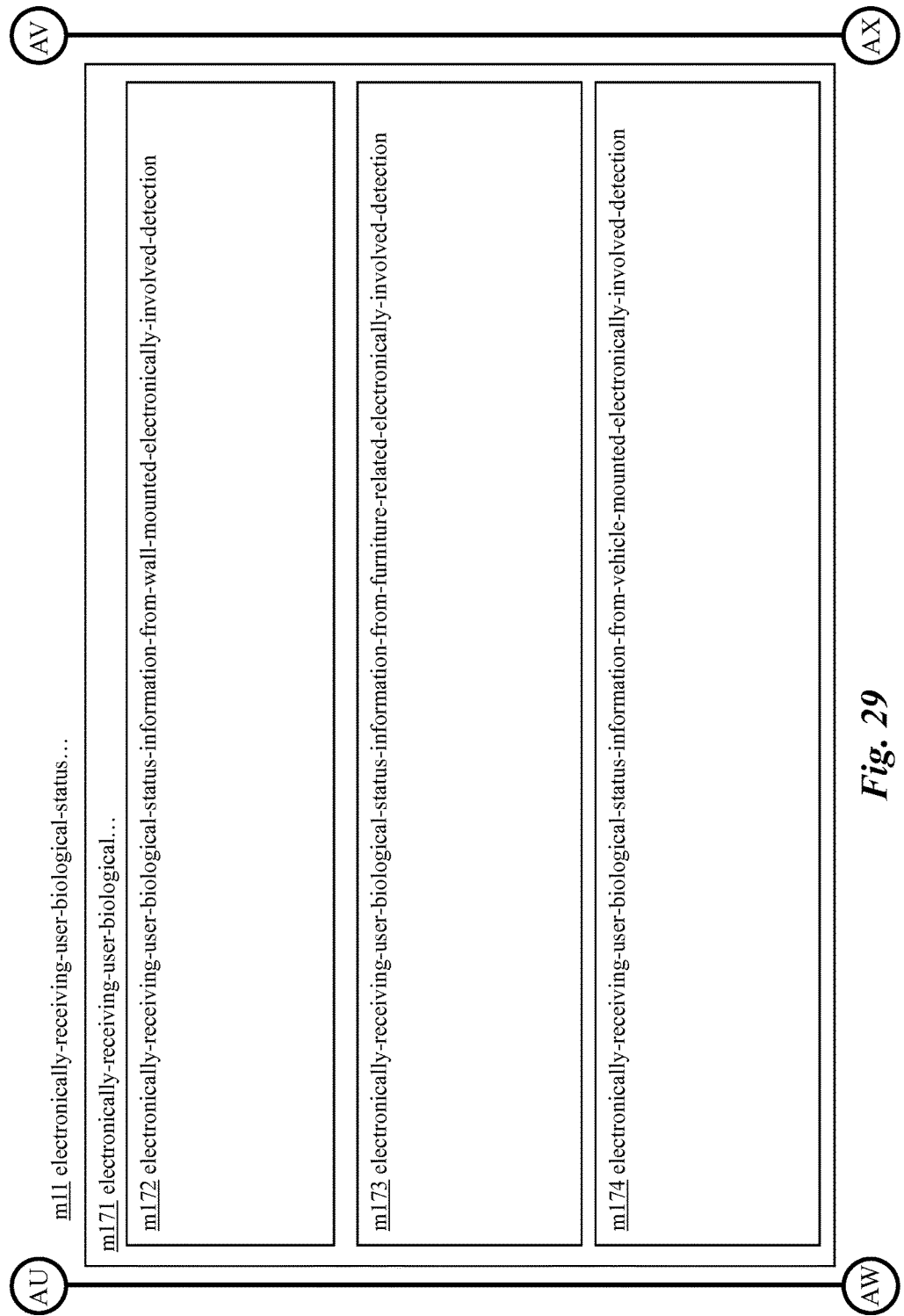

In one or more implementations, as shown in FIG. 29, module m171 may include electronically-receiving-user-biological-status-information-from-wall-mounted-electronically-involved-detection module m172.

In one or more implementations, as shown in FIG. 29, module m171 may include electronically-receiving-user-biological-status-information-from-furniture-related-electronically-involved-detection module m173.

In one or more implementations, as shown in FIG. 29, module m171 may include electronically-receiving-user-biological-status-information-from-vehicle-mounted-electronically-involved-detection module m174.

Figure 30:
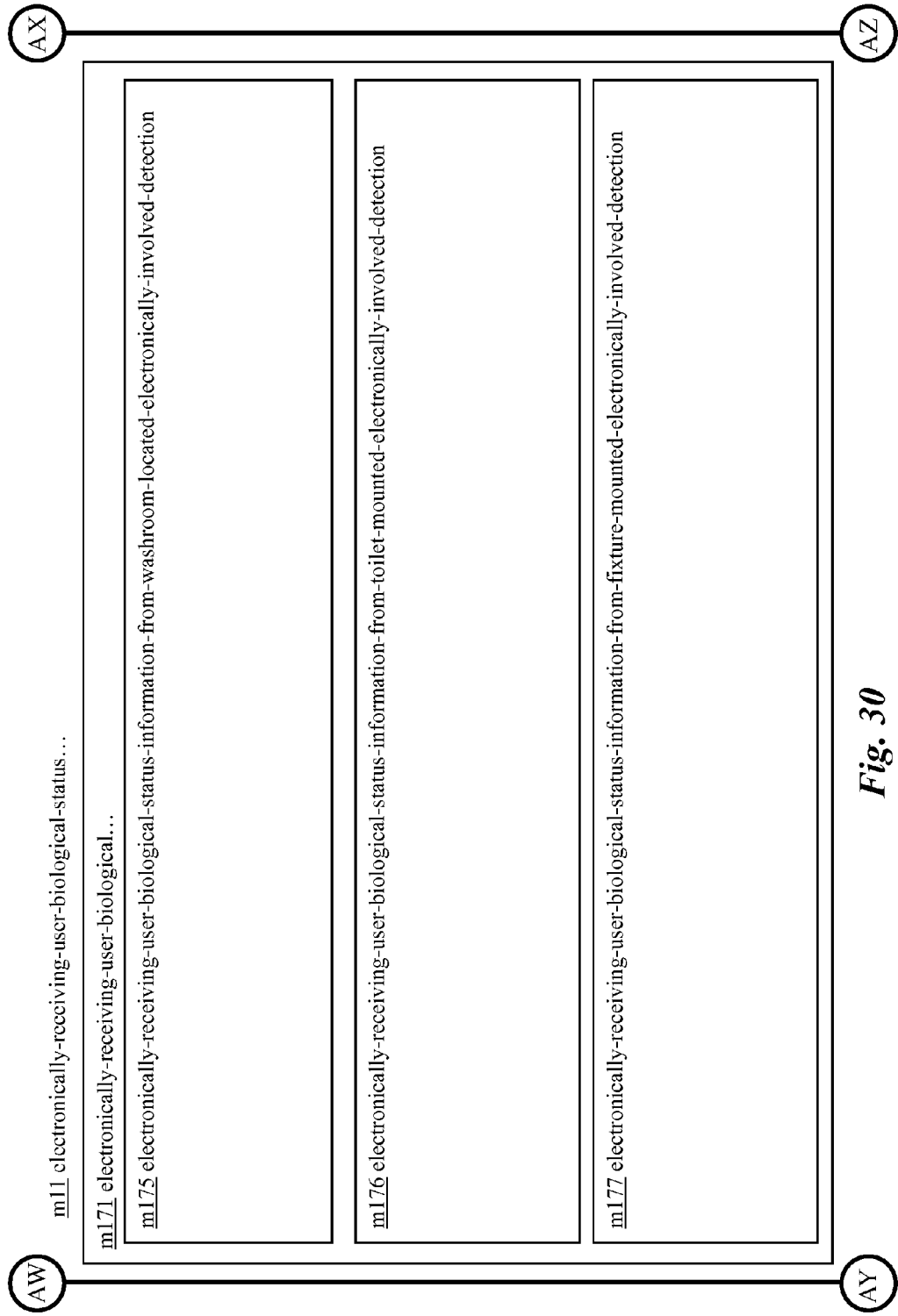

In one or more implementations, as shown in FIG. 30, module m171 may include electronically-receiving-user-biological-status-information-from-washroom-located-electronically-involved-detection module m175.

In one or more implementations, as shown in FIG. 30, module m171 may include electronically-receiving-user-biological-status-information-from-toilet-mounted-electronically-involved-detection module m176.

In one or more implementations, as shown in FIG. 30, module m171 may include electronically-receiving-user-biological-status-information-from-fixture-mounted-electronically-involved-detection module m177.

In one or more implementations, as shown in FIG. 25, module m11 may include electronically-receiving-user-biological-status-information-from-electronically-involved-invasive-detection module m178.

Figure 31:
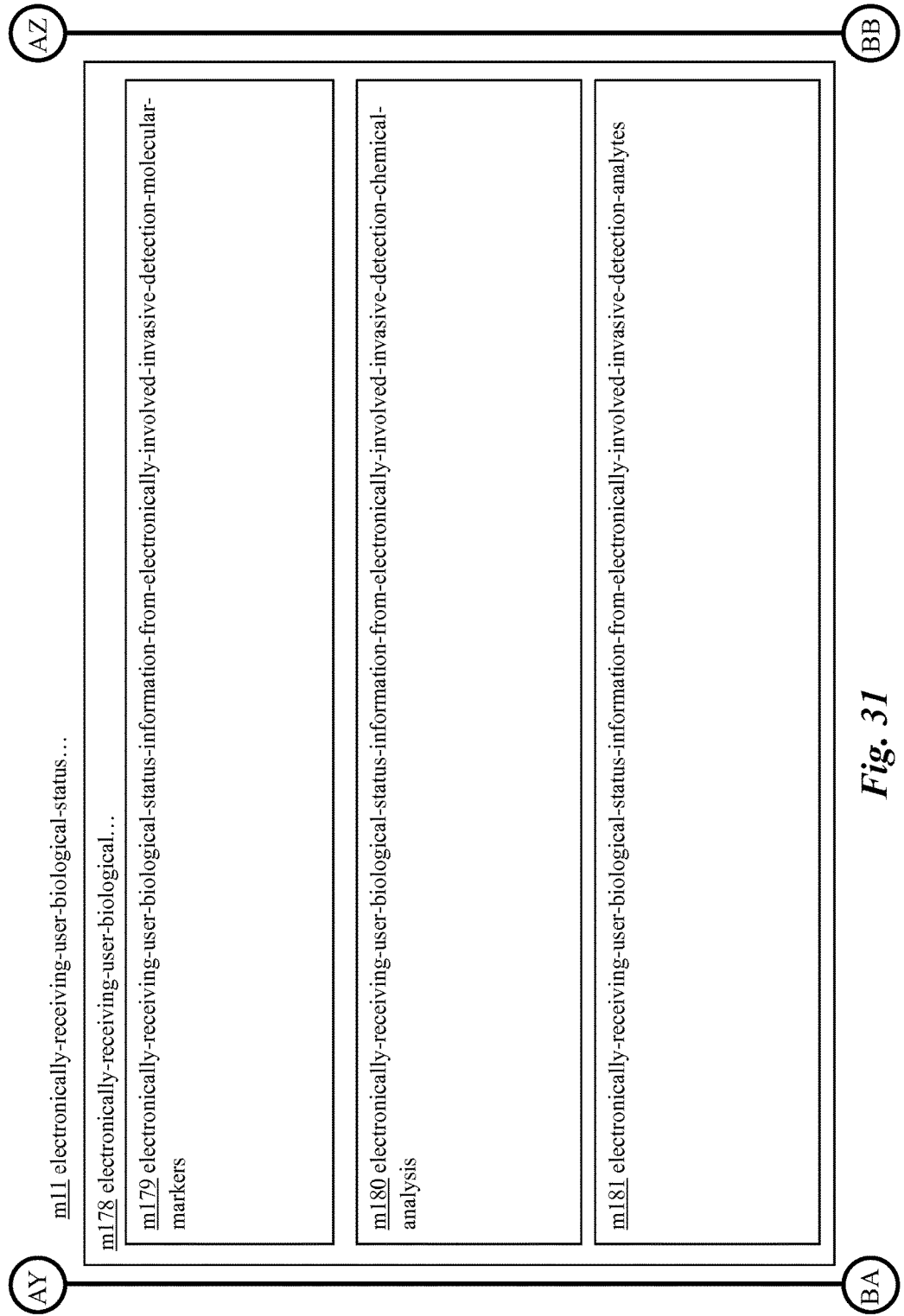

In one or more implementations, as shown in FIG. 31, module m178 may include electronically-receiving-user-biological-status-information-from-electronically-involved-invasive-detection-molecular-markers module m179.

In one or more implementations, as shown in FIG. 31, module m178 may include electronically-receiving-user-biological-status-information-from-electronically-involved-invasive-detection-chemical-analysis module m180.

In one or more implementations, as shown in FIG. 31, module m178 may include electronically-receiving-user-biological-status-information-from-electronically-involved-invasive-detection-analytes module m181.

Figure 32:
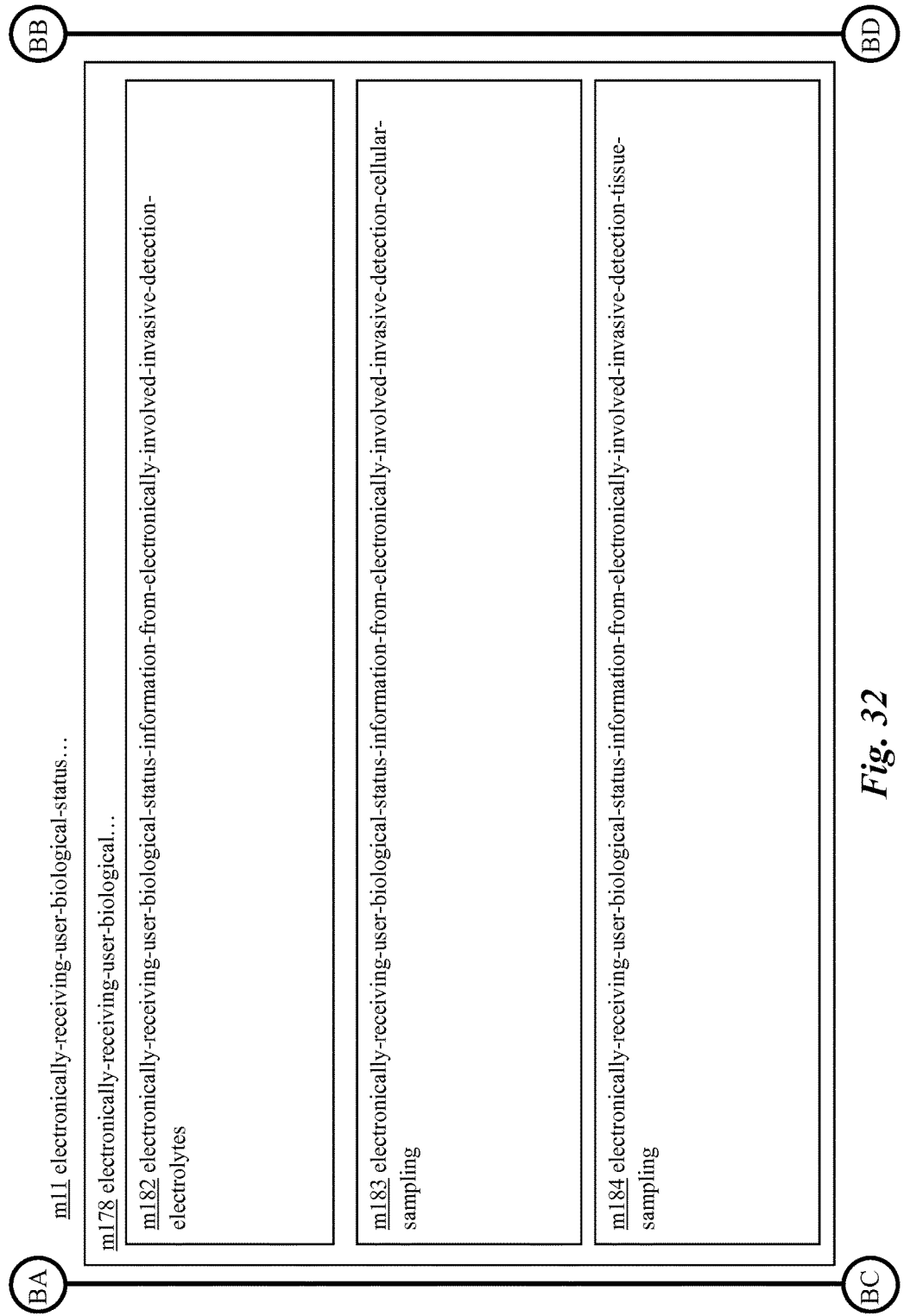

In one or more implementations, as shown in FIG. 32, module m178 may include electronically-receiving-user-biological-status-information-from-electronically-involved-invasive-detection-electrolytes module m182.

In one or more implementations, as shown in FIG. 32, module m178 may include electronically-receiving-user-biological-status-information-from-electronically-involved-invasive-detection-cellular-sampling module m183.

In one or more implementations, as shown in FIG. 32, module m178 may include electronically-receiving-user-biological-status-information-from-electronically-involved-invasive-detection-tissue-sampling module m184.

Figure 33:
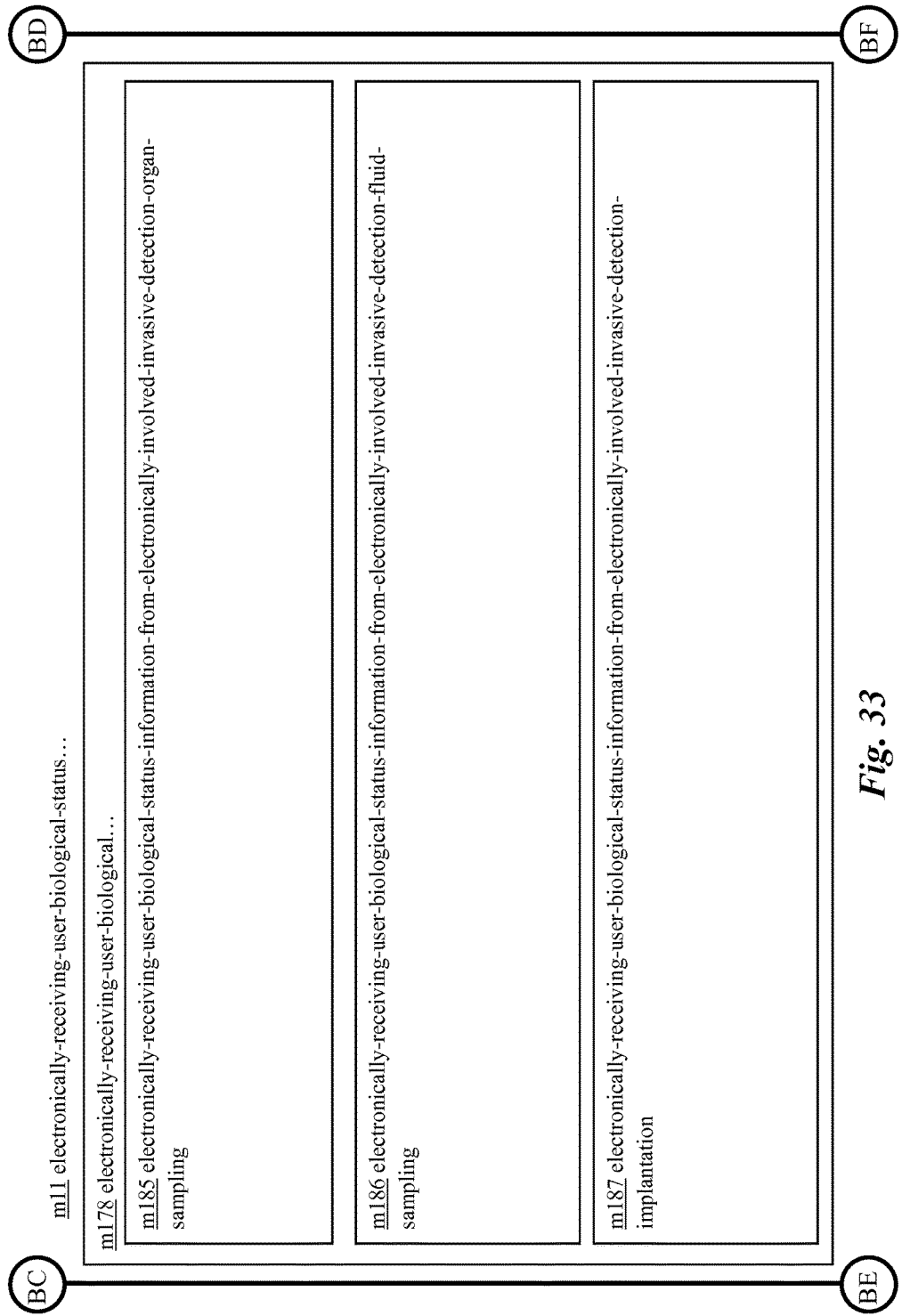

In one or more implementations, as shown in FIG. 33, module m178 may include electronically-receiving-user-biological-status-information-from-electronically-involved-invasive-detection-organ-sampling module m185.

In one or more implementations, as shown in FIG. 33, module m178 may include electronically-receiving-user-biological-status-information-from-electronically-involved-invasive-detection-fluid-sampling module m186.

In one or more implementations, as shown in FIG. 33, module m178 may include electronically-receiving-user-biological-status-information-from-electronically-involved-invasive-detection-implantation module m187.

Figure 34:
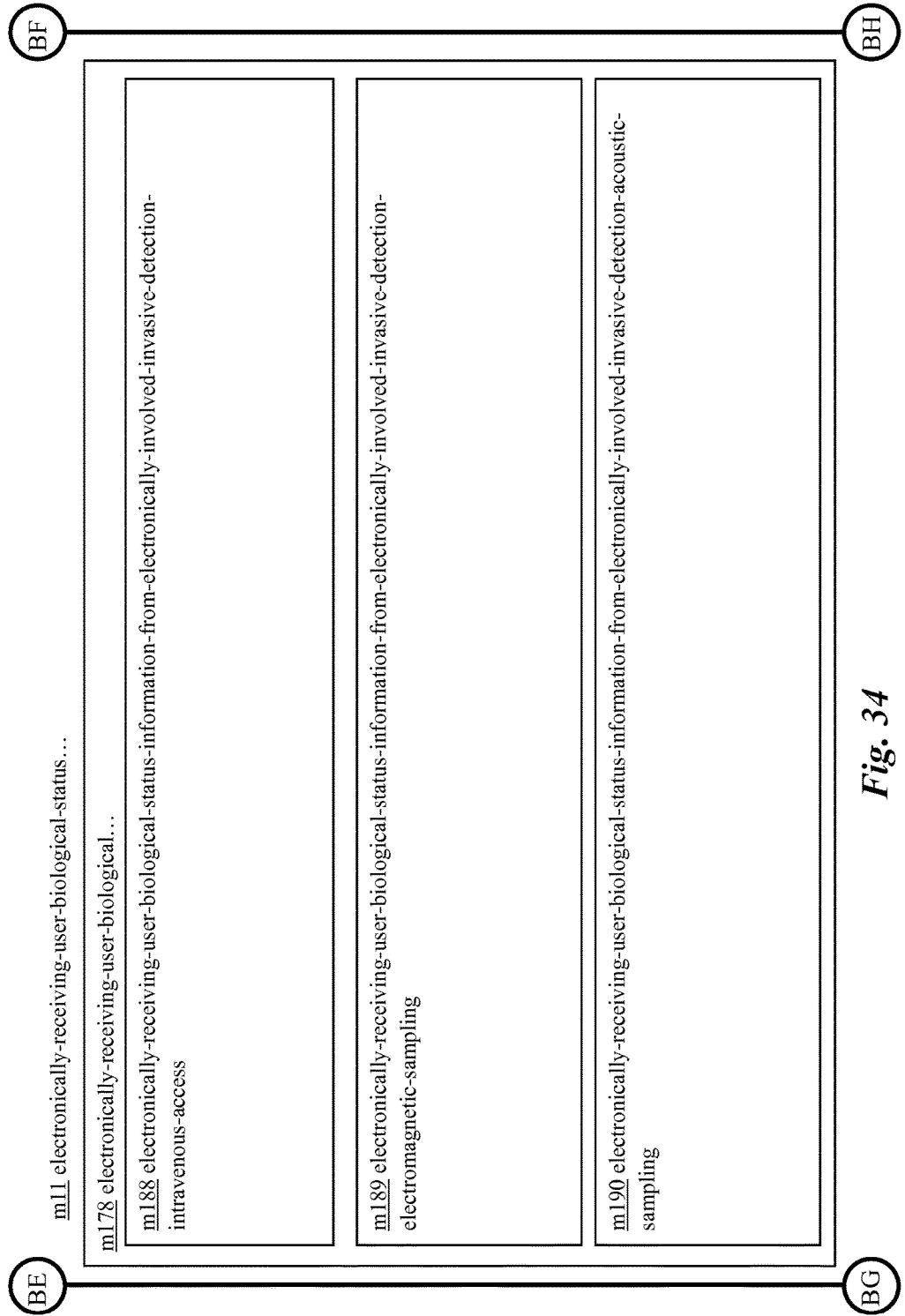

In one or more implementations, as shown in FIG. 34, module m178 may include electronically-receiving-user-biological-status-information-from-electronically-involved-invasive-detection-intravenous-access module m188.

In one or more implementations, as shown in FIG. 34, module m178 may include electronically-receiving-user-biological-status-information-from-electronically-involved-invasive-detection-electromagnetic-sampling module m189.

In one or more implementations, as shown in FIG. 34, module m178 may include electronically-receiving-user-biological-status-information-from-electronically-involved-invasive-detection-acoustic-sampling module m190.

Figure 35:
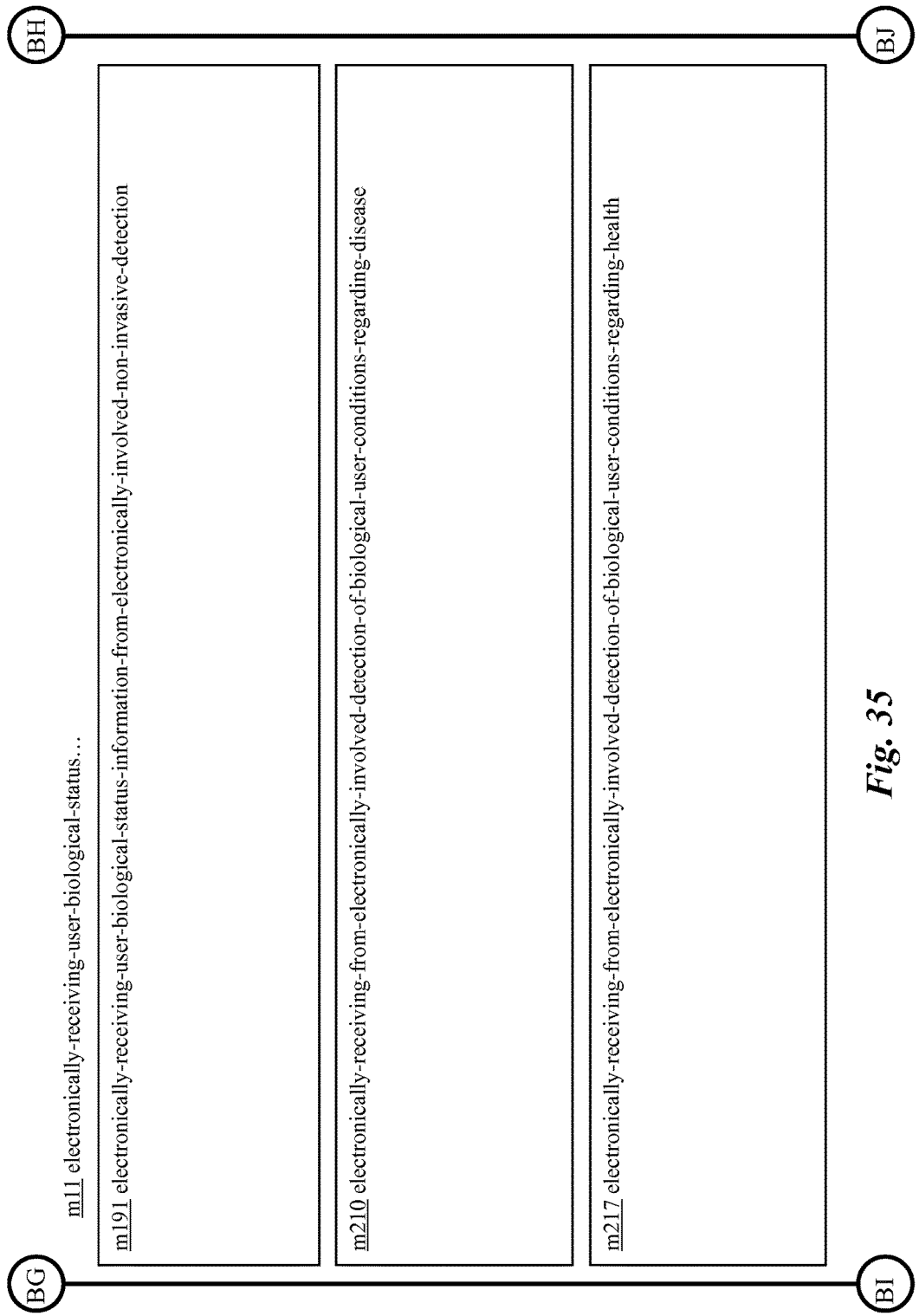

In one or more implementations, as shown in FIG. 35, module m11 may include electronically-receiving-user-biological-status-information-from-electronically-involved-non-invasive-detection module m191.

Figure 36:
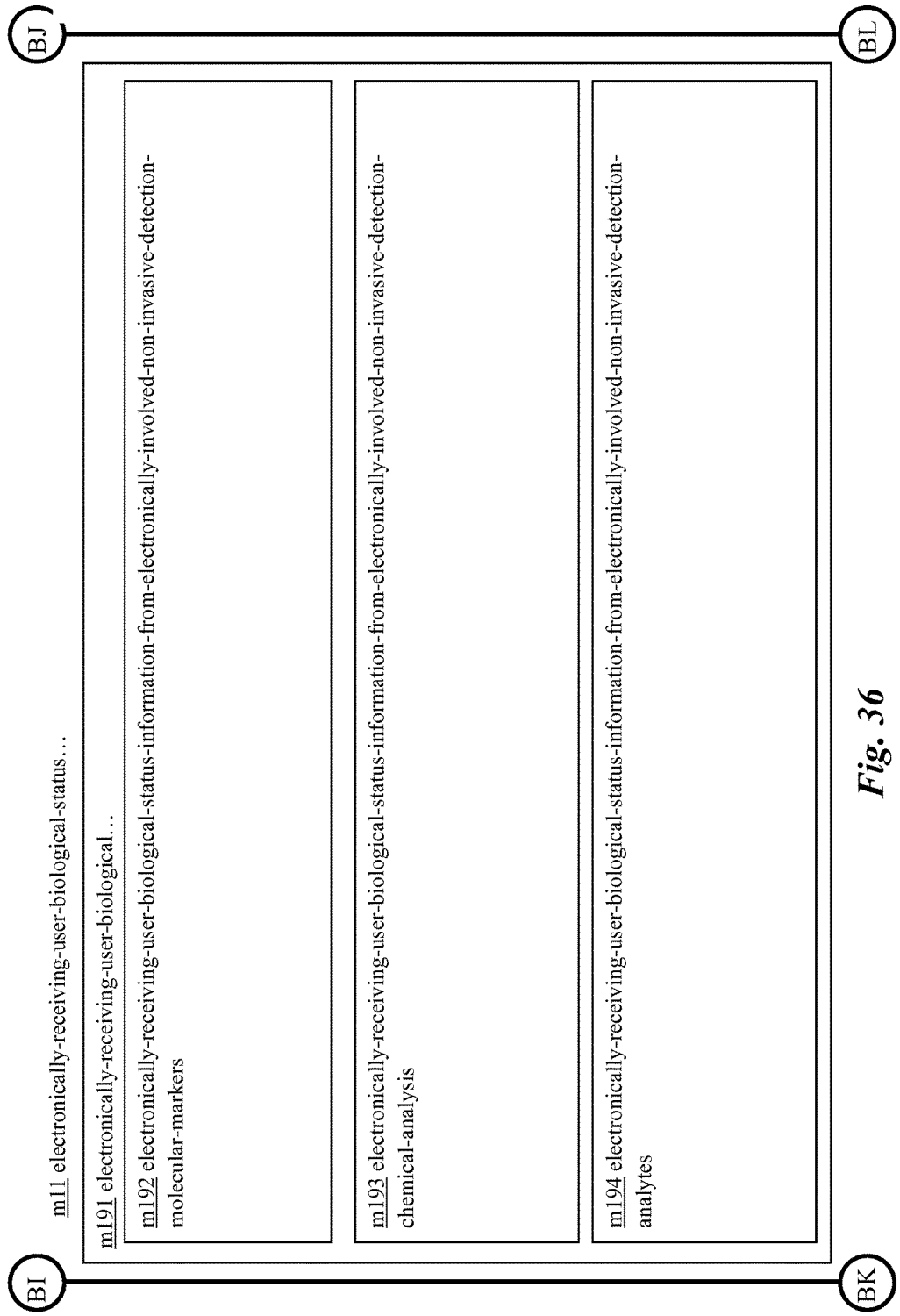

In one or more implementations, as shown in FIG. 36, module m191 may include electronically-receiving-user-biological-status-information-from-electronically-involved-non-invasive-detection-molecular-markers module m192.

In one or more implementations, as shown in FIG. 36, module m191 may include electronically-receiving-user-biological-status-information-from-electronically-involved-non-invasive-detection-chemical-analysis module m193.

In one or more implementations, as shown in FIG. 36, module m191 may include electronically-receiving-user-biological-status-information-from-electronically-involved-non-invasive-detection-analytes module m194.

Figure 37:
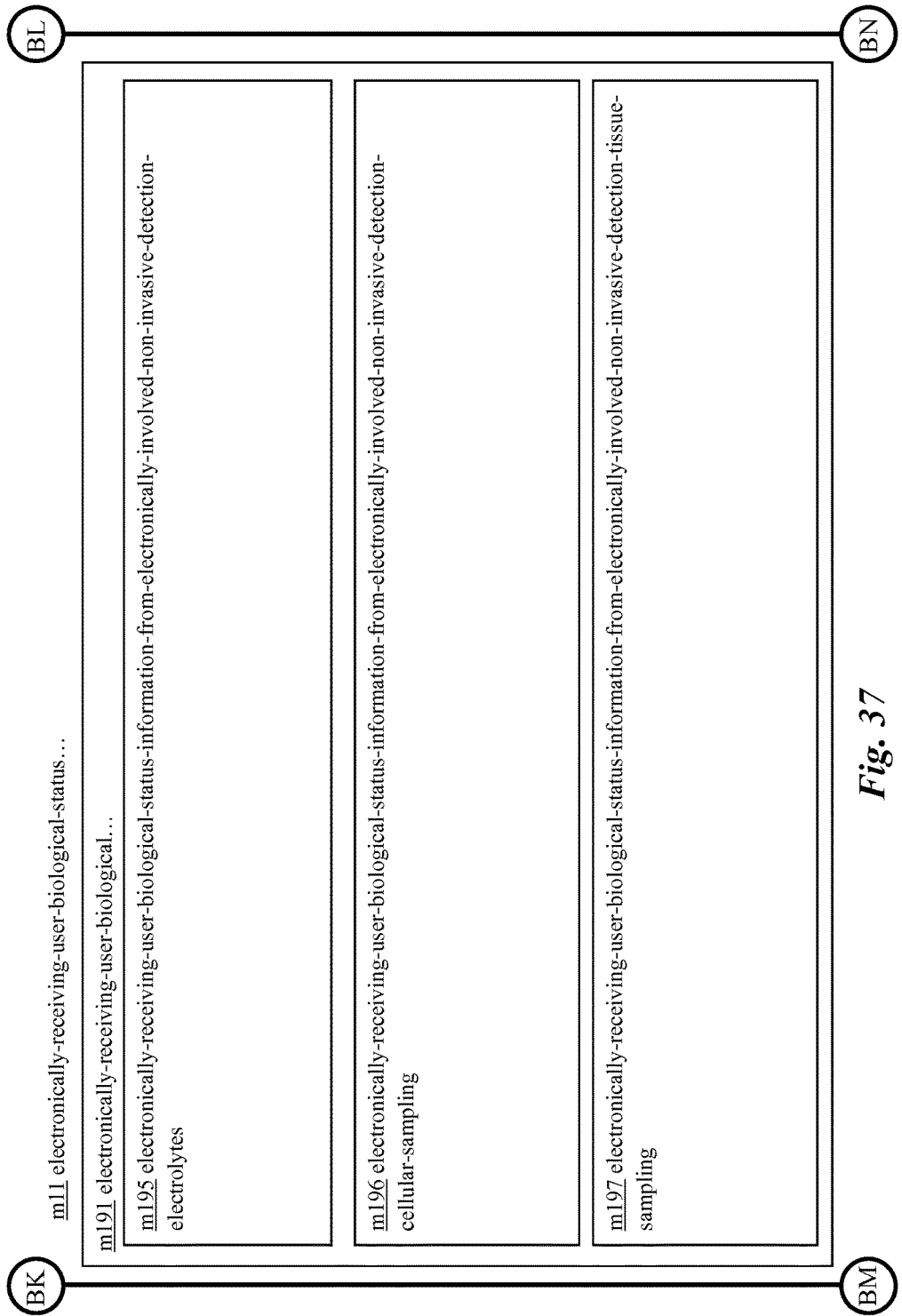

In one or more implementations, as shown in FIG. 37, module m191 may include electronically-receiving-user-biological-status-information-from-electronically-involved-non-invasive-detection-electrolytes module m195.

In one or more implementations, as shown in FIG. 37, module m191 may include electronically-receiving-user-biological-status-information-from-electronically-involved-non-invasive-detection-cellular-sampling module m196.

In one or more implementations, as shown in FIG. 37, module m191 may include electronically-receiving-user-biological-status-information-from-electronically-involved-non-invasive-detection-tissue-sampling module m197.

Figure 38:
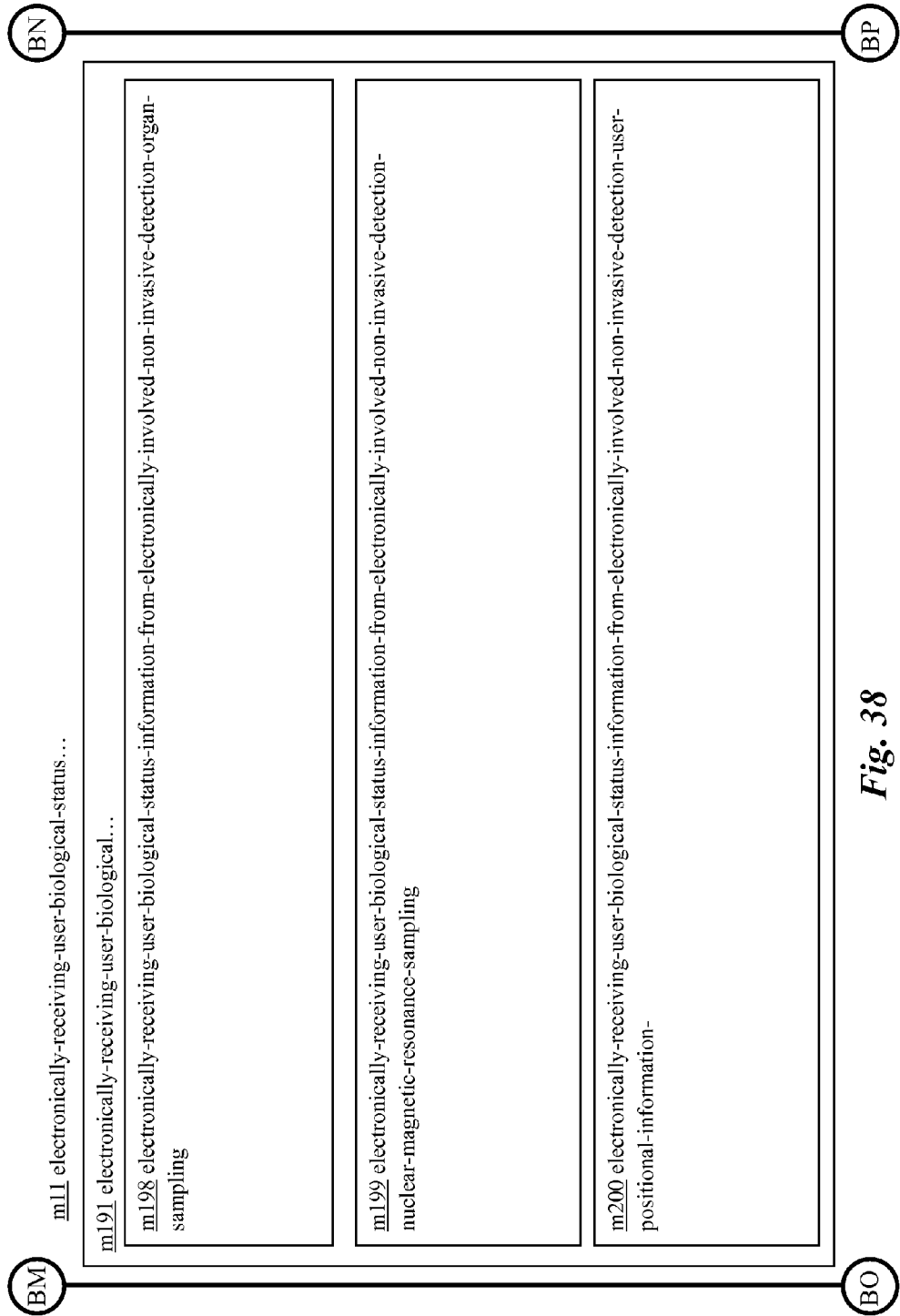

In one or more implementations, as shown in FIG. 38, module m191 may include electronically-receiving-user-biological-status-information-from-electronically-involved-non-invasive-detection-organ-sampling module m198.

In one or more implementations, as shown in FIG. 38, module m191 may include electronically-receiving-user-biological-status-information-from-electronically-involved-non-invasive-detection-nuclear-magnetic-resonance-sampling module m199.

In one or more implementations, as shown in FIG. 38, module m191 may include electronically-receiving-user-biological-status-information-from-electronically-involved-non-invasive-detection-user-positional-information-module m200.

Figure 39:
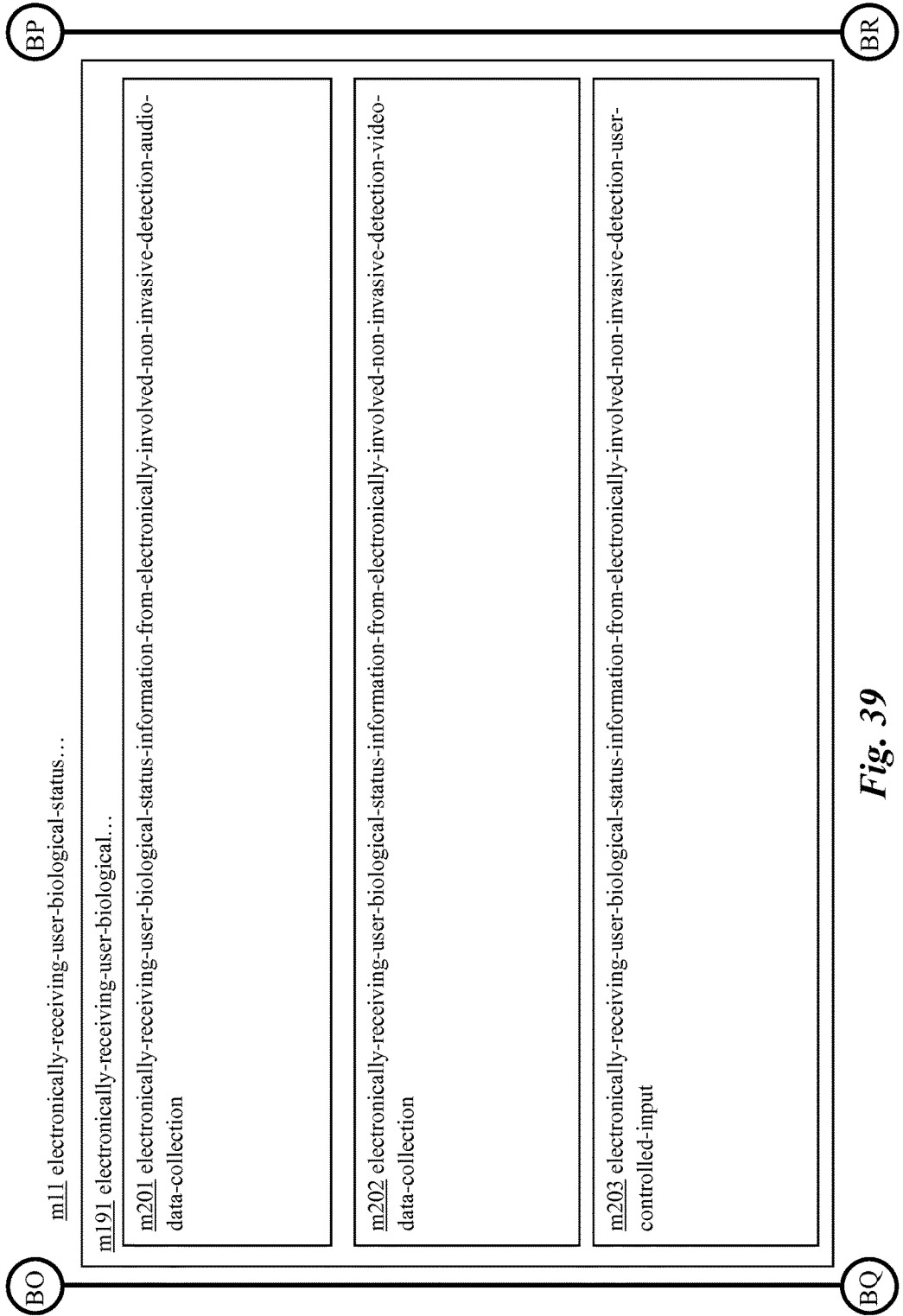

In one or more implementations, as shown in FIG. 39, module m191 may include electronically-receiving-user-biological-status-information-from-electronically-involved-non-invasive-detection-audio-data-collection module m201.

In one or more implementations, as shown in FIG. 39, module m191 may include electronically-receiving-user-biological-status-information-from-electronically-involved-non-invasive-detection-video-data-collection module m202.

In one or more implementations, as shown in FIG. 39, module m191 may include electronically-receiving-user-biological-status-information-from-electronically-involved-non-invasive-detection-user-controlled-input module m203.

Figure 40:
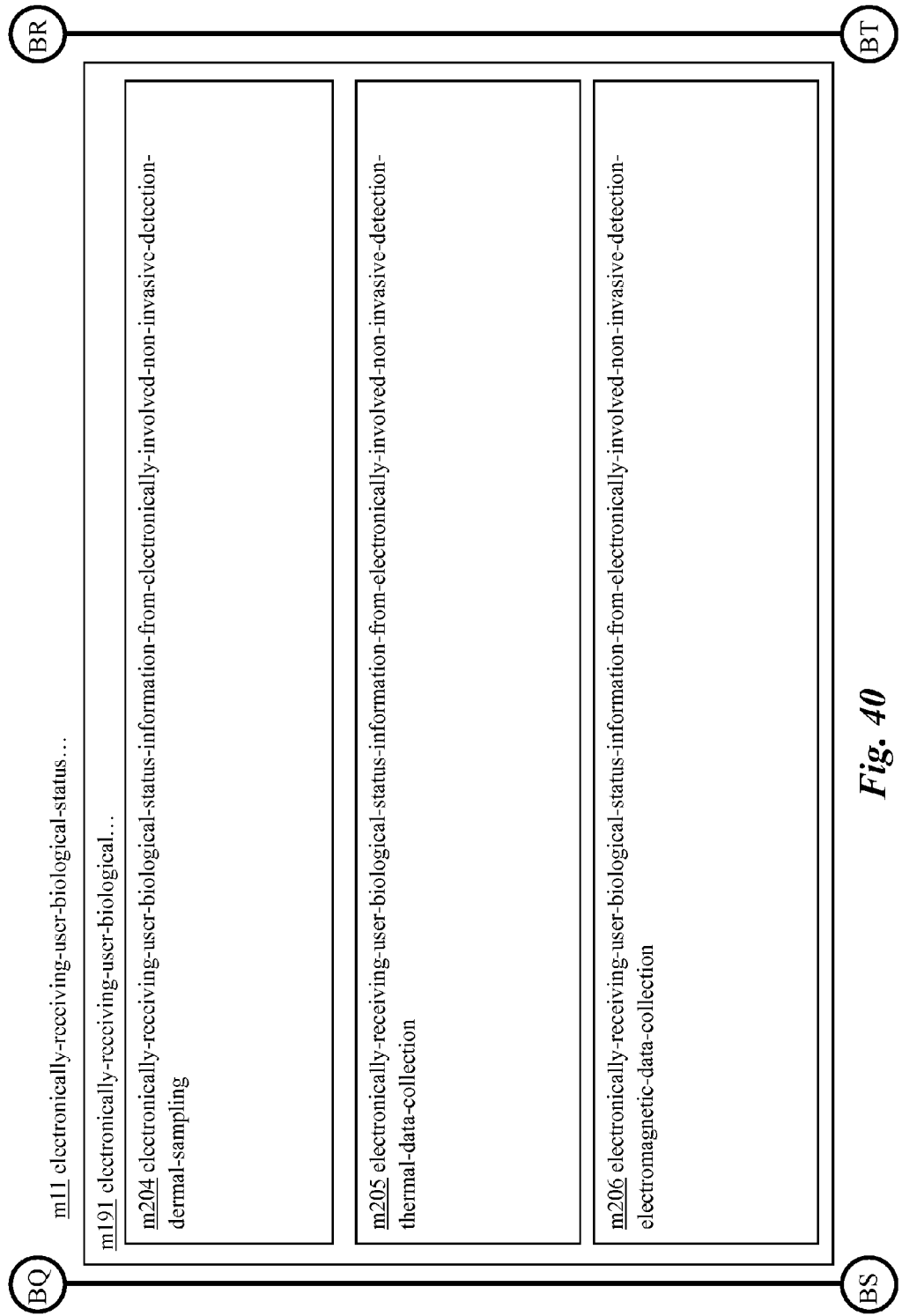

In one or more implementations, as shown in FIG. 40, module m191 may include electronically-receiving-user-biological-status-information-from-electronically-involved-non-invasive-detection-dermal-sampling module m204.

In one or more implementations, as shown in FIG. 40, module m191 may include electronically-receiving-userbiological-status-information-from-electronically-involved-non-invasive-detection-thermal-data-collection module m205.

In one or more implementations, as shown in FIG. 40, module m191 may include electronically-receiving-user-biological-status-information-from-electronically-involved-non-invasive-detection-electromagnetic-data-collection module m206.

Figure 41:
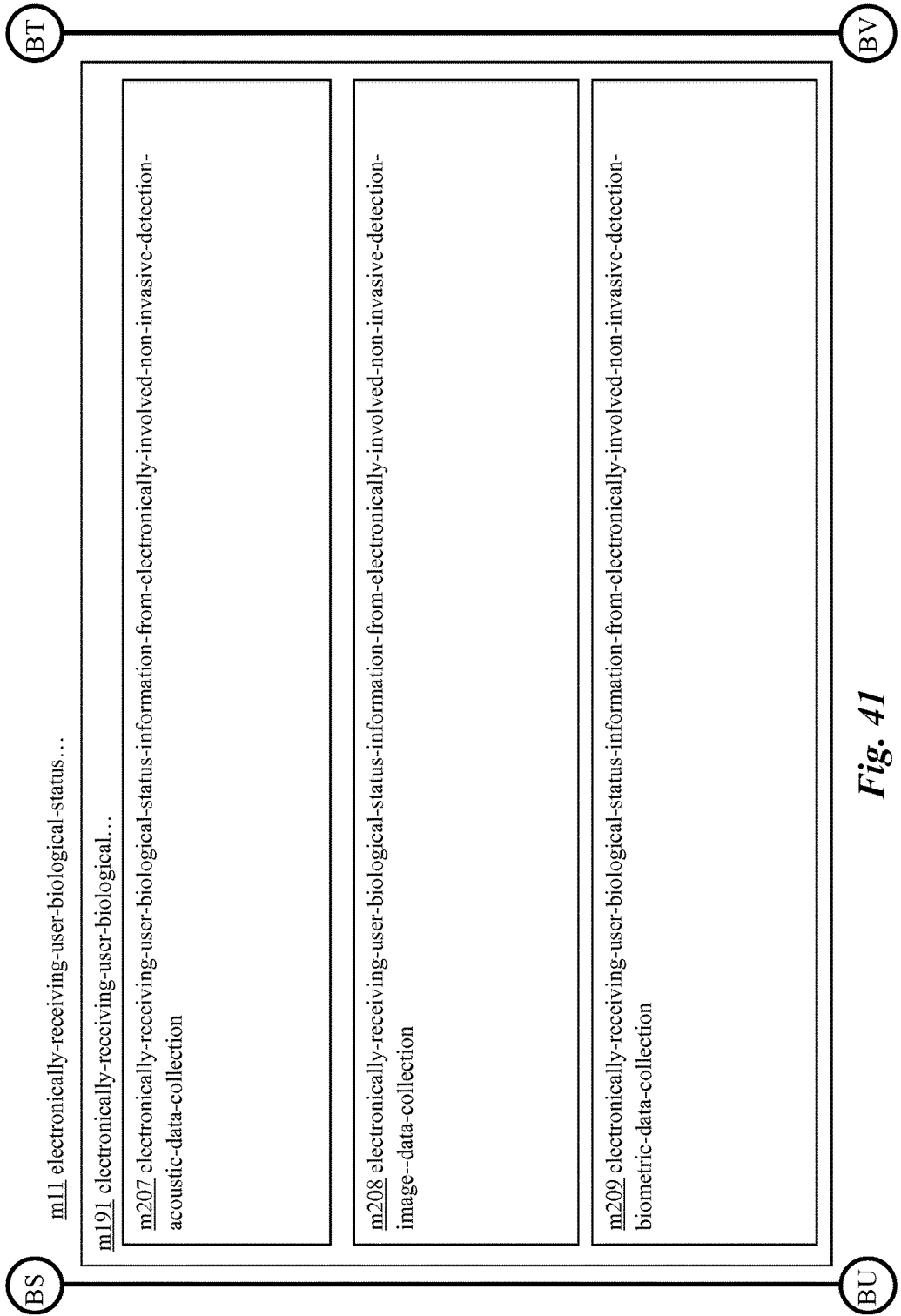

In one or more implementations, as shown in FIG. 41, module m191 may include electronically-receiving-user-biological-status-information-from-electronically-involved-non-invasive-detection-acoustic-data-collection module m207.

In one or more implementations, as shown in FIG. 41, module m191 may include electronically-receiving-user-biological-status-information-from-electronically-involved-non-invasive-detection-image-data-collection module m208.

In one or more implementations, as shown in FIG. 41, module m191 may include electronically-receiving-user-biological-status-information-from-electronically-involved-non-invasive-detection-biometric-data-collection module m209.

In one or more implementations, as shown in FIG. 35, module m11 may include electronically-receiving-from-electronically-involved-detection-of-biological-user-conditions-regarding-disease module m210.

Figure 42:
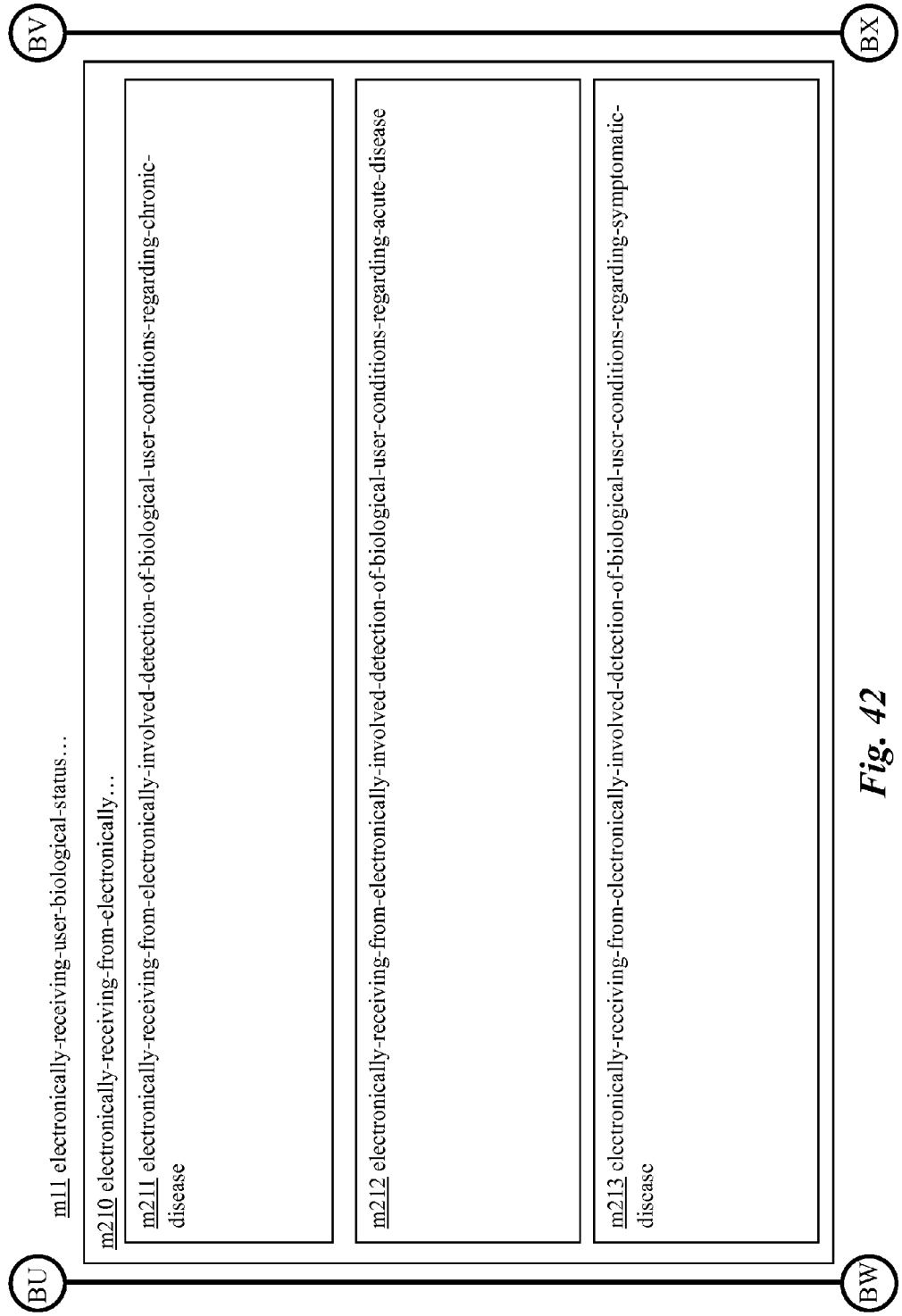

In one or more implementations, as shown in FIG. 42, module m210 may include electronically-receiving-from-electronically-involved-detection-of-biological-user-conditions-regarding-chronic-disease module m211.

In one or more implementations, as shown in FIG. 42, module m210 may include electronically-receiving-from-electronically-involved-detection-of-biological-user-conditions-regarding-acute-disease module m212.

In one or more implementations, as shown in FIG. 42, module m210 may include electronically-receiving-from-electronically-involved-detection-of-biological-user-conditions-regarding-symptomatic-disease module m213.

Figure 43:
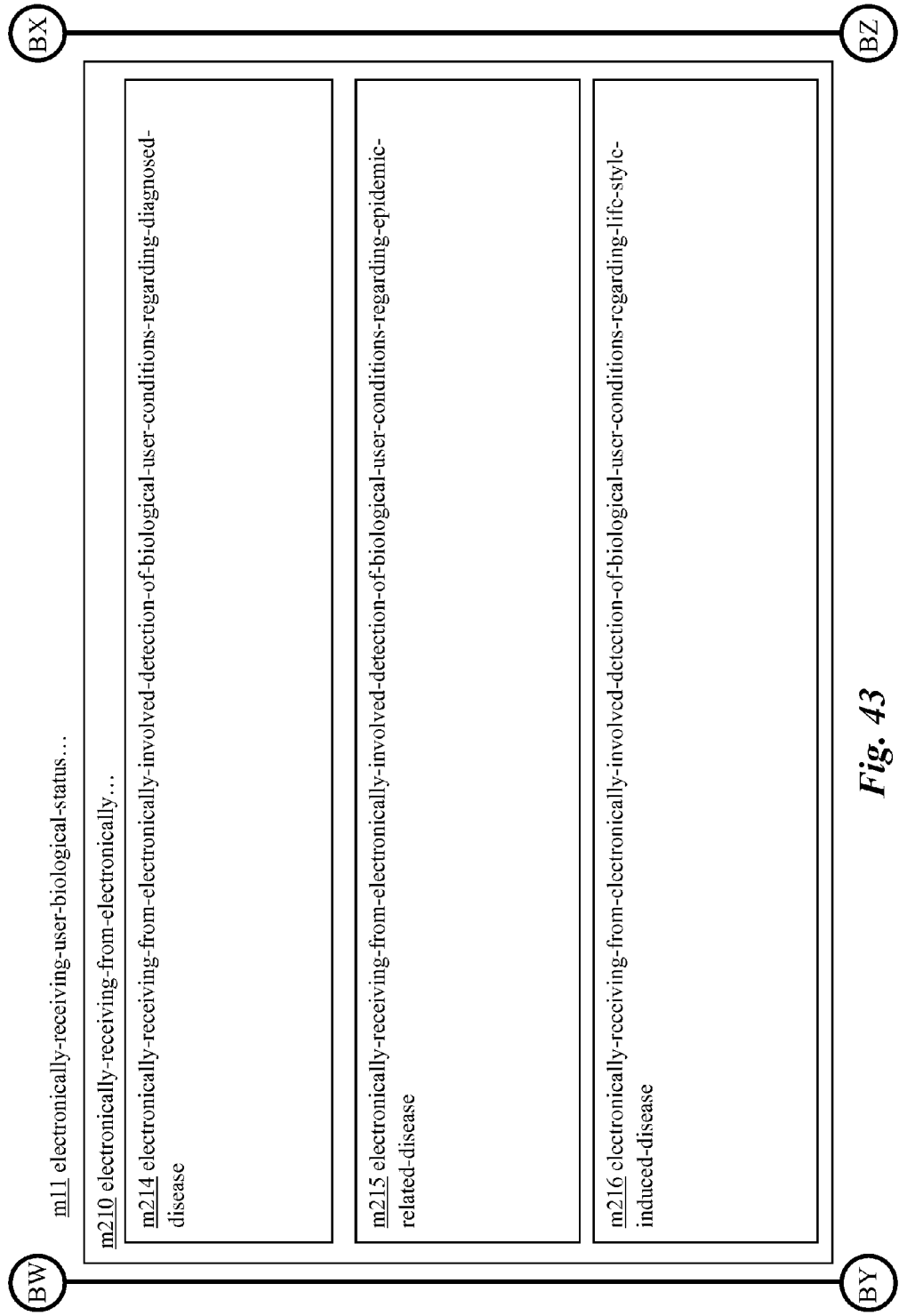

In one or more implementations, as shown in FIG. 43, module m210 may include electronically-receiving-from-electronically-involved-detection-of-biological-user-conditions-regarding-diagnosed-disease module m214.

In one or more implementations, as shown in FIG. 43, module m210 may include electronically-receiving-from-electronically-involved-detection-of-biological-user-conditions-regarding-epidemic-related-disease module m215.

In one or more implementations, as shown in FIG. 43, module m210 may include electronically-receiving-from-electronically-involved-detection-of-biological-user-conditions-regarding-life-style-induced-disease module m216.

In one or more implementations, as shown in FIG. 35, module m11 may include electronically-receiving-from-electronically-involved-detection-of-biological-user-conditions-regarding-health module m217.

Figure 44:
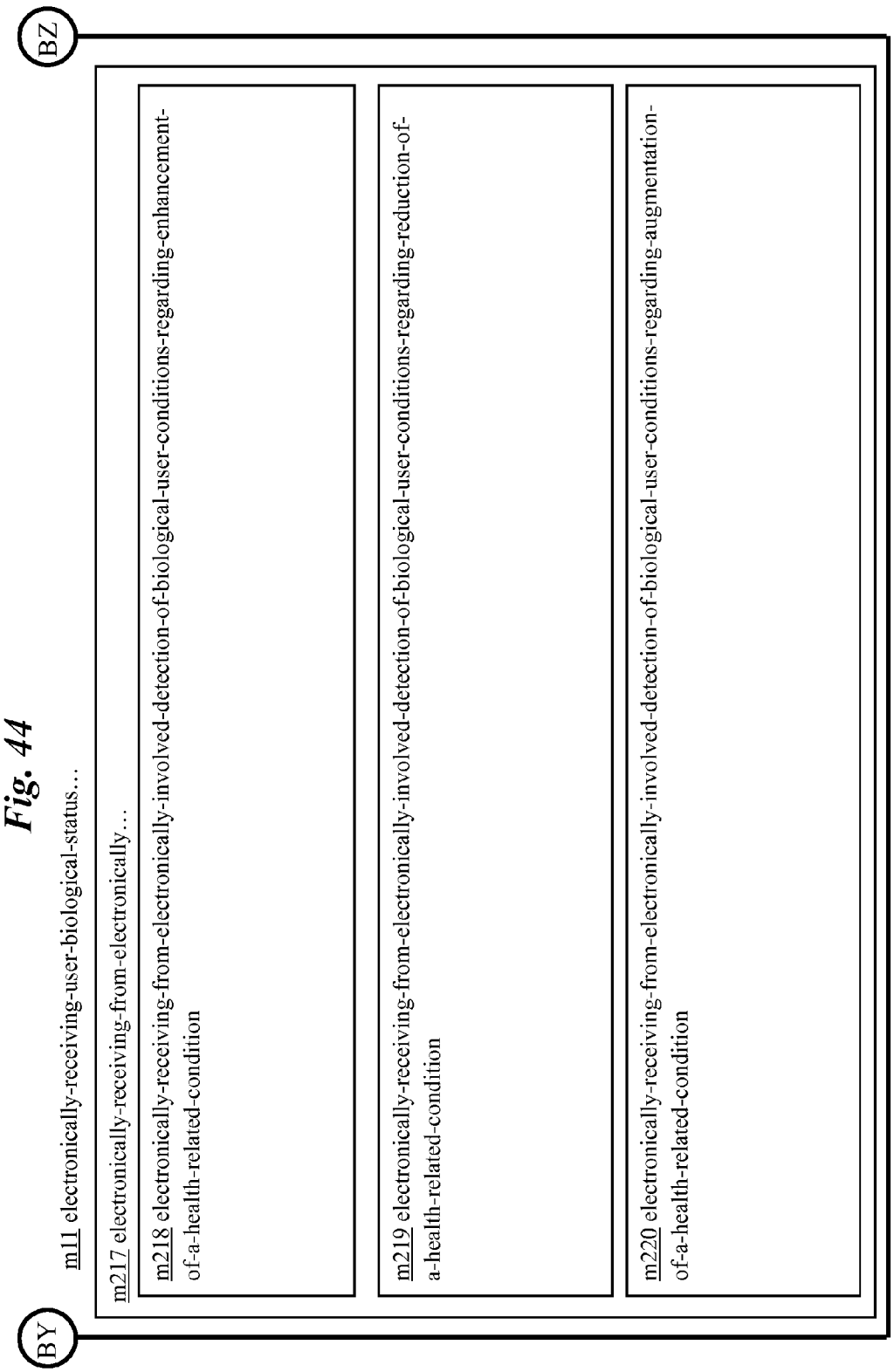

In one or more implementations, as shown in FIG. 44, module m217 may include electronically-receiving-from-electronically-involved-detection-of-biological-user-conditions-regarding-enhancement-of-a-health-related-condition module m218.

In one or more implementations, as shown in FIG. 44, module m217 may include electronically-receiving-from-electronically-involved-detection-of-biological-user-conditions-regarding-reduction-of-a-health-related-condition module m219.

In one or more implementations, as shown in FIG. 44, module m217 may include electronically-receiving-from-electronically-involved-detection-of-biological-user-conditions-regarding-augmentation-of-a-health-related-condition module m220.

Figure 45:
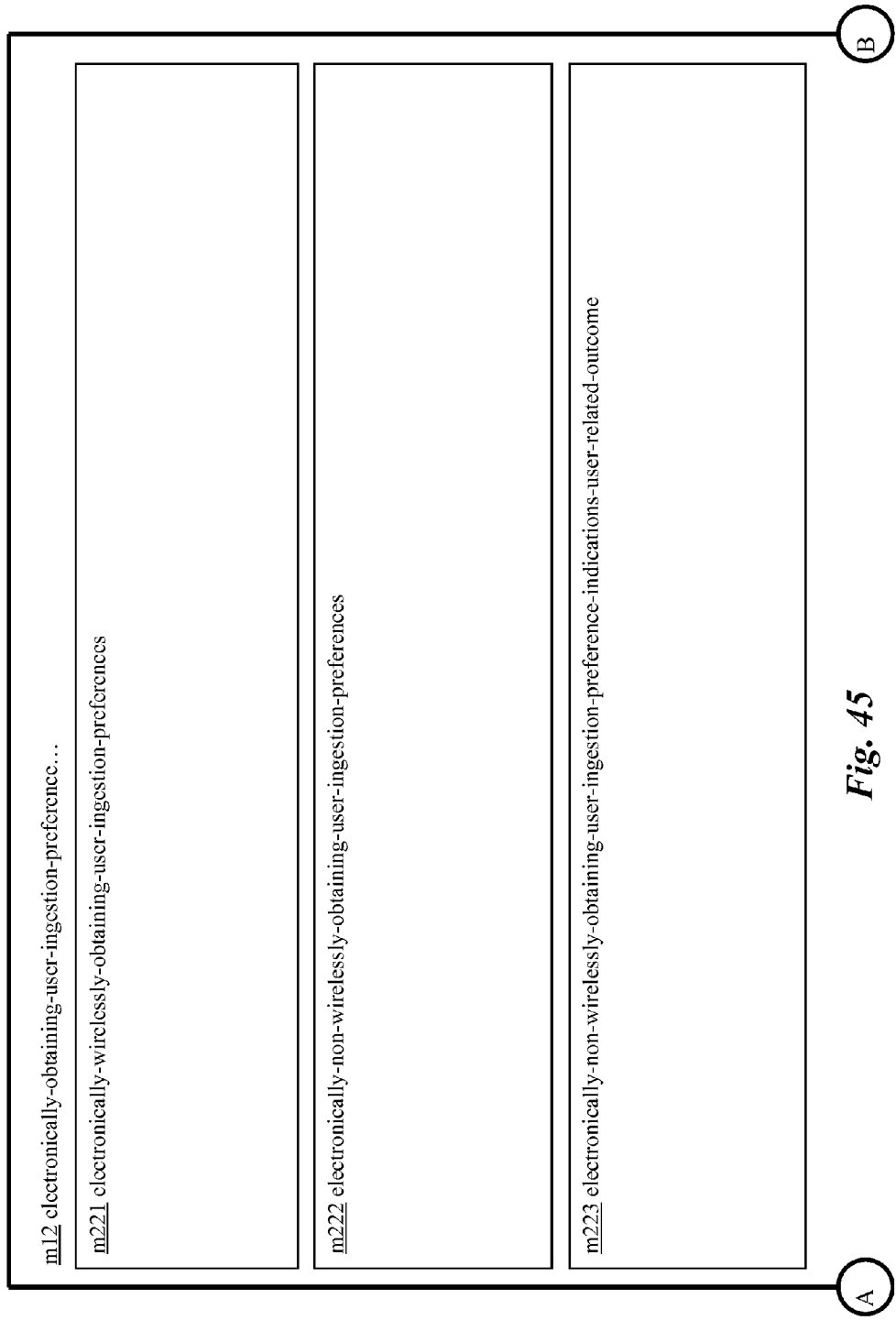

In one or more implementations, as shown in FIG. 45, module m12 may include electronically-wirelessly-obtaining-user-ingestion-preferences module m221.

In one or more implementations, as shown in FIG. 45, module m12 may include electronically-non-wirelessly-obtaining-user-ingestion-preferences module m222.

In one or more implementations, as shown in FIG. 45, module m12 may include electronically-non-wirelessly-obtaining-user-ingestion-preference-indications-user-related-outcome module m223.

Figure 46:
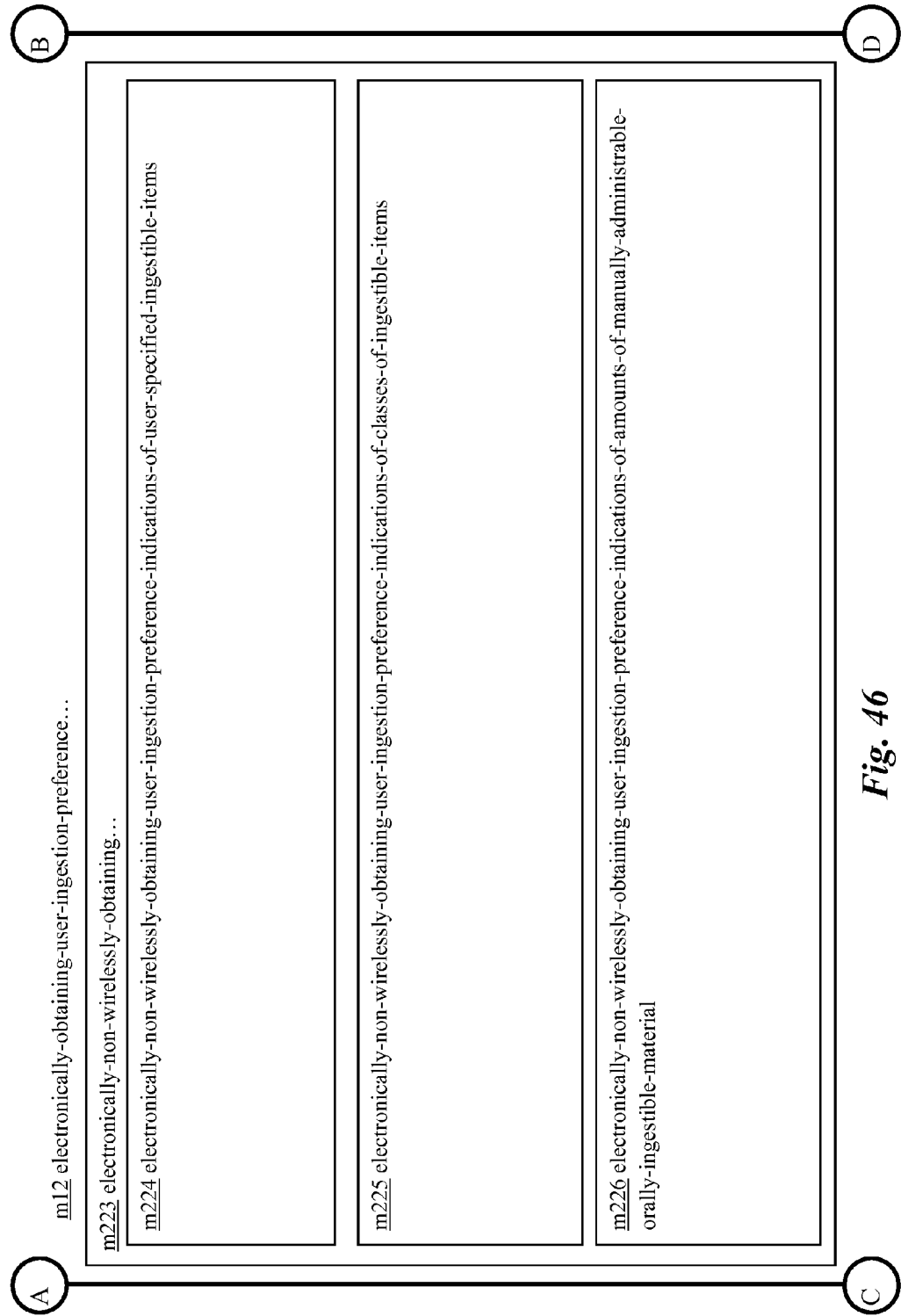

In one or more implementations, as shown in FIG. 46, module m223 may include electronically-non-wirelessly-obtaining-user-ingestion-preference-indications-of-user-specified-ingestible-items module m224.

In one or more implementations, as shown in FIG. 46, module m223 may include electronically-non-wirelessly-obtaining-user-ingestion-preference-indications-of-classes-of-ingestible-items module m225.

In one or more implementations, as shown in FIG. 46, module m223 may include electronically-non-wirelessly-obtaining-user-ingestion-preference-indications-of-amounts-of-manually-administrable-orally-ingestible-material module m226.

Figure 47:
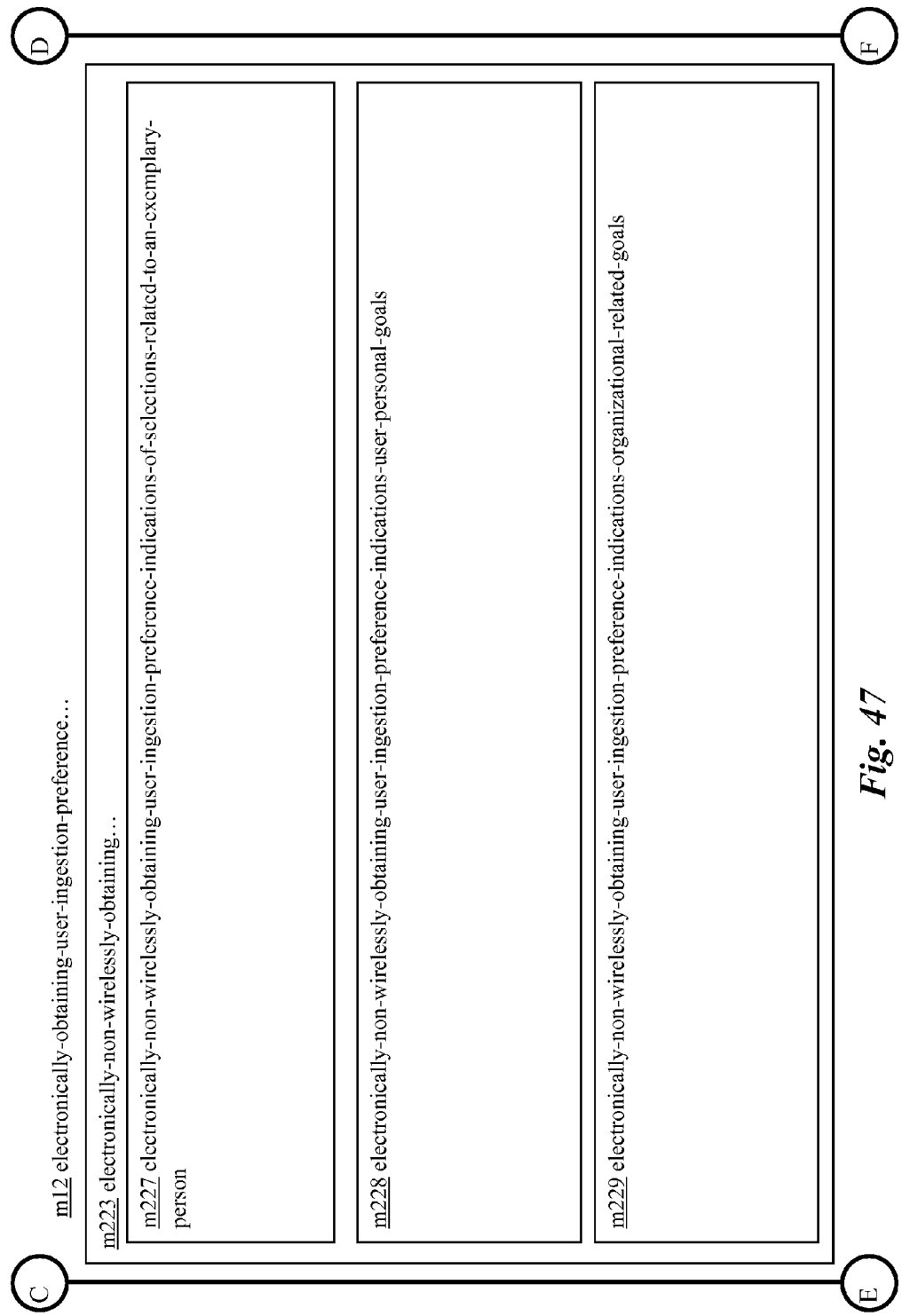

In one or more implementations, as shown in FIG. 47, module m223 may include electronically-non-wirelessly-obtaining-user-ingestion-preference-indications-of-selections-related-to-an-exemplary-person module m227.

In one or more implementations, as shown in FIG. 47, module m223 may include electronically-non-wirelessly-obtaining-user-ingestion-preference-indications-user-personal-goals module m228.

In one or more implementations, as shown in FIG. 47, module m223 may include electronically-non-wirelessly-obtaining-user-ingestion-preference-indications-organizational-related-goals module m229.

Figure 48:
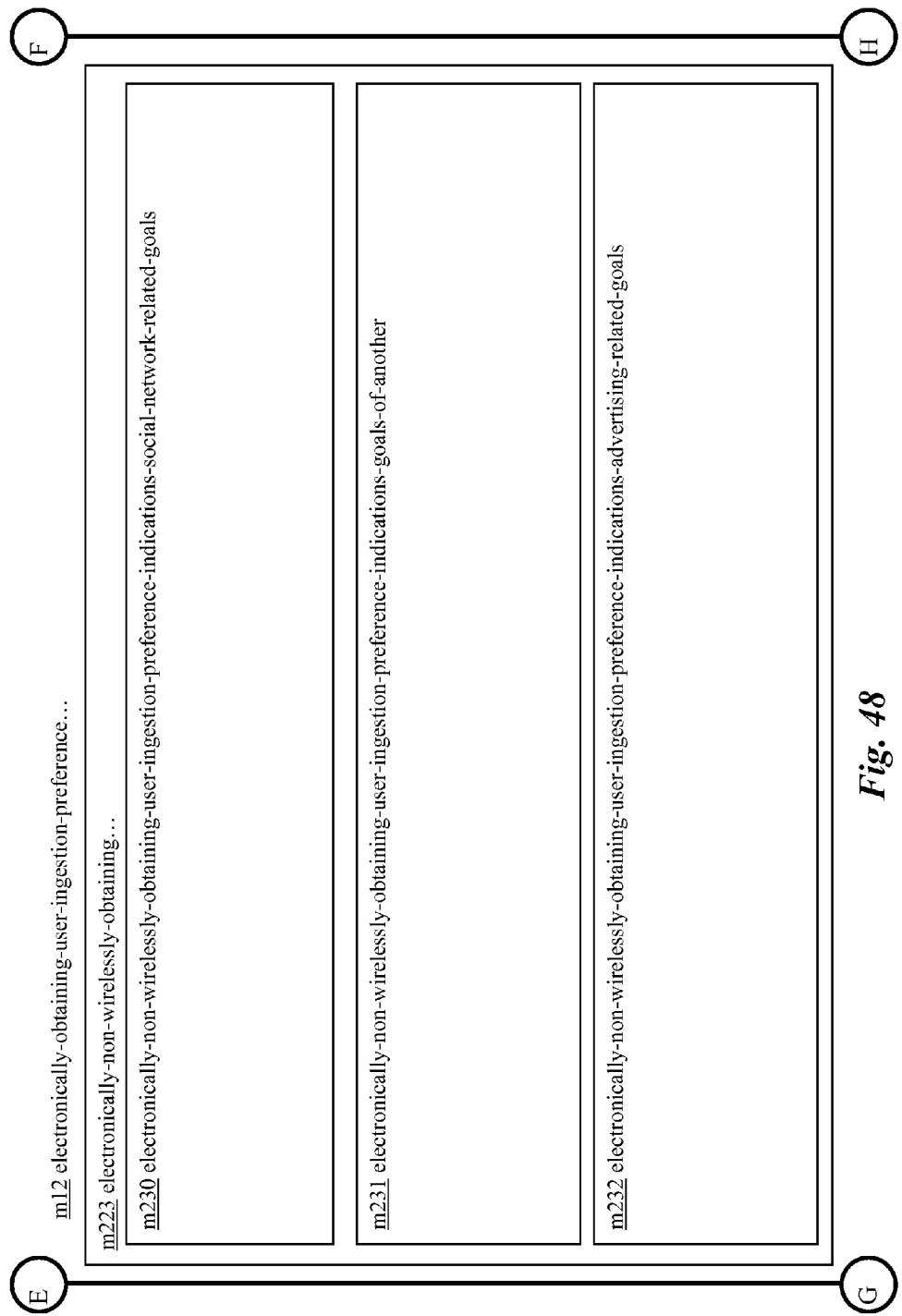

In one or more implementations, as shown in FIG. 48, module m223 may include electronically-non-wirelessly-obtaining-user-ingestion-preference-indications-social-network-related-goals module m230.

In one or more implementations, as shown in FIG. 48, module m223 may include electronically-non-wirelessly-obtaining-user-ingestion-preference-indications-goals-of-another module m231.

In one or more implementations, as shown in FIG. 48, module m223 may include electronically-non-wirelessly-obtaining-user-ingestion-preference-indications-advertising-related-goals module m232.

Figure 49:
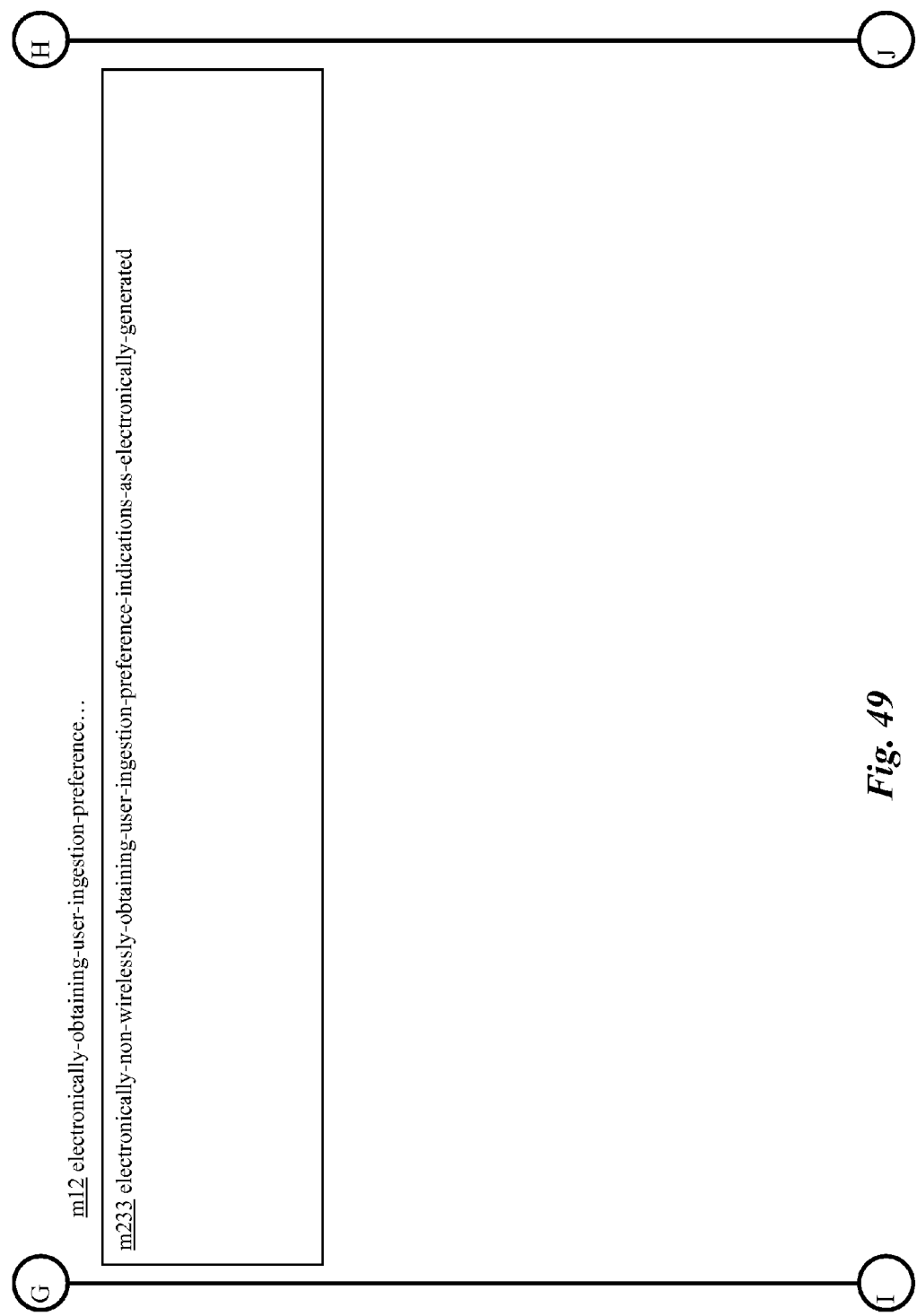

In one or more implementations, as shown in FIG. 49, module m12 may include electronically-non-wirelessly-obtaining-user-ingestion-preference-indications-as-electronically-generated module m233.

Figure 50:
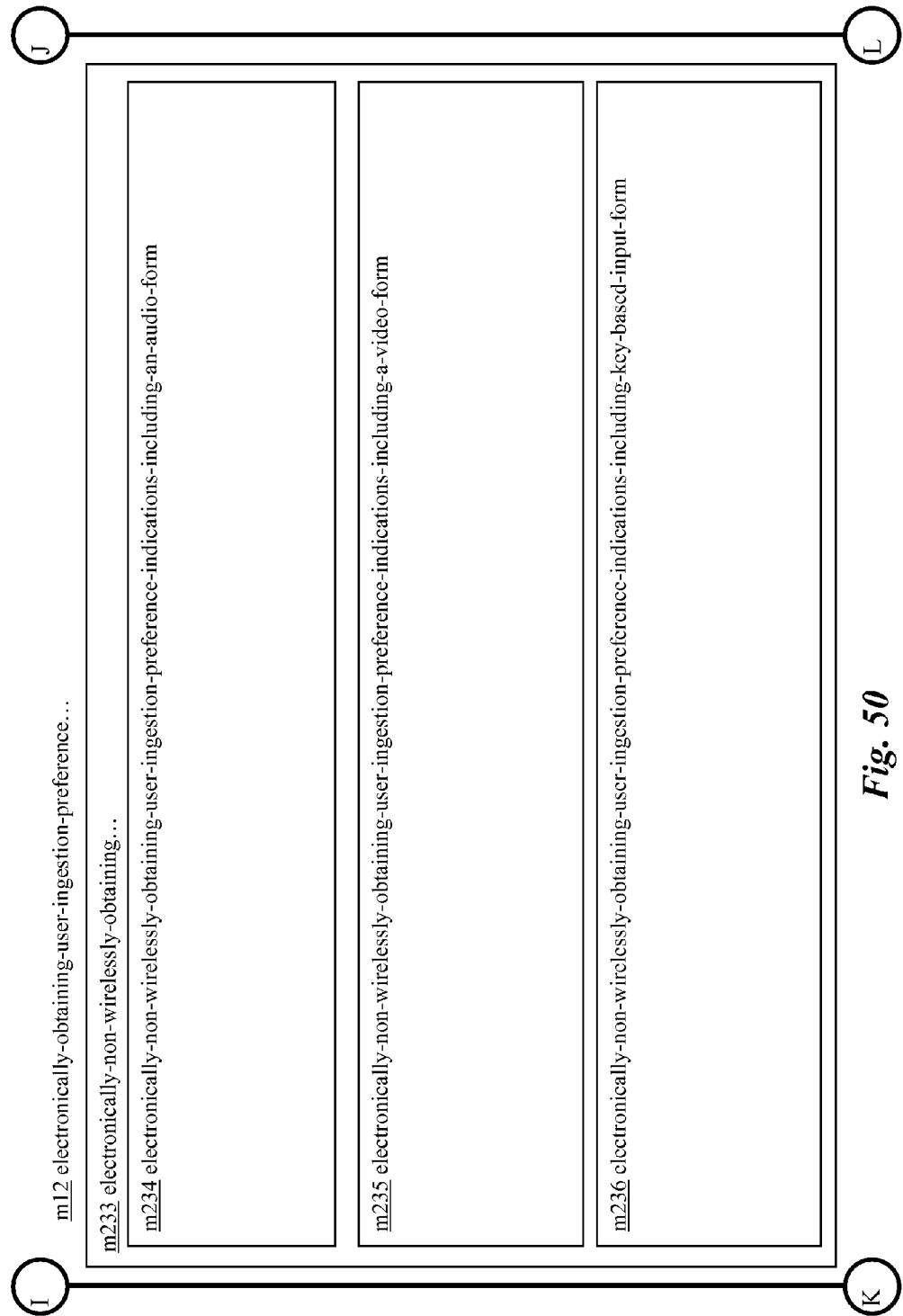

In one or more implementations, as shown in FIG. 50, module m233 may include electronically-non-wirelessly-obtaining-user-ingestion-preference-indications-including-an-audio-form module m234.

In one or more implementations, as shown in FIG. 50, module m233 may include electronically-non-wirelessly-obtaining-user-ingestion-preference-indications-including-a-video-form module m235.

In one or more implementations, as shown in FIG. 50, module m233 may include electronically-non-wirelessly-obtaining-user-ingestion-preference-indications-including-key-based-input-form module m236.

Figure 51:
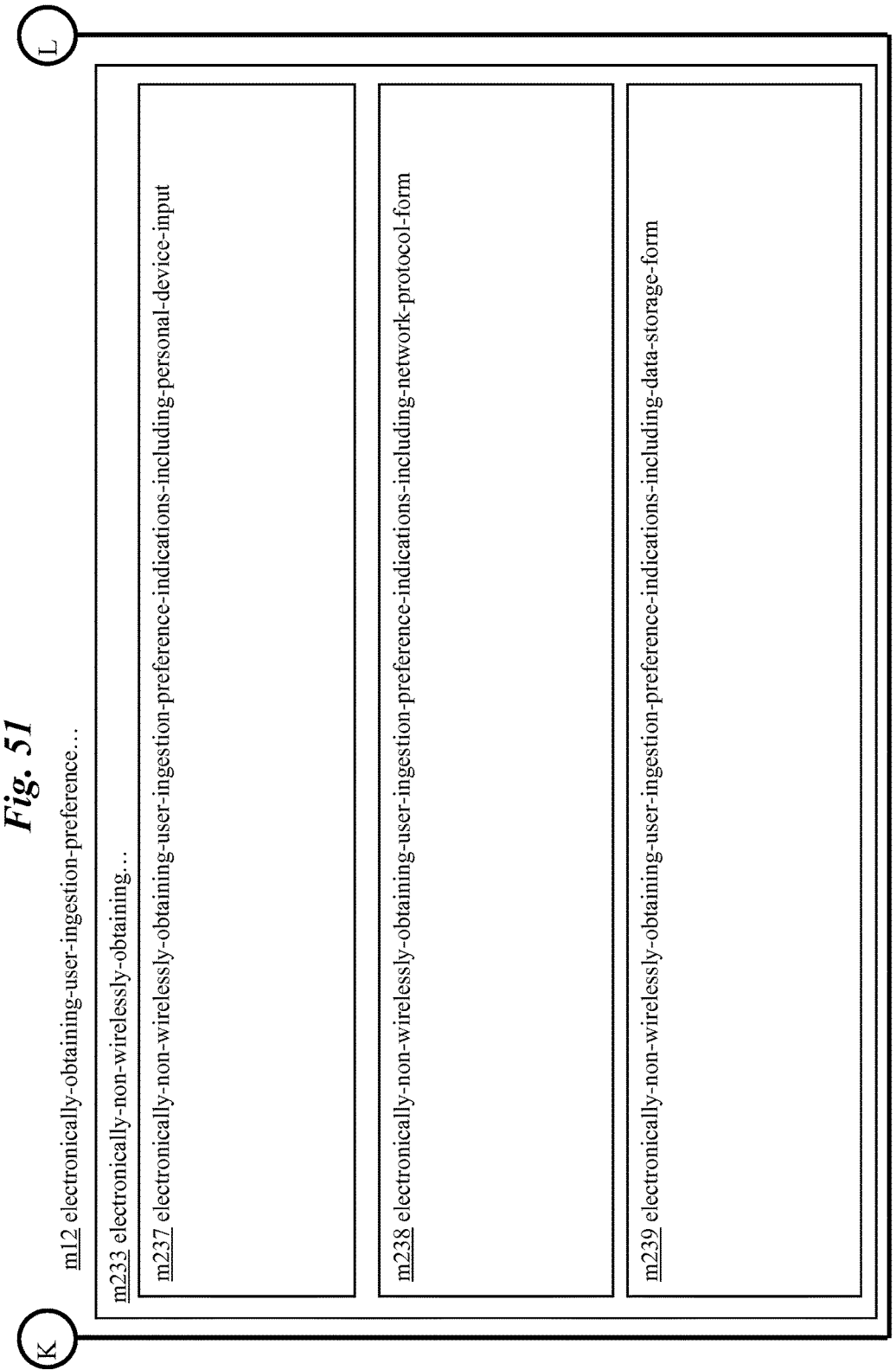

In one or more implementations, as shown in FIG. 51, module m233 may include electronically-non-wirelessly-obtaining-user-ingestion-preference-indications-including-personal-device-input module m237.

In one or more implementations, as shown in FIG. 51, module m233 may include electronically-non-wirelessly-obtaining-user-ingestion-preference-indications-including-network-protocol-form module m238.

In one or more implementations, as shown in FIG. 51, module m233 may include electronically-non-wirelessly-obtaining-user-ingestion-preference-indications-including-data-storage-form module m239.

Figure 52:
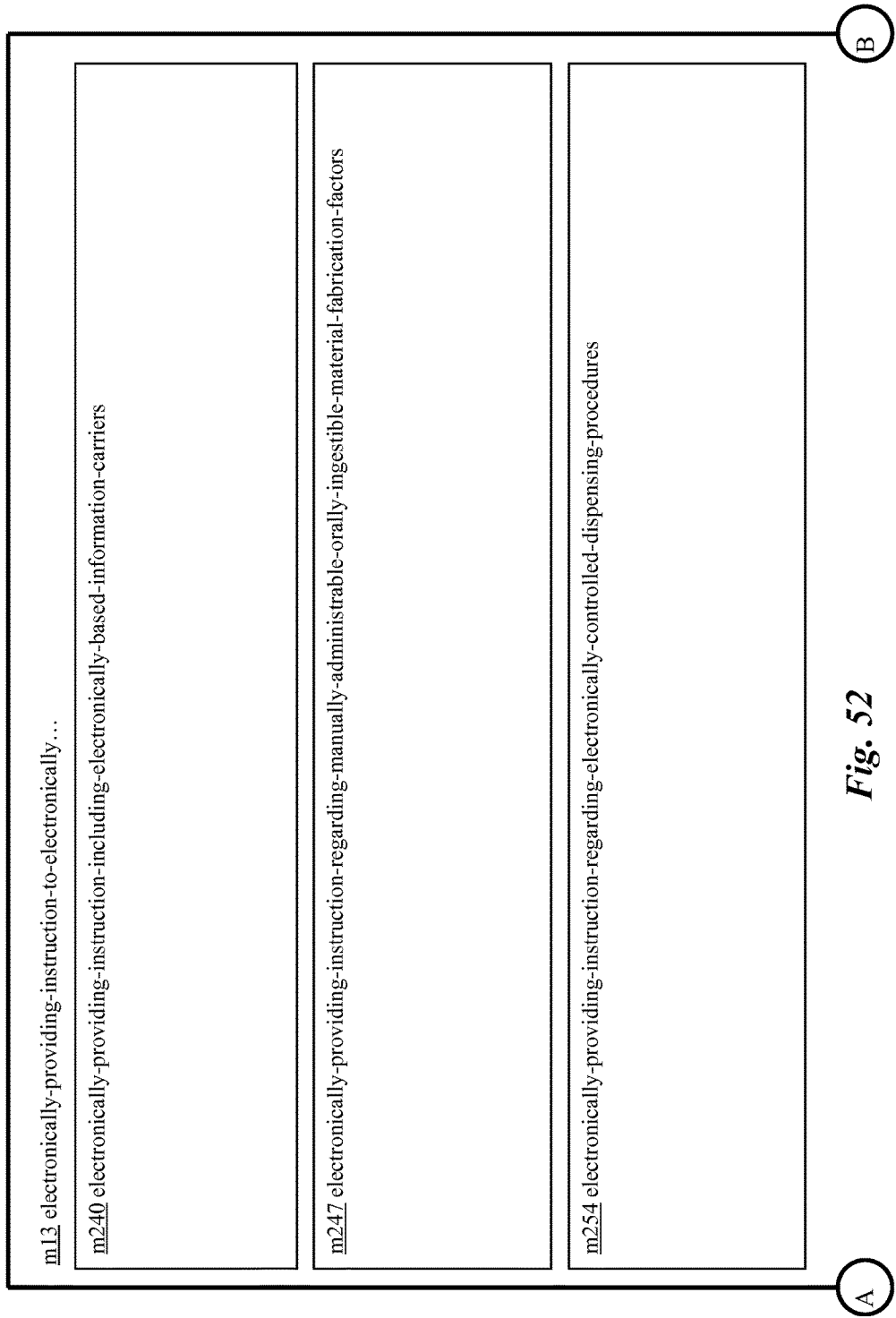

In one or more implementations, as shown in FIG. 52, module m13 may include electronically-providing-instruction-including-electronically-based-information-carriers module m240.

Figure 53:
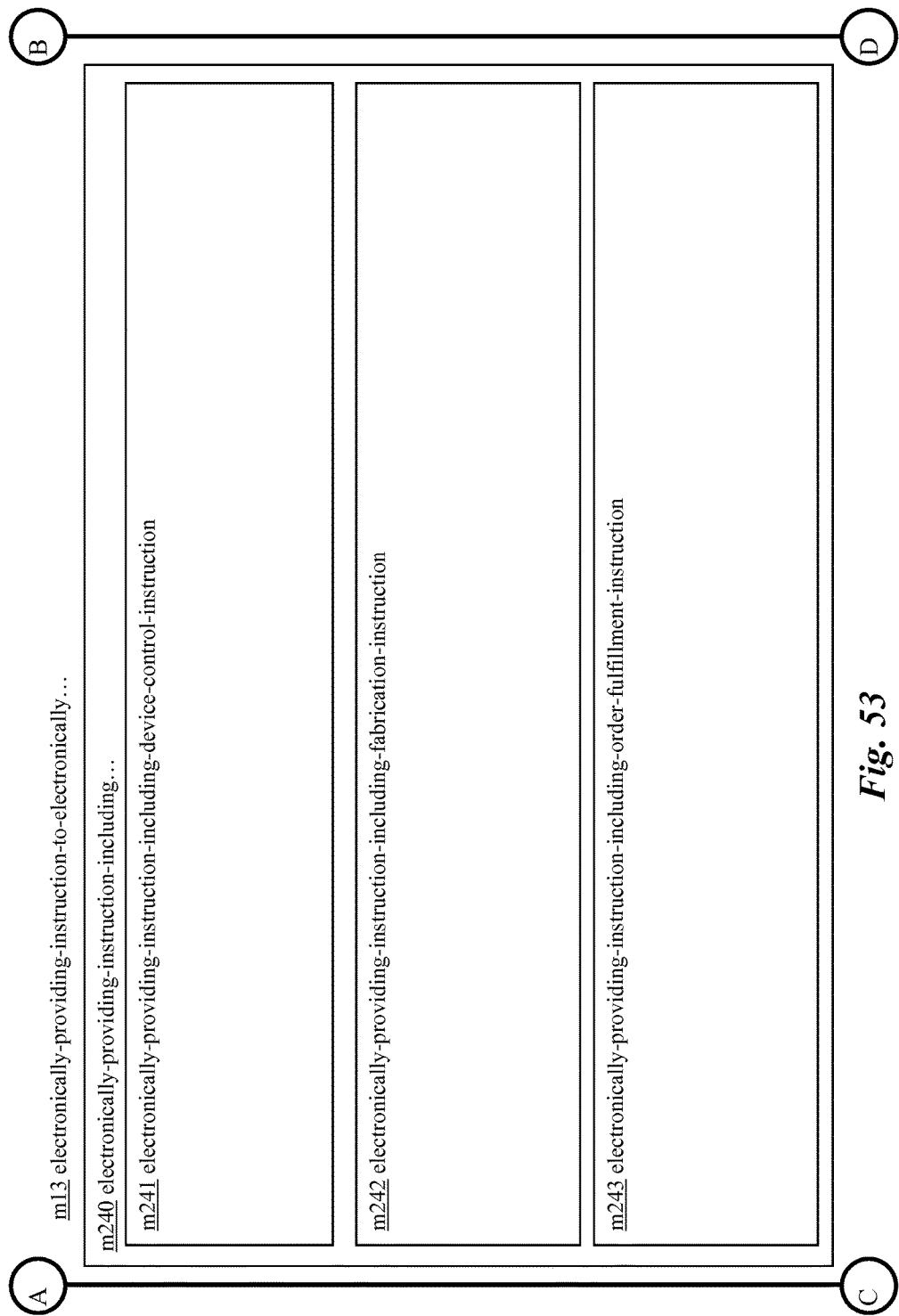

In one or more implementations, as shown in FIG. 53, module m240 may include electronically-providing-instruction-including-device-control-instruction module m241.

In one or more implementations, as shown in FIG. 53, module m240 may include electronically-providing-instruction-including-fabrication-instruction module m242.

In one or more implementations, as shown in FIG. 53, module m240 may include electronically-providing-instruction-including-order-fulfillment-instruction module m243.

Figure 54:
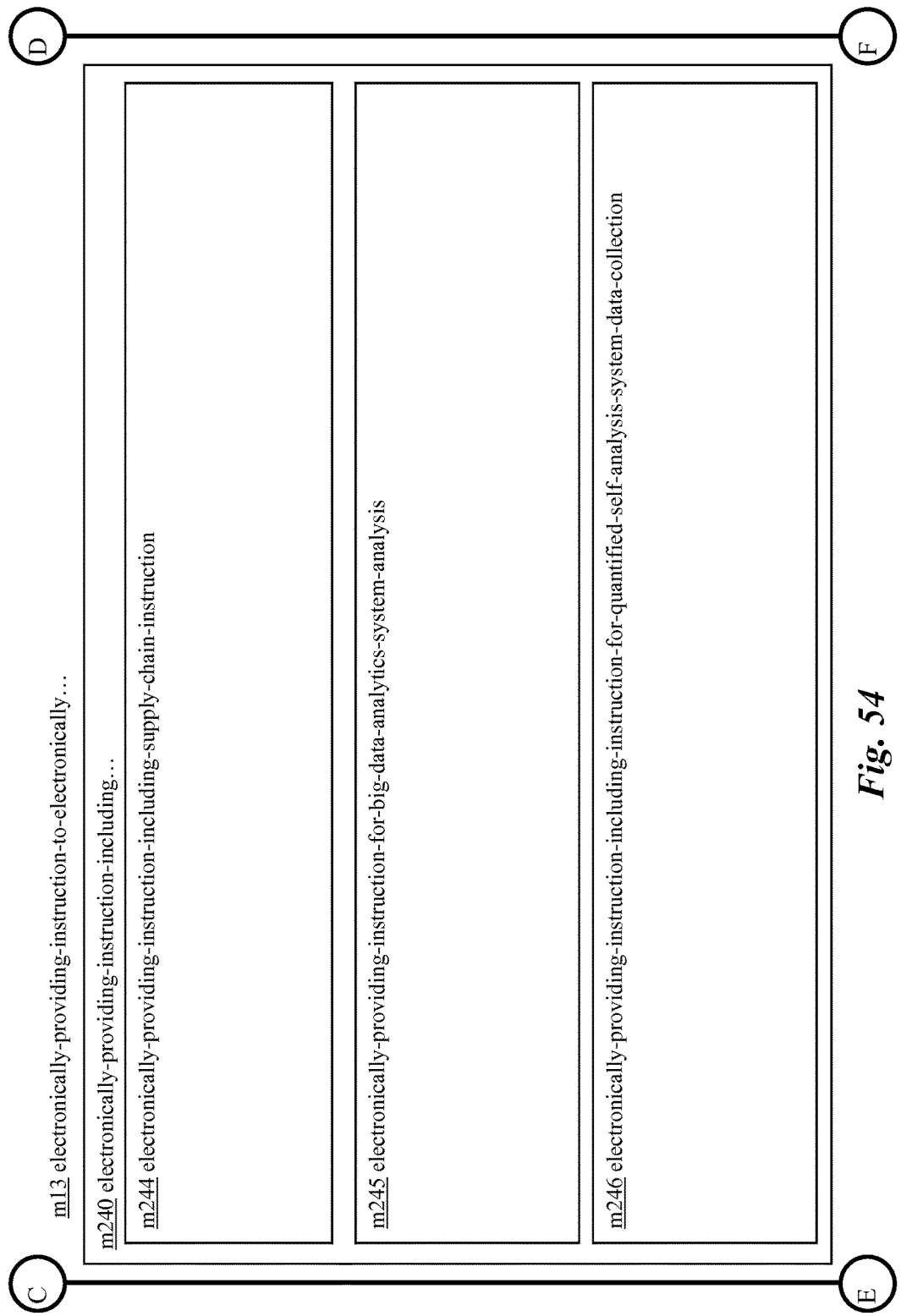

In one or more implementations, as shown in FIG. 54, module m240 may include electronically-providing-instruction-including-supply-chain-instruction module m244.

In one or more implementations, as shown in FIG. 54, module m240 may include electronically-providing-instruction-for-big-data-analytics-system-analysis module m245.

In one or more implementations, as shown in FIG. 54, module m240 may include electronically-providing-instruction-including-instruction-for-quantified-self-analysis-system-data-collection module m246.

In one or more implementations, as shown in FIG. 52, module m13 may include electronically-providing-instruction-regarding-manually-administrable-orally-ingestible-material-fabrication-factors module m247.

Figure 55:
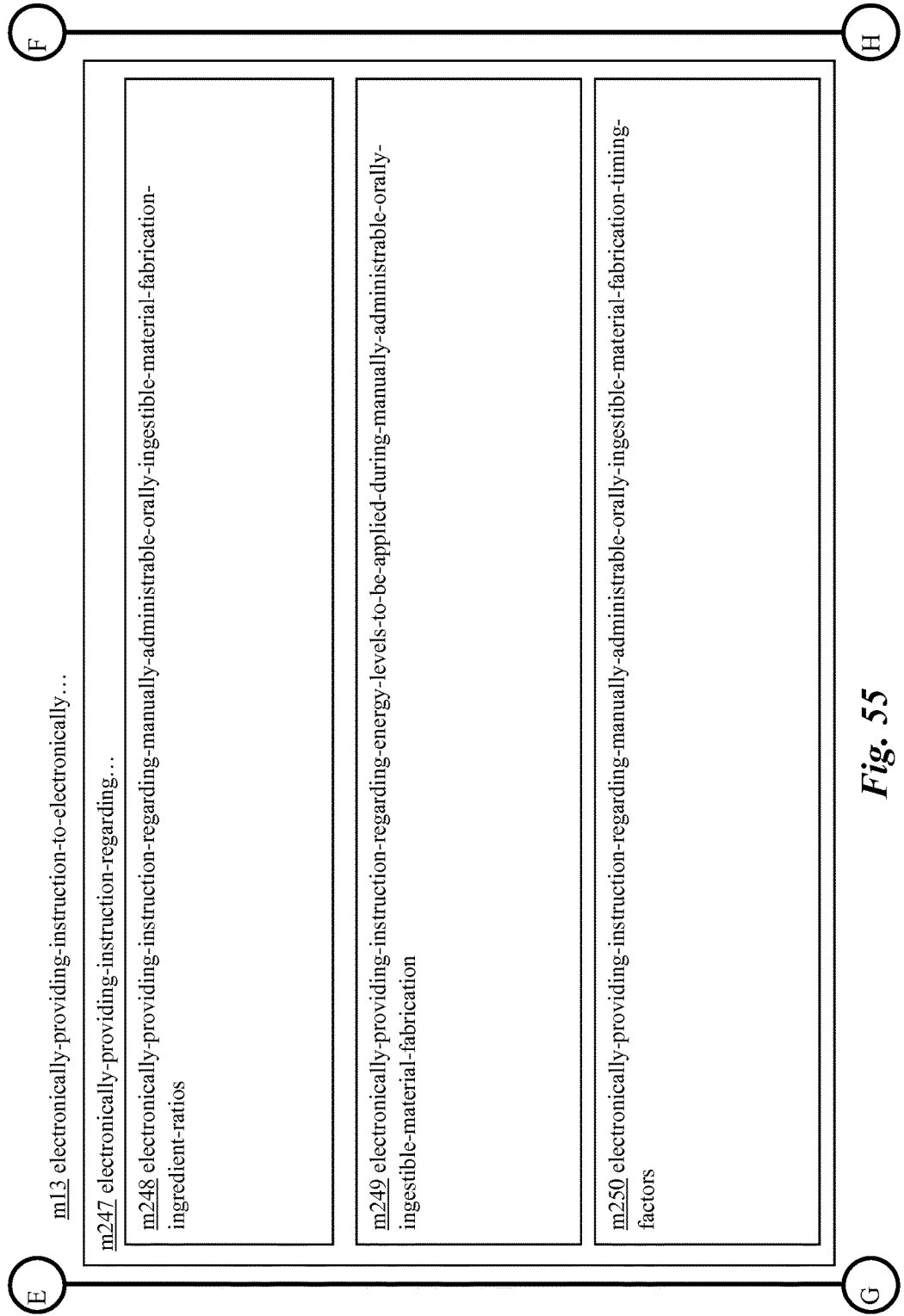

In one or more implementations, as shown in FIG. 55, module m247 may include electronically-providing-instruction-regarding-manually-administrable-orally-ingestible-material-fabrication-ingredient-ratios module m248.

In one or more implementations, as shown in FIG. 55, module m247 may include electronically-providing-instruction-regarding-energy-levels-to-be-applied-during-manually-administrable-orally-ingestible-material-fabrication module m249.

In one or more implementations, as shown in FIG. 55, module m247 may include electronically-providing-instruction-regarding-manually-administrable-orally-ingestible-material-fabrication-timing-factors module m250.

Figure 56:
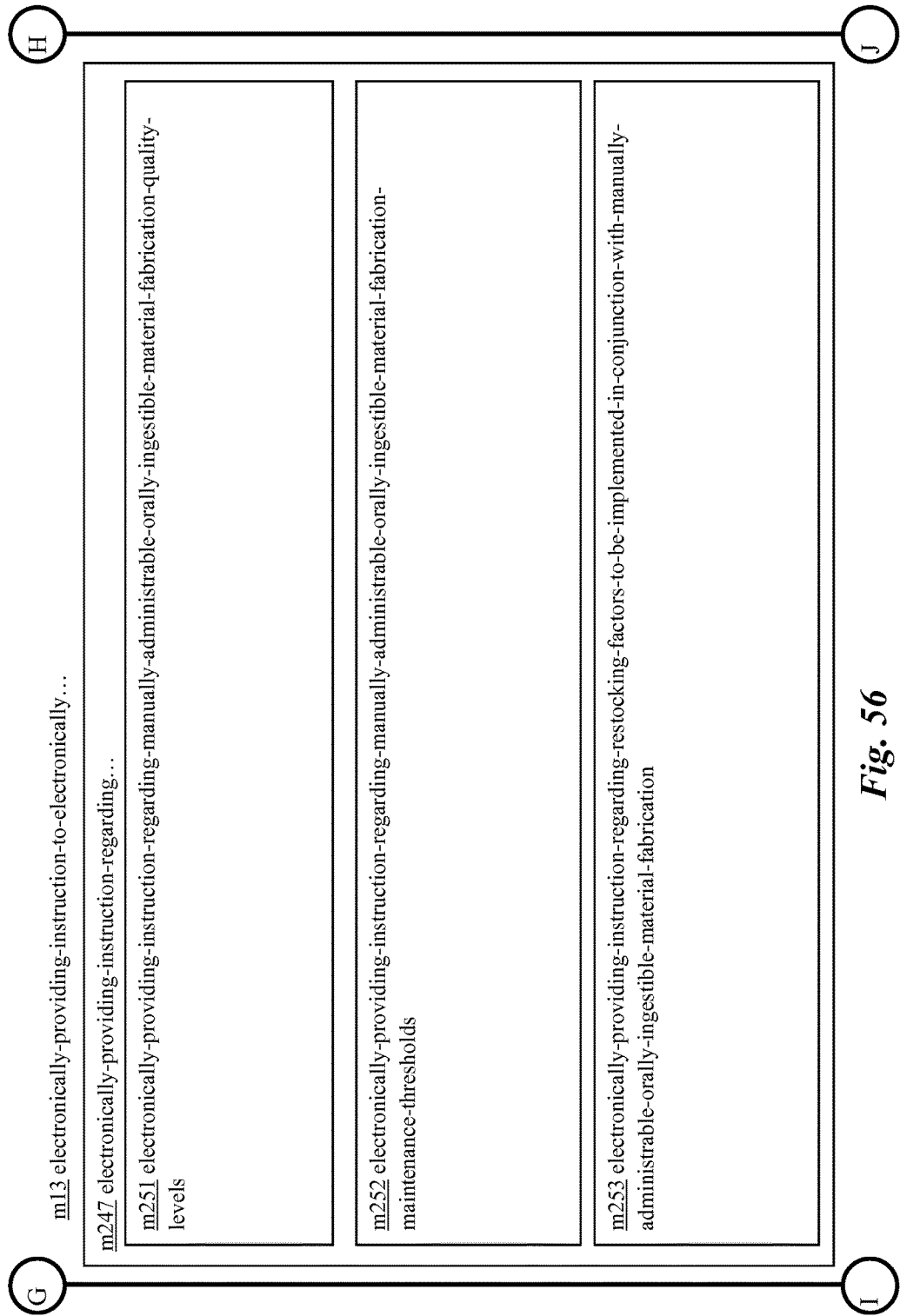

In one or more implementations, as shown in FIG. 56, module m247 may include electronically-providing-instruction-regarding-manually-administrable-orally-ingestible-material-fabrication-quality-levels module m251.

In one or more implementations, as shown in FIG. 56, module m247 may include electronically-providing-instruction-regarding-manually-administrable-orally-ingestible-material-fabrication-maintenance-thresholds module m252.

In one or more implementations, as shown in FIG. 56, module m247 may include electronically-providing-instruction-regarding-restocking-factors-to-be-implemented-in-conjunction-with-manually-administrable-orally-ingestible-material-fabrication module m253.

In one or more implementations, as shown in FIG. 52, module m13 may include electronically-providing-instruction-regarding-electronically-controlled-dispensing-procedures module m254.

Figure 57:
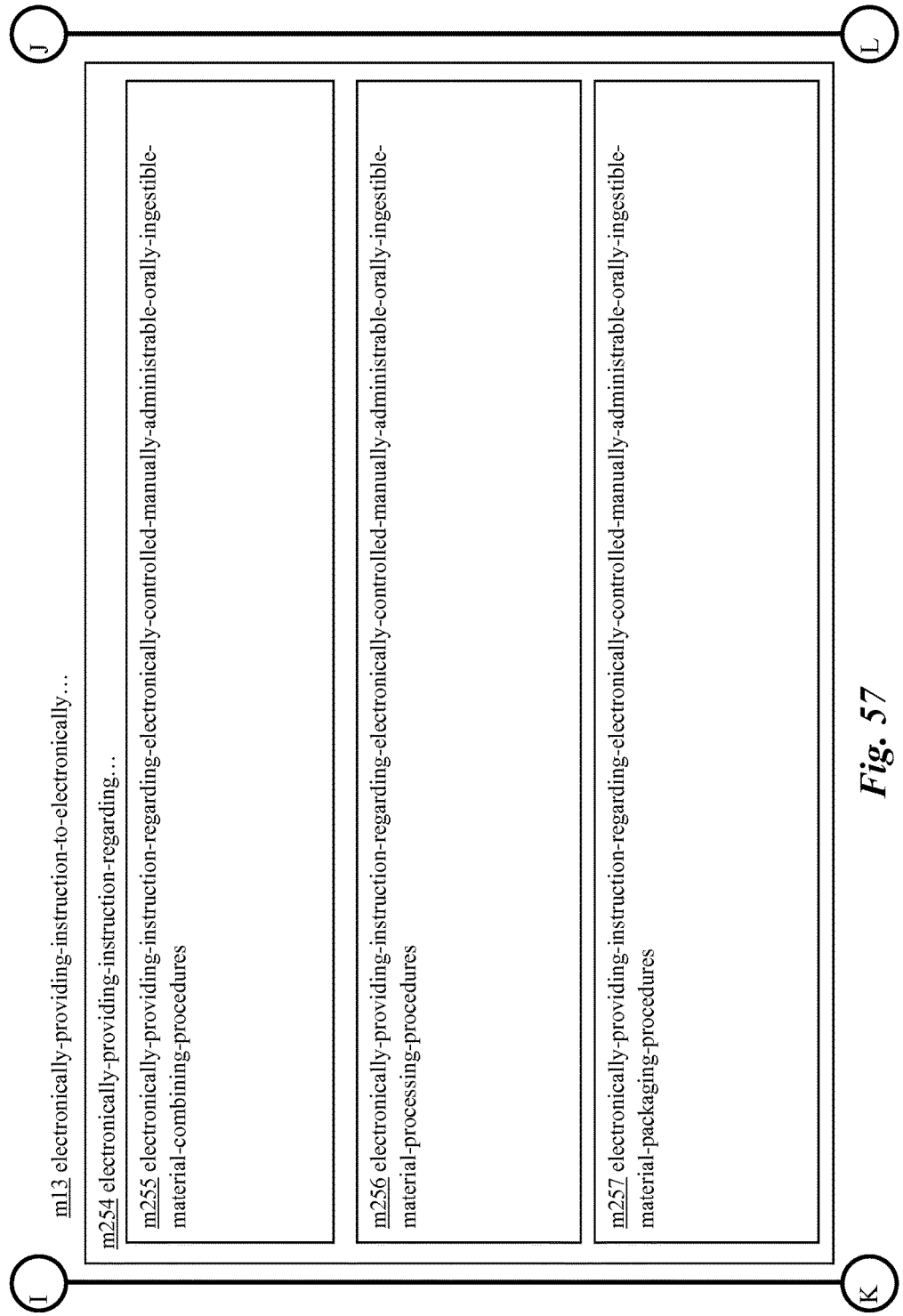

In one or more implementations, as shown in FIG. 57, module m254 may include electronically-providing-instruction-regarding-electronically-controlled-manually-administrable-orally-ingestible-material-combining-procedures module m255.

In one or more implementations, as shown in FIG. 57, module m254 may include electronically-providing-instruction-regarding-electronically-controlled-manually-administrable-orally-ingestible-material-processing-procedures module m256.

In one or more implementations, as shown in FIG. 57, module m254 may include electronically-providing-instruction-regarding-electronically-controlled-manually-administrable-orally-ingestible-material-packaging-procedures module m257.

Figure 58:
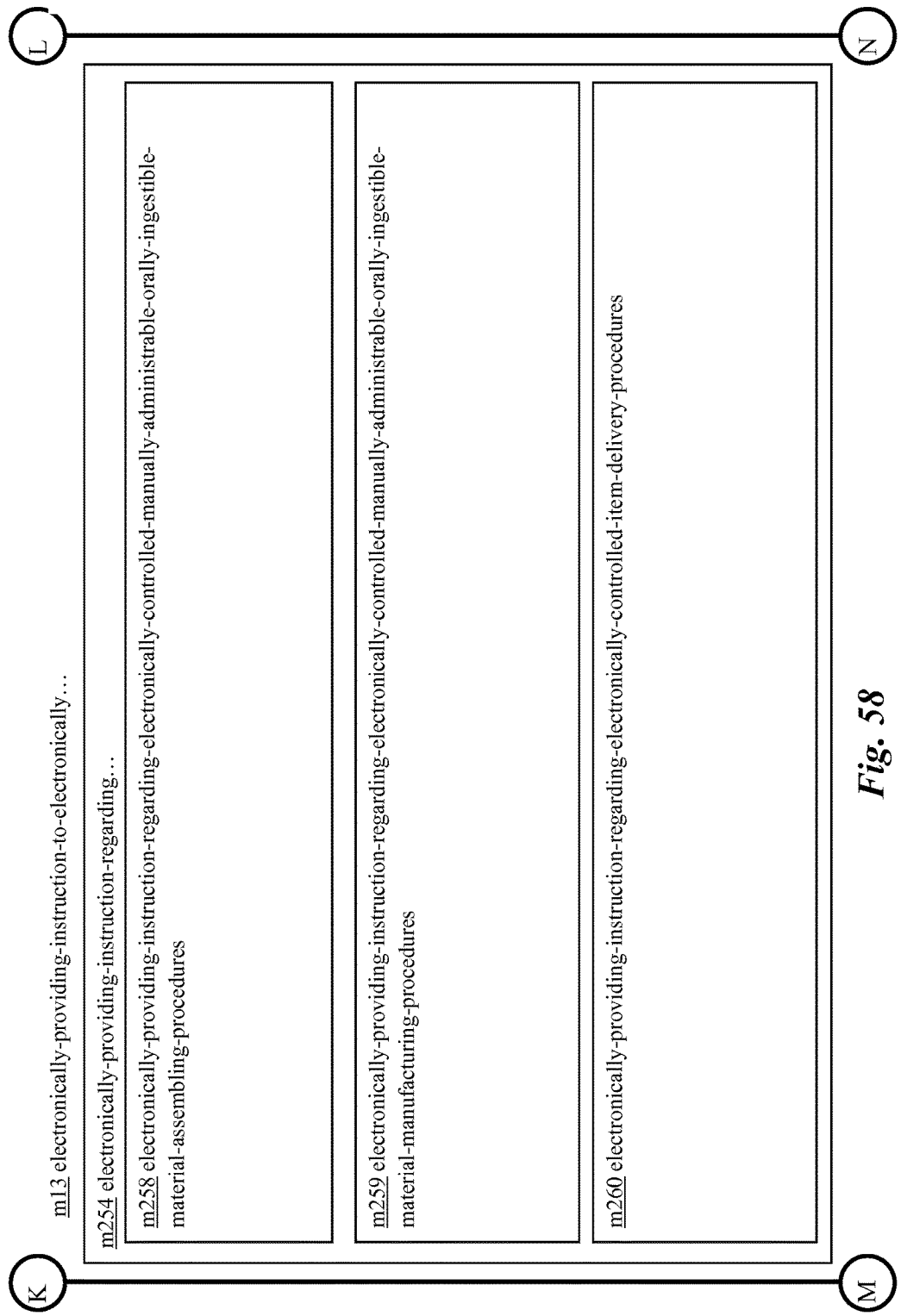

In one or more implementations, as shown in FIG. 58, module m254 may include electronically-providing-instruction-regarding-electronically-controlled-manually-administrable-orally-ingestible-material-assembling-procedures module m258.

In one or more implementations, as shown in FIG. 58, module m254 may include electronically-providing-instruction-regarding-electronically-controlled-manually-administrable-orally-ingestible-material-manufacturing-procedures module m259.

In one or more implementations, as shown in FIG. 58, module m254 may include electronically-providing-instruction-regarding-electronically-controlled-item-delivery-procedures module m260.

Figure 59:
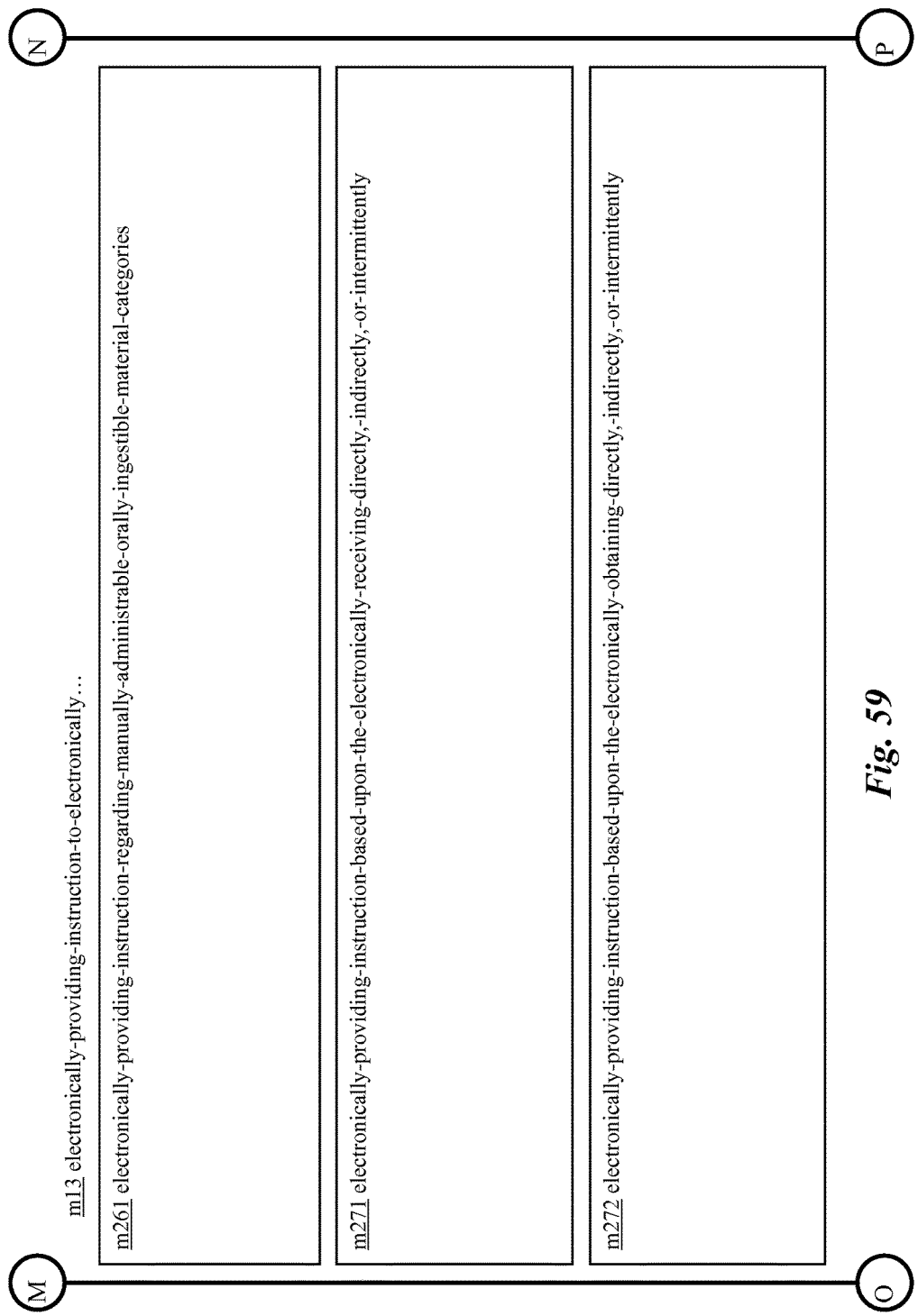

In one or more implementations, as shown in FIG. 59, module m13 may include electronically-providing-instruction-regarding-manually-administrable-orally-ingestible-material-categories module m261.

Figure 60:
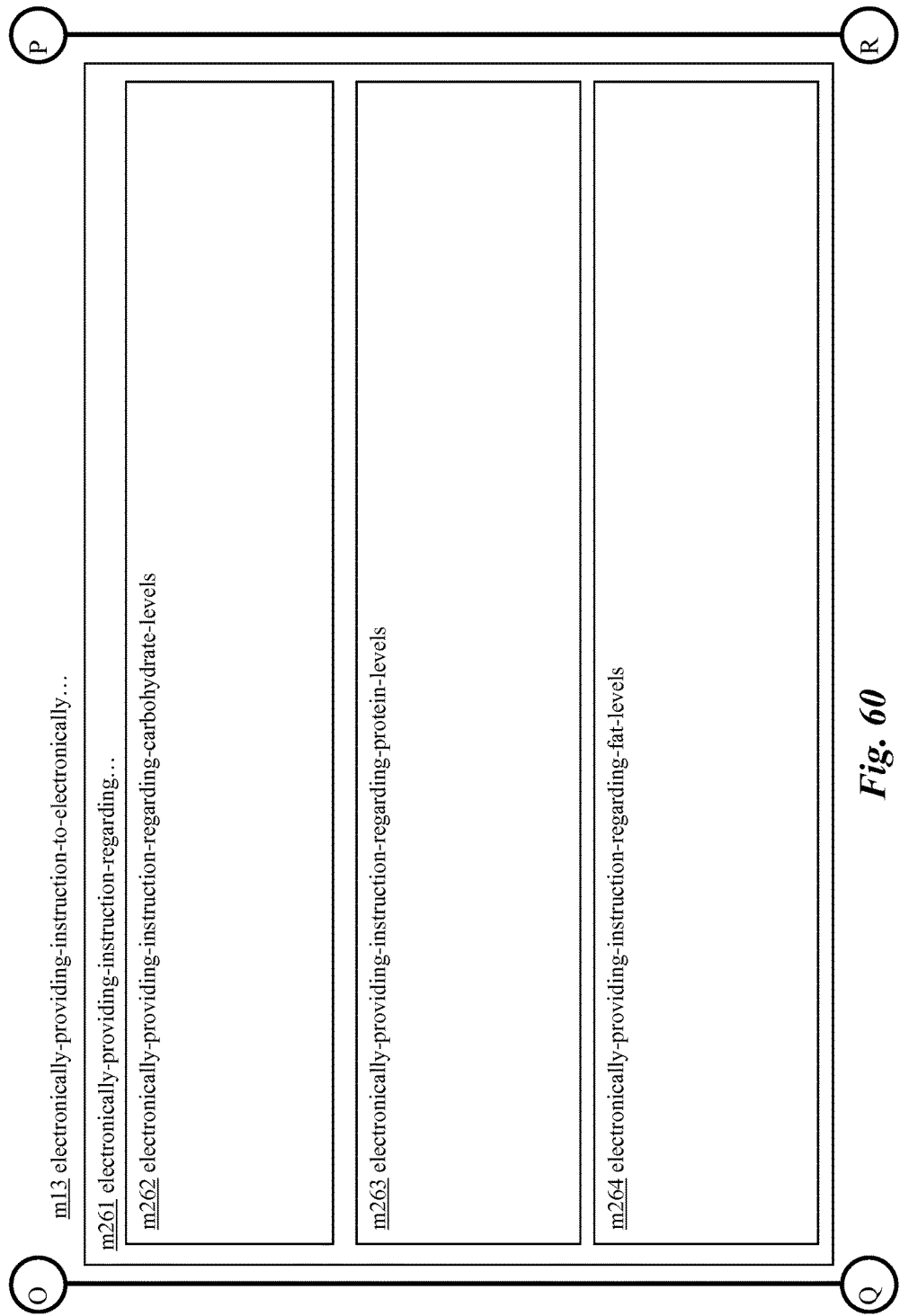

In one or more implementations, as shown in FIG. 60, module m261 may include electronically-providing-instruction-regarding-carbohydrate-levels module m262.

In one or more implementations, as shown in FIG. 60, module m261 may include electronically-providing-instruction-regarding-protein-levels module m263.

In one or more implementations, as shown in FIG. 60, module m261 may include electronically-providing-instruction-regarding-fat-levels module m264.

Figure 61:
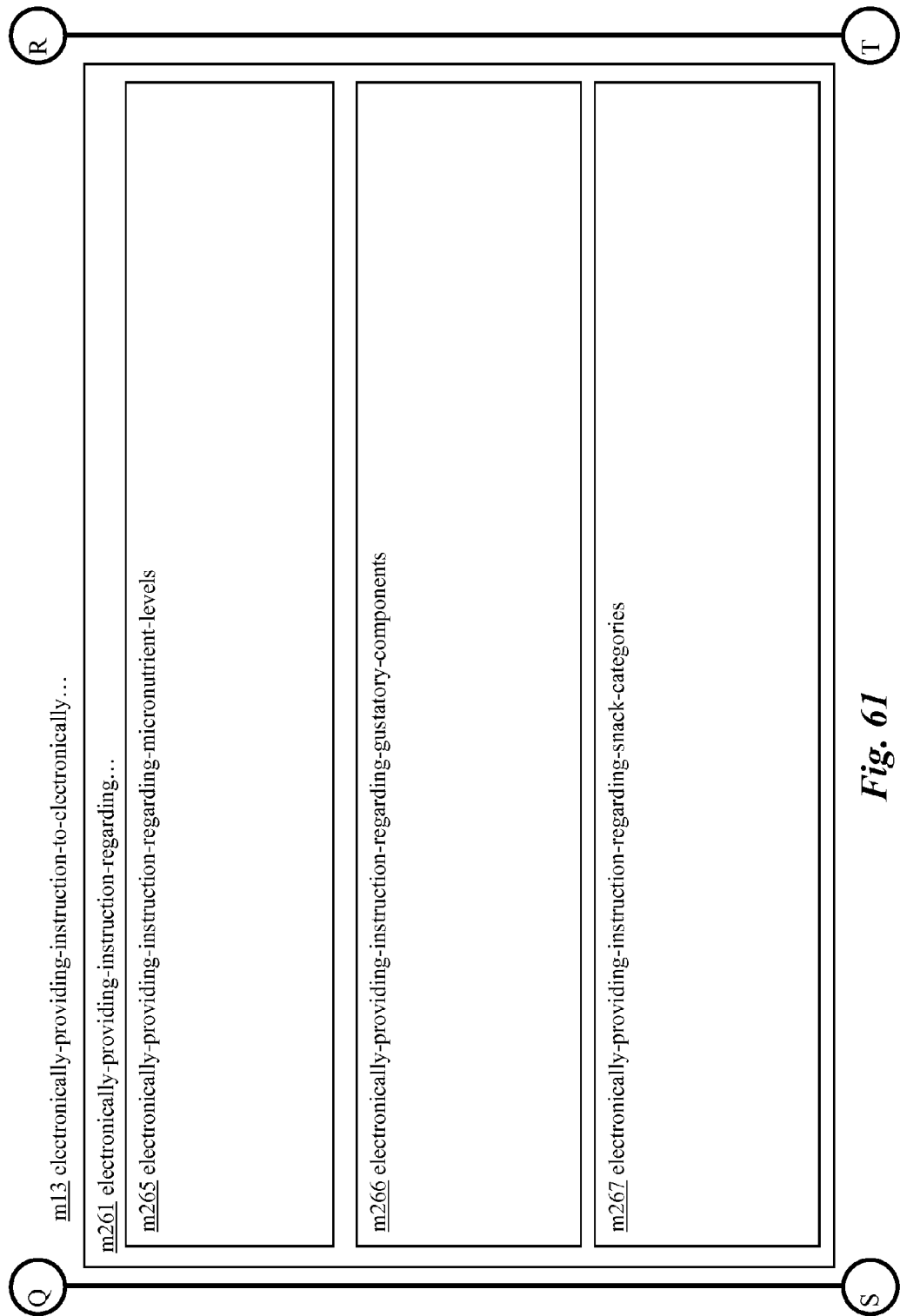

In one or more implementations, as shown in FIG. 61, module m261 may include electronically-providing-instruction-regarding-micronutrient-levels module m265.

In one or more implementations, as shown in FIG. 61, module m261 may include electronically-providing-instruction-regarding-gustatory-components module m266.

In one or more implementations, as shown in FIG. 61, module m261 may include electronically-providing-instruction-regarding-snack-categories module m267.

Figure 62:
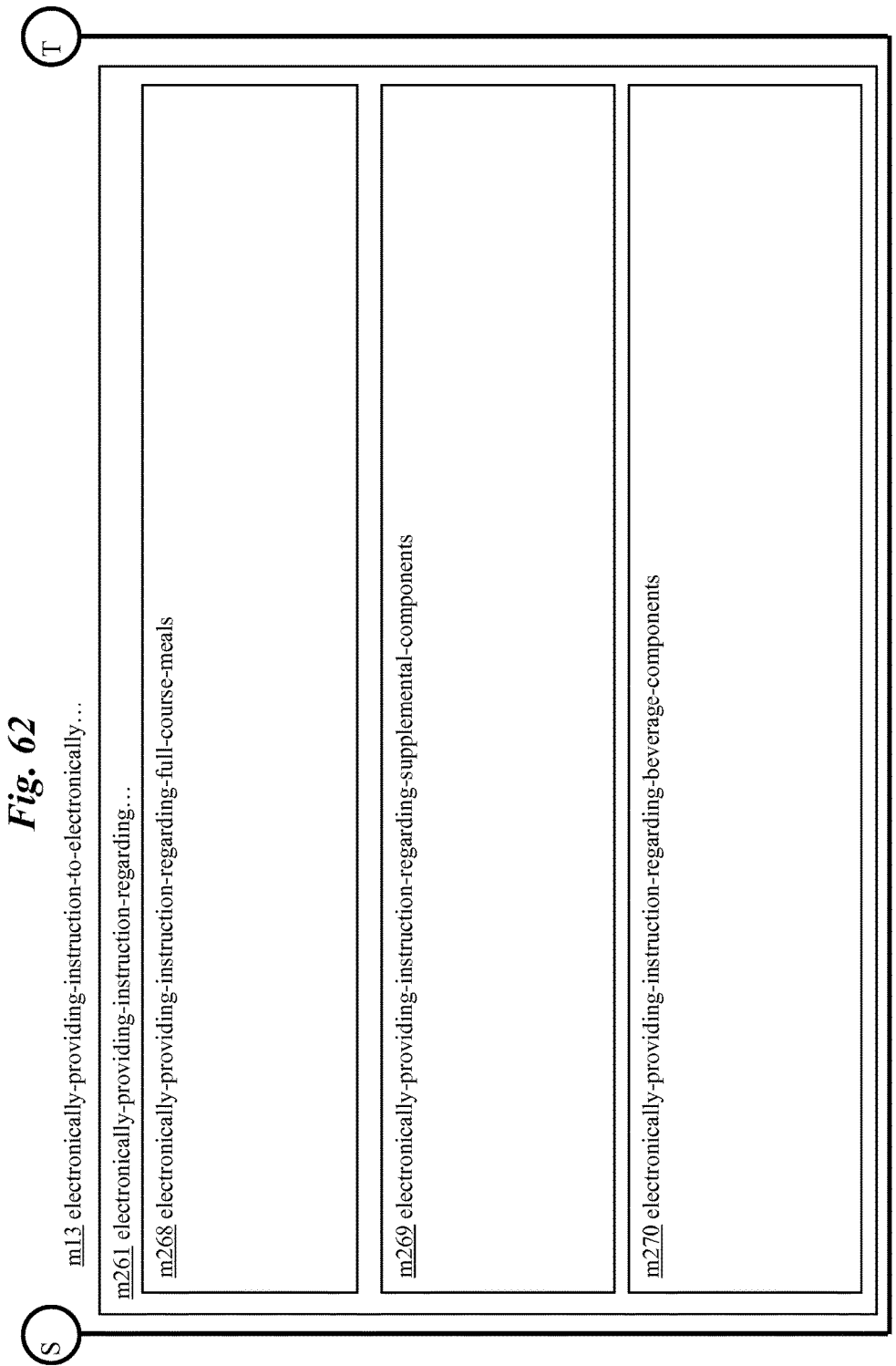

In one or more implementations, as shown in FIG. 62, module m261 may include electronically-providing-instruction-regarding-full-course-meals module m268.

In one or more implementations, as shown in FIG. 62, module m261 may include electronically-providing-instruction-regarding-supplemental-components module m269.

In one or more implementations, as shown in FIG. 62, module m261 may include electronically-providing-instruction-regarding-beverage-components module m270.

In one or more implementations, as shown in FIG. 59, module m13 may include electronically-providing-instruction-based-upon-the-electronically-receiving-directly,-indirectly,-or-intermittently module m271.

In one or more implementations, as shown in FIG. 59, module m13 may include electronically-providing-instruction-based-upon-the-electronically-obtaining-directly,-indirectly,-or-intermittently module m272.

An operational flow o10 as shown in FIG. 63 represents example operations related to electronically receiving user biological status information from electronically involved detection of one or more biological user conditions; electronically obtaining one or more user ingestion preference indications; and electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications.

FIG. 63 and those figures that follow may have various examples of operational flows, and explanation may be provided with respect to the above-described examples and/or with respect to other examples and contexts. Nonetheless, it should be understood that the operational flows may be executed in a number of other environments and contexts, and/or in modified versions. Furthermore, although the various operational flows are presented in the sequence(s) illustrated, it should be understood that the various operations may be performed in other orders than those which are illustrated, or may be performed concurrently.

In FIG. 63 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

In one or more implementations, as shown in FIG. 63, the operational flow o10 proceeds to operation o11 for electronically receiving user biological status information from electronically involved detection of one or more biological user conditions. Origination of a physically tangible component group can be accomplished through skilled in the art design choice selection including use of one or more components and/or subsystems explicitly and/or implicitly referred to herein for at least in part implementing execution of one or more instructions of the operation o11, for performance of the operation o11 by an electrical circuitry arrangement as activated thereto, and/or otherwise fulfillment of the operation o11. One or more non-transitory signal bearing physical media can bear the one or more instructions that when executed can direct performance of the operation o11. Furthermore, electronically-receiving-user-biological-status-information-from-electronically-involved-detection-of-biological-user-conditions module m11 depicted in FIG. 4 as being included in the processing module m10, when executed and/or activated, can direct performance of and/or perform the operation o11. Illustratively, in one or more implementations, the operation o11 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.).

In one or more implementations, as shown in FIG. 63, the operational flow o10 proceeds to operation o12 for electronically obtaining one or more user ingestion preference indications. Origination of a physically tangible component group can be accomplished through skilled in the art design choice selection including use of one or more components and/or subsystems explicitly and/or implicitly referred to herein for at least in part implementing execution of one or more instructions of the operation o12, for performance of the operation o12 by an electrical circuitry arrangement as activated thereto, and/or otherwise fulfillment of the operation o12. One or more non-transitory signal bearing physical media can bear the one or more instructions that when executed can direct performance of the operation o12. Furthermore, electronically-obtaining-user-ingestion-preference-indications module m12 depicted in FIG. 4 as being included in the processing module m10, when executed and/or activated, can direct performance of and/or perform the operation o12. Illustratively, in one or more implementations, the operation o12 can be carried out, for example, by electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.).

In one or more implementations, as shown in FIG. 63, the operational flow o10 proceeds to operation o13 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications. Origination of a physically tangible component group can be accomplished through skilled in the art design choice selection including use of one or more components and/or subsystems explicitly and/or implicitly referred to herein for at least in part implementing execution of one or more instructions of the operation o13, for performance of the operation o13 by an electrical circuitry arrangement as activated thereto, and/or otherwise fulfillment of the operation o13. One or more non-transitory signal bearing physical media can bear the one or more instructions that when executed can direct performance of the operation o13. Furthermore, electronically-providing-instruction-to-electronically-direct-factors-of-electronically-controlled-dispensing-of-manually-administrable-orally-ingestible-material-based-upon-the-electronically-receiving-user-biological-status-information-from-electronically-involved-detection-of-biological-user-conditions-and-based-upon-the-electronically-obtaining-user-ingestion-preference-indications module m13 depicted in FIG. 4 as being included in the processing module m10, when executed and/or activated, can direct performance of and/or perform the operation o13. Illustratively, in one or more implementations, the operation o13 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.).

Figure 64:
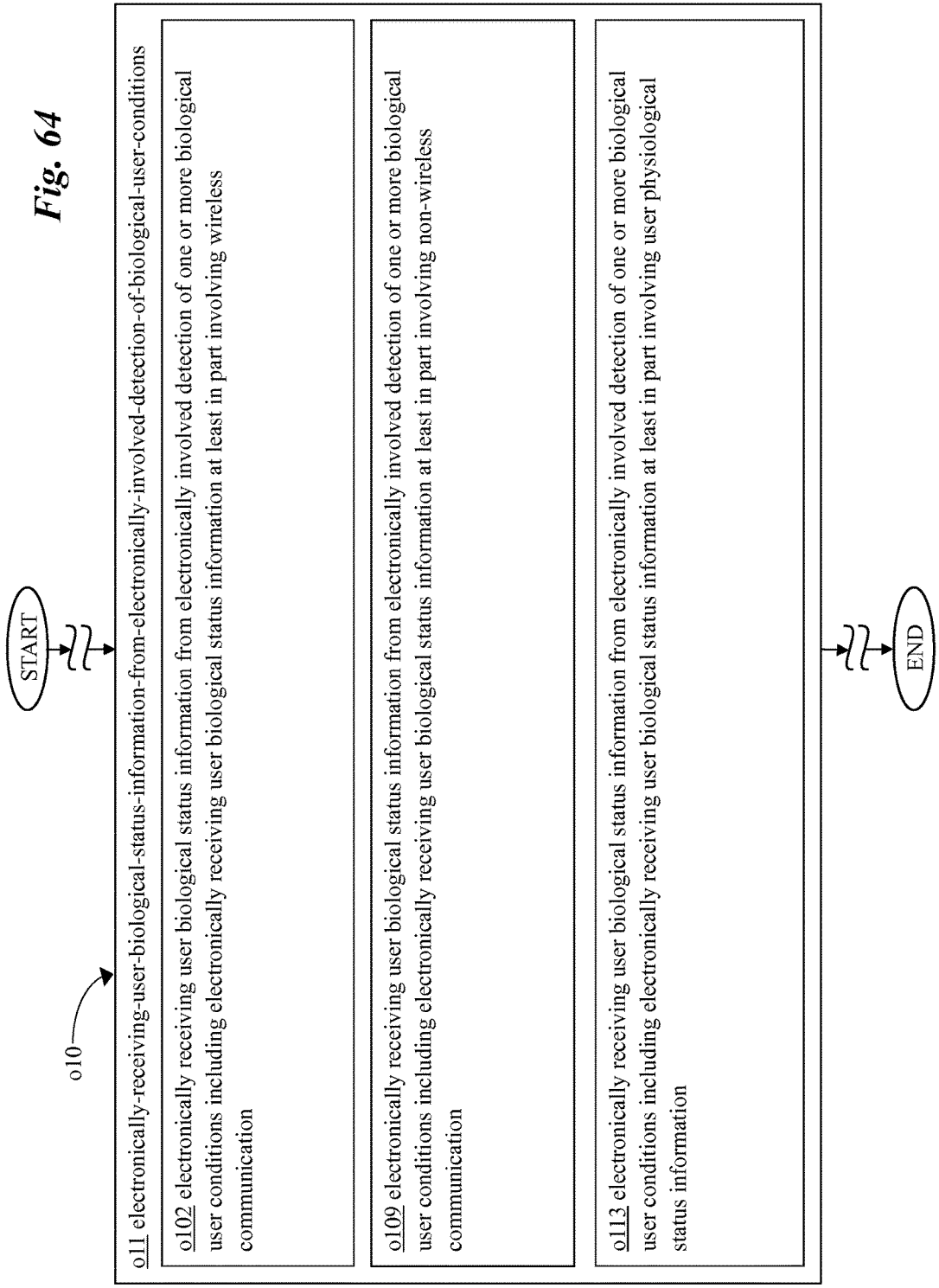

In one or more implementations, as shown in FIG. 64, the operation o11 can include operation o102 for electronically receiving user biological status information from electronically involved detection of one or more biological user conditions including electronically receiving user biological status information at least in part involving wireless communication. Origination of a physically tangible component group can be accomplished through skilled in the art design choice selection including use of one or more components and/or subsystems explicitly and/or implicitly referred to herein for at least in part implementing execution of one or more instructions of the operation o102, for performance of the operation o102 by an electrical circuitry arrangement as activated thereto, and/or otherwise fulfillment of the operation o102. One or more non-transitory signal bearing physical media can bear the one or more instructions that when executed can direct performance of the operation o102. Furthermore, electronically-receiving-user-biological-status-information-wireless-communication module m102 depicted in FIG. 5 as being included in the module m11, when executed and/or activated, can direct performance of and/or perform the operation o102. Illustratively, in one or more implementations, the operation o102 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 65:
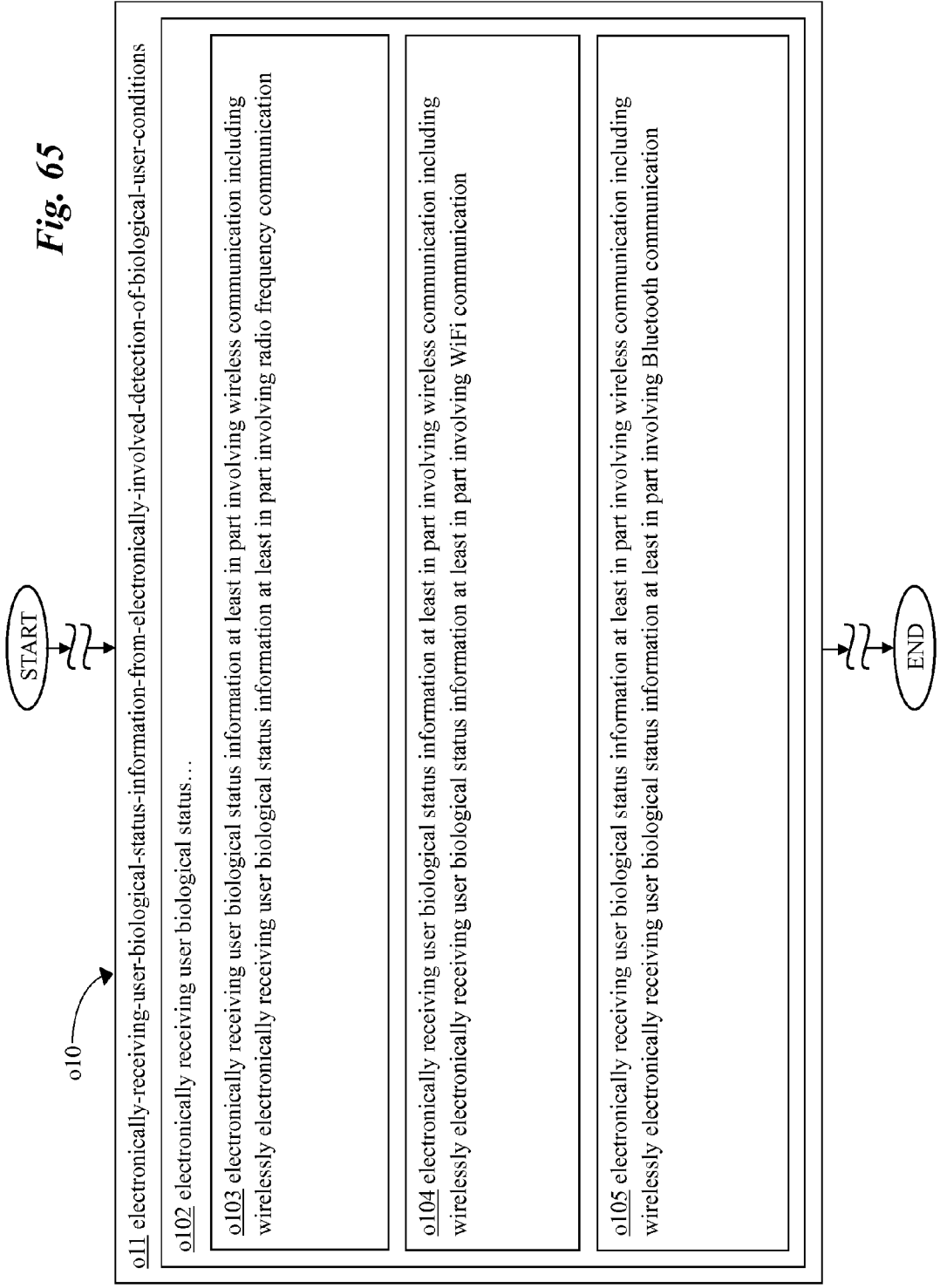
Figure 66:
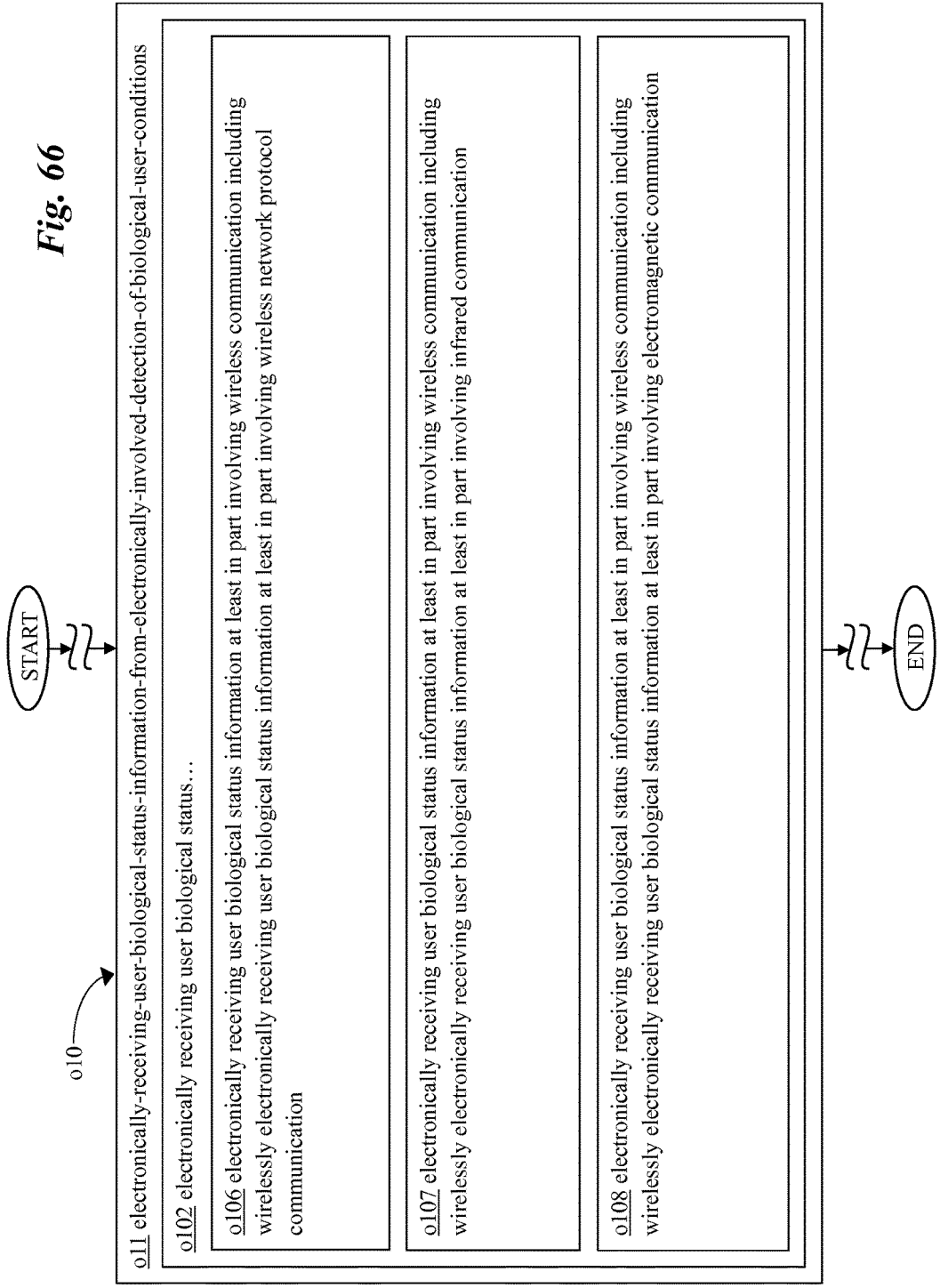

In one or more implementations, as shown in FIG. 65, the operation o102 can include operation o103 for electronically receiving user biological status information at least in part involving wireless communication including wirelessly electronically receiving user biological status information at least in part involving radio frequency communication. Origination of a physically tangible component group can be accomplished through skilled in the art design choice selection including use of one or more components and/or subsystems explicitly and/or implicitly referred to herein for at least in part implementing execution of one or more instructions of the operation o103, for performance of the operation o103 by an electrical circuitry arrangement as activated thereto, and/or otherwise fulfillment of the operation o103. One or more non-transitory signal bearing physical media can bear the one or more instructions that when executed can direct performance of the operation o103. Furthermore, wirelessly-electronically-receiving-user-biological-status-information-radio-frequency-communication module m103 depicted in FIG. 6 as being included in the module m102, when executed and/or activated, can direct performance of and/or perform the operation o103. Illustratively, in one or more implementations, the operation o103 can be carried out, for example, by electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including wirelessly electronically receiving (e.g. electromagnetic, infrared, wireless protocols, data packets, Bluetooth, WiFi, radio frequency, etc.) user biological status information (e.g. quantified-self data, group, behavior life data, individual, functional, historical, physiological, current, etc.) at least in part involving radio frequency communication (e.g. receiving packetized radio frequency communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 65, the operation o102 can include operation o104 for electronically receiving user biological status information at least in part involving wireless communication including wirelessly electronically receiving user biological status information at least in part involving WiFi communication. Origination of a physically tangible component group can be accomplished through skilled in the art design choice selection including use of one or more components and/or subsystems explicitly and/or implicitly referred to herein for at least in part implementing execution of one or more instructions of the operation o104, for performance of the operation o104 by an electrical circuitry arrangement as activated thereto, and/or otherwise fulfillment of the operation o104. One or more non-transitory signal bearing physical media can bear the one or more instructions that when executed can direct performance of the operation o104. Furthermore, wirelessly-electronically-receiving-user-biological-status-information-WiFi-communication module m104 depicted in FIG. 6 as being included in the module m102, when executed and/or activated, can direct performance of and/or perform the operation o104. Illustratively, in one or more implementations, the operation o104 can be carried out, for example, by electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including wirelessly electronically receiving (e.g. radio frequency, WiFi, Bluetooth, packetized data, wireless protocols, infrared, electromagnetic, other transmission, etc.) user biological status information (e.g. current, physiological, historical, functional, etc.) at least in part involving WiFi communication (e.g. receiving short range WiFi communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 65, the operation o102 can include operation o105 for electronically receiving user biological status information at least in part involving wireless communication including wirelessly electronically receiving user biological status information at least in part involving Bluetooth communication. Origination of a physically tangible component group can be accomplished through skilled in the art design choice selection including use of one or more components and/or subsystems explicitly and/or implicitly referred to herein for at least in part implementing execution of one or more instructions of the operation o105, for performance of the operation o105 by an electrical circuitry arrangement as activated thereto, and/or otherwise fulfillment of the operation o105. One or more non-transitory signal bearing physical media can bear the one or more instructions that when executed can direct performance of the operation o105. Furthermore, wirelessly-electronically-receiving-user-biological-status-information-Bluetooth-communication module m105 depicted in FIG. 6 as being included in the module m102, when executed and/or activated, can direct performance of and/or perform the operation o105. Illustratively, in one or more implementations, the operation o105 can be carried out, for example, by electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including wirelessly electronically receiving (e.g. electromagnetic, infrared, wireless protocols, data packets, Bluetooth, WiFi, radio frequency, etc.) user biological status information (e.g. quantified-self data, group, behavior life data, individual, functional, historical, physiological, current, etc.) at least in part involving Bluetooth communication (e.g. receiving Bluetooth personal data communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 56, the operation o102 can include operation o106 for electronically receiving user biological status information at least in part involving wireless communication including wirelessly electronically receiving user biological status information at least in part involving wireless network protocol communication. Origination of a physically tangible component group can be accomplished through skilled in the art design choice selection including use of one or more components and/or subsystems explicitly and/or implicitly referred to herein for at least in part implementing execution of one or more instructions of the operation o106, for performance of the operation o106 by an electrical circuitry arrangement as activated thereto, and/or otherwise fulfillment of the operation o106. One or more non-transitory signal bearing physical media can bear the one or more instructions that when executed can direct performance of the operation o106. Furthermore, wirelessly-electronically-receiving-user-biological-status-information-wireless-network-protocol-communication module m106 depicted in FIG. 7 as being included in the module m102, when executed and/or activated, can direct performance of and/or perform the operation o106. Illustratively, in one or more implementations, the operation o106 can be carried out, for example, by electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including wirelessly electronically receiving (e.g. radio frequency, WiFi, Bluetooth, packetized data, wireless protocols, infrared, electromagnetic, other transmission, etc.) user biological status information (e.g. current, physiological, historical, functional, etc.) at least in part involving wireless network protocol communication (e.g. receiving wireless Ethernet communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 56, the operation o102 can include operation o107 for electronically receiving user biological status information at least in part involving wireless communication including wirelessly electronically receiving user biological status information at least in part involving infrared communication. Origination of a physically tangible component group can be accomplished through skilled in the art design choice selection including use of one or more components and/or subsystems explicitly and/or implicitly referred to herein for at least in part implementing execution of one or more instructions of the operation o107, for performance of the operation o107 by an electrical circuitry arrangement as activated thereto, and/or otherwise fulfillment of the operation o107. One or more non-transitory signal bearing physical media can bear the one or more instructions that when executed can direct performance of the operation o107. Furthermore, wirelessly-electronically-receiving-user-biological-status-information-infrared-communication module m107 depicted in FIG. 7 as being included in the module m102, when executed and/or activated, can direct performance of and/or perform the operation o107. Illustratively, in one or more implementations, the operation o107 can be carried out, for example, by electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including wirelessly electronically receiving (e.g. electromagnetic, infrared, wireless protocols, data packets, Bluetooth, WiFi, radio frequency, etc.) user biological status information (e.g. quantified-self data, group, behavior life data, individual, functional, historical, physiological, current, etc.) at least in part involving infrared communication (e.g. receiving point-to-point infrared communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 56, the operation o102 can include operation o108 for electronically receiving user biological status information at least in part involving wireless communication including wirelessly electronically receiving user biological status information at least in part involving electromagnetic communication. Origination of a physically tangible component group can be accomplished through skilled in the art design choice selection including use of one or more components and/or subsystems explicitly and/or implicitly referred to herein for at least in part implementing execution of one or more instructions of the operation o108, for performance of the operation o108 by an electrical circuitry arrangement as activated thereto, and/or otherwise fulfillment of the operation o108. One or more non-transitory signal bearing physical media can bear the one or more instructions that when executed can direct performance of the operation o108. Furthermore, wirelessly-electronically-receiving-user-biological-status-information-electromagnetic-communication module m108 depicted in FIG. 7 as being included in the module m102, when executed and/or activated, can direct performance of and/or perform the operation o108. Illustratively, in one or more implementations, the operation o108 can be carried out, for example, by electronically receiving (e.g. electromagnetic, infrared, wireless protocols, data packets, Bluetooth, WiFi, radio frequency, etc.) user biological status information (e.g. current, physiological, historical, functional, etc.) at least in part involving wireless communication (e.g. receiving wireless point-to-point communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including wirelessly electronically receiving (e.g. radio frequency, WiFi, Bluetooth, packetized data, wireless protocols, infrared, electromagnetic, other transmission, etc.) user biological status information (e.g. current, physiological, historical, functional, etc.) at least in part involving electromagnetic communication (e.g. receiving short range point-to-point electromagnetic communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 64, the operation o11 can include operation o109 for electronically receiving user biological status information from electronically involved detection of one or more biological user conditions including electronically receiving user biological status information at least in part involving non-wireless communication. Origination of a physically tangible component group can be accomplished through skilled in the art design choice selection including use of one or more components and/or subsystems explicitly and/or implicitly referred to herein for at least in part implementing execution of one or more instructions of the operation o109, for performance of the operation o109 by an electrical circuitry arrangement as activated thereto, and/or otherwise fulfillment of the operation o109. One or more non-transitory signal bearing physical media can bear the one or more instructions that when executed can direct performance of the operation o109. Furthermore, electronically-receiving-user-biological-status-information-non-wireless-communication module m109 depicted in FIG. 5 as being included in the module m11, when executed and/or activated, can direct performance of and/or perform the operation o109. Illustratively, in one or more implementations, the operation o109 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. swipes, scans, network, direct device-to-device, other transfers, etc.) user biological status information (e.g. quantified-self data, group, behavior life data, individual, functional, historical, physiological, current, etc.) at least in part involving non-wireless communication (e.g. receiving momentary contact non-wireless communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 67:
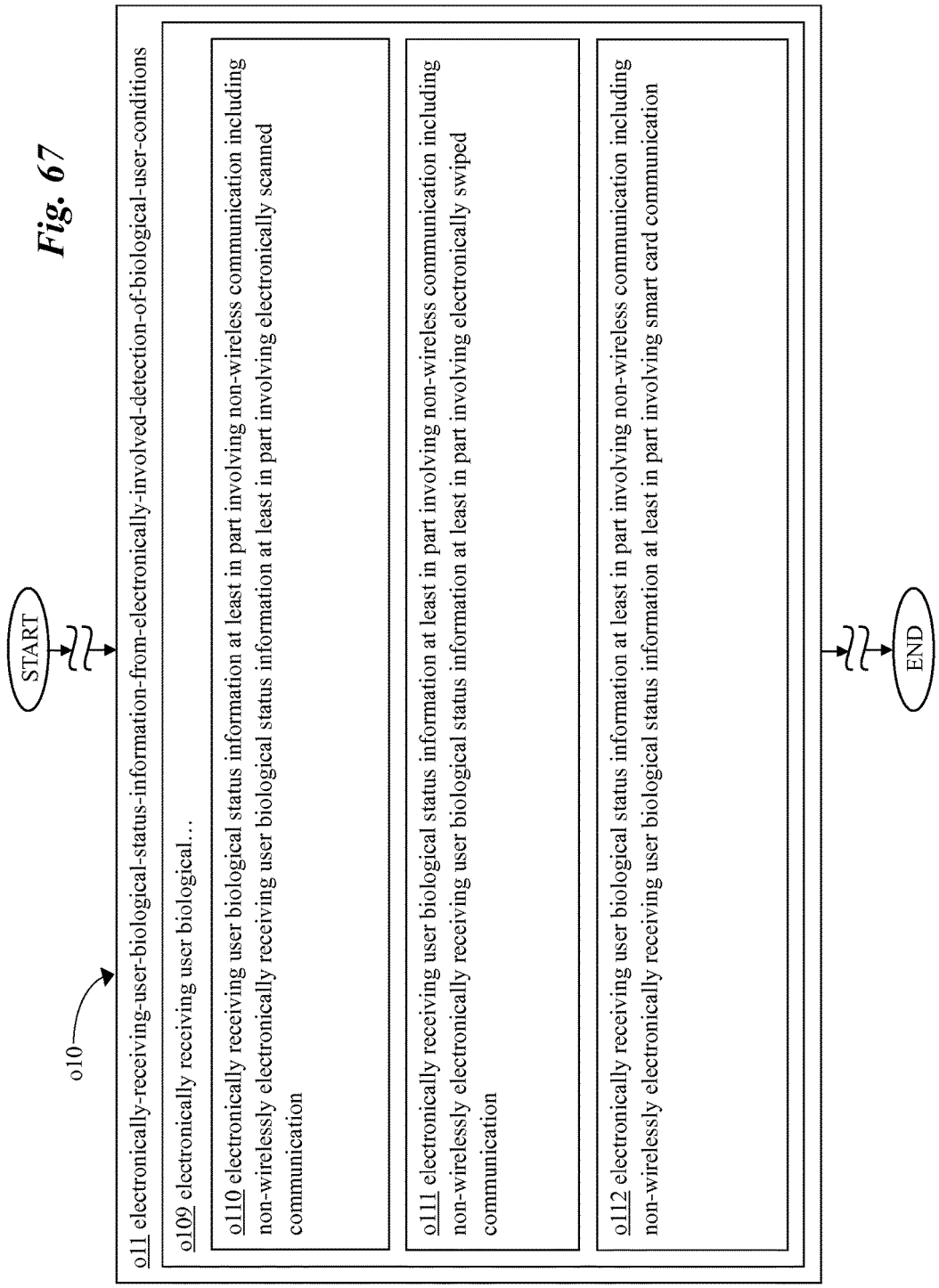

In one or more implementations, as shown in FIG. 67, the operation o109 can include operation o110 for electronically receiving user biological status information at least in part involving non-wireless communication including non-wirelessly electronically receiving user biological status information at least in part involving electronically scanned communication. Origination of a physically tangible component group can be accomplished through skilled in the art design choice selection including use of one or more components and/or subsystems explicitly and/or implicitly referred to herein for at least in part implementing execution of one or more instructions of the operation o110, for performance of the operation o110 by an electrical circuitry arrangement as activated thereto, and/or otherwise fulfillment of the operation o110. One or more non-transitory signal bearing physical media can bear the one or more instructions that when executed can direct performance of the operation o110. Furthermore, non-wirelessly-electronically-receiving-user-biological-status-information-electronically-scanned-communication module m110 depicted in FIG. 8 as being included in the module m109, when executed and/or activated, can direct performance of and/or perform the operation o110. Illustratively, in one or more implementations, the operation o110 can be carried out, for example, by electronically receiving (e.g. swipes, scans, network, direct device-to-device, other transfers, etc.) user biological status information (e.g. quantified-self data, group, behavior life data, individual, functional, historical, physiological, current, etc.) at least in part involving non-wireless communication (e.g. receiving momentary contact non-wireless communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including non-wirelessly electronically receiving (e.g. direct device-to-device, network, non-wireless, scans, swipes, other transfers, etc.) user biological status information (e.g. current, physiological, historical, functional, etc.) at least in part involving electronically scanned communication (e.g. receiving electromagnetic or optical scan from smart phone, personal device, or dedicated data collection device at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 67, the operation o109 can include operation o111 for electronically receiving user biological status information at least in part involving non-wireless communication including non-wirelessly electronically receiving user biological status information at least in part involving electronically swiped communication. Origination of a physically tangible component group can be accomplished through skilled in the art design choice selection including use of one or more components and/or subsystems explicitly and/or implicitly referred to herein for at least in part implementing execution of one or more instructions of the operation o111, for performance of the operation o111 by an electrical circuitry arrangement as activated thereto, and/or otherwise fulfillment of the operation o111. One or more non-transitory signal bearing physical media can bear the one or more instructions that when executed can direct performance of the operation o111. Furthermore, non-wirelessly-electronically-receiving-user-biological-status-information-electronically-swiped-communication module m111 depicted in FIG. 8 as being included in the module m109, when executed and/or activated, can direct performance of and/or perform the operation o111. Illustratively, in one or more implementations, the operation o111 can be carried out, for example, by electronically receiving (e.g. swipes, scans, network, direct device-to-device, other transfers, etc.) user biological status information (e.g. quantified-self data, group, behavior life data, individual, functional, historical, physiological, current, etc.) at least in part involving non-wireless communication (e.g. receiving momentary contact non-wireless communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including non-wirelessly electronically receiving (e.g. swipes, scans, network, direct device-to-device, other transfers, etc.) user biological status information (e.g. quantified-self data, group, behavior life data, individual, functional, historical, physiological, current, etc.) at least in part involving electronically swiped communication (e.g. receiving electromagnetic or optical scan from swipe of data collection device such as smart card, smart phone, personal device, or other data collection device at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 67, the operation o109 can include operation o112 for electronically receiving user biological status information at least in part involving non-wireless communication including non-wirelessly electronically receiving user biological status information at least in part involving smart card communication. Origination of a physically tangible component group can be accomplished through skilled in the art design choice selection including use of one or more components and/or subsystems explicitly and/or implicitly referred to herein for at least in part implementing execution of one or more instructions of the operation o112, for performance of the operation o112 by an electrical circuitry arrangement as activated thereto, and/or otherwise fulfillment of the operation o112. One or more non-transitory signal bearing physical media can bear the one or more instructions that when executed can direct performance of the operation o112. Furthermore, non-wirelessly-electronically-receiving-user-biological-status-information-smart-card-communication module m112 depicted in FIG. 8 as being included in the module m109, when executed and/or activated, can direct performance of and/or perform the operation o112. Illustratively, in one or more implementations, the operation o112 can be carried out, for example, by electronically receiving (e.g. swipes, scans, network, direct device-to-device, other transfers, etc.) user biological status information (e.g. quantified-self data, group, behavior life data, individual, functional, historical, physiological, current, etc.) at least in part involving non-wireless communication (e.g. receiving momentary contact non-wireless communication at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including non-wirelessly electronically receiving (e.g. direct device-to-device, network, non-wireless, scans, swipes, other transfers, etc.) user biological status information (e.g. current, physiological, historical, functional, etc.) at least in part involving smart card communication (e.g. receiving electromagnetic or optical scan from smart card data collection device at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 65, the operation o11 can include operation o113 for electronically receiving user biological status information from electronically involved detection of one or more biological user conditions including electronically receiving user biological status information at least in part involving user physiological status information. Origination of a physically tangible component group can be accomplished through skilled in the art design choice selection including use of one or more components and/or subsystems explicitly and/or implicitly referred to herein for at least in part implementing execution of one or more instructions of the operation o113, for performance of the operation o113 by an electrical circuitry arrangement as activated thereto, and/or otherwise fulfillment of the operation o113. One or more non-transitory signal bearing physical media can bear the one or more instructions that when executed can direct performance of the operation o113. Furthermore, electronically-receiving-user-biological-status-information-user-physiological-status-information module m113 depicted in FIG. 5 as being included in the module m11, when executed and/or activated, can direct performance of and/or perform the operation o113. Illustratively, in one or more implementations, the operation o113 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, lifestyle, health, enhancement, reduction, augmentation, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 68:
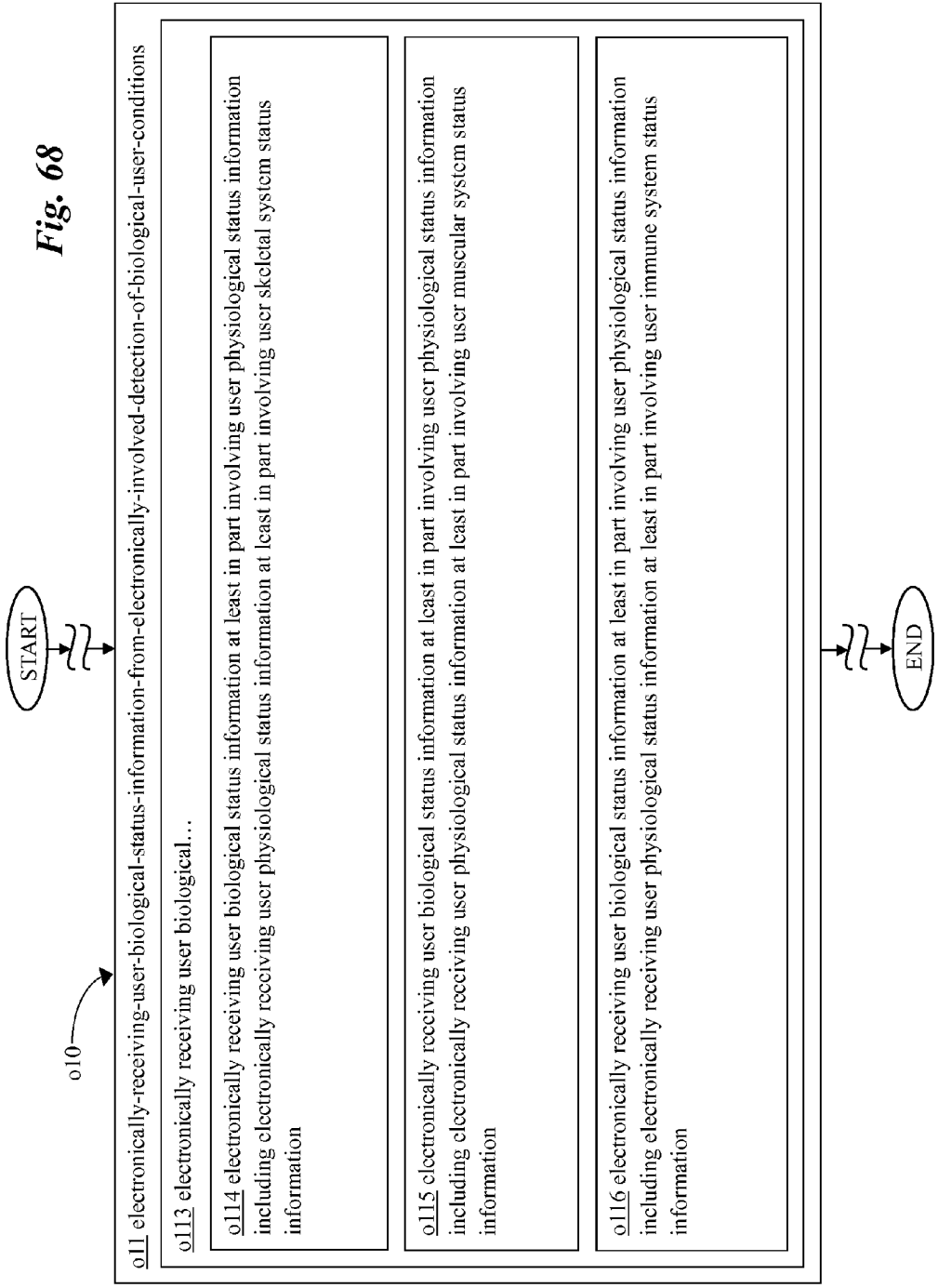

In one or more implementations, as shown in FIG. 68, the operation o113 can include operation o114 for electronically receiving user biological status information at least in part involving user physiological status information including electronically receiving user physiological status information at least in part involving user skeletal system status information. Origination of a physically tangible component group can be accomplished through skilled in the art design choice selection including use of one or more components and/or subsystems explicitly and/or implicitly referred to herein for at least in part implementing execution of one or more instructions of the operation o114, for performance of the operation o114 by an electrical circuitry arrangement as activated thereto, and/or otherwise fulfillment of the operation o114. One or more non-transitory signal bearing physical media can bear the one or more instructions that when executed can direct performance of the operation o114. Furthermore, electronically-receiving-user-physiological-status-information-user-skeletal-system-status-information module m114 depicted in FIG. 9 as being included in the module m113, when executed and/or activated, can direct performance of and/or perform the operation o114. Illustratively, in one or more implementations, the operation o114 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user physiological status information (e.g. skeletal, muscular, immune, lymphatic, cardiovascular, urinary, etc.) at least in part involving user skeletal system status information (e.g. receiving historical or current skeletal system status information such as bone density, fracture statistics, bone growth rates, spinal disk data, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 68, the operation o113 can include operation o115 for electronically receiving user biological status information at least in part involving user physiological status information including electronically receiving user physiological status information at least in part involving user muscular system status information. Origination of a physically tangible component group can be accomplished through skilled in the art design choice selection including use of one or more components and/or subsystems explicitly and/or implicitly referred to herein for at least in part implementing execution of one or more instructions of the operation o115, for performance of the operation o115 by an electrical circuitry arrangement as activated thereto, and/or otherwise fulfillment of the operation o115. One or more non-transitory signal bearing physical media can bear the one or more instructions that when executed can direct performance of the operation o115. Furthermore, electronically-receiving-user-physiological-status-information-user-muscular-system-status-information module m115 depicted in FIG. 9 as being included in the module m113, when executed and/or activated, can direct performance of and/or perform the operation o115. Illustratively, in one or more implementations, the operation o115 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user physiological status information (e.g. digestive, respiratory, nervous, endocrine, reproductive, integumentary, etc.) at least in part involving user muscular system status information (e.g. receiving historical or current muscular system status information such as lactic acid levels, myoelectric activity, weight lifting routines, protein intake, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 68, the operation o113 can include operation o116 for electronically receiving user biological status information at least in part involving user physiological status information including electronically receiving user physiological status information at least in part involving user immune system status information. Origination of a physically tangible component group can be accomplished through skilled in the art design choice selection including use of one or more components and/or subsystems explicitly and/or implicitly referred to herein for at least in part implementing execution of one or more instructions of the operation o116, for performance of the operation o116 by an electrical circuitry arrangement as activated thereto, and/or otherwise fulfillment of the operation o116. One or more non-transitory signal bearing physical media can bear the one or more instructions that when executed can direct performance of the operation o116. Furthermore, electronically-receiving-user-physiological-status-information-user-immune-system-status-information module m116 depicted in FIG. 9 as being included in the module m113, when executed and/or activated, can direct performance of and/or perform the operation o116. Illustratively, in one or more implementations, the operation o116 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user physiological status information (e.g. skeletal, muscular, immune, lymphatic, cardiovascular, urinary, etc.) at least in part involving user immune system status information (e.g. receiving historical or current immune system status information such as infection records, antibody data, autoimmune data, allergy data, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 69:
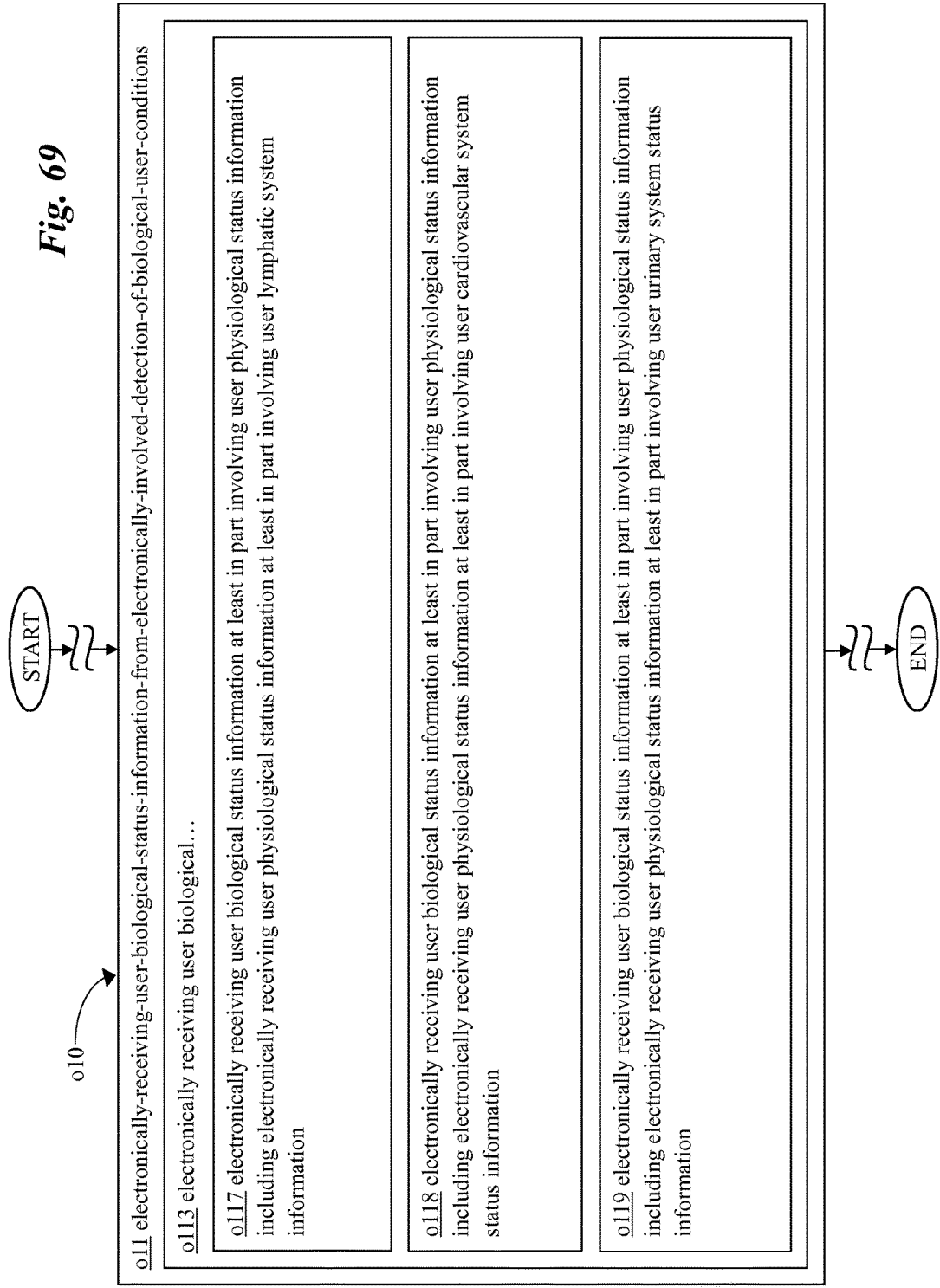

In one or more implementations, as shown in FIG. 69, the operation o113 can include operation o117 for electronically receiving user biological status information at least in part involving user physiological status information including electronically receiving user physiological status information at least in part involving user lymphatic system information. Origination of a physically tangible component group can be accomplished through skilled in the art design choice selection including use of one or more components and/or subsystems explicitly and/or implicitly referred to herein for at least in part implementing execution of one or more instructions of the operation o117, for performance of the operation o117 by an electrical circuitry arrangement as activated thereto, and/or otherwise fulfillment of the operation o117. One or more non-transitory signal bearing physical media can bear the one or more instructions that when executed can direct performance of the operation o117. Furthermore, electronically-receiving-user-physiological-status-information-user-lymphatic-system-information module m117 depicted in FIG. 10 as being included in the module m113, when executed and/or activated, can direct performance of and/or perform the operation o117. Illustratively, in one or more implementations, the operation o117 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user physiological status information (e.g. digestive, respiratory, nervous, endocrine, reproductive, integumentary, etc.) at least in part involving user lymphatic system information (e.g. receiving historical or current lymphatic system status information such as lymph node drainage levels, lymph node size, amount of time spent trampolining, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 69, the operation o113 can include operation o118 for electronically receiving user biological status information at least in part involving user physiological status information including electronically receiving user physiological status information at least in part involving user cardiovascular system status information. Origination of a physically tangible component group can be accomplished through skilled in the art design choice selection including use of one or more components and/or subsystems explicitly and/or implicitly referred to herein for at least in part implementing execution of one or more instructions of the operation o118, for performance of the operation o118 by an electrical circuitry arrangement as activated thereto, and/or otherwise fulfillment of the operation o118. One or more non-transitory signal bearing physical media can bear the one or more instructions that when executed can direct performance of the operation o118. Furthermore, electronically-receiving-user-physiological-status-information-user-cardiovascular-system-status-information module m118 depicted in FIG. 10 as being included in the module m113, when executed and/or activated, can direct performance of and/or perform the operation o118. Illustratively, in one or more implementations, the operation o118 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user physiological status information (e.g. skeletal, muscular, immune, lymphatic, cardiovascular, urinary, etc.) at least in part involving user cardiovascular system status information (e.g. receiving historical or current cardiovascular system status information such as heart rate variability data, resting pulse data, VO2 max data, blood pressure data, blood lipids data, blood chemistry data, stent sensor data, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 69, the operation o113 can include operation o119 for electronically receiving user biological status information at least in part involving user physiological status information including electronically receiving user physiological status information at least in part involving user urinary system status information. Origination of a physically tangible component group can be accomplished through skilled in the art design choice selection including use of one or more components and/or subsystems explicitly and/or implicitly referred to herein for at least in part implementing execution of one or more instructions of the operation o119, for performance of the operation o119 by an electrical circuitry arrangement as activated thereto, and/or otherwise fulfillment of the operation o119. One or more non-transitory signal bearing physical media can bear the one or more instructions that when executed can direct performance of the operation o119. Furthermore, electronically-receiving-user-physiological-status-information-user-urinary-system-status-information module m119 depicted in FIG. 10 as being included in the module m113, when executed and/or activated, can direct performance of and/or perform the operation o119. Illustratively, in one or more implementations, the operation o119 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user physiological status information (e.g. digestive, respiratory, nervous, endocrine, reproductive, integumentary, etc.) at least in part involving user urinary system status information (e.g. receiving historical or current urinary system status information such as incontinence data, amount of blood in urine, urine sugar, protein, etc. levels, bladder infection records, number of times urinating, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 70:
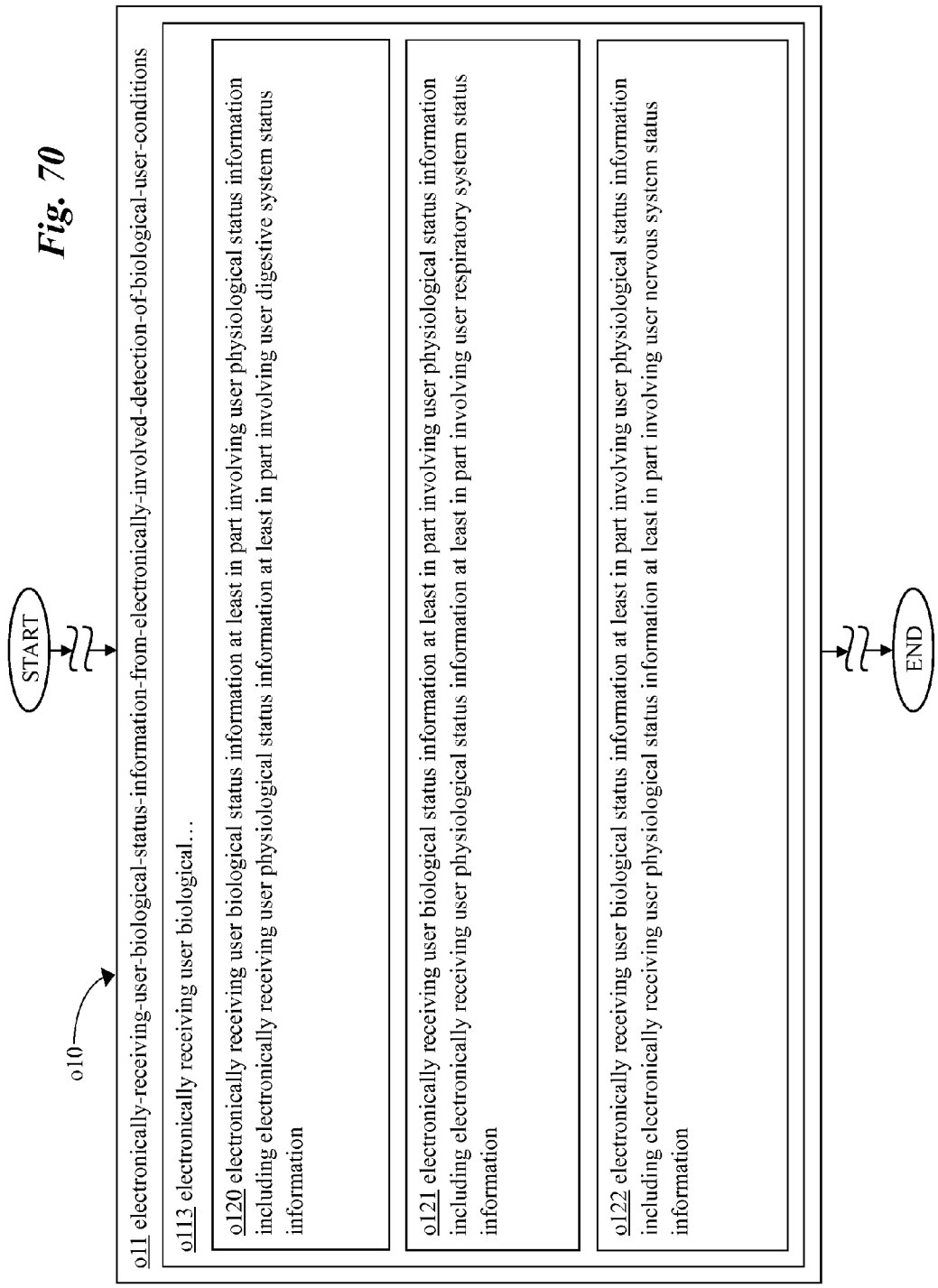

In one or more implementations, as shown in FIG. 70, the operation o113 can include operation o120 for electronically receiving user biological status information at least in part involving user physiological status information including electronically receiving user physiological status information at least in part involving user digestive system status information. Origination of a physically tangible component group can be accomplished through skilled in the art design choice selection including use of one or more components and/or subsystems explicitly and/or implicitly referred to herein for at least in part implementing execution of one or more instructions of the operation o120, for performance of the operation o120 by an electrical circuitry arrangement as activated thereto, and/or otherwise fulfillment of the operation o120. One or more non-transitory signal bearing physical media can bear the one or more instructions that when executed can direct performance of the operation o120. Furthermore, electronically-receiving-user-physiological-status-information-user-digestive-system-status-information module m120 depicted in FIG. 11 as being included in the module m113, when executed and/or activated, can direct performance of and/or perform the operation o120. Illustratively, in one or more implementations, the operation o120 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user physiological status information (e.g. skeletal, muscular, immune, lymphatic, cardiovascular, urinary, etc.) at least in part involving user digestive system status information (e.g. receiving historical or current digestive system status information such as hydrochloric acid levels, enzyme levels, levels of undigested matter, acid reflux levels, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 70, the operation o113 can include operation o121 for electronically receiving user biological status information at least in part involving user physiological status information including electronically receiving user physiological status information at least in part involving user respiratory system status information. Origination of a physically tangible component group can be accomplished through skilled in the art design choice selection including use of one or more components and/or subsystems explicitly and/or implicitly referred to herein for at least in part implementing execution of one or more instructions of the operation o121, for performance of the operation o121 by an electrical circuitry arrangement as activated thereto, and/or otherwise fulfillment of the operation o121. One or more non-transitory signal bearing physical media can bear the one or more instructions that when executed can direct performance of the operation o121. Furthermore, electronically-receiving-user-physiological-status-information-user-respiratory-system-status-information module m121 depicted in FIG. 11 as being included in the module m113, when executed and/or activated, can direct performance of and/or perform the operation o121. Illustratively, in one or more implementations, the operation o121 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user physiological status information (e.g. digestive, respiratory, nervous, endocrine, reproductive, integumentary, etc.) at least in part involving user respiratory system status information (e.g. receiving historical or current respiratory system status information such as amount or degree of asthmatic episodes, respiration rate, lung volume, air pollution exposure, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 70, the operation o113 can include operation o122 for electronically receiving user biological status information at least in part involving user physiological status information including electronically receiving user physiological status information at least in part involving user nervous system status information. Origination of a physically tangible component group can be accomplished through skilled in the art design choice selection including use of one or more components and/or subsystems explicitly and/or implicitly referred to herein for at least in part implementing execution of one or more instructions of the operation o122, for performance of the operation o122 by an electrical circuitry arrangement as activated thereto, and/or otherwise fulfillment of the operation o122. One or more non-transitory signal bearing physical media can bear the one or more instructions that when executed can direct performance of the operation o122. Furthermore, electronically-receiving-user-physiological-status-information-user-nervous-system-status-information module m122 depicted in FIG. 11 as being included in the module m113, when executed and/or activated, can direct performance of and/or perform the operation o122. Illustratively, in one or more implementations, the operation o122 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user physiological status information (e.g. skeletal, muscular, immune, lymphatic, cardiovascular, urinary, etc.) at least in part involving user nervous system status information (e.g. receiving historical or current nervous system status information such as nerve enervation levels, nerve signaling data, sciatica incident records, tremor incident records, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 71:
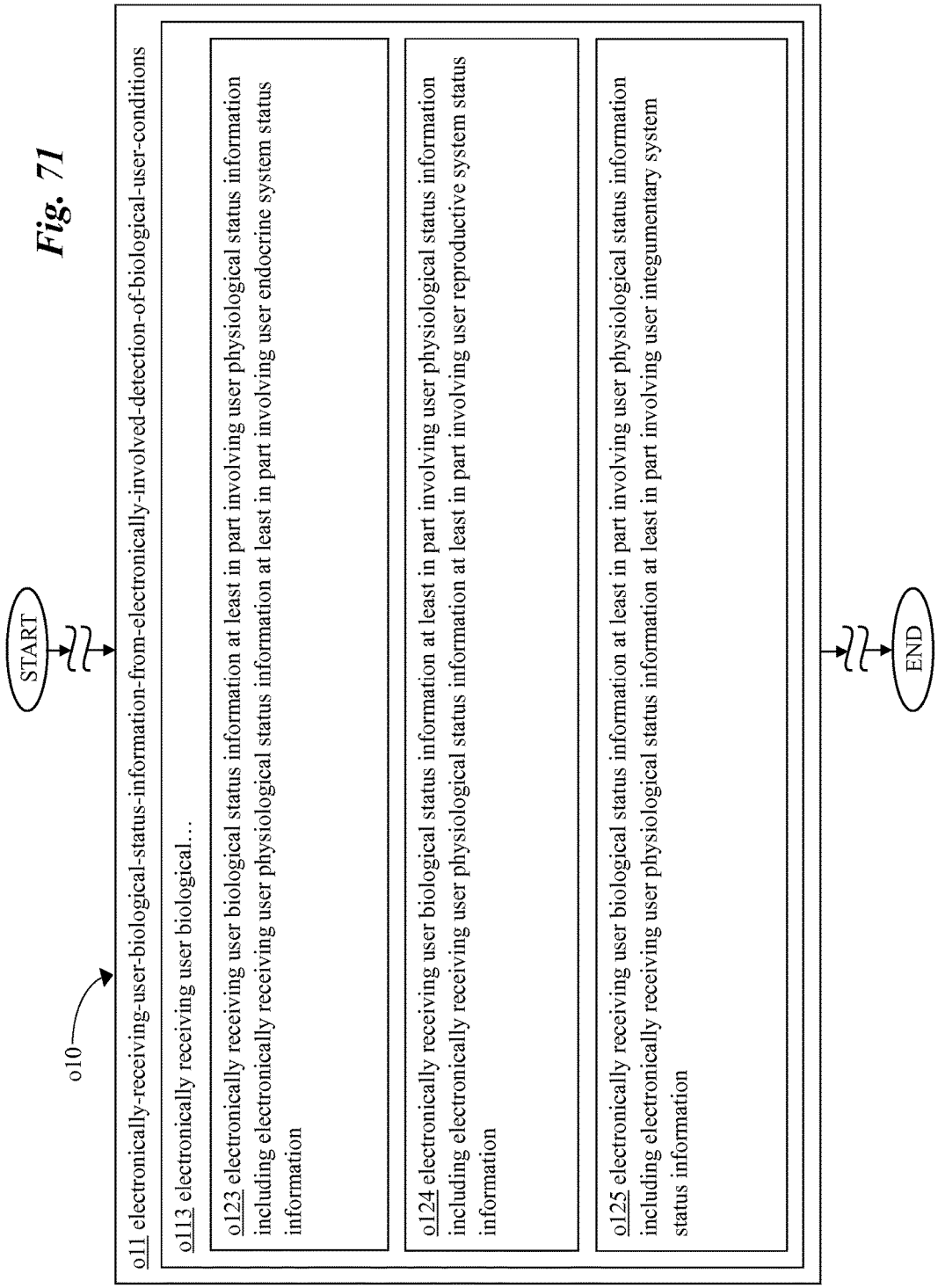

In one or more implementations, as shown in FIG. 71, the operation o113 can include operation o123 for electronically receiving user biological status information at least in part involving user physiological status information including electronically receiving user physiological status information at least in part involving user endocrine system status information. Origination of a physically tangible component group can be accomplished through skilled in the art design choice selection including use of one or more components and/or subsystems explicitly and/or implicitly referred to herein for at least in part implementing execution of one or more instructions of the operation o123, for performance of the operation o123 by an electrical circuitry arrangement as activated thereto, and/or otherwise fulfillment of the operation o123. One or more non-transitory signal bearing physical media can bear the one or more instructions that when executed can direct performance of the operation o123. Furthermore, electronically-receiving-user-physiological-status-information-user-endocrine-system-status-information module m123 depicted in FIG. 12 as being included in the module m113, when executed and/or activated, can direct performance of and/or perform the operation o123. Illustratively, in one or more implementations, the operation o123 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user physiological status information (e.g. digestive, respiratory, nervous, endocrine, reproductive, integumentary, etc.) at least in part involving user endocrine system status information (e.g. receiving historical or current endocrine system status information such as thyroid T3, T4, TPO, etc. levels, adrenal related cortisol levels, pancreas related blood sugar levels or proteolytic enzyme levels, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 71, the operation o113 can include operation o124 for electronically receiving user biological status information at least in part involving user physiological status information including electronically receiving user physiological status information at least in part involving user reproductive system status information. Origination of a physically tangible component group can be accomplished through skilled in the art design choice selection including use of one or more components and/or subsystems explicitly and/or implicitly referred to herein for at least in part implementing execution of one or more instructions of the operation o124, for performance of the operation o124 by an electrical circuitry arrangement as activated thereto, and/or otherwise fulfillment of the operation o124. One or more non-transitory signal bearing physical media can bear the one or more instructions that when executed can direct performance of the operation o124. Furthermore, electronically-receiving-user-physiological-status-information-user-reproductive-system-status-information module m124 depicted in FIG. 12 as being included in the module m113, when executed and/or activated, can direct performance of and/or perform the operation o124. Illustratively, in one or more implementations, the operation o124 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user physiological status information (e.g. skeletal, muscular, immune, lymphatic, cardiovascular, urinary, etc.) at least in part involving user reproductive system status information (e.g. receiving historical or current reproductive system status information such as pregnancy duration records, pregnancy status records, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 71, the operation o113 can include operation o125 for electronically receiving user biological status information at least in part involving user physiological status information including electronically receiving user physiological status information at least in part involving user integumentary system status information. Origination of a physically tangible component group can be accomplished through skilled in the art design choice selection including use of one or more components and/or subsystems explicitly and/or implicitly referred to herein for at least in part implementing execution of one or more instructions of the operation o125, for performance of the operation o125 by an electrical circuitry arrangement as activated thereto, and/or otherwise fulfillment of the operation o125. One or more non-transitory signal bearing physical media can bear the one or more instructions that when executed can direct performance of the operation o125. Furthermore, electronically-receiving-user-physiological-status-information-user-integumentary-system-status-information module m125 depicted in FIG. 12 as being included in the module m113, when executed and/or activated, can direct performance of and/or perform the operation o125. Illustratively, in one or more implementations, the operation o125 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user physiological status information (e.g. receiving historical or current physiological status information such as heart activity, blood sugar levels, exercise recovery, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user physiological status information (e.g. digestive, respiratory, nervous, endocrine, reproductive, integumentary, etc.) at least in part involving user integumentary system status information (e.g. receiving historical or current integumentary system status information such as hair growth rate, hair cut frequency, hair thickness measurements, skin wound healing rates, skin integrity levels, skin scaling levels, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 72:
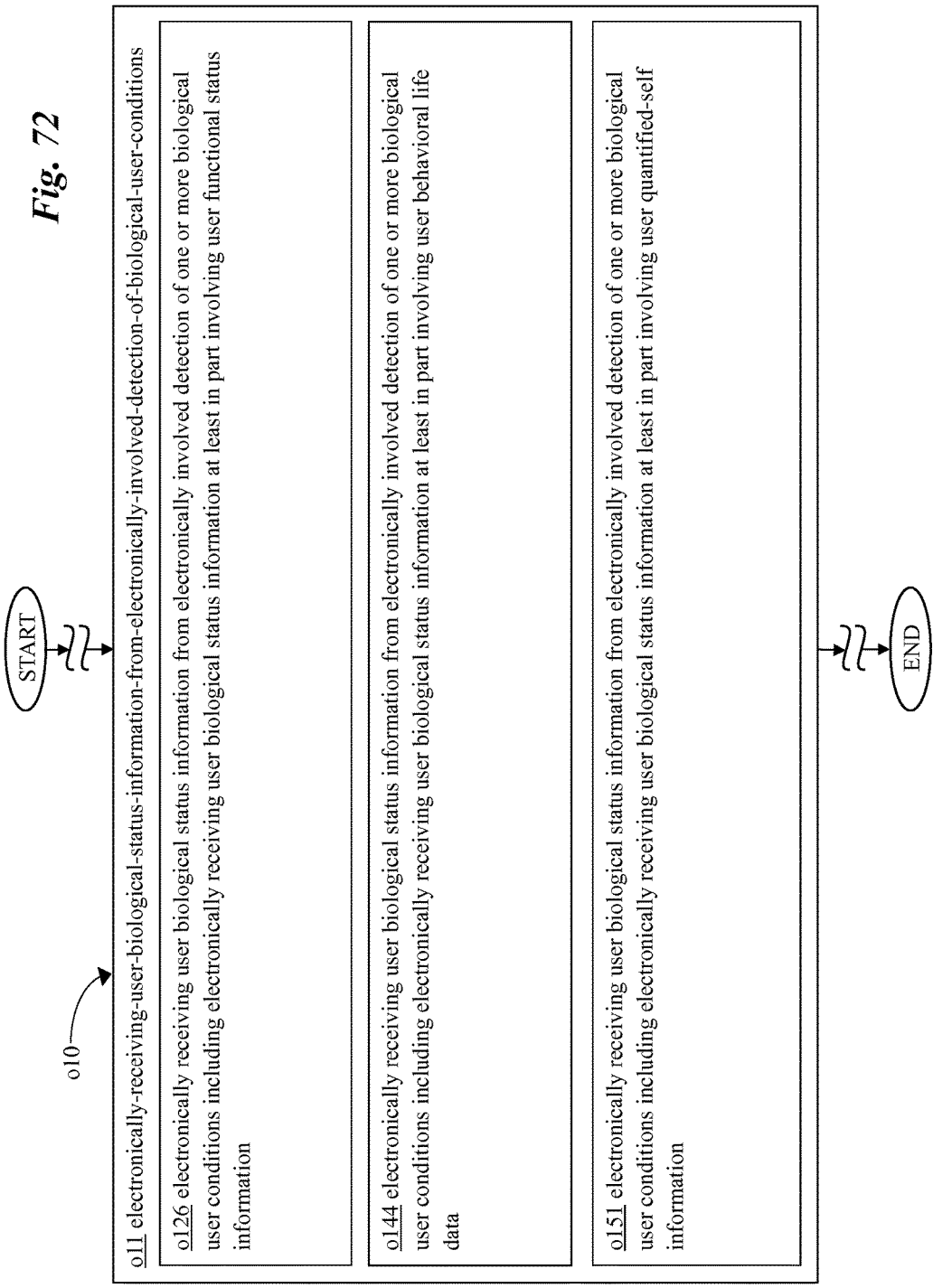

In one or more implementations, as shown in FIG. 72, the operation o11 can include operation o126 for electronically receiving user biological status information from electronically involved detection of one or more biological user conditions including electronically receiving user biological status information at least in part involving user functional status information. Origination of a physically tangible component group can be accomplished through skilled in the art design choice selection including use of one or more components and/or subsystems explicitly and/or implicitly referred to herein for at least in part implementing execution of one or more instructions of the operation o126, for performance of the operation o126 by an electrical circuitry arrangement as activated thereto, and/or otherwise fulfillment of the operation o126. One or more non-transitory signal bearing physical media can bear the one or more instructions that when executed can direct performance of the operation o126. Furthermore, electronically-receiving-user-biological-status-information-user-functional-status-information module m126 depicted in FIG. 13 as being included in the module m11, when executed and/or activated, can direct performance of and/or perform the operation o126. Illustratively, in one or more implementations, the operation o126 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, lifestyle, health, enhancement, reduction, augmentation, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user functional status information (e.g. receiving historical or current functional status information such as ambulatory functional status records of walking, running, climbing, sleeping, housework, educational, musical, athletic, recreational, vocational, etc. functional performance, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 73:
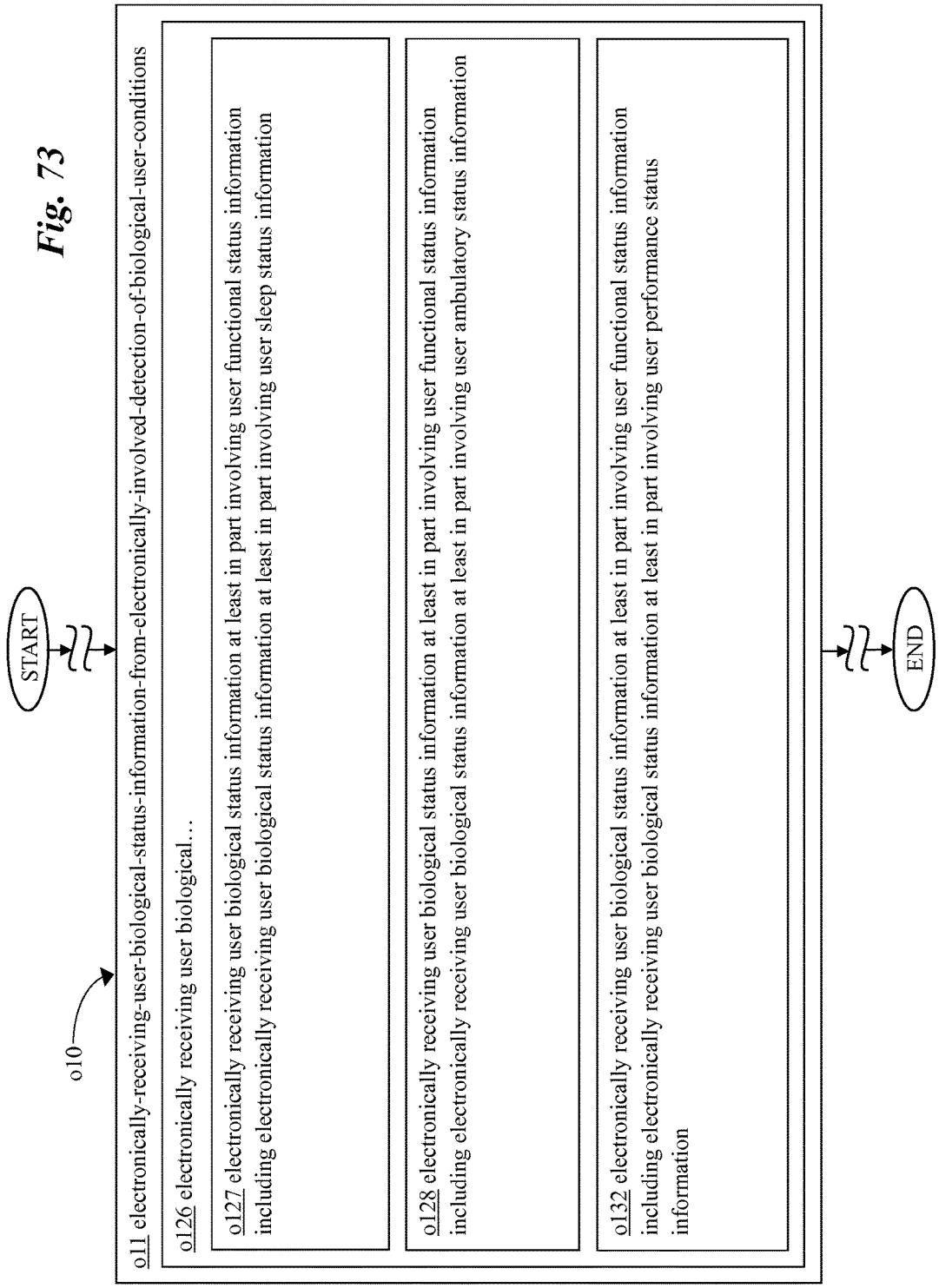

In one or more implementations, as shown in FIG. 73, the operation o126 can include operation o127 for electronically receiving user biological status information at least in part involving user functional status information including electronically receiving user biological status information at least in part involving user sleep status information. Origination of a physically tangible component group can be accomplished through skilled in the art design choice selection including use of one or more components and/or subsystems explicitly and/or implicitly referred to herein for at least in part implementing execution of one or more instructions of the operation o127, for performance of the operation o127 by an electrical circuitry arrangement as activated thereto, and/or otherwise fulfillment of the operation o127. One or more non-transitory signal bearing physical media can bear the one or more instructions that when executed can direct performance of the operation o127. Furthermore, electronically-receiving-user-biological-status-information-user-sleep-status-information module m127 depicted in FIG. 14 as being included in the module m126, when executed and/or activated, can direct performance of and/or perform the operation o127. Illustratively, in one or more implementations, the operation o127 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user functional status information (e.g. receiving historical or current functional status information such as ambulatory functional status records of walking, running, climbing, sleeping, housework, educational, musical, athletic, recreational, vocational, etc. functional performance, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user sleep status information (e.g. receiving sleep status information such as amount of sleep, amount of movement during sleep, times of sleep, times of doziness while awake, amount of stimulants ingested, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 73, the operation o126 can include operation o128 for electronically receiving user biological status information at least in part involving user functional status information including electronically receiving user biological status information at least in part involving user ambulatory status information. Origination of a physically tangible component group can be accomplished through skilled in the art design choice selection including use of one or more components and/or subsystems explicitly and/or implicitly referred to herein for at least in part implementing execution of one or more instructions of the operation o128, for performance of the operation o128 by an electrical circuitry arrangement as activated thereto, and/or otherwise fulfillment of the operation o128. One or more non-transitory signal bearing physical media can bear the one or more instructions that when executed can direct performance of the operation o128. Furthermore, electronically-receiving-user-biological-status-information-user-ambulatory-status-information module m128 depicted in FIG. 14 as being included in the module m126, when executed and/or activated, can direct performance of and/or perform the operation o128. Illustratively, in one or more implementations, the operation o128 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user functional status information (e.g. receiving historical or current functional status information such as ambulatory functional status records of walking, running, climbing, sleeping, housework, educational, musical, athletic, recreational, vocational, etc. functional performance, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user ambulatory status information (e.g. receiving historical or current ambulatory status information such as ambulatory functional status records of walking, running, climbing, using a wheelchair, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 74:
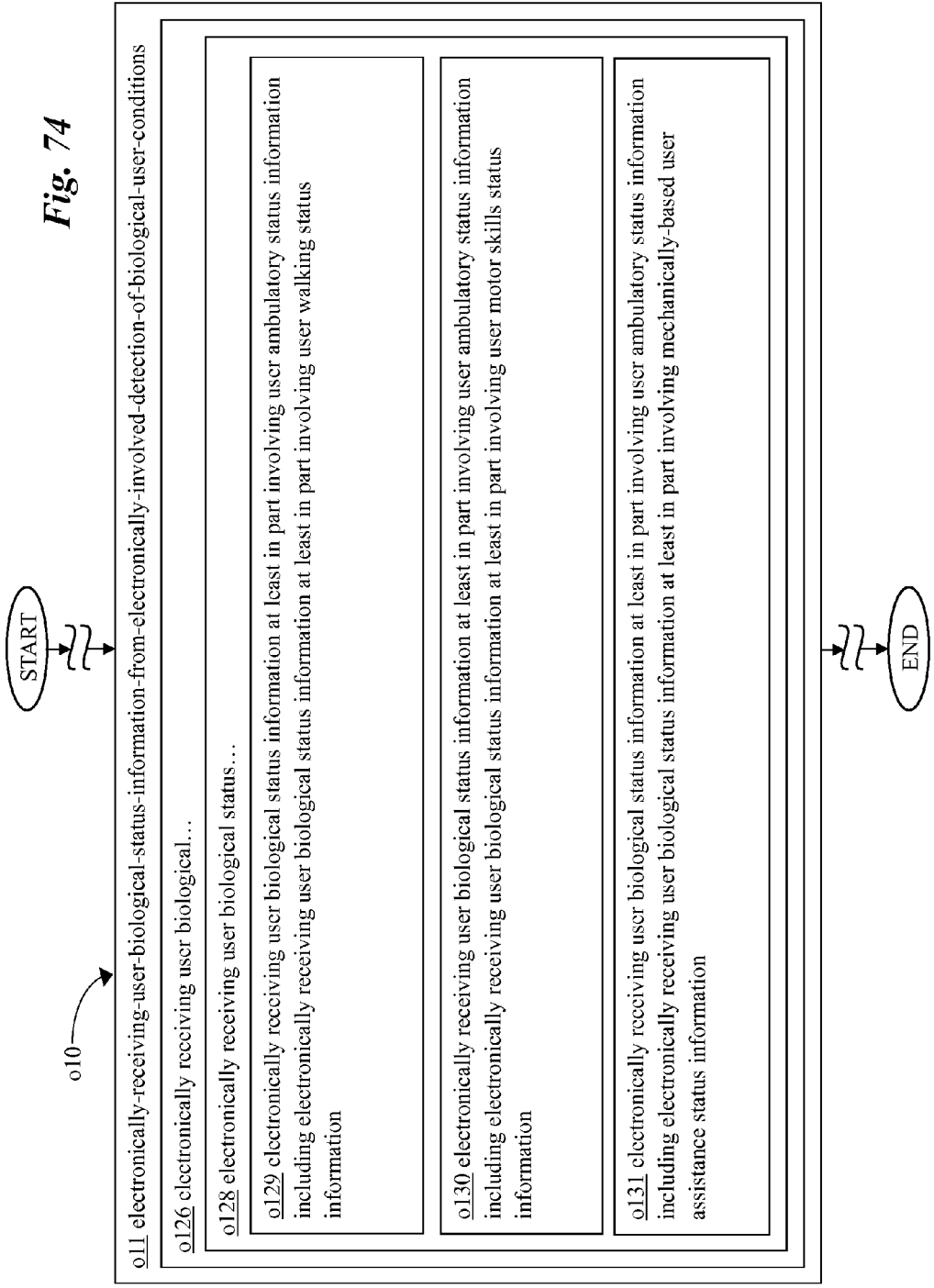

In one or more implementations, as shown in FIG. 74, the operation o128 can include operation o129 for electronically receiving user biological status information at least in part involving user ambulatory status information including electronically receiving user biological status information at least in part involving user walking status information. Origination of a physically tangible component group can be accomplished through skilled in the art design choice selection including use of one or more components and/or subsystems explicitly and/or implicitly referred to herein for at least in part implementing execution of one or more instructions of the operation o129, for performance of the operation o129 by an electrical circuitry arrangement as activated thereto, and/or otherwise fulfillment of the operation o129. One or more non-transitory signal bearing physical media can bear the one or more instructions that when executed can direct performance of the operation o129. Furthermore, electronically-receiving-user-biological-status-information-user-walking-status-information module m129 depicted in FIG. 15 as being included in the module m128, when executed and/or activated, can direct performance of and/or perform the operation o129. Illustratively, in one or more implementations, the operation o129 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user ambulatory status information (e.g. receiving historical or current ambulatory status information such as ambulatory functional status records of walking, running, climbing, using a wheelchair, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user walking status information (e.g. receiving historical or current walking status information such as distance, duration, timing, elevation change, gate length, geographical region, environmental, climate, gaps between, use of mechanical assistant devices, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 74, the operation o128 can include operation o130 for electronically receiving user biological status information at least in part involving user ambulatory status information including electronically receiving user biological status information at least in part involving user motor skills status information. Origination of a physically tangible component group can be accomplished through skilled in the art design choice selection including use of one or more components and/or subsystems explicitly and/or implicitly referred to herein for at least in part implementing execution of one or more instructions of the operation o130, for performance of the operation o130 by an electrical circuitry arrangement as activated thereto, and/or otherwise fulfillment of the operation o130. One or more non-transitory signal bearing physical media can bear the one or more instructions that when executed can direct performance of the operation o130. Furthermore, electronically-receiving-user-biological-status-information-user-motor-skills-status-information module m130 depicted in FIG. 15 as being included in the module m128, when executed and/or activated, can direct performance of and/or perform the operation o130. Illustratively, in one or more implementations, the operation o130 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user ambulatory status information (e.g. receiving historical or current ambulatory status information such as ambulatory functional status records of walking, running, climbing, using a wheelchair, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user motor skills status information (e.g. receiving historical or current motor skills status information such as data regarding eye-hand coordination, distribution of weight in standing, walking, sitting, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 74, the operation o128 can include operation o131 for electronically receiving user biological status information at least in part involving user ambulatory status information including electronically receiving user biological status information at least in part involving mechanically-based user assistance status information. Origination of a physically tangible component group can be accomplished through skilled in the art design choice selection including use of one or more components and/or subsystems explicitly and/or implicitly referred to herein for at least in part implementing execution of one or more instructions of the operation o131, for performance of the operation o131 by an electrical circuitry arrangement as activated thereto, and/or otherwise fulfillment of the operation o131. One or more non-transitory signal bearing physical media can bear the one or more instructions that when executed can direct performance of the operation o131. Furthermore, electronically-receiving-user-biological-status-information-mechanically-based-user-assistance-status-information module m131 depicted in FIG. 15 as being included in the module m128, when executed and/or activated, can direct performance of and/or perform the operation o131. Illustratively, in one or more implementations, the operation o131 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user ambulatory status information (e.g. receiving historical or current ambulatory status information such as ambulatory functional status records of walking, running, climbing, using a wheelchair, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving mechanically-based user assistance status information (e.g. receiving historical or current mechanically-based user assistance status information such as amount of time spent using mechanically-based user assistance, amount of time spent without assistance in similar activities, change in amount or degree of mechanically-based user assistance, etc. regarding wheelchair use, cane use, walker use, grabbing device use, manipulation device use, transporter device use, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 73, the operation o126 can include operation o132 for electronically receiving user biological status information at least in part involving user functional status information including electronically receiving user biological status information at least in part involving user performance status information. Origination of a physically tangible component group can be accomplished through skilled in the art design choice selection including use of one or more components and/or subsystems explicitly and/or implicitly referred to herein for at least in part implementing execution of one or more instructions of the operation o132, for performance of the operation o132 by an electrical circuitry arrangement as activated thereto, and/or otherwise fulfillment of the operation o132. One or more non-transitory signal bearing physical media can bear the one or more instructions that when executed can direct performance of the operation o132. Furthermore, electronically-receiving-user-biological-status-information-user-performance-status-information module m132 depicted in FIG. 14 as being included in the module m126, when executed and/or activated, can direct performance of and/or perform the operation o132. Illustratively, in one or more implementations, the operation o132 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user functional status information (e.g. receiving historical or current functional status information such as ambulatory functional status records of walking, running, climbing, sleeping, housework, educational, musical, athletic, recreational, vocational, etc. functional performance, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 75:
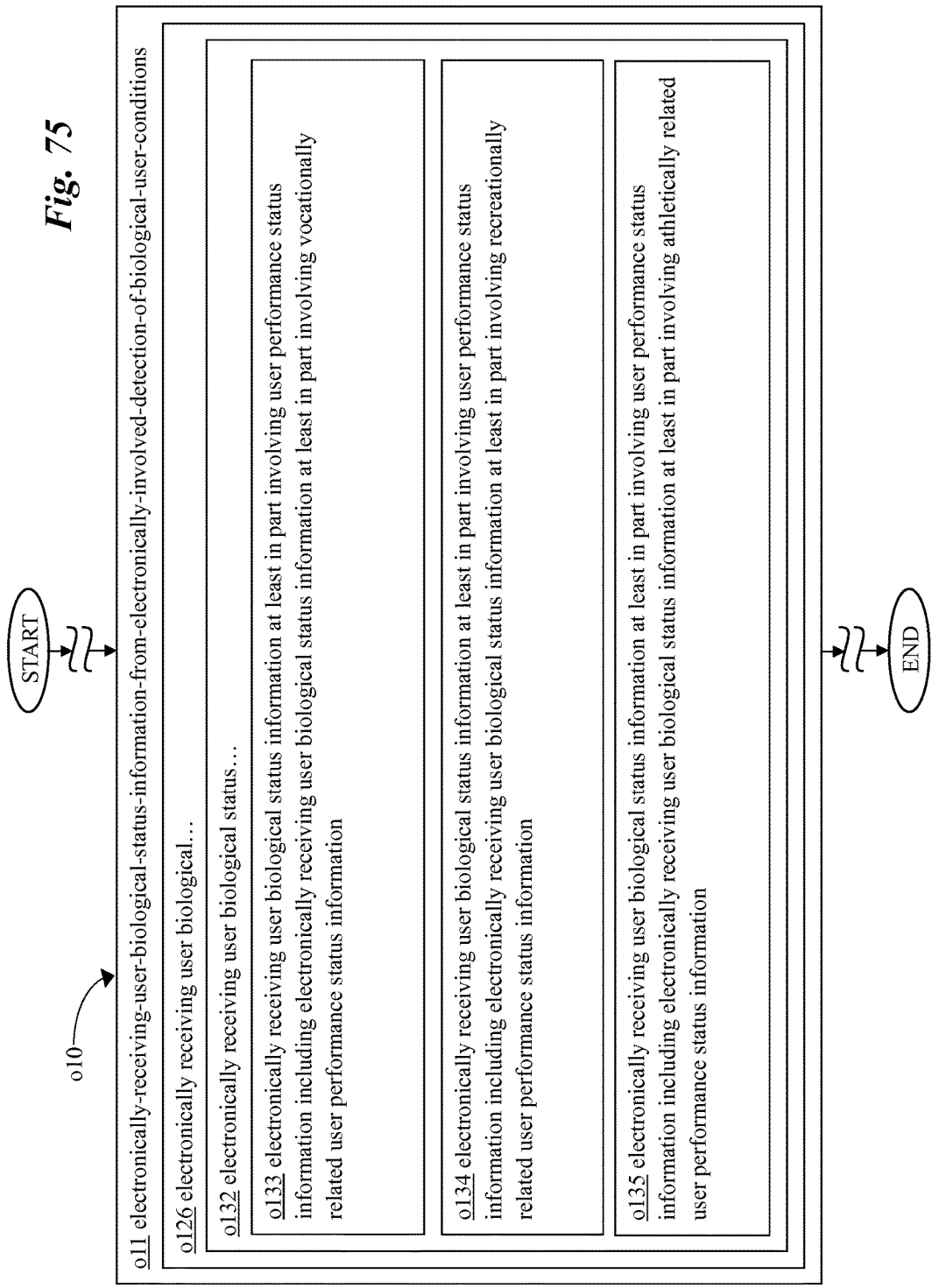

In one or more implementations, as shown in FIG. 75, the operation o132 can include operation o133 for electronically receiving user biological status information at least in part involving user performance status information including electronically receiving user biological status information at least in part involving vocationally related user performance status information. Origination of a physically tangible component group can be accomplished through skilled in the art design choice selection including use of one or more components and/or subsystems explicitly and/or implicitly referred to herein for at least in part implementing execution of one or more instructions of the operation o133, for performance of the operation o133 by an electrical circuitry arrangement as activated thereto, and/or otherwise fulfillment of the operation o133. One or more non-transitory signal bearing physical media can bear the one or more instructions that when executed can direct performance of the operation o133. Furthermore, electronically-receiving-user-biological-status-information-vocationally-related-user-performance-status-information module m133 depicted in FIG. 16 as being included in the module m132, when executed and/or activated, can direct performance of and/or perform the operation o133. Illustratively, in one or more implementations, the operation o133 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving vocationally related user performance status information (e.g. such as number of hours worked per week or other time period, amount of defined type of work produced, amount of income brought into company such as through sales, number of customers served, changes in income levels, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 75, the operation o132 can include operation o134 for electronically receiving user biological status information at least in part involving user performance status information including electronically receiving user biological status information at least in part involving recreationally related user performance status information. Origination of a physically tangible component group can be accomplished through skilled in the art design choice selection including use of one or more components and/or subsystems explicitly and/or implicitly referred to herein for at least in part implementing execution of one or more instructions of the operation o134, for performance of the operation o134 by an electrical circuitry arrangement as activated thereto, and/or otherwise fulfillment of the operation o134. One or more non-transitory signal bearing physical media can bear the one or more instructions that when executed can direct performance of the operation o134. Furthermore, electronically-receiving-user-biological-status-information-user-performance-status-information-including-electronically-receiving-user-biological-status-information-recreationally-related-user-performance-status- information module m134 depicted in FIG. 16 as being included in the module m132, when executed and/or activated, can direct performance of and/or perform the operation o134. Illustratively, in one or more implementations, the operation o134 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving recreationally related user performance status information (e.g. receiving historical or current recreationally related user performance status information such as hours spent on family outings, number of vacation trips taken, amount of time spent with particular individuals such as family members, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 75, the operation o132 can include operation o135 for electronically receiving user biological status information at least in part involving user performance status information including electronically receiving user biological status information at least in part involving athletically related user performance status information. Origination of a physically tangible component group can be accomplished through skilled in the art design choice selection including use of one or more components and/or subsystems explicitly and/or implicitly referred to herein for at least in part implementing execution of one or more instructions of the operation o135, for performance of the operation o135 by an electrical circuitry arrangement as activated thereto, and/or otherwise fulfillment of the operation o135. One or more non-transitory signal bearing physical media can bear the one or more instructions that when executed can direct performance of the operation o135. Furthermore, electronically-receiving-user-biological-status-information-user-performance-status-information-including-electronically-receiving-user-biological-status-information-athletically-related-user-performance-status- information module m135 depicted in FIG. 16 as being included in the module m132, when executed and/or activated, can direct performance of and/or perform the operation o135. Illustratively, in one or more implementations, the operation o135 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving athletically related user performance status information (e.g. such as number of hours worked per week or other time period, amount of defined type of work produced, amount of income brought into company such as through sales, number of customers served, changes in income levels, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 76:
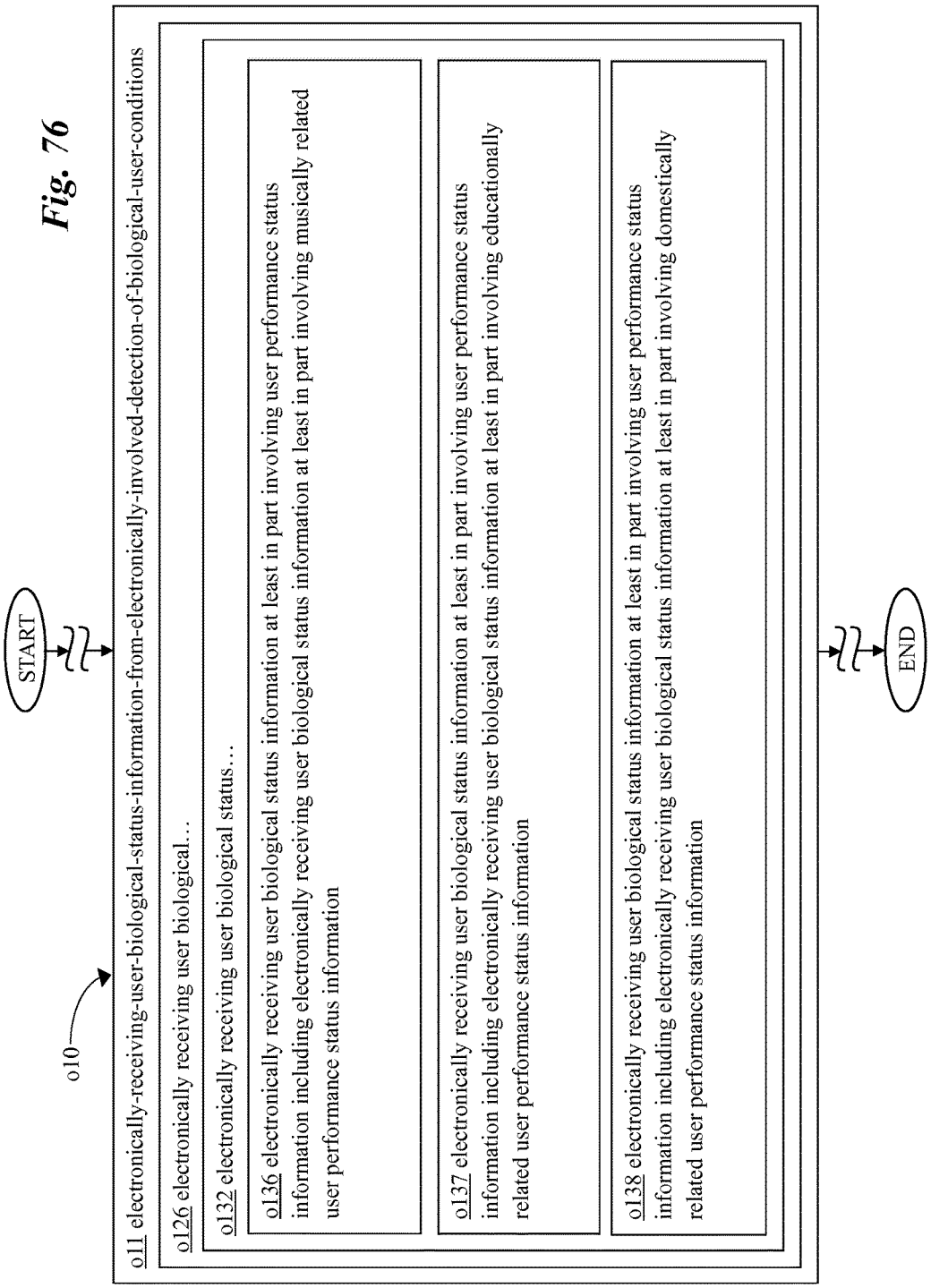

In one or more implementations, as shown in FIG. 76, the operation o132 can include operation o136 for electronically receiving user biological status information at least in part involving user performance status information including electronically receiving user biological status information at least in part involving musically related user performance status information. Origination of a physically tangible component group can be accomplished through skilled in the art design choice selection including use of one or more components and/or subsystems explicitly and/or implicitly referred to herein for at least in part implementing execution of one or more instructions of the operation o136, for performance of the operation o136 by an electrical circuitry arrangement as activated thereto, and/or otherwise fulfillment of the operation o136. One or more non-transitory signal bearing physical media can bear the one or more instructions that when executed can direct performance of the operation o136. Furthermore, electronically-receiving-user-biological-status-information-user-performance-status-information-including-electronically-receiving-user-biological-status-information-musically-related-user-performance-status- information module m136 depicted in FIG. 17 as being included in the module m132, when executed and/or activated, can direct performance of and/or perform the operation o136. Illustratively, in one or more implementations, the operation o136 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving musically related user performance status information (e.g. receiving historical or current musically related user performance status information such as data regarding amount of time spent practicing particular sections of a song, data regarding note accuracy, adherence to goals regarding tempo, articulation, phrasing, dynamics, etc. for instrumental or vocal performance of one or more portions of music, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 76, the operation o132 can include operation o137 for electronically receiving user biological status information at least in part involving user performance status information including electronically receiving user biological status information at least in part involving educationally related user performance status information. Origination of a physically tangible component group can be accomplished through skilled in the art design choice selection including use of one or more components and/or subsystems explicitly and/or implicitly referred to herein for at least in part implementing execution of one or more instructions of the operation o137, for performance of the operation o137 by an electrical circuitry arrangement as activated thereto, and/or otherwise fulfillment of the operation o137. One or more non-transitory signal bearing physical media can bear the one or more instructions that when executed can direct performance of the operation o137. Furthermore, electronically-receiving-user-biological-status-information-educationally-related-user-performance-status-information module m137 depicted in FIG. 17 as being included in the module m132, when executed and/or activated, can direct performance of and/or perform the operation o137. Illustratively, in one or more implementations, the operation o137 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving educationally related user performance status information (e.g. such as grades achieved, degrees earned, number of courses taken per period, degree of difficulty of classes, weekly class load, number of tests or papers scheduled in a period, number of outbursts in classroom, number of truancies per period, amount of extracurricular activity, progress rate in learning, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 76, the operation o132 can include operation o138 for electronically receiving user biological status information at least in part involving user performance status information including electronically receiving user biological status information at least in part involving domestically related user performance status information. Origination of a physically tangible component group can be accomplished through skilled in the art design choice selection including use of one or more components and/or subsystems explicitly and/or implicitly referred to herein for at least in part implementing execution of one or more instructions of the operation o138, for performance of the operation o138 by an electrical circuitry arrangement as activated thereto, and/or otherwise fulfillment of the operation o138. One or more non-transitory signal bearing physical media can bear the one or more instructions that when executed can direct performance of the operation o138. Furthermore, electronically-receiving-user-biological-status-information-domestically-related-user-performance-status-information module m138 depicted in FIG. 17 as being included in the module m132, when executed and/or activated, can direct performance of and/or perform the operation o138. Illustratively, in one or more implementations, the operation o138 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user performance status information (e.g. receiving historical or current user performance status information such as data regarding amount of sales made on job, school grades, number of trips taken, hours spent practicing a skill, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving domestically related user performance status information (e.g. receiving historical or current domestically related user performance status information regarding decibel levels of conversation, amount of time household occupants converse with each other, amount of time family members spend time with each other, activities that family members spend time with each other, positional data regarding various family members locations through the day, week, or longer, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 77:
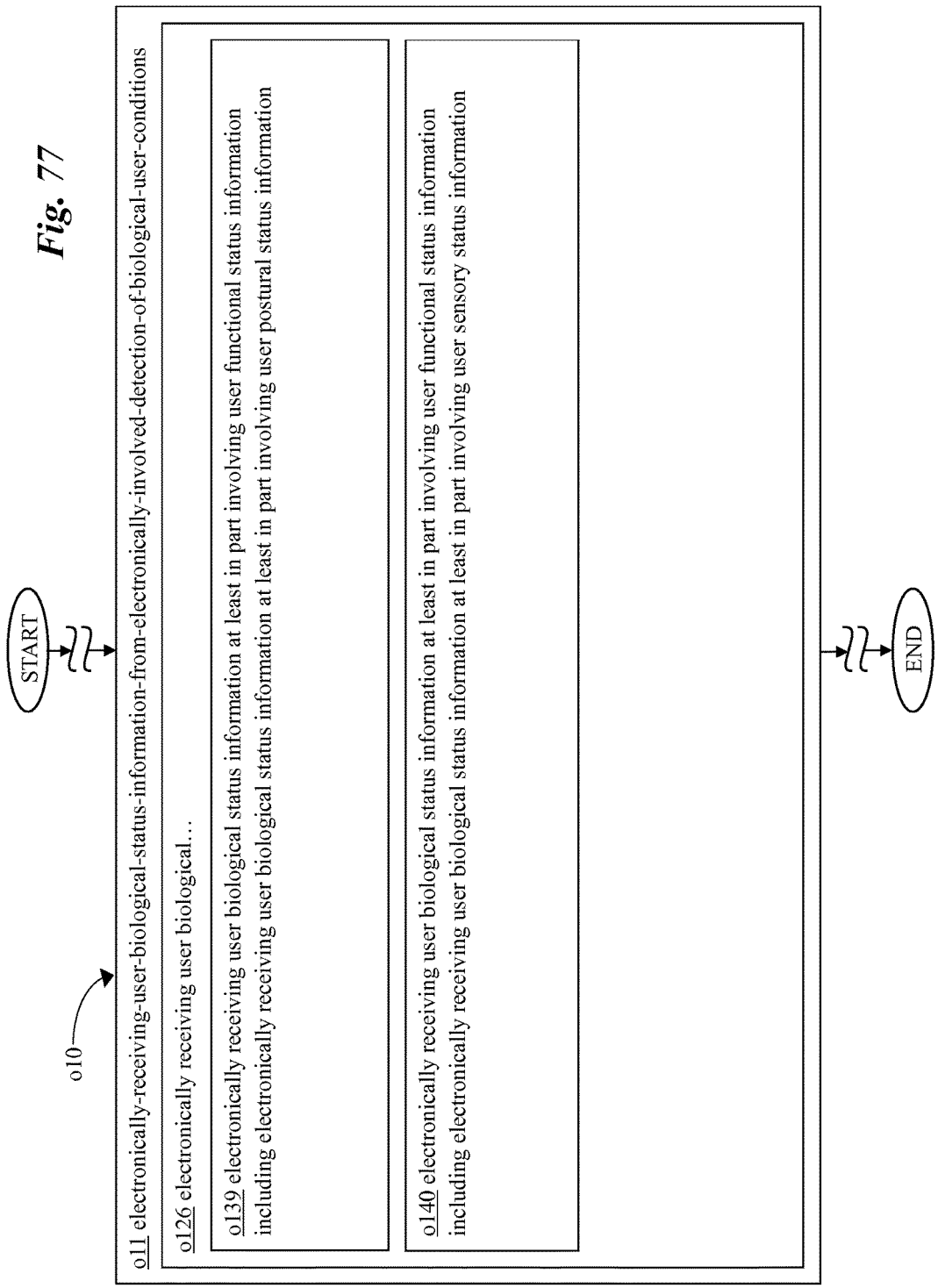

In one or more implementations, as shown in FIG. 77, the operation o126 can include operation o139 for electronically receiving user biological status information at least in part involving user functional status information including electronically receiving user biological status information at least in part involving user postural status information. Origination of a physically tangible component group can be accomplished through skilled in the art design choice selection including use of one or more components and/or subsystems explicitly and/or implicitly referred to herein for at least in part implementing execution of one or more instructions of the operation o139, for performance of the operation o139 by an electrical circuitry arrangement as activated thereto, and/or otherwise fulfillment of the operation o139. One or more non-transitory signal bearing physical media can bear the one or more instructions that when executed can direct performance of the operation o139. Furthermore, electronically-receiving-user-biological-status-information-user-postural-status-information module m139 depicted in FIG. 18 as being included in the module m126, when executed and/or activated, can direct performance of and/or perform the operation o139. Illustratively, in one or more implementations, the operation o139 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user functional status information (e.g. receiving historical or current functional status information such as ambulatory functional status records of walking, running, climbing, sleeping, housework, educational, musical, athletic, recreational, vocational, etc. functional performance, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user postural status information (e.g. such as amount of time spent sitting between periods of movement out of chair, posture expressed in sitting, walking, standing, lying, driving, office work, manual labor, recreating, athletics, in relation to furniture, equipment, fixtures, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 77, the operation o126 can include operation o140 for electronically receiving user biological status information at least in part involving user functional status information including electronically receiving user biological status information at least in part involving user sensory status information. Origination of a physically tangible component group can be accomplished through skilled in the art design choice selection including use of one or more components and/or subsystems explicitly and/or implicitly referred to herein for at least in part implementing execution of one or more instructions of the operation o140, for performance of the operation o140 by an electrical circuitry arrangement as activated thereto, and/or otherwise fulfillment of the operation o140. One or more non-transitory signal bearing physical media can bear the one or more instructions that when executed can direct performance of the operation o140. Furthermore, electronically-receiving-user-biological-status-information-user-sensory-status-information module m140 depicted in FIG. 18 as being included in the module m126, when executed and/or activated, can direct performance of and/or perform the operation o140. Illustratively, in one or more implementations, the operation o140 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user functional status information (e.g. receiving historical or current functional status information such as ambulatory functional status records of walking, running, climbing, sleeping, housework, educational, musical, athletic, recreational, vocational, etc. functional performance, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user sensory status information (e.g. receiving historical or current sensory status information such as data regarding acuity, sensitivity, or other parameters in hearing or eyesight, touch, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 78:
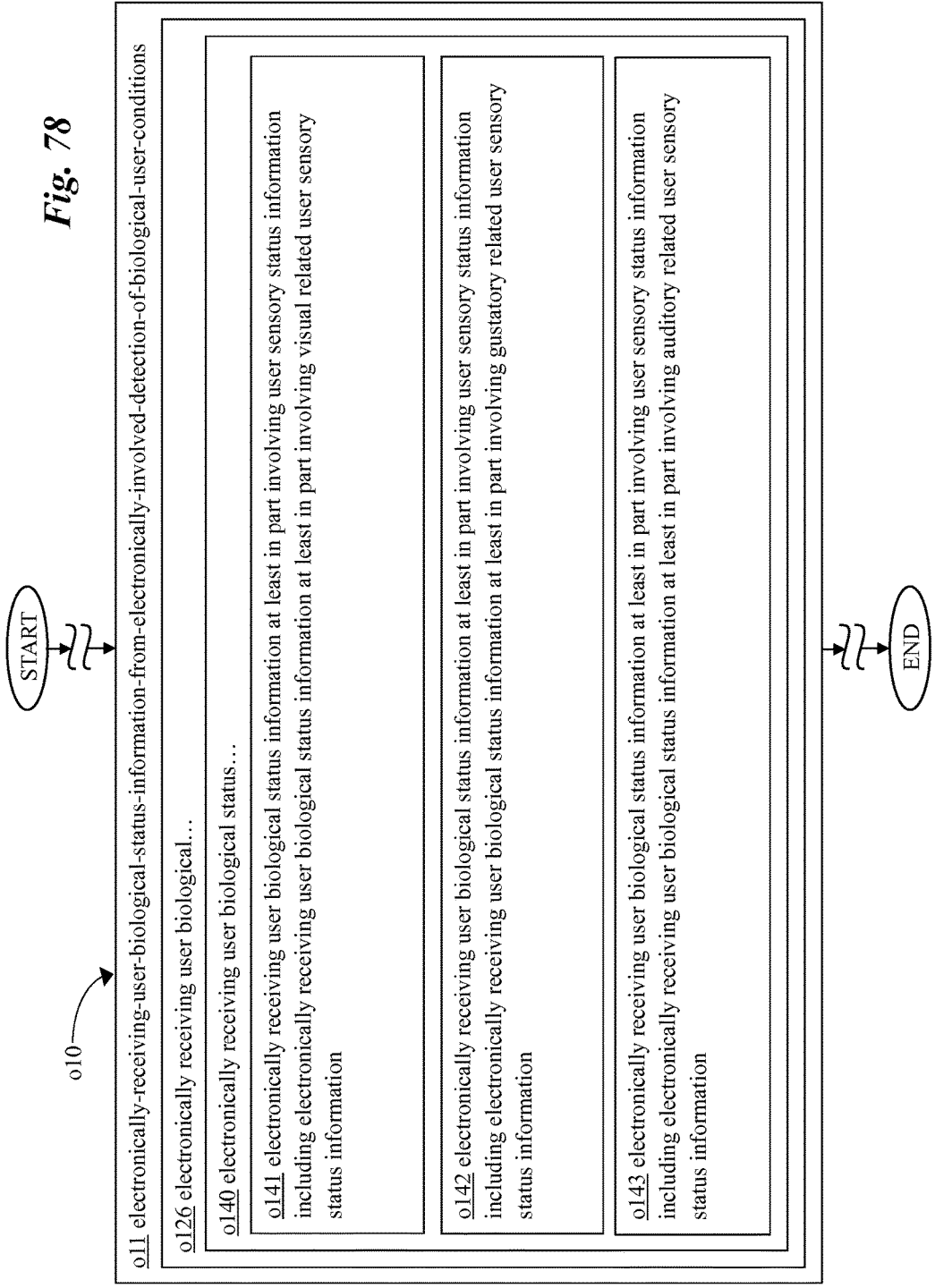

In one or more implementations, as shown in FIG. 78, the operation o140 can include operation o141 for electronically receiving user biological status information at least in part involving user sensory status information including electronically receiving user biological status information at least in part involving visual related user sensory status information. Origination of a physically tangible component group can be accomplished through skilled in the art design choice selection including use of one or more components and/or subsystems explicitly and/or implicitly referred to herein for at least in part implementing execution of one or more instructions of the operation o141, for performance of the operation o141 by an electrical circuitry arrangement as activated thereto, and/or otherwise fulfillment of the operation o141. One or more non-transitory signal bearing physical media can bear the one or more instructions that when executed can direct performance of the operation o141. Furthermore, electronically-receiving-user-biological-status-information-visual-related-user-sensory-status-information module m141 depicted in FIG. 19 as being included in the module m140, when executed and/or activated, can direct performance of and/or perform the operation o141. Illustratively, in one or more implementations, the operation o141 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user sensory status information (e.g. receiving historical or current sensory status information such as data regarding acuity, sensitivity, or other parameters in hearing or eyesight, touch, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving visual related user sensory status information (e.g. such as time spent with various visual environments such as monitors or other displays, reading books, driving, relaxing, outdoor activities, concentration, eyewear used at various times, corrective surgery or other surgical procedures performed or anticipated, infections involved, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, theater, school, hospital, park, restaurant, food court, etc. from a data collection device worn by a person or located elsewhere such as furniture, building fixtures, etc.).

In one or more implementations, as shown in FIG. 78, the operation o140 can include operation o142 for electronically receiving user biological status information at least in part involving user sensory status information including electronically receiving user biological status information at least in part involving gustatory related user sensory status information. Origination of a physically tangible component group can be accomplished through skilled in the art design choice selection including use of one or more components and/or subsystems explicitly and/or implicitly referred to herein for at least in part implementing execution of one or more instructions of the operation o142, for performance of the operation o142 by an electrical circuitry arrangement as activated thereto, and/or otherwise fulfillment of the operation o142. One or more non-transitory signal bearing physical media can bear the one or more instructions that when executed can direct performance of the operation o142. Furthermore, electronically-receiving-user-biological-status-information-gustatory-related-user-sensory-status-information module m142 depicted in FIG. 19 as being included in the module m140, when executed and/or activated, can direct performance of and/or perform the operation o142. Illustratively, in one or more implementations, the operation o142 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user sensory status information (e.g. receiving historical or current sensory status information such as data regarding acuity, sensitivity, or other parameters in hearing or eyesight, touch, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving gustatory related user sensory status information (e.g. receiving historical or current gustatory status information such as data regarding amount of salt, sugar, or taste modifiers, etc. typically used, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 78, the operation o140 can include operation o143 for electronically receiving user biological status information at least in part involving user sensory status information including electronically receiving user biological status information at least in part involving auditory related user sensory status information. Origination of a physically tangible component group can be accomplished through skilled in the art design choice selection including use of one or more components and/or subsystems explicitly and/or implicitly referred to herein for at least in part implementing execution of one or more instructions of the operation o143, for performance of the operation o143 by an electrical circuitry arrangement as activated thereto, and/or otherwise fulfillment of the operation o143. One or more non-transitory signal bearing physical media can bear the one or more instructions that when executed can direct performance of the operation o143. Furthermore, electronically-receiving-user-biological-status-information-auditory-related-user-sensory-status-information module m143 depicted in FIG. 19 as being included in the module m140, when executed and/or activated, can direct performance of and/or perform the operation o143. Illustratively, in one or more implementations, the operation o143 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user sensory status information (e.g. receiving historical or current sensory status information such as data regarding acuity, sensitivity, or other parameters in hearing or eyesight, touch, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving auditory related user sensory status information (e.g. such as decibel level exposure in various audio environments, accustomed audio levels in hearing speech, audio devices such as computer, phone, radio, etc. infections involved, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures).

In one or more implementations, as shown in FIG. 72, the operation o11 can include operation o144 for electronically receiving user biological status information from electronically involved detection of one or more biological user conditions including electronically receiving user biological status information at least in part involving user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o144, for performance of the operation o144 by an electrical circuitry arrangement as activated thereto, and/or otherwise fulfillment of the operation o144. One or more non-transitory signal bearing physical media can bear the one or more instructions that when executed can direct performance of the operation o144. Furthermore, electronically-receiving-user-biological-status-information-user-behavioral-life-data module m144 depicted in FIG. 13 as being included in the module m11, when executed and/or activated, can direct performance of and/or perform the operation o144. Illustratively, in one or more implementations, the operation o144 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 79:
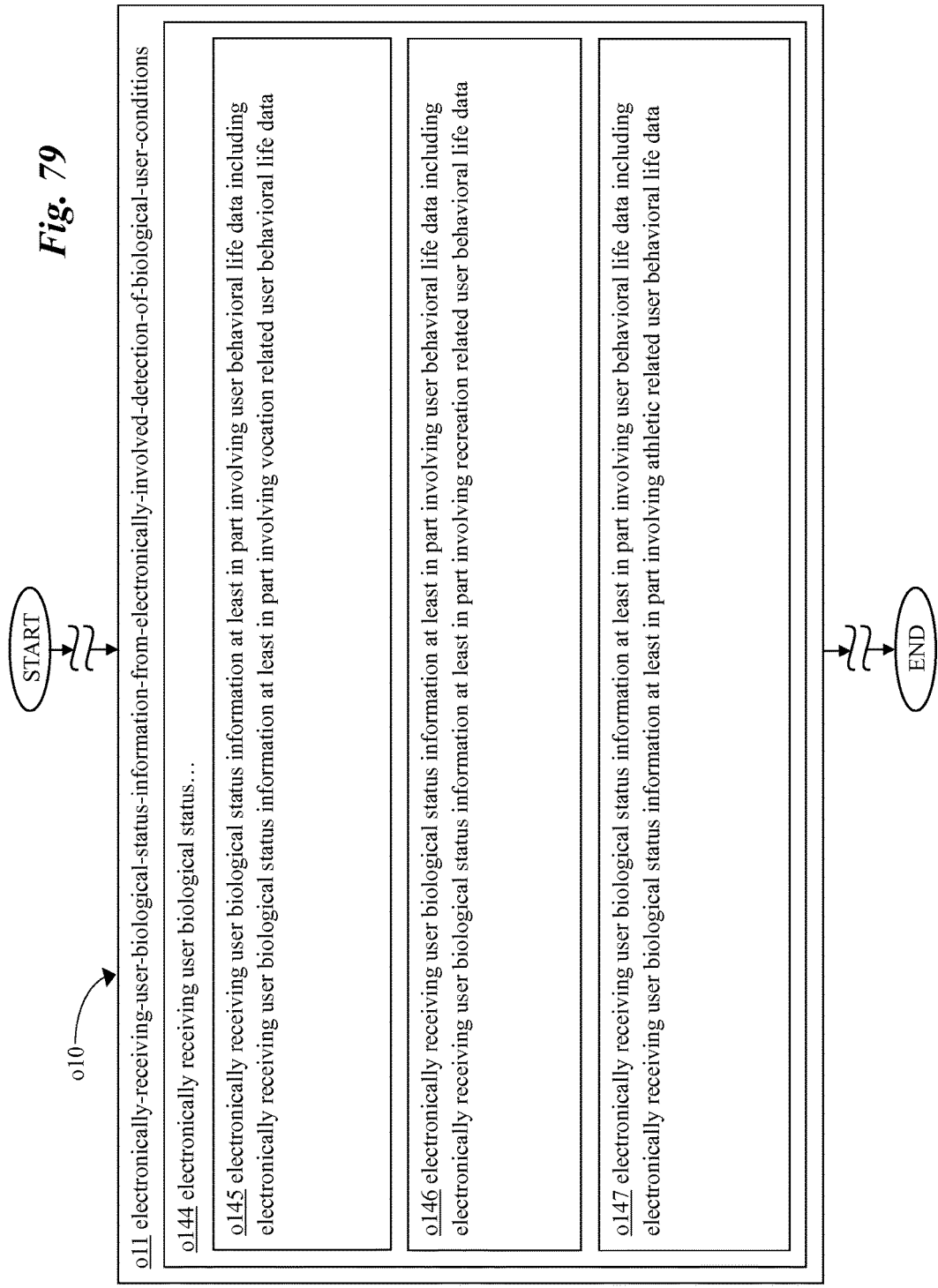

In one or more implementations, as shown in FIG. 79, the operation o144 can include operation o145 for electronically receiving user biological status information at least in part involving user behavioral life data including electronically receiving user biological status information at least in part involving vocation related user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o145, for performance of the operation o145 by an electrical circuitry arrangement as activated thereto, and/or otherwise fulfillment of the operation o145. One or more non-transitory signal bearing physical media can bear the one or more instructions that when executed can direct performance of the operation o145. Furthermore, electronically-receiving-user-biological-status-information-vocation-related-user-behavioral-life-data module m145 depicted in FIG. 20 as being included in the module m144, when executed and/or activated, can direct performance of and/or perform the operation o145. Illustratively, in one or more implementations, the operation o145 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving vocation related user behavioral life data (e.g. such as attendance periods at vocation, vocational stress levels, vocational advancement levels, number of business trips taken, duration of business trips, commuting hours expended, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 79, the operation o144 can include operation o146 for electronically receiving user biological status information at least in part involving user behavioral life data including electronically receiving user biological status information at least in part involving recreation related user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o146, for performance of the operation o146 by an electrical circuitry arrangement as activated thereto, and/or otherwise fulfillment of the operation o146. One or more non-transitory signal bearing physical media can bear the one or more instructions that when executed can direct performance of the operation o146. Furthermore, electronically-receiving-user-biological-status-information-recreation-related-user-behavioral-life-data module m146 depicted in FIG. 20 as being included in the module m144, when executed and/or activated, can direct performance of and/or perform the operation o146. Illustratively, in one or more implementations, the operation o146 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving recreation related user behavioral life data (e.g. receiving historical or current recreation related user behavioral life data such as data regarding desired or undesirable behavior of individual, family member, employee recreation activities such as vacation, hobbies, etc. regarding such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 79, the operation o144 can include operation o147 for electronically receiving user biological status information at least in part involving user behavioral life data including electronically receiving user biological status information at least in part involving athletic related user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o147, for performance of the operation o147 by an electrical circuitry arrangement as activated thereto, and/or otherwise fulfillment of the operation o147. One or more non-transitory signal bearing physical media can bear the one or more instructions that when executed can direct performance of the operation o147. Furthermore, electronically-receiving-user-biological-status-information-athletic-related-user-behavioral-life-data module m147 depicted in FIG. 20 as being included in the module m144, when executed and/or activated, can direct performance of and/or perform the operation o147. Illustratively, in one or more implementations, the operation o147 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving athletic related user behavioral life data (e.g. such as number of points scored, number of assists executed, duration or scheduling of training or games, accomplishments, recovery ability, days of rest, type of sport(s), current part of season, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 80:
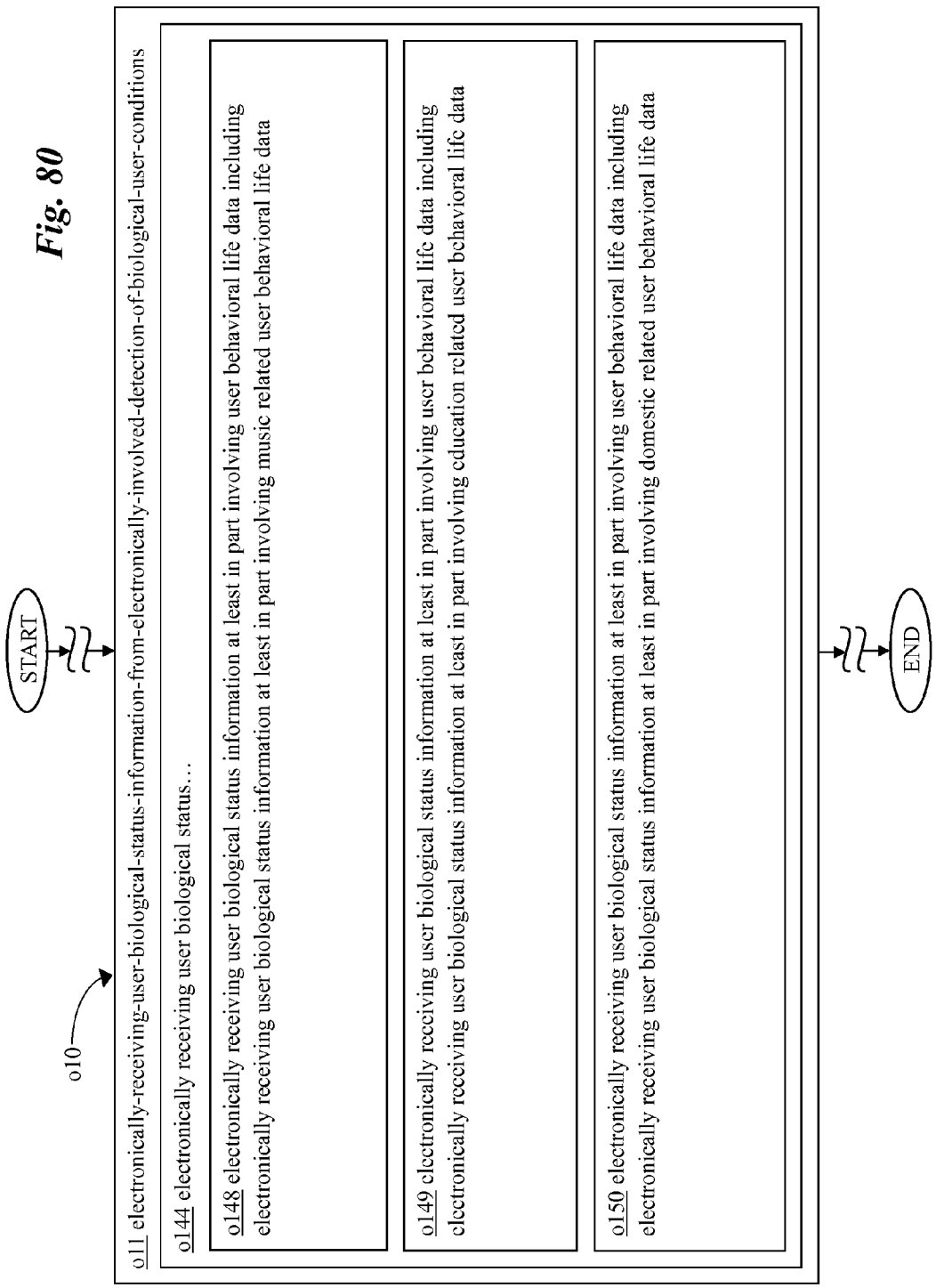

In one or more implementations, as shown in FIG. 80, the operation o144 can include operation o148 for electronically receiving user biological status information at least in part involving user behavioral life data including electronically receiving user biological status information at least in part involving music related user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o148, for performance of the operation o148 by an electrical circuitry arrangement as activated thereto, and/or otherwise fulfillment of the operation o148. One or more non-transitory signal bearing physical media can bear the one or more instructions that when executed can direct performance of the operation o148. Furthermore, electronically-receiving-user-biological-status-information-music-related-user-behavioral-life-data module m148 depicted in FIG. 21 as being included in the module m144, when executed and/or activated, can direct performance of and/or perform the operation o148. Illustratively, in one or more implementations, the operation o148 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving music related user behavioral life data (e.g. receiving historical or current music related user behavioral life data such as data regarding desired or undesirable behavior of individual, family member, groups in music lessons, performances, such as words, phrases, verbalization, body language, practicing habits, instrumental or vocal technique, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 80, the operation o144 can include operation o149 for electronically receiving user biological status information at least in part involving user behavioral life data including electronically receiving user biological status information at least in part involving education related user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o149, for performance of the operation o149 by an electrical circuitry arrangement as activated thereto, and/or otherwise fulfillment of the operation o149. One or more non-transitory signal bearing physical media can bear the one or more instructions that when executed can direct performance of the operation o149. Furthermore, electronically-receiving-user-biological-status-information-education-related-user-behavioral-life-data module m149 depicted in FIG. 21 as being included in the module m144, when executed and/or activated, can direct performance of and/or perform the operation o149. Illustratively, in one or more implementations, the operation o149 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving education related user behavioral life data (e.g. such as time spent or degree of involvement in class, studying, doing homework, extra-curricular activity, encouraged activities, discouraged activities, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 80, the operation o144 can include operation o150 for electronically receiving user biological status information at least in part involving user behavioral life data including electronically receiving user biological status information at least in part involving domestic related user behavioral life data. Origination of a physically tangible component group can be accomplished through skilled in the art design choice selection including use of one or more components and/or subsystems explicitly and/or implicitly referred to herein for at least in part implementing execution of one or more instructions of the operation o150, for performance of the operation o150 by an electrical circuitry arrangement as activated thereto, and/or otherwise fulfillment of the operation o150. One or more non-transitory signal bearing physical media can bear the one or more instructions that when executed can direct performance of the operation o150. Furthermore, electronically-receiving-user-biological-status-information-domestic-related-user-behavioral-life-data module m150 depicted in FIG. 21 as being included in the module m144, when executed and/or activated, can direct performance of and/or perform the operation o150. Illustratively, in one or more implementations, the operation o150 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user behavioral life data (e.g. receiving historical or current user behavioral life data such as data regarding desired or undesirable behavior of individual, family member, organizational member, company employee in groups, family, work setting, school, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving domestic related user behavioral life data (e.g. receiving historical or current domestic related user behavioral life data such as data regarding desired or undesirable behavior of individual, family member, child, parent, etc. in home, family setting, such as words, phrases, verbalization, body language, written products, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 72, the operation o11 can include operation o151 for electronically receiving user biological status information from electronically involved detection of one or more biological user conditions including electronically receiving user biological status information at least in part involving user quantified-self information. Origination of a physically tangible component group can be accomplished through skilled in the art design choice selection including use of one or more components and/or subsystems explicitly and/or implicitly referred to herein for at least in part implementing execution of one or more instructions of the operation o151, for performance of the operation o151 by an electrical circuitry arrangement as activated thereto, and/or otherwise fulfillment of the operation o151. One or more non-transitory signal bearing physical media can bear the one or more instructions that when executed can direct performance of the operation o151. Furthermore, electronically-receiving-user-biological-status-information-user-quantified-self-information module m151 depicted in FIG. 13 as being included in the module m11, when executed and/or activated, can direct performance of and/or perform the operation o151. Illustratively, in one or more implementations, the operation o151 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user quantified-self information (e.g. such as amount, intensity, duration, frequency, etc. involving an activity or measurement of an individual, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 81:
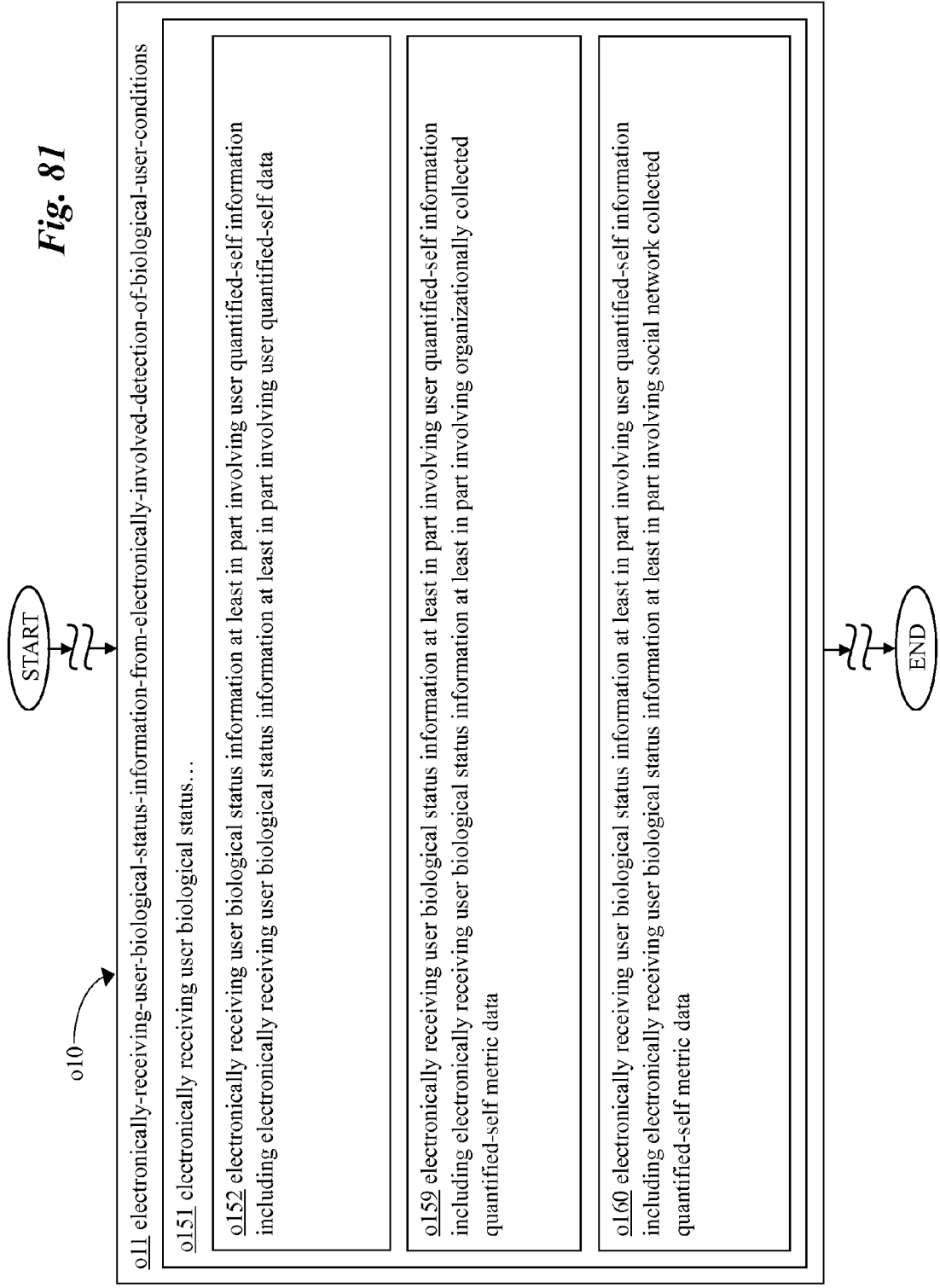

In one or more implementations, as shown in FIG. 81, the operation o151 can include operation o152 for electronically receiving user biological status information at least in part involving user quantified-self information including electronically receiving user biological status information at least in part involving user quantified-self data. Origination of a physically tangible component group can be accomplished through skilled in the art design choice selection including use of one or more components and/or subsystems explicitly and/or implicitly referred to herein for at least in part implementing execution of one or more instructions of the operation o152, for performance of the operation o152 by an electrical circuitry arrangement as activated thereto, and/or otherwise fulfillment of the operation o152. One or more non-transitory signal bearing physical media can bear the one or more instructions that when executed can direct performance of the operation o152. Furthermore, electronically-receiving-user-biological-status-information-user-quantified-self-data-module m152 depicted in FIG. 22 as being included in the module m151, when executed and/or activated, can direct performance of and/or perform the operation o152. Illustratively, in one or more implementations, the operation o152 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user quantified-self information (e.g. such as amount, intensity, duration, frequency, etc. involving an activity or measurement of an individual, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 82:
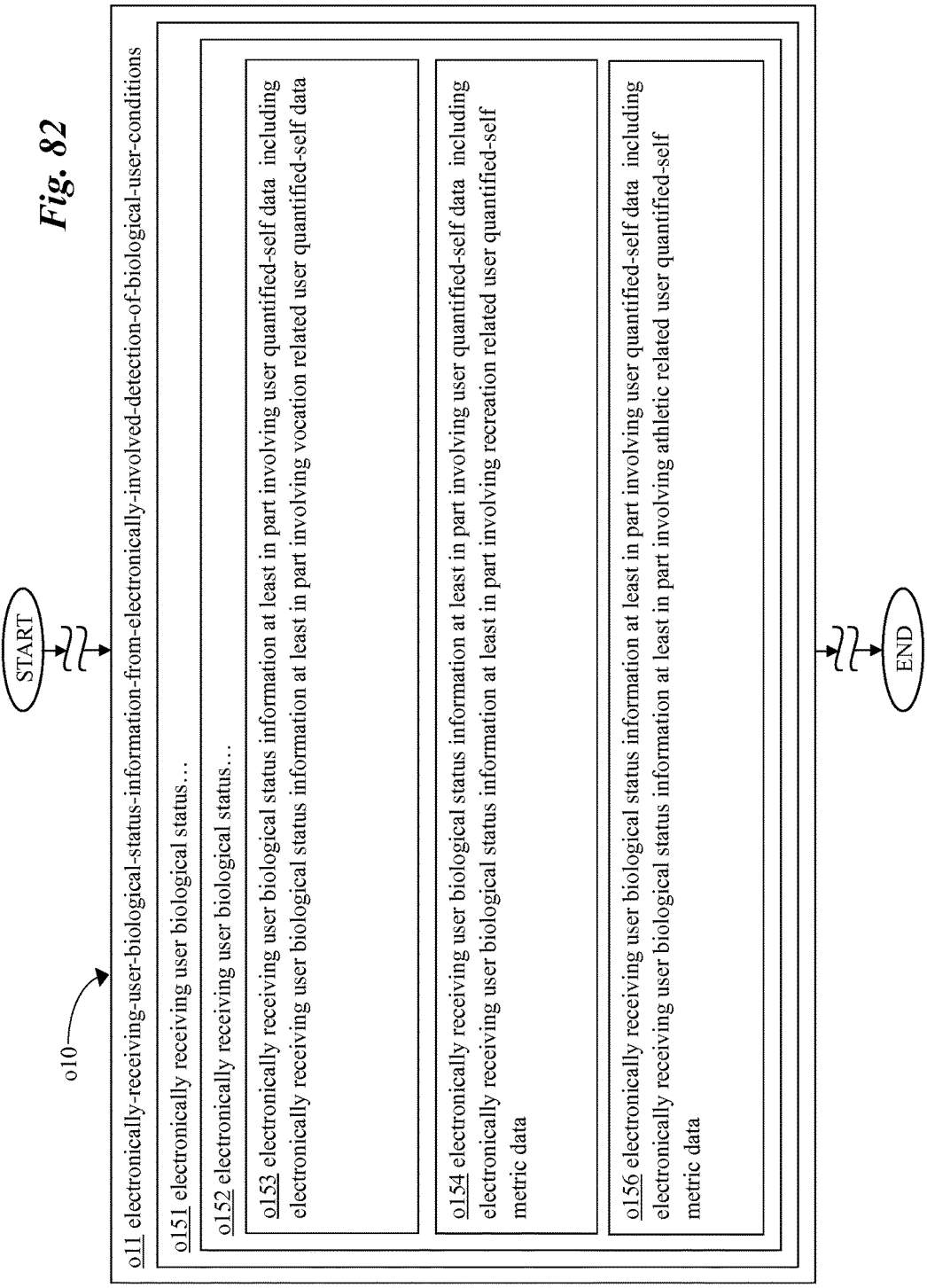

In one or more implementations, as shown in FIG. 82, the operation o152 can include operation o153 for electronically receiving user biological status information at least in part involving user quantified-self data including electronically receiving user biological status information at least in part involving vocation related user quantified-self data. Origination of a physically tangible component group can be accomplished through skilled in the art design choice selection including use of one or more components and/or subsystems explicitly and/or implicitly referred to herein for at least in part implementing execution of one or more instructions of the operation o153, for performance of the operation o153 by an electrical circuitry arrangement as activated thereto, and/or otherwise fulfillment of the operation o153. One or more non-transitory signal bearing physical media can bear the one or more instructions that when executed can direct performance of the operation o153. Furthermore, electronically-receiving-user-biological-status-information-vocation-related-user-quantified-self module m153 depicted in FIG. 23 as being included in the module m152, when executed and/or activated, can direct performance of and/or perform the operation o153. Illustratively, in one or more implementations, the operation o153 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving vocation related user quantified-self data (e.g. such as amount, intensity, duration, frequency, etc. involving an vocational activity or measurement of an individual such as related to a tasks of a job, interaction with workers, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 82, the operation o152 can include operation o154 for electronically receiving user biological status information at least in part involving user quantified-self data including electronically receiving user biological status information at least in part involving recreation related user quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o154, for performance of the operation o154 by an electrical circuitry arrangement as activated thereto, and/or otherwise fulfillment of the operation o154. One or more non-transitory signal bearing physical media can bear the one or more instructions that when executed can direct performance of the operation o154. Furthermore, electronically-receiving-user-biological-status-information-recreation-related-user-quantified-self-metric-data module m154 depicted in FIG. 23 as being included in the module m152, when executed and/or activated, can direct performance of and/or perform the operation o154. Illustratively, in one or more implementations, the operation o154 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving recreation related user quantified-self metric data (e.g. receiving historical or current recreation related user quantified-self data as personal data of an individual collected through wearable or non-wearable sensors as directed or managed by the individual regarding life-style influences such as personal maintenance habits such as eating, social interaction habits, etc. regarding the individual's recreational activities regarding such as hobbies, sports events, vacation, trips, clubs, family outings, family reunions, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 82, the operation o152 can include operation o155 for electronically receiving user biological status information at least in part involving user quantified-self data including electronically receiving user biological status information at least in part involving athletic related user quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o155, for performance of the operation o155 by an electrical circuitry arrangement as activated thereto, and/or otherwise fulfillment of the operation o155. One or more non-transitory signal bearing physical media can bear the one or more instructions that when executed can direct performance of the operation o155. Furthermore, electronically-receiving-user-biological-status-information-athletic-related-user-quantified-self-metric-data module m155 depicted in FIG. 23 as being included in the module m152, when executed and/or activated, can direct performance of and/or perform the operation o155. Illustratively, in one or more implementations, the operation o155 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving athletic related user quantified-self metric data (e.g. such as amount, intensity, duration, frequency, etc. involving an activity or measurement of an individual such as involving training, playing a game, practicing, interaction with team mates or opponents, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 83:
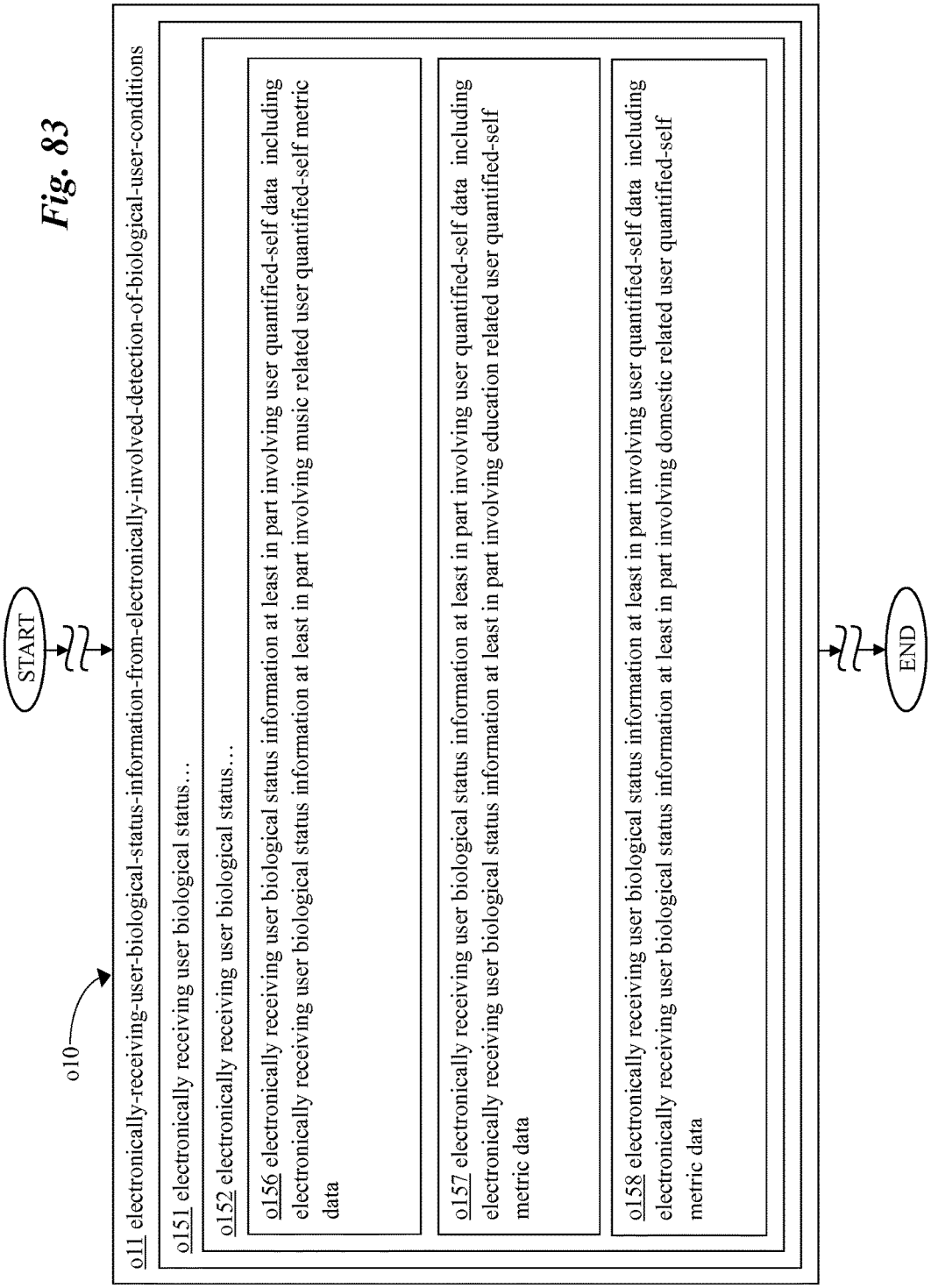

In one or more implementations, as shown in FIG. 83, the operation o152 can include operation o156 for electronically receiving user biological status information at least in part involving user quantified-self data including electronically receiving user biological status information at least in part involving music related user quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o156, for performance of the operation o156 by an electrical circuitry arrangement as activated thereto, and/or otherwise fulfillment of the operation o156. One or more non-transitory signal bearing physical media can bear the one or more instructions that when executed can direct performance of the operation o156. Furthermore, electronically-receiving-user-biological-status-information-music-related-user-quantified-self-metric-data module m156 depicted in FIG. 24 as being included in the module m152, when executed and/or activated, can direct performance of and/or perform the operation o156. Illustratively, in one or more implementations, the operation o156 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving music related user quantified-self metric data (e.g. receiving historical or current recreation related user quantified-self data as personal data of an individual collected through wearable or non-wearable sensors as directed or managed by the individual regarding life-style influences such as personal practicing, listening, performing, etc. habits such as instrumental playing, singing, composing, listening, social interaction habits, etc. regarding the individual's music activities of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 83, the operation o152 can include operation o157 for electronically receiving user biological status information at least in part involving user quantified-self data including electronically receiving user biological status information at least in part involving education related user quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o157, for performance of the operation o157 by an electrical circuitry arrangement as activated thereto, and/or otherwise fulfillment of the operation o157. One or more non-transitory signal bearing physical media can bear the one or more instructions that when executed can direct performance of the operation o157. Furthermore, electronically-receiving-user-biological-status-information-education-related-user-quantified-self-metric-data module m157 depicted in FIG. 24 as being included in the module m152, when executed and/or activated, can direct performance of and/or perform the operation o157. Illustratively, in one or more implementations, the operation o157 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving education related user quantified-self metric data (e.g. such as amount, intensity, duration, frequency, etc. involving an activity or measurement of an individual such as test performance, classroom involvement, interaction with peers, interaction with teachers, extracurricular activity involvement, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 83, the operation o152 can include operation o158 for electronically receiving user biological status information at least in part involving user quantified-self data including electronically receiving user biological status information at least in part involving domestic related user quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o158, for performance of the operation o158 by an electrical circuitry arrangement as activated thereto, and/or otherwise fulfillment of the operation o158. One or more non-transitory signal bearing physical media can bear the one or more instructions that when executed can direct performance of the operation o158. Furthermore, electronically-receiving-user-biological-status-information-domestic-related-user-quantified-self-metric-data module m158 depicted in FIG. 24 as being included in the module m152, when executed and/or activated, can direct performance of and/or perform the operation o158. Illustratively, in one or more implementations, the operation o158 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) at least in part involving user quantified-self data (e.g. receiving historical or current user quantified-self data as personal data of an individual collected through wearable or non-wearable sensors as directed or managed by the individual regarding life-style influences regarding the individual such as eating habits, movement habits, interaction with others, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving domestic related user quantified-self metric data (e.g. receiving historical or current domestic related user quantified-self data as personal data of an individual collected through wearable or non-wearable sensors as directed or managed by the individual regarding life-style influences such as personal maintenance habits such as eating, social interaction habits, etc. regarding the individual's domestic activities regarding such as housework, family activities such as dining, leisure, dialog, spectator activity, yard work, vacations, outings, gatherings, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 81, the operation o151 can include operation o159 for electronically receiving user biological status information at least in part involving user quantified-self information including electronically receiving user biological status information at least in part involving organizationally collected quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o159, for performance of the operation o159 by an electrical circuitry arrangement as activated thereto, and/or otherwise fulfillment of the operation o159. One or more non-transitory signal bearing physical media can bear the one or more instructions that when executed can direct performance of the operation o159. Furthermore, electronically-receiving-user-biological-status-information-organizationally-collected-quantified-self-metric-data module m159 depicted in FIG. 22 as being included in the module m151, when executed and/or activated, can direct performance of and/or perform the operation o159. Illustratively, in one or more implementations, the operation o159 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user quantified-self information (e.g. such as amount, intensity, duration, frequency, etc. involving an activity or measurement of an individual, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving organizationally collected quantified-self metric data (e.g. such as amount, intensity, duration, frequency, etc. involving an activity or measurement of an individual such as involving business group, military company, athletic team, regarding amount of work collectively done, amount of sales collectively achieved, number of games collectively won, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

In one or more implementations, as shown in FIG. 81, the operation o151 can include operation o160 for electronically receiving user biological status information at least in part involving user quantified-self information including electronically receiving user biological status information at least in part involving social network collected quantified-self metric data. Origination of a physically tangible component group can be accomplished through skilled in the art design choice selection including use of one or more components and/or subsystems explicitly and/or implicitly referred to herein for at least in part implementing execution of one or more instructions of the operation o160, for performance of the operation o160 by an electrical circuitry arrangement as activated thereto, and/or otherwise fulfillment of the operation o160. One or more non-transitory signal bearing physical media can bear the one or more instructions that when executed can direct performance of the operation o160. Furthermore, electronically-receiving-user-biological-status-information-social-network-collected-quantified-self-metric-data module m160 depicted in FIG. 22 as being included in the module m151, when executed and/or activated, can direct performance of and/or perform the operation o160. Illustratively, in one or more implementations, the operation o160 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) at least in part involving user quantified-self information (e.g. such as amount, intensity, duration, frequency, etc. involving an activity or measurement of an individual, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.) including electronically receiving (e.g. radio frequency, WiFi, Bluetooth, packetized data, wireless protocols, infrared, electromagnetic, etc.) user biological status information (e.g. current, physiological, historical, functional, etc.) at least in part involving social network collected quantified-self metric data (e.g. receiving historical or current social network collected user quantified-self data as personal data of an individual collected through wearable or non-wearable sensors as directed or managed by the individual regarding life-style influences as reported to a social network group such as personal maintenance habits such as eating, social interaction habits, etc. or other activities regarding such as hobbies, sports events, vacation, trips, clubs, family outings, family reunions, etc. of medical patient, student, businessperson, customer, office worker, family member, passenger, guest, attendee, etc. at a kiosk, personal, community, or other type vending, dispensing, or food fabricating machine located in a home, business, transportation facility, market, sports facility, office building, theater, school, hospital, park, restaurant, food court, etc. from a data collection device worn by a person or located elsewhere such as furniture, building fixtures, etc.).

Figure 84:
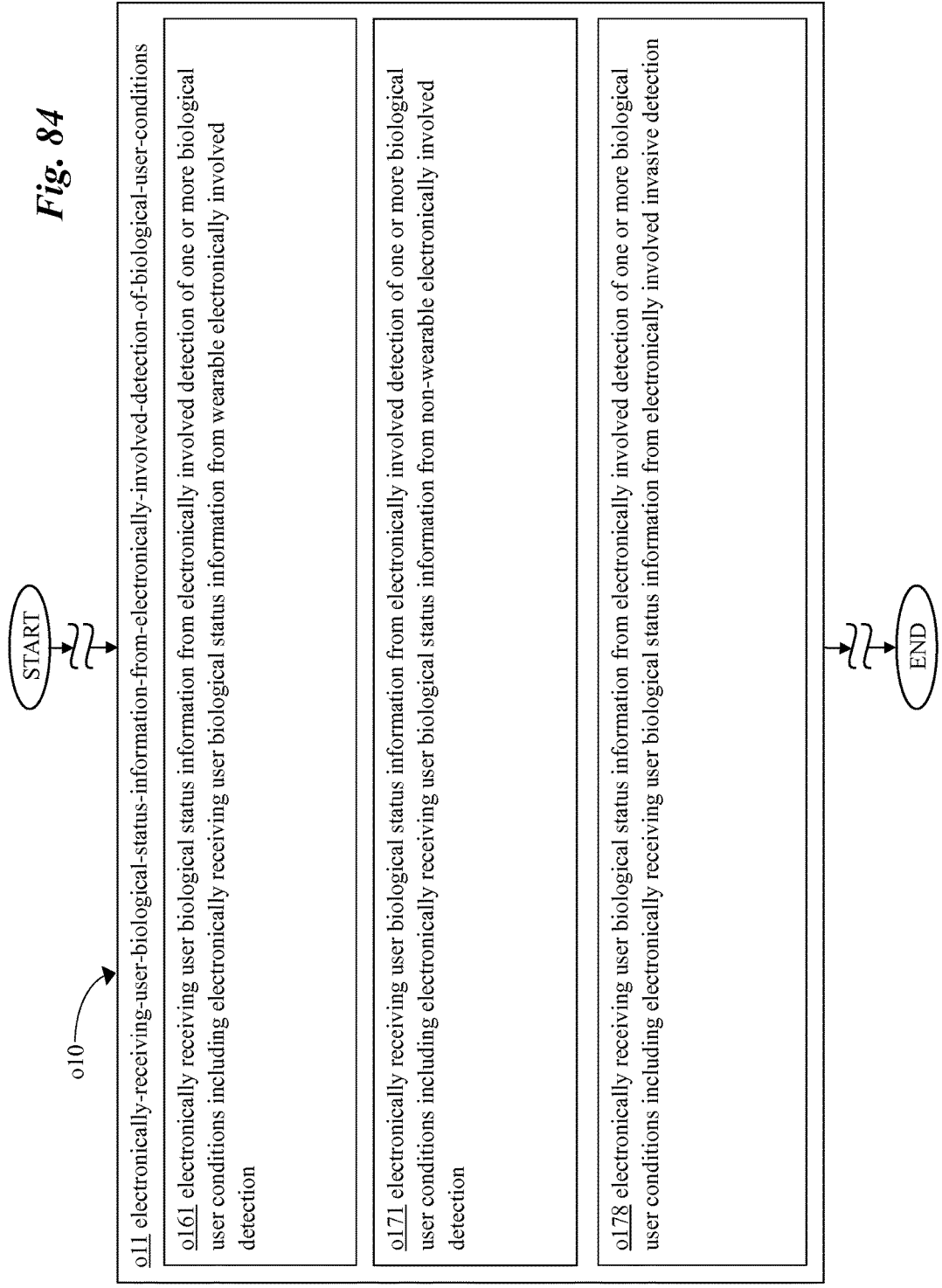

In one or more implementations, as shown in FIG. 84, the operation o11 can include operation o161 for electronically receiving user biological status information from electronically involved detection of one or more biological user conditions including electronically receiving user biological status information from wearable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o161, for performance of the operation o161 by an electrical circuitry arrangement as activated thereto, and/or otherwise fulfillment of the operation o161. One or more non-transitory signal bearing physical media can bear the one or more instructions that when executed can direct performance of the operation o161. Furthermore, electronically-receiving-user-biological-status-information-from-wearable-electronically-involved-detection module m161 depicted in FIG. 25 as being included in the module m11, when executed and/or activated, can direct performance of and/or perform the operation o161. Illustratively, in one or more implementations, the operation o161 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.).

Figure 85:
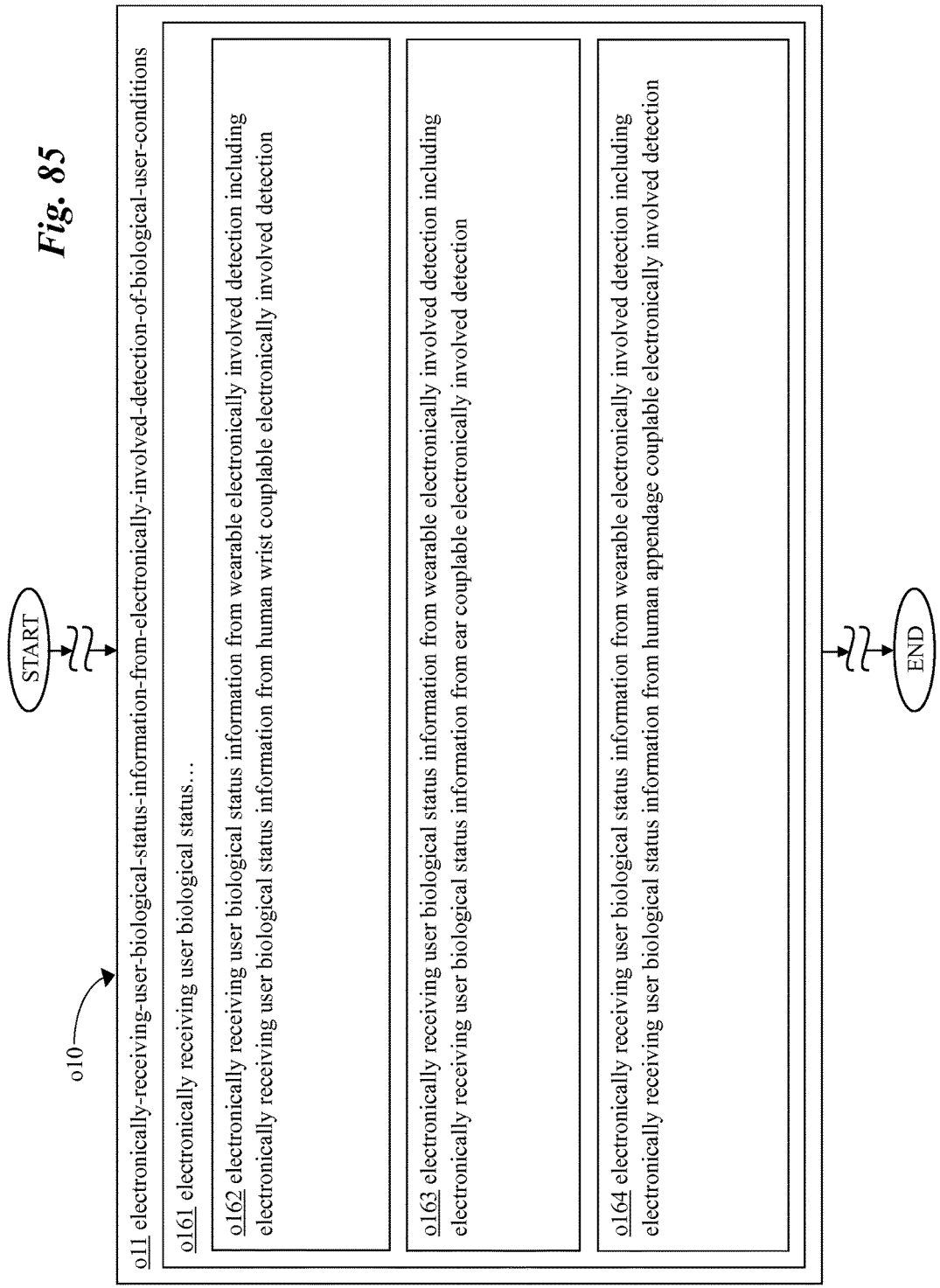

In one or more implementations, as shown in FIG. 85, the operation o161 can include operation o162 for electronically receiving user biological status information from wearable electronically involved detection including electronically receiving user biological status information from human wrist couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o162, for performance of the operation o162 by an electrical circuitry arrangement as activated thereto, and/or otherwise fulfillment of the operation o162. One or more non-transitory signal bearing physical media can bear the one or more instructions that when executed can direct performance of the operation o162. Furthermore, electronically-receiving-user-biological-status-information-from-human-wrist-couplable-electronically-involved-detection module m162 depicted in FIG. 26 as being included in the module m161, when executed and/or activated, can direct performance of and/or perform the operation o162. Illustratively, in one or more implementations, the operation o162 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from human wrist couplable electronically involved detection (e.g. detection integrated with bracelet, wristwatch, wristband, jewelry regarding invasive, non-invasive, device, sensor, nanosensor, electromechanical, chemical, electrical, biological, surgical, other sensing, etc.).

In one or more implementations, as shown in FIG. 85, the operation o161 can include operation o163 for electronically receiving user biological status information from wearable electronically involved detection including electronically receiving user biological status information from ear couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o163, for performance of the operation o163 by an electrical circuitry arrangement as activated thereto, and/or otherwise fulfillment of the operation o163. One or more non-transitory signal bearing physical media can bear the one or more instructions that when executed can direct performance of the operation o163. Furthermore, electronically-receiving-user-biological-status-information-from-ear-couplable-electronically-involved-detection module m163 depicted in FIG. 26 as being included in the module m161, when executed and/or activated, can direct performance of and/or perform the operation o163. Illustratively, in one or more implementations, the operation o163 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from ear couplable electronically involved detection (e.g. from ear couplable detection such as earrings, headphones, ear clips, ear plugs, ear buds, ear muffs clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 85, the operation o161 can include operation o164 for electronically receiving user biological status information from wearable electronically involved detection including electronically receiving user biological status information from human appendage couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o164, for performance of the operation o164 by an electrical circuitry arrangement as activated thereto, and/or otherwise fulfillment of the operation o164. One or more non-transitory signal bearing physical media can bear the one or more instructions that when executed can direct performance of the operation o164. Furthermore, electronically-receiving-user-biological-status-information-from-human-appendage-couplable-electronically-involved-detection module m164 depicted in FIG. 26 as being included in the module m161, when executed and/or activated, can direct performance of and/or perform the operation o164. Illustratively, in one or more implementations, the operation o164 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from human appendage couplable electronically involved detection (e.g. detection integrated with arm, leg, neck attachments, etc. brace, leggings, socks, sleeves, strapped, etc. invasive, non-invasive, device, sensor, nanosensor, electromechanical, chemical, electrical, biological, surgical, other sensing, etc.).

Figure 86:
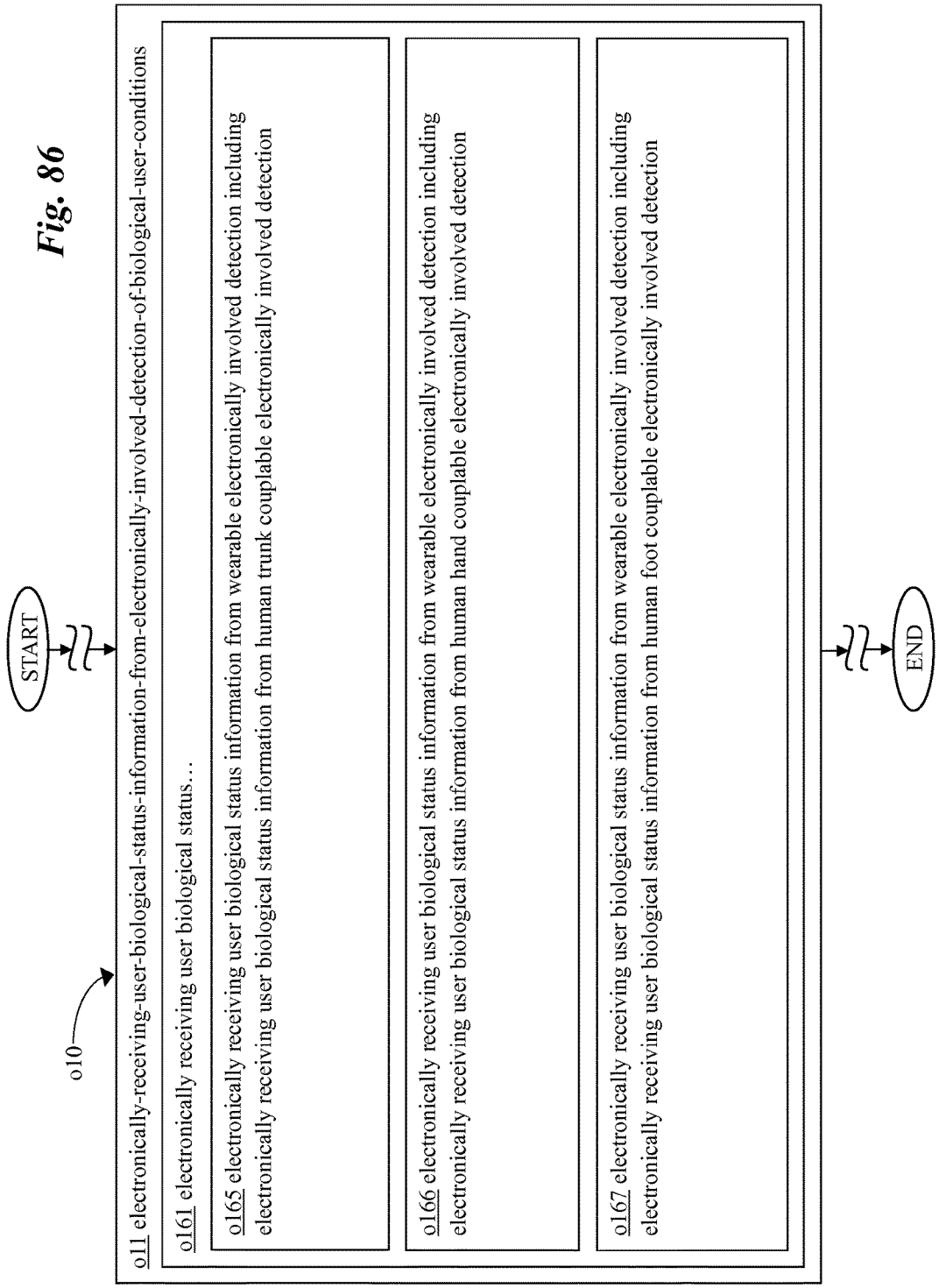

In one or more implementations, as shown in FIG. 86, the operation o161 can include operation o165 for electronically receiving user biological status information from wearable electronically involved detection including electronically receiving user biological status information from human trunk couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o165, for performance of the operation o165 by an electrical circuitry arrangement as activated thereto, and/or otherwise fulfillment of the operation o165. One or more non-transitory signal bearing physical media can bear the one or more instructions that when executed can direct performance of the operation o165. Furthermore, electronically-receiving-user-biological-status-information-from-human-trunk-couplable-electronically-involved-detection module m165 depicted in FIG. 27 as being included in the module m161, when executed and/or activated, can direct performance of and/or perform the operation o165. Illustratively, in one or more implementations, the operation o165 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from human trunk couplable electronically involved detection (e.g. from human trunk couplable detection such as belts, fanny packs, vests, straps, backpacks, electrode pads, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 86, the operation o161 can include operation o166 for electronically receiving user biological status information from wearable electronically involved detection including electronically receiving user biological status information from human hand couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o166, for performance of the operation o166 by an electrical circuitry arrangement as activated thereto, and/or otherwise fulfillment of the operation o166. One or more non-transitory signal bearing physical media can bear the one or more instructions that when executed can direct performance of the operation o166. Furthermore, electronically-receiving-user-biological-status-information-from-human-hand-couplable-electronically-involved-detection module m166 depicted in FIG. 27 as being included in the module m161, when executed and/or activated, can direct performance of and/or perform the operation o166. Illustratively, in one or more implementations, the operation o166 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from human hand couplable electronically involved detection (e.g. detection integrated with gloves, rings, pads, straps, etc. invasive, non-invasive, device, sensor, nanosensor, electromechanical, chemical, electrical, biological, surgical, other sensing, etc.).

In one or more implementations, as shown in FIG. 86, the operation o161 can include operation o167 for electronically receiving user biological status information from wearable electronically involved detection including electronically receiving user biological status information from human foot couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o167, for performance of the operation o167 by an electrical circuitry arrangement as activated thereto, and/or otherwise fulfillment of the operation o167. One or more non-transitory signal bearing physical media can bear the one or more instructions that when executed can direct performance of the operation o167. Furthermore, electronically-receiving-user-biological-status-information-from-human-foot-couplable-electronically-involved-detection module m167 depicted in FIG. 27 as being included in the module m161, when executed and/or activated, can direct performance of and/or perform the operation o167. Illustratively, in one or more implementations, the operation o167 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from human foot couplable electronically involved detection (e.g. from foot couplable detection such as shoes, socks, sandals, toe-rings, ankle bracelets, electrode pads, etc. to a kiosk, personal, community, or other type vending, dispensing, or food fabricating machine located in a home, business, transportation facility, market, sports facility, office building, theater, school, hospital, park, restaurant, food court, etc.).

Figure 87:
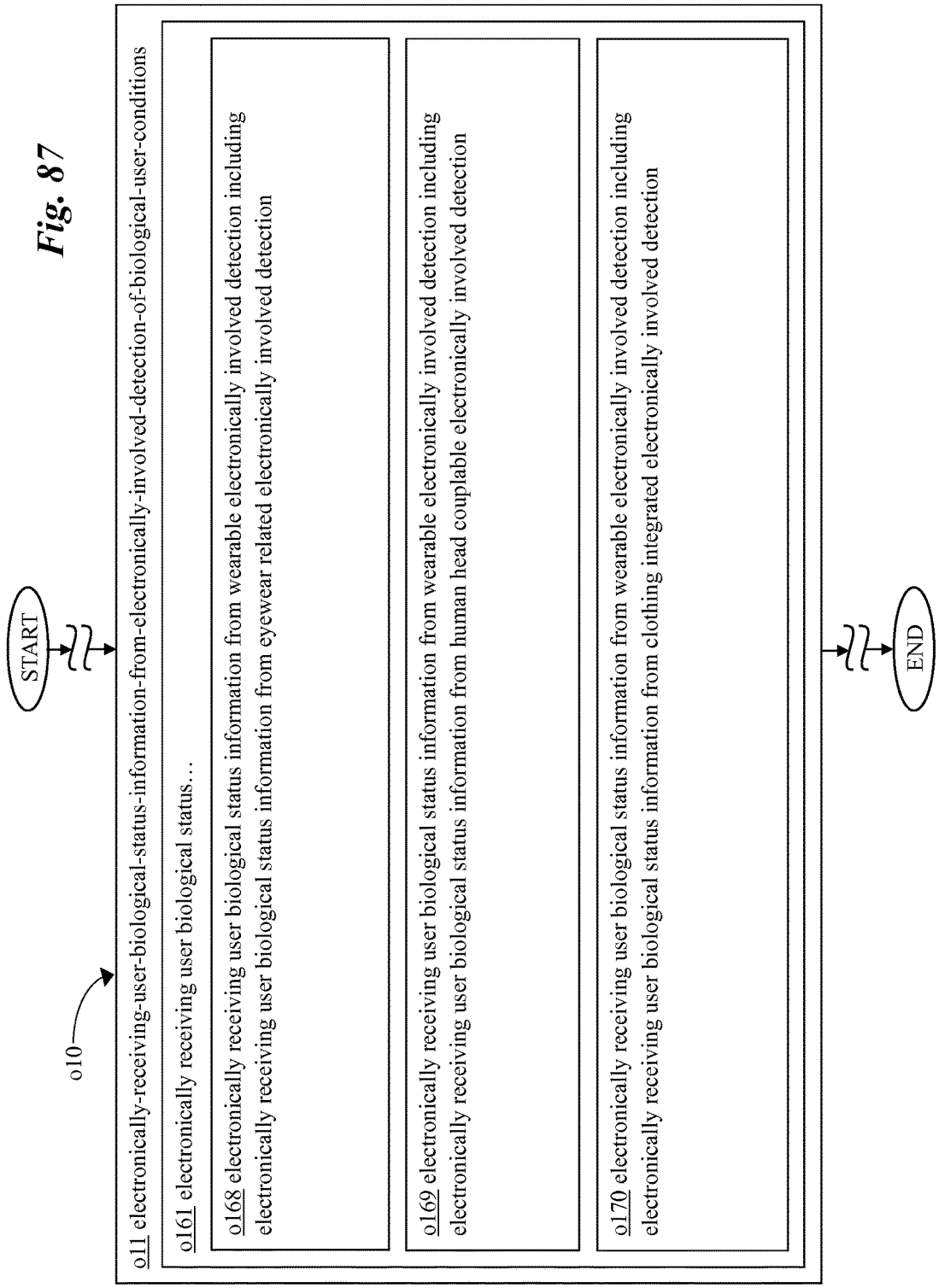

In one or more implementations, as shown in FIG. 87, the operation o161 can include operation o168 for electronically receiving user biological status information from wearable electronically involved detection including electronically receiving user biological status information from eyewear related electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o168, for performance of the operation o168 by an electrical circuitry arrangement as activated thereto, and/or otherwise fulfillment of the operation o168. One or more non-transitory signal bearing physical media can bear the one or more instructions that when executed can direct performance of the operation o168. Furthermore, electronically-receiving-user-biological-status-information-from-eyewear-related-electronically-involved-detection module m168 depicted in FIG. 28 as being included in the module m161, when executed and/or activated, can direct performance of and/or perform the operation o168. Illustratively, in one or more implementations, the operation o168 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from eyewear related electronically involved detection (e.g. detection integrated with glasses, contacts, lens, frames, monocle, etc. invasive, non-invasive, device, sensor, nanosensor, electromechanical, chemical, electrical, biological, surgical, other sensing, etc.).

In one or more implementations, as shown in FIG. 87, the operation o161 can include operation o169 for electronically receiving user biological status information from wearable electronically involved detection including electronically receiving user biological status information from human head couplable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o169, for performance of the operation o169 by an electrical circuitry arrangement as activated thereto, and/or otherwise fulfillment of the operation o169. One or more non-transitory signal bearing physical media can bear the one or more instructions that when executed can direct performance of the operation o169. Furthermore, electronically-receiving-user-biological-status-information-from-human-head-couplable-electronically-involved-detection module m169 depicted in FIG. 28 as being included in the module m161, when executed and/or activated, can direct performance of and/or perform the operation o169. Illustratively, in one or more implementations, the operation o169 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from human head couplable electronically involved detection (e.g. from head couplable detection such as hats, head bands, face masks, hair combs or other accessories, necklaces, nanosensor impregnated make-up, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 87, the operation o161 can include operation o170 for electronically receiving user biological status information from wearable electronically involved detection including electronically receiving user biological status information from clothing integrated electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o170, for performance of the operation o170 by an electrical circuitry arrangement as activated thereto, and/or otherwise fulfillment of the operation o170. One or more non-transitory signal bearing physical media can bear the one or more instructions that when executed can direct performance of the operation o170. Furthermore, electronically-receiving-user-biological-status-information-from-clothing-integrated-electronically-involved-detection module m170 depicted in FIG. 28 as being included in the module m161, when executed and/or activated, can direct performance of and/or perform the operation o170. Illustratively, in one or more implementations, the operation o170 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from wearable electronically involved detection (e.g. from wearable detection such as clothing, apparel accessories, luggage, handbags, wallets, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from clothing integrated electronically involved detection (e.g. detection integrated with shirts, pants, underwear, jackets, natural fabrics, synthetics, etc. invasive, non-invasive, device, sensor, nanosensor, electromechanical, chemical, electrical, biological, surgical, other sensing, etc.).

In one or more implementations, as shown in FIG. 84, the operation o11 can include operation o171 for electronically receiving user biological status information from electronically involved detection of one or more biological user conditions including electronically receiving user biological status information from non-wearable electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o171, for performance of the operation o171 by an electrical circuitry arrangement as activated thereto, and/or otherwise fulfillment of the operation o171. One or more non-transitory signal bearing physical media can bear the one or more instructions that when executed can direct performance of the operation o171. Furthermore, electronically-receiving-user-biological-status-information-from-non-wearable-electronically-involved-detection module m171 depicted in FIG. 25 as being included in the module m11, when executed and/or activated, can direct performance of and/or perform the operation o171. Illustratively, in one or more implementations, the operation o171 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.).

Figure 88:
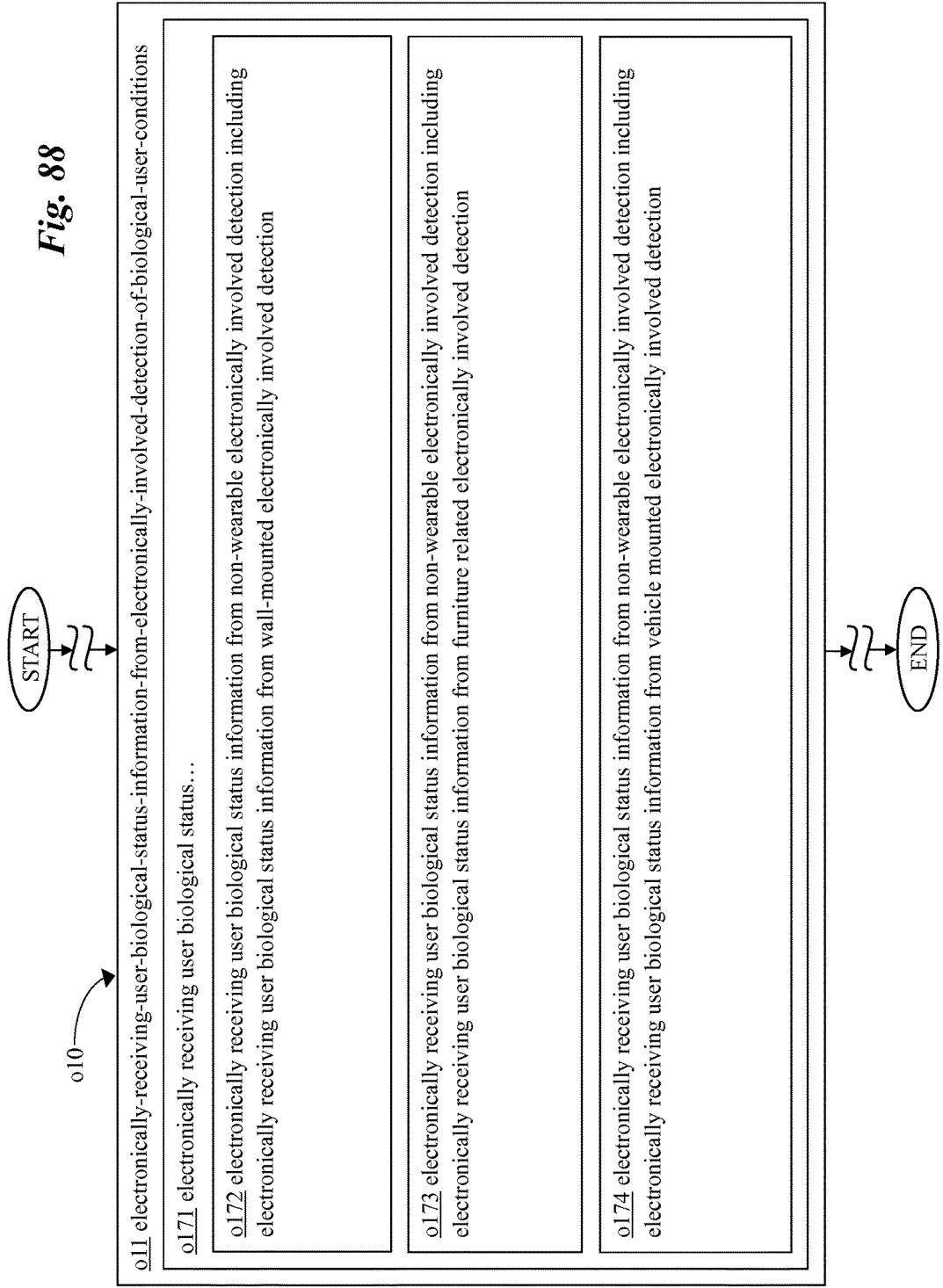

In one or more implementations, as shown in FIG. 88, the operation o171 can include operation o172 for electronically receiving user biological status information from non-wearable electronically involved detection including electronically receiving user biological status information from wall-mounted electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o172, for performance of the operation o172 by an electrical circuitry arrangement as activated thereto, and/or otherwise fulfillment of the operation o172. One or more non-transitory signal bearing physical media can bear the one or more instructions that when executed can direct performance of the operation o172. Furthermore, electronically-receiving-user-biological-status-information-from-wall-mounted-electronically-involved-detection module m172 depicted in FIG. 29 as being included in the module m171, when executed and/or activated, can direct performance of and/or perform the operation o172. Illustratively, in one or more implementations, the operation o172 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from wall-mounted electronically involved detection (e.g. detection integrated with paintings, cabinets, mirrors, posters, infrared heating panels, suspended, etc. invasive, non-invasive, device, sensor, nanosensor, electromechanical, chemical, electrical, biological, surgical, other sensing, etc.).

In one or more implementations, as shown in FIG. 88, the operation o171 can include operation o173 for electronically receiving user biological status information from non-wearable electronically involved detection including electronically receiving user biological status information from furniture related electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o173, for performance of the operation o173 by an electrical circuitry arrangement as activated thereto, and/or otherwise fulfillment of the operation o173. One or more non-transitory signal bearing physical media can bear the one or more instructions that when executed can direct performance of the operation o173. Furthermore, electronically-receiving-user-biological-status-information-from-furniture-related-electronically-involved-detection module m173 depicted in FIG. 29 as being included in the module m171, when executed and/or activated, can direct performance of and/or perform the operation o173. Illustratively, in one or more implementations, the operation o173 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from furniture related electronically involved detection (e.g. from furniture related detection such as tables, chairs, stools, benches, couches, beds, desks, computer stands, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 88, the operation o171 can include operation o174 for electronically receiving user biological status information from non-wearable electronically involved detection including electronically receiving user biological status information from vehicle mounted electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o174, for performance of the operation o174 by an electrical circuitry arrangement as activated thereto, and/or otherwise fulfillment of the operation o174. One or more non-transitory signal bearing physical media can bear the one or more instructions that when executed can direct performance of the operation o174. Furthermore, electronically-receiving-user-biological-status-information-from-vehicle-mounted-electronically-involved-detection module m174 depicted in FIG. 29 as being included in the module m171, when executed and/or activated, can direct performance of and/or perform the operation o174. Illustratively, in one or more implementations, the operation o174 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from vehicle mounted electronically involved detection (e.g. detection integrated with steering wheel, dashboard, windshield, seat, car door, window, mirror, etc. invasive, non-invasive, device, sensor, nanosensor, electromechanical, chemical, electrical, biological, surgical, other sensing, etc.).

Figure 89:
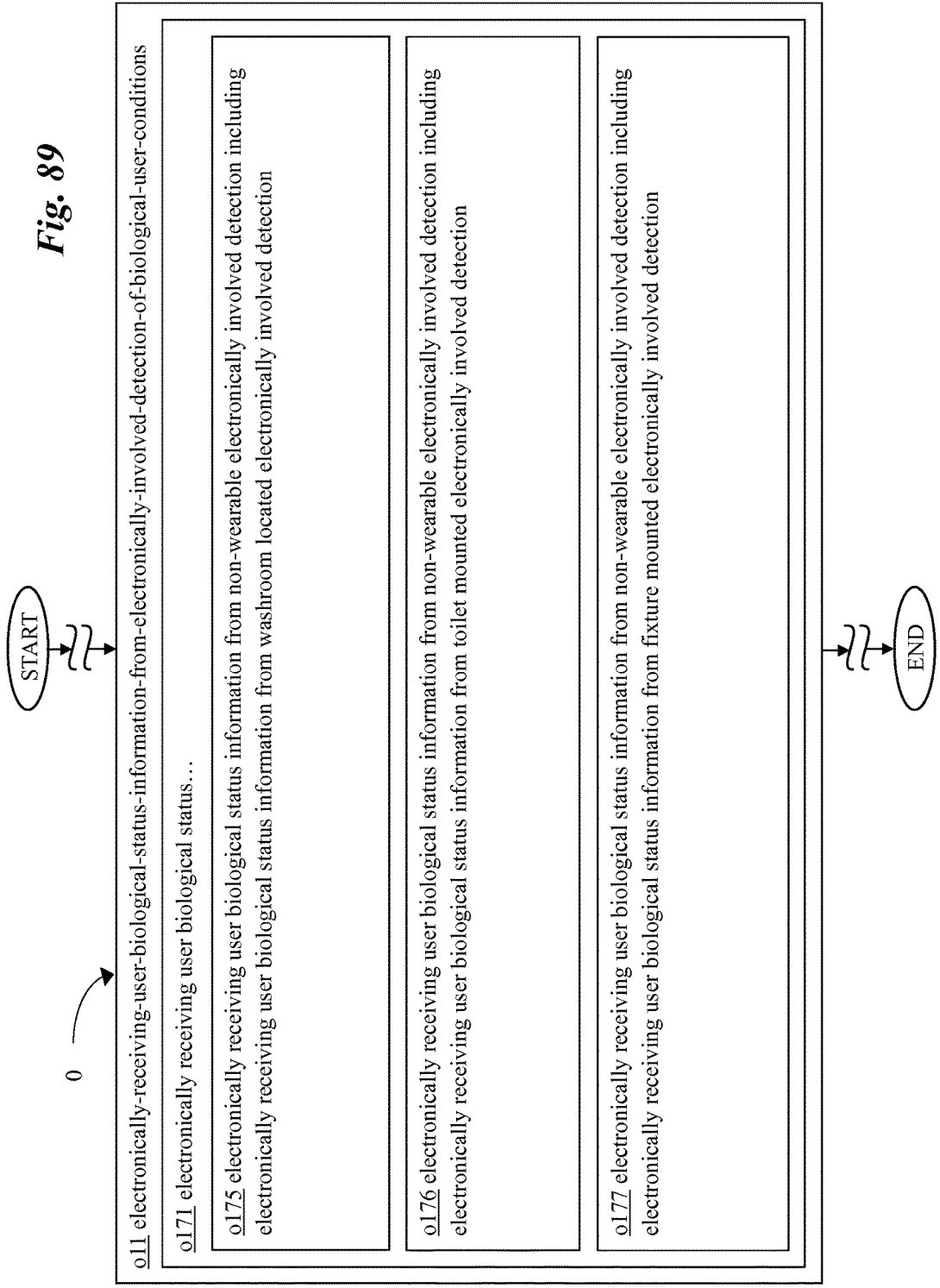

In one or more implementations, as shown in FIG. 89, the operation o171 can include operation o175 for electronically receiving user biological status information from non-wearable electronically involved detection including electronically receiving user biological status information from washroom located electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o175, for performance of the operation o175 by an electrical circuitry arrangement as activated thereto, and/or otherwise fulfillment of the operation o175. One or more non-transitory signal bearing physical media can bear the one or more instructions that when executed can direct performance of the operation o175. Furthermore, electronically-receiving-user-biological-status-information-from-washroom-located-electronically-involved-detection module m175 depicted in FIG. 30 as being included in the module m171, when executed and/or activated, can direct performance of and/or perform the operation o175. Illustratively, in one or more implementations, the operation o175 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from washroom located electronically involved detection (e.g. from washroom located detection such as toilets, bathtubs, sinks, closets, dispensers of toiletries, towel bars, mirrors, light fixtures, fans, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 89, the operation o171 can include operation o176 for electronically receiving user biological status information from non-wearable electronically involved detection including electronically receiving user biological status information from toilet mounted electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o176, for performance of the operation o176 by an electrical circuitry arrangement as activated thereto, and/or otherwise fulfillment of the operation o176. One or more non-transitory signal bearing physical media can bear the one or more instructions that when executed can direct performance of the operation o176. Furthermore, electronically-receiving-user-biological-status-information-from-toilet-mounted-electronically-involved-detection module m176 depicted in FIG. 30 as being included in the module m171, when executed and/or activated, can direct performance of and/or perform the operation o176. Illustratively, in one or more implementations, the operation o176 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) user biological status information (e.g. current, physiological, historical, functional, etc.) from toilet mounted electronically involved detection (e.g. detection integrated with toilet seat, toilet bowl, toilet tank, toilet accessories, etc. invasive, non-invasive, device, sensor, nanosensor, electromechanical, chemical, electrical, biological, surgical, other sensing, etc.).

In one or more implementations, as shown in FIG. 89, the operation o171 can include operation o177 for electronically receiving user biological status information from non-wearable electronically involved detection including electronically receiving user biological status information from fixture mounted electronically involved detection. Origination of a physically tangible component group can be accomplished through skilled in the art design choice selection including use of one or more components and/or subsystems explicitly and/or implicitly referred to herein for at least in part implementing execution of one or more instructions of the operation o177, for performance of the operation o177 by an electrical circuitry arrangement as activated thereto, and/or otherwise fulfillment of the operation o177. One or more non-transitory signal bearing physical media can bear the one or more instructions that when executed can direct performance of the operation o177. Furthermore, electronically-receiving-user-biological-status-information-from-fixture-mounted-electronically-involved-detection module m177 depicted in FIG. 30 as being included in the module m171, when executed and/or activated, can direct performance of and/or perform the operation o177. Illustratively, in one or more implementations, the operation o177 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from non-wearable electronically involved detection (e.g. from non-wearable detection such as building fixtures, washroom equipment, furniture, building construction, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from fixture mounted electronically involved detection (e.g. from fixture mounted detection lights, plumbing, electrical, carpeting, wall accessories, ceiling attachments, counters, cabinets, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 84, the operation o11 can include operation o178 for electronically receiving user biological status information from electronically involved detection of one or more biological user conditions including electronically receiving user biological status information from electronically involved invasive detection. Origination of a physically tangible component group can be accomplished through skilled in the art design choice selection including use of one or more components and/or subsystems explicitly and/or implicitly referred to herein for at least in part implementing execution of one or more instructions of the operation o178, for performance of the operation o178 by an electrical circuitry arrangement as activated thereto, and/or otherwise fulfillment of the operation o178. One or more non-transitory signal bearing physical media can bear the one or more instructions that when executed can direct performance of the operation o178. Furthermore, electronically-receiving-user-biological-status-information-from-electronically-involved-invasive-detection module m178 depicted in FIG. 25 as being included in the module m11, when executed and/or activated, can direct performance of and/or perform the operation o178. Illustratively, in one or more implementations, the operation o178 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.).

Figure 90:
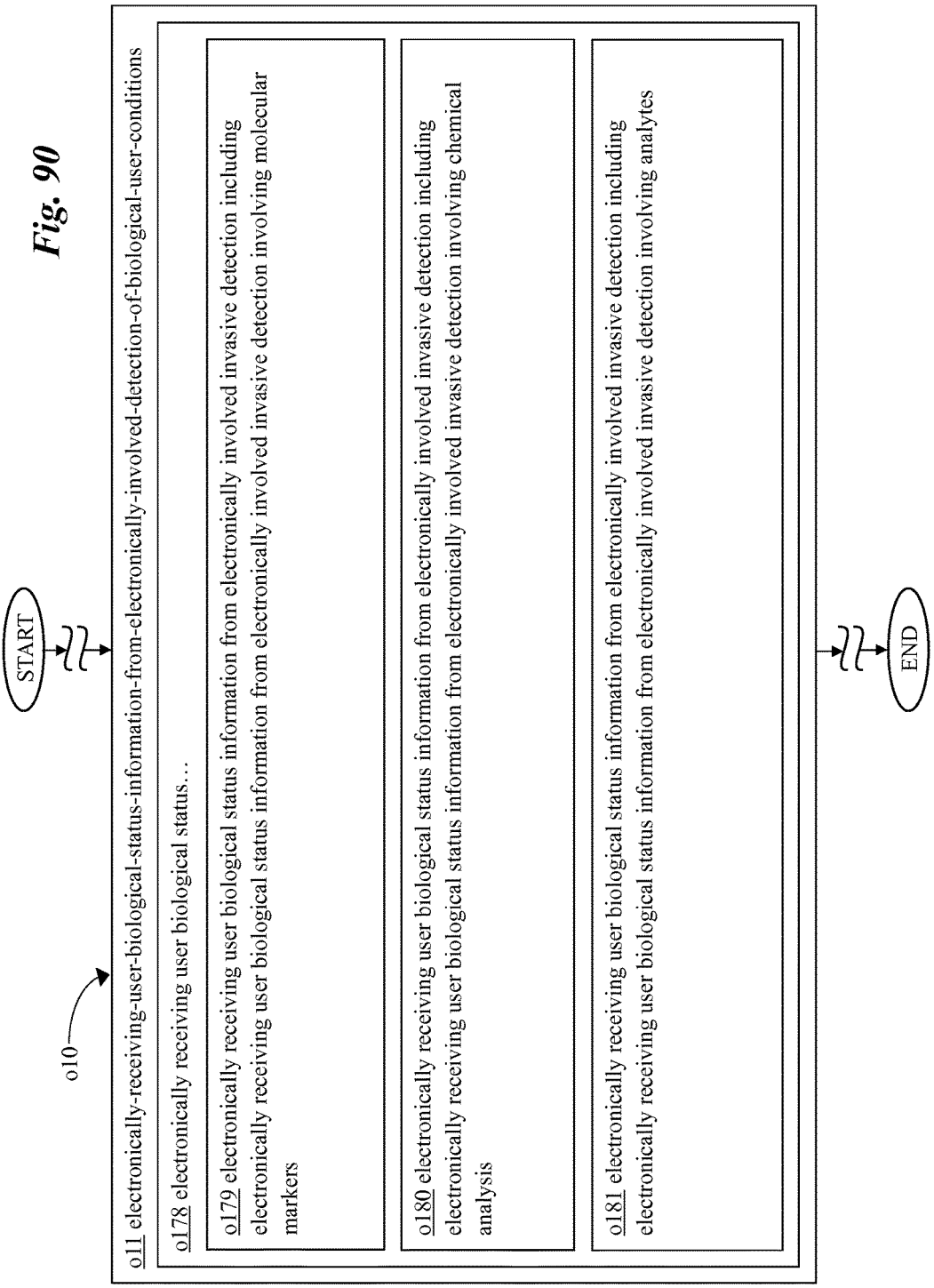

In one or more implementations, as shown in FIG. 90, the operation o178 can include operation o179 for electronically receiving user biological status information from electronically involved invasive detection including electronically receiving user biological status information from electronically involved invasive detection involving molecular markers. Origination of a physically tangible component group can be accomplished through skilled in the art design choice selection including use of one or more components and/or subsystems explicitly and/or implicitly referred to herein for at least in part implementing execution of one or more instructions of the operation o179, for performance of the operation o179 by an electrical circuitry arrangement as activated thereto, and/or otherwise fulfillment of the operation o179. One or more non-transitory signal bearing physical media can bear the one or more instructions that when executed can direct performance of the operation o179. Furthermore, electronically-receiving-user-biological-status-information-from-electronically-involved-invasive-detection-molecular-markers module m179 depicted in FIG. 31 as being included in the module m178, when executed and/or activated, can direct performance of and/or perform the operation o179. Illustratively, in one or more implementations, the operation o179 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved invasive detection (e.g. nanosensors such as electronic, mechanical, surgical, chemical, biological, or other, devices, sensors, tubes, probes, needles, etc. insertable into body, cavity, other, etc.) involving molecular markers (e.g. from detection regarding proteins, antibodies, hormonal, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 90, the operation o178 can include operation o180 for electronically receiving user biological status information from electronically involved invasive detection including electronically receiving user biological status information from electronically involved invasive detection involving chemical analysis. Origination of a physically tangible component group can be accomplished through skilled in the art design choice selection including use of one or more components and/or subsystems explicitly and/or implicitly referred to herein for at least in part implementing execution of one or more instructions of the operation o180, for performance of the operation o180 by an electrical circuitry arrangement as activated thereto, and/or otherwise fulfillment of the operation o180. One or more non-transitory signal bearing physical media can bear the one or more instructions that when executed can direct performance of the operation o180. Furthermore, electronically-receiving-user-biological-status-information-from-electronically-involved-invasive-detection-chemical-analysis module m180 depicted in FIG. 31 as being included in the module m178, when executed and/or activated, can direct performance of and/or perform the operation o180. Illustratively, in one or more implementations, the operation o180 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) involving chemical analysis (e.g. from chemical analysis detection such as blood lipids, toxin levels, glucose concentration, steroid concentration, uric acid concentration, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 90, the operation o178 can include operation o181 for electronically receiving user biological status information from electronically involved invasive detection including electronically receiving user biological status information from electronically involved invasive detection involving analytes. Origination of a physically tangible component group can be accomplished through skilled in the art design choice selection including use of one or more components and/or subsystems explicitly and/or implicitly referred to herein for at least in part implementing execution of one or more instructions of the operation o181, for performance of the operation o181 by an electrical circuitry arrangement as activated thereto, and/or otherwise fulfillment of the operation o181. One or more non-transitory signal bearing physical media can bear the one or more instructions that when executed can direct performance of the operation o181. Furthermore, electronically-receiving-user-biological-status-information-from-electronically-involved-invasive-detection-analytes module m181 depicted in FIG. 31 as being included in the module m178, when executed and/or activated, can direct performance of and/or perform the operation o181. Illustratively, in one or more implementations, the operation o181 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved invasive detection (e.g. nanosensors such as electronic, mechanical, surgical, chemical, biological, or other, devices, sensors, tubes, probes, needles, etc. insertable into body, cavity, other, etc.) involving analytes (e.g. from analyte detection such as glucose concentration, steroid concentration, uric acid concentration, etc. to a kiosk, personal, community, or other type vending, dispensing, or food fabricating machine located in a home, business, transportation facility, market, sports facility, office building, theater, school, hospital, park, restaurant, food court, etc.).

Figure 91:
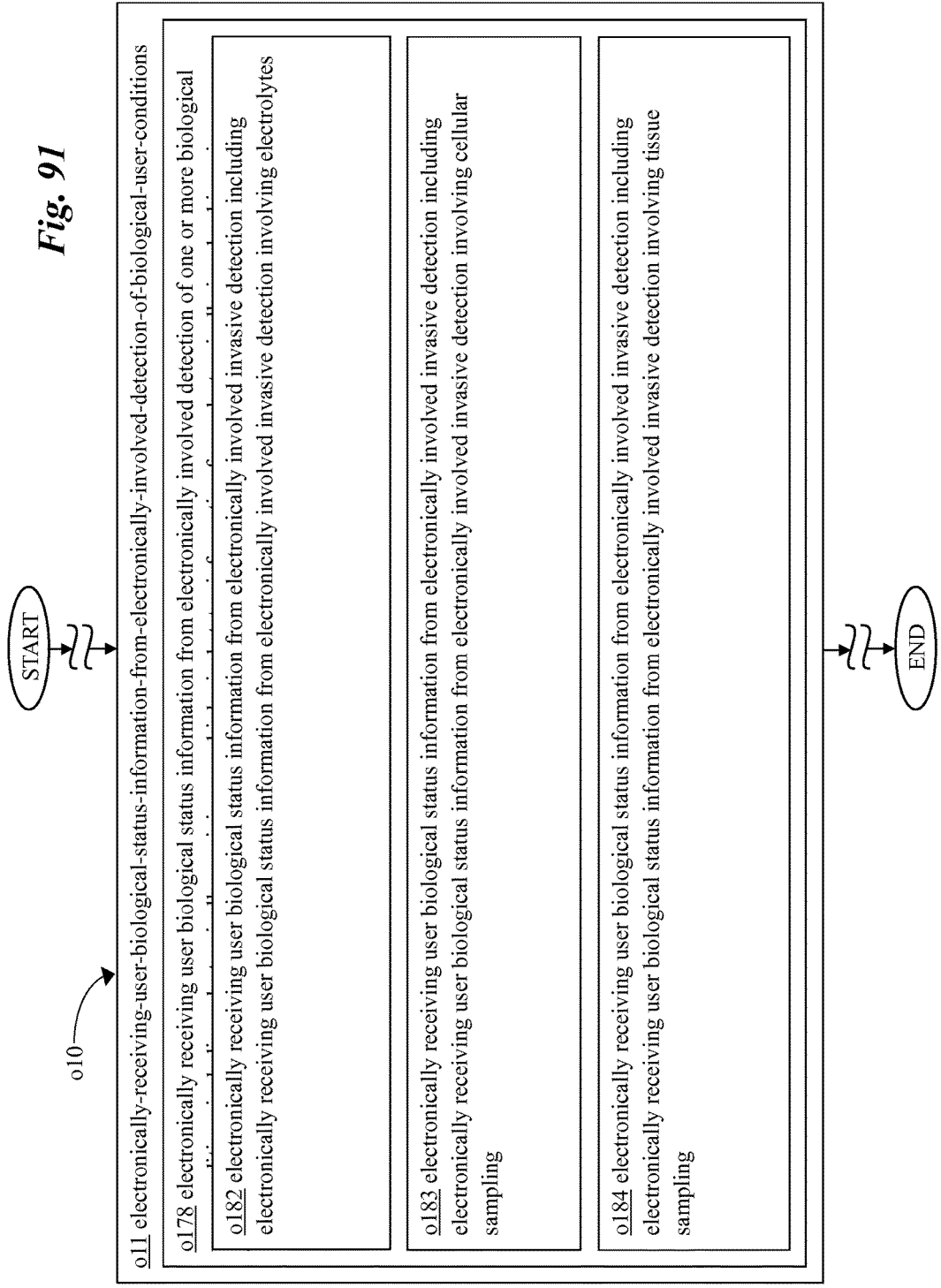

In one or more implementations, as shown in FIG. 91, the operation o178 can include operation o182 for electronically receiving user biological status information from electronically involved invasive detection including electronically receiving user biological status information from electronically involved invasive detection involving electrolytes. Origination of a physically tangible component group can be accomplished through skilled in the art design choice selection including use of one or more components and/or subsystems explicitly and/or implicitly referred to herein for at least in part implementing execution of one or more instructions of the operation o182, for performance of the operation o182 by an electrical circuitry arrangement as activated thereto, and/or otherwise fulfillment of the operation o182. One or more non-transitory signal bearing physical media can bear the one or more instructions that when executed can direct performance of the operation o182. Furthermore, electronically-receiving-user-biological-status-information-from-electronically-involved-invasive-detection-electrolytes module m182 depicted in FIG. 32 as being included in the module m178, when executed and/or activated, can direct performance of and/or perform the operation o182. Illustratively, in one or more implementations, the operation o182 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) involving electrolytes (e.g. from of electrolyte detection of potassium, sodium, magnesium, or other blood mineral levels, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 91, the operation o178 can include operation o183 for electronically receiving user biological status information from electronically involved invasive detection including electronically receiving user biological status information from electronically involved invasive detection involving cellular sampling. Origination of a physically tangible component group can be accomplished through skilled in the art design choice selection including use of one or more components and/or subsystems explicitly and/or implicitly referred to herein for at least in part implementing execution of one or more instructions of the operation o183, for performance of the operation o183 by an electrical circuitry arrangement as activated thereto, and/or otherwise fulfillment of the operation o183. One or more non-transitory signal bearing physical media can bear the one or more instructions that when executed can direct performance of the operation o183. Furthermore, electronically-receiving-user-biological-status-information-from-electronically-involved-invasive-detection-cellular-sampling module m183 depicted in FIG. 32 as being included in the module m178, when executed and/or activated, can direct performance of and/or perform the operation o183. Illustratively, in one or more implementations, the operation o183 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved invasive detection (e.g. nanosensors such as electronic, mechanical, surgical, chemical, biological, or other, devices, sensors, tubes, probes, needles, etc. insertable into body, cavity, other, etc.) involving cellular sampling (e.g. from cellular sampling such as DNA sampling, mitochrondrial sampling, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 91, the operation o178 can include operation o184 for electronically receiving user biological status information from electronically involved invasive detection including electronically receiving user biological status information from electronically involved invasive detection involving tissue sampling. Origination of a physically tangible component group can be accomplished through skilled in the art design choice selection including use of one or more components and/or subsystems explicitly and/or implicitly referred to herein for at least in part implementing execution of one or more instructions of the operation o184, for performance of the operation o184 by an electrical circuitry arrangement as activated thereto, and/or otherwise fulfillment of the operation o184. One or more non-transitory signal bearing physical media can bear the one or more instructions that when executed can direct performance of the operation o184. Furthermore, electronically-receiving-user-biological-status-information-from-electronically-involved-invasive-detection-tissue-sampling module m184 depicted in FIG. 32 as being included in the module m178, when executed and/or activated, can direct performance of and/or perform the operation o184. Illustratively, in one or more implementations, the operation o184 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) involving tissue sampling (e.g. from tissue sampling such as mineral hair analysis, biopsies, etc., etc. to a kiosk, personal, community, or other type vending, dispensing, or food fabricating machine located in a home, business, transportation facility, market, sports facility, office building, theater, school, hospital, park, restaurant, food court, etc.).

Figure 92:
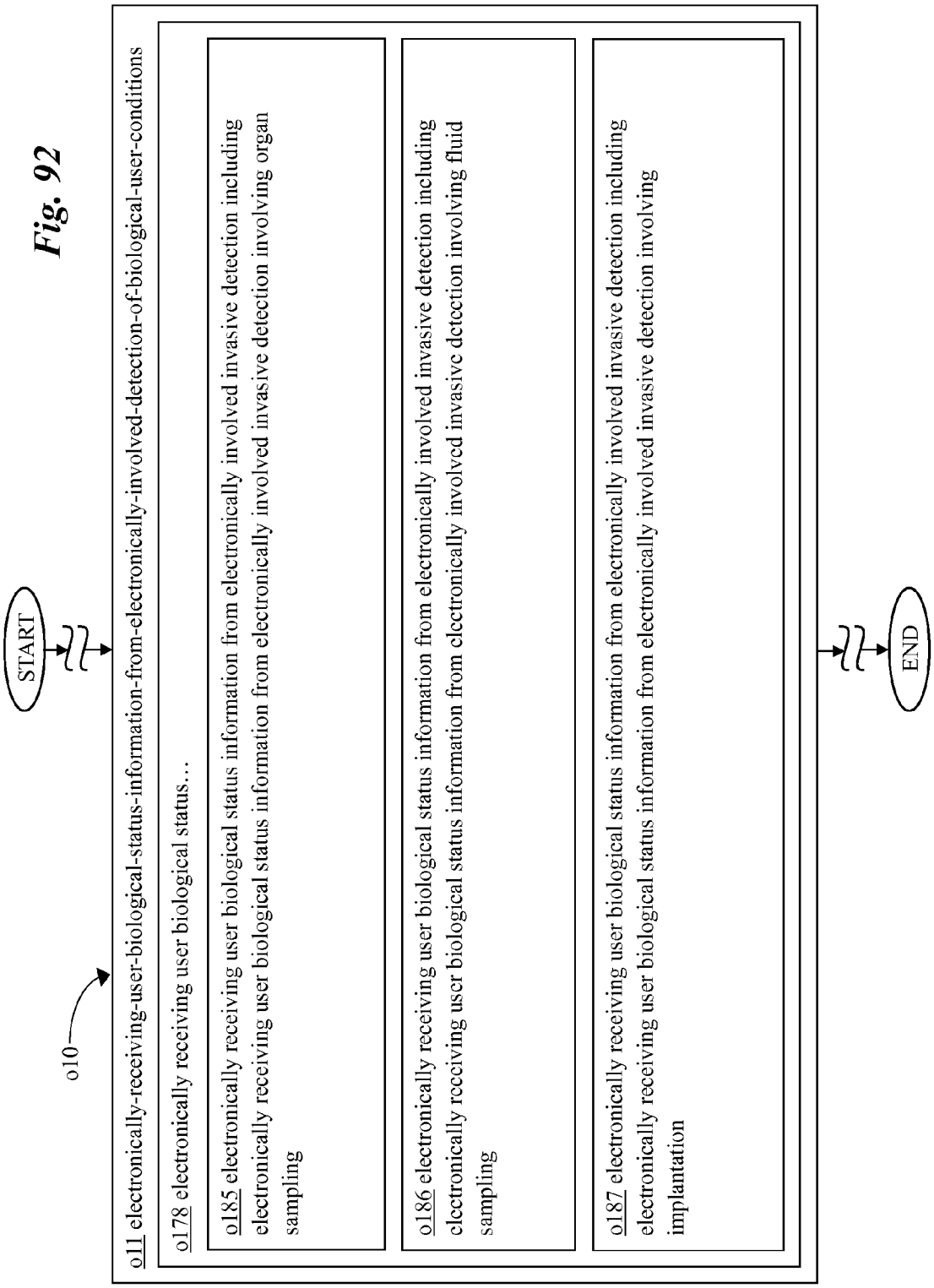

In one or more implementations, as shown in FIG. 92, the operation o178 can include operation o185 for electronically receiving user biological status information from electronically involved invasive detection including electronically receiving user biological status information from electronically involved invasive detection involving organ sampling. Origination of a physically tangible component group can be accomplished through skilled in the art design choice selection including use of one or more components and/or subsystems explicitly and/or implicitly referred to herein for at least in part implementing execution of one or more instructions of the operation o185, for performance of the operation o185 by an electrical circuitry arrangement as activated thereto, and/or otherwise fulfillment of the operation o185. One or more non-transitory signal bearing physical media can bear the one or more instructions that when executed can direct performance of the operation o185. Furthermore, electronically-receiving-user-biological-status-information-from-electronically-involved-invasive-detection-organ-sampling module m185 depicted in FIG. 33 as being included in the module m178, when executed and/or activated, can direct performance of and/or perform the operation o185. Illustratively, in one or more implementations, the operation o185 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved invasive detection (e.g. nanosensors such as electronic, mechanical, surgical, chemical, biological, or other, devices, sensors, tubes, probes, needles, etc. insertable into body, cavity, other, etc.) involving organ sampling (e.g. from nanosensor direct sampling of kidney or lung function to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 92, the operation o178 can include operation o186 for electronically receiving user biological status information from electronically involved invasive detection including electronically receiving user biological status information from electronically involved invasive detection involving fluid sampling. Origination of a physically tangible component group can be accomplished through skilled in the art design choice selection including use of one or more components and/or subsystems explicitly and/or implicitly referred to herein for at least in part implementing execution of one or more instructions of the operation o186, for performance of the operation o186 by an electrical circuitry arrangement as activated thereto, and/or otherwise fulfillment of the operation o186. One or more non-transitory signal bearing physical media can bear the one or more instructions that when executed can direct performance of the operation o186. Furthermore, electronically-receiving-user-biological-status-information-from-electronically-involved-invasive-detection-fluid-sampling module m186 depicted in FIG. 33 as being included in the module m178, when executed and/or activated, can direct performance of and/or perform the operation o186. Illustratively, in one or more implementations, the operation o186 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) involving fluid sampling (e.g. from fluid sampling detection such as blood, saliva, urine, etc. sampling, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 92, the operation o178 can include operation o187 for electronically receiving user biological status information from electronically involved invasive detection including electronically receiving user biological status information from electronically involved invasive detection involving implantation. Origination of a physically tangible component group can be accomplished through skilled in the art design choice selection including use of one or more components and/or subsystems explicitly and/or implicitly referred to herein for at least in part implementing execution of one or more instructions of the operation o187, for performance of the operation o187 by an electrical circuitry arrangement as activated thereto, and/or otherwise fulfillment of the operation o187. One or more non-transitory signal bearing physical media can bear the one or more instructions that when executed can direct performance of the operation o187. Furthermore, electronically-receiving-user-biological-status-information-from-electronically-involved-invasive-detection-implantation module m187 depicted in FIG. 33 as being included in the module m178, when executed and/or activated, can direct performance of and/or perform the operation o187. Illustratively, in one or more implementations, the operation o187 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved invasive detection (e.g. nanosensors such as electronic, mechanical, surgical, chemical, biological, or other, devices, sensors, tubes, probes, needles, etc. insertable into body, cavity, other, etc.) involving implantation (e.g. blood pressure and flow rate data from implantation of sensor containing stents, etc. to a kiosk, personal, community, or other type vending, dispensing, or food fabricating machine located in a home, business, transportation facility, market, sports facility, office building, theater, school, hospital, park, restaurant, food court, etc.).

Figure 93:
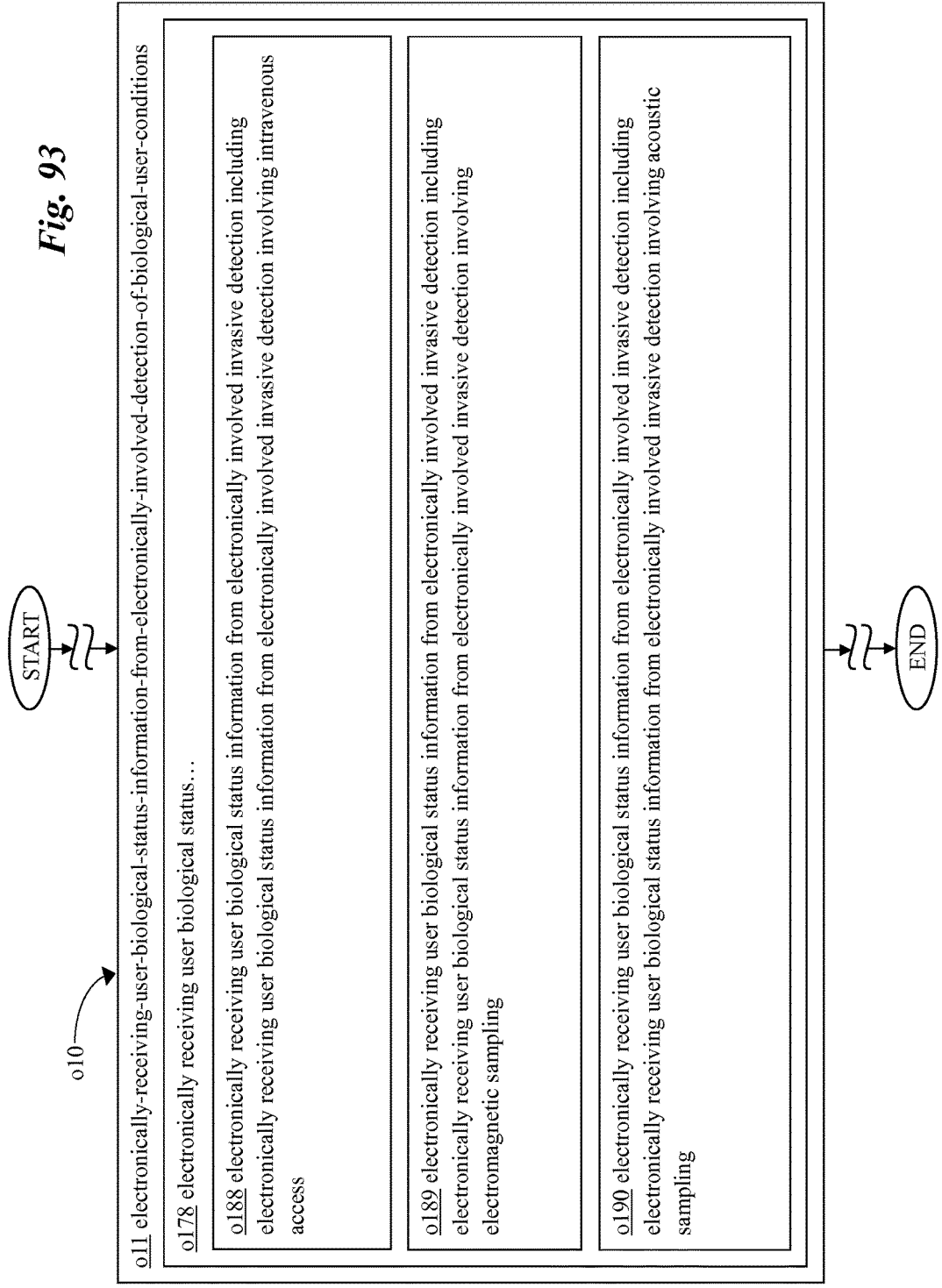

In one or more implementations, as shown in FIG. 93, the operation o178 can include operation o188 for electronically receiving user biological status information from electronically involved invasive detection including electronically receiving user biological status information from electronically involved invasive detection involving intravenous access. Origination of a physically tangible component group can be accomplished through skilled in the art design choice selection including use of one or more components and/or subsystems explicitly and/or implicitly referred to herein for at least in part implementing execution of one or more instructions of the operation o188, for performance of the operation o188 by an electrical circuitry arrangement as activated thereto, and/or otherwise fulfillment of the operation o188. One or more non-transitory signal bearing physical media can bear the one or more instructions that when executed can direct performance of the operation o188. Furthermore, electronically-receiving-user-biological-status-information-from-electronically-involved-invasive-detection-intravenous-access module m188 depicted in FIG. 34 as being included in the module m178, when executed and/or activated, can direct performance of and/or perform the operation o188. Illustratively, in one or more implementations, the operation o188 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) involving intravenous access (e.g. from intravenous access detection such as blood sampling detection, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 93, the operation o178 can include operation o189 for electronically receiving user biological status information from electronically involved invasive detection including electronically receiving user biological status information from electronically involved invasive detection involving electromagnetic sampling. Origination of a physically tangible component group can be accomplished through skilled in the art design choice selection including use of one or more components and/or subsystems explicitly and/or implicitly referred to herein for at least in part implementing execution of one or more instructions of the operation o189, for performance of the operation o189 by an electrical circuitry arrangement as activated thereto, and/or otherwise fulfillment of the operation o189. One or more non-transitory signal bearing physical media can bear the one or more instructions that when executed can direct performance of the operation o189. Furthermore, electronically-receiving-user-biological-status-information-from-electronically-involved-invasive-detection-electromagnetic-sampling module m189 depicted in FIG. 34 as being included in the module m178, when executed and/or activated, can direct performance of and/or perform the operation o189. Illustratively, in one or more implementations, the operation o189 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved invasive detection (e.g. nanosensors such as electronic, mechanical, surgical, chemical, biological, or other, devices, sensors, tubes, probes, needles, etc. insertable into body, cavity, other, etc.) involving electromagnetic sampling (e.g. from inserted electromagnetic nanoprobes for electromagnetic brain wave activity or monitoring of electric current through electrically conductive connective tissue, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 93, the operation o178 can include operation o190 for electronically receiving user biological status information from electronically involved invasive detection including electronically receiving user biological status information from electronically involved invasive detection involving acoustic sampling. Origination of a physically tangible component group can be accomplished through skilled in the art design choice selection including use of one or more components and/or subsystems explicitly and/or implicitly referred to herein for at least in part implementing execution of one or more instructions of the operation o190, for performance of the operation o190 by an electrical circuitry arrangement as activated thereto, and/or otherwise fulfillment of the operation o190. One or more non-transitory signal bearing physical media can bear the one or more instructions that when executed can direct performance of the operation o190. Furthermore, electronically-receiving-user-biological-status-information-from-electronically-involved-invasive-detection-acoustic-sampling module m190 depicted in FIG. 34 as being included in the module m178, when executed and/or activated, can direct performance of and/or perform the operation o190. Illustratively, in one or more implementations, the operation o190 can be carried out, for example, by electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved invasive detection (e.g. insertion of instrument, object, etc. into body, cavity, etc. such as needles, probes, tubes, sensors, devices, nanosensors such as biological, chemical, surgical, mechanical, electronic or other, etc.) involving acoustic sampling (e.g. from acoustic sampling such as ultrasound sampling, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 94*o*, the operation o11 can include operation o191 for electronically receiving user biological status information from electronically involved detection of one or more biological user conditions including electronically receiving user biological status information from electronically involved non-invasive detection. Origination of a physically tangible component group can be accomplished through skilled in the art design choice selection including use of one or more components and/or subsystems explicitly and/or implicitly referred to herein for at least in part implementing execution of one or more instructions of the operation o191, for performance of the operation o191 by an electrical circuitry arrangement as activated thereto, and/or otherwise fulfillment of the operation o191. One or more non-transitory signal bearing physical media can bear the one or more instructions that when executed can direct performance of the operation o191. Furthermore, electronically-receiving-user-biological-status-information-from-electronically-involved-non-invasive-detection module m191 depicted in FIG. 35 as being included in the module m11, when executed and/or activated, can direct performance of and/or perform the operation o191. Illustratively, in one or more implementations, the operation o191 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.).

Figure 95:
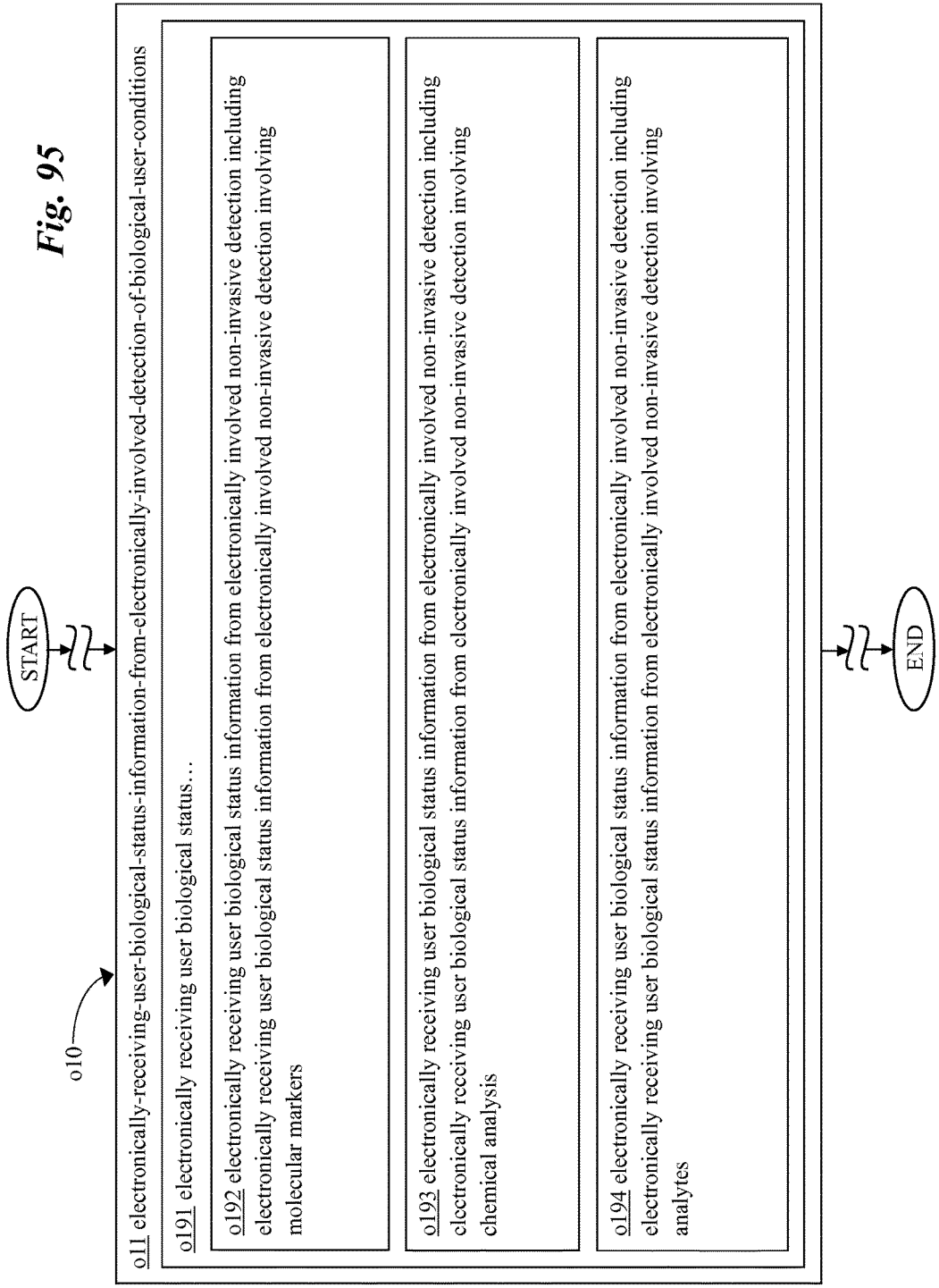

In one or more implementations, as shown in FIG. 95, the operation o191 can include operation o192 for electronically receiving user biological status information from electronically involved non-invasive detection including electronically receiving user biological status information from electronically involved non-invasive detection involving molecular markers. Origination of a physically tangible component group can be accomplished through skilled in the art design choice selection including use of one or more components and/or subsystems explicitly and/or implicitly referred to herein for at least in part implementing execution of one or more instructions of the operation o192, for performance of the operation o192 by an electrical circuitry arrangement as activated thereto, and/or otherwise fulfillment of the operation o192. One or more non-transitory signal bearing physical media can bear the one or more instructions that when executed can direct performance of the operation o192. Furthermore, electronically-receiving-user-biological-status-information-from-electronically-involved-non-invasive-detection-molecular-markers module m192 depicted in FIG. 36 as being included in the module m191, when executed and/or activated, can direct performance of and/or perform the operation o192. Illustratively, in one or more implementations, the operation o192 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving molecular markers (e.g. from detection of molecular markers such as biochemical markers regarding change in gene product level such as in proteins and amino acids and molecular markers regarding change at the DNA level such as nucleotide deletion, duplication, inversion and/or insertion, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 95, the operation o191 can include operation o193 for electronically receiving user biological status information from electronically involved non-invasive detection including electronically receiving user biological status information from electronically involved non-invasive detection involving chemical analysis. Origination of a physically tangible component group can be accomplished through skilled in the art design choice selection including use of one or more components and/or subsystems explicitly and/or implicitly referred to herein for at least in part implementing execution of one or more instructions of the operation o193, for performance of the operation o193 by an electrical circuitry arrangement as activated thereto, and/or otherwise fulfillment of the operation o193. One or more non-transitory signal bearing physical media can bear the one or more instructions that when executed can direct performance of the operation o193. Furthermore, electronically-receiving-user-biological-status-information-from-electronically-involved-non-invasive-detection-chemical-analysis module m193 depicted in FIG. 36 as being included in the module m191, when executed and/or activated, can direct performance of and/or perform the operation o193. Illustratively, in one or more implementations, the operation o193 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving chemical analysis (e.g. from chemical analysis data of breath, saliva, urine, hair, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 95, the operation o191 can include operation o194 for electronically receiving user biological status information from electronically involved non-invasive detection including electronically receiving user biological status information from electronically involved non-invasive detection involving analytes. Origination of a physically tangible component group can be accomplished through skilled in the art design choice selection including use of one or more components and/or subsystems explicitly and/or implicitly referred to herein for at least in part implementing execution of one or more instructions of the operation o194, for performance of the operation o194 by an electrical circuitry arrangement as activated thereto, and/or otherwise fulfillment of the operation o194. One or more non-transitory signal bearing physical media can bear the one or more instructions that when executed can direct performance of the operation o194. Furthermore, electronically-receiving-user-biological-status-information-from-electronically-involved-non-invasive-detection-analytes module m194 depicted in FIG. 36 as being included in the module m191, when executed and/or activated, can direct performance of and/or perform the operation o194. Illustratively, in one or more implementations, the operation o194 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving analytes (e.g. from analyte detection such as blood sugar concentration, uric acid concentration, acoustic sampling such as ultrasound sampling, etc. to a kiosk, personal, community, or other type vending, dispensing, or food fabricating machine located in a home, business, transportation facility, market, sports facility, office building, theater, school, hospital, park, restaurant, food court, etc.).

Figure 96:
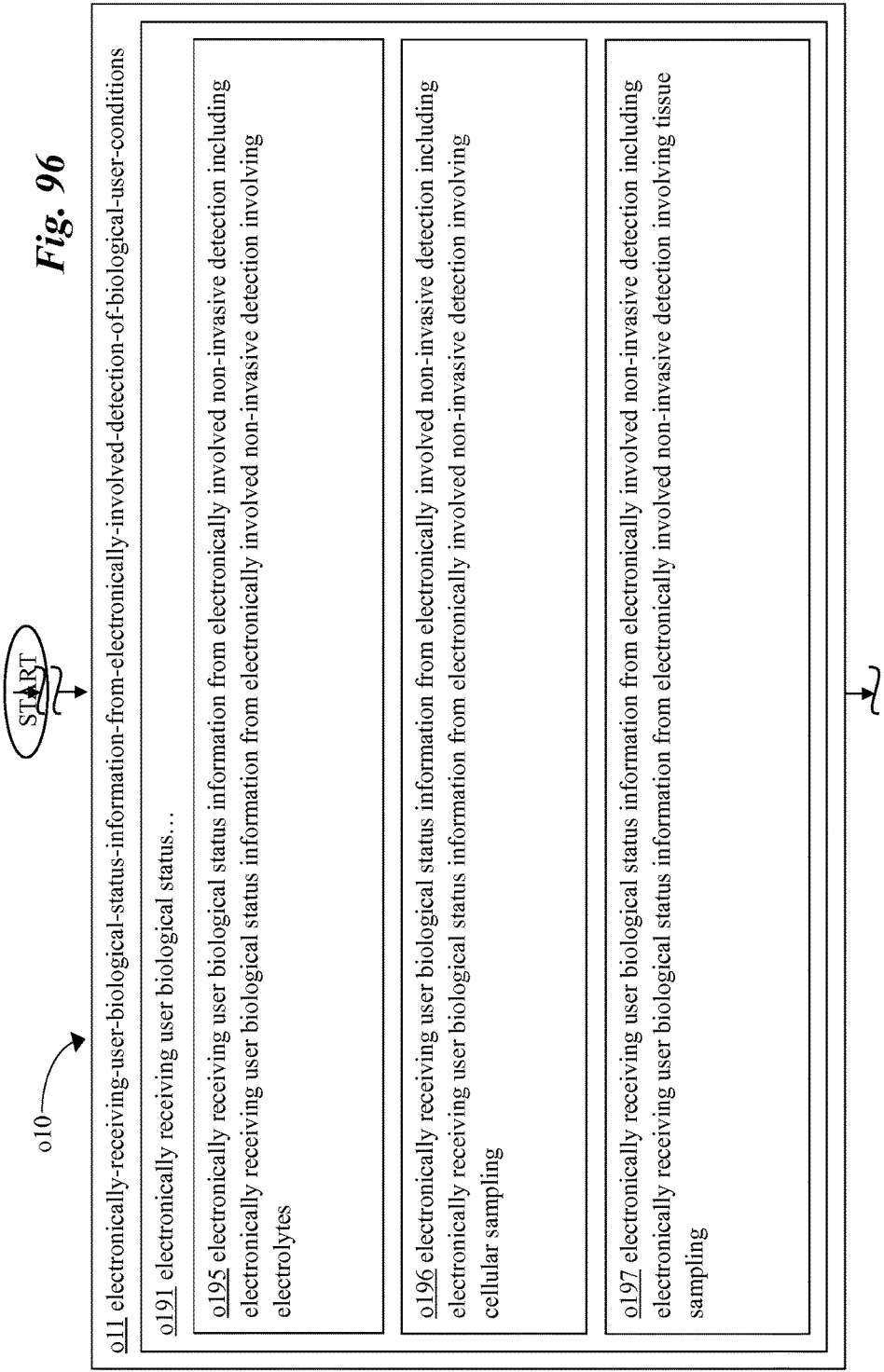

In one or more implementations, as shown in FIG. 96, the operation o191 can include operation o195 for electronically receiving user biological status information from electronically involved non-invasive detection including electronically receiving user biological status information from electronically involved non-invasive detection involving electrolytes. Origination of a physically tangible component group can be accomplished through skilled in the art design choice selection including use of one or more components and/or subsystems explicitly and/or implicitly referred to herein for at least in part implementing execution of one or more instructions of the operation o195, for performance of the operation o195 by an electrical circuitry arrangement as activated thereto, and/or otherwise fulfillment of the operation o195. One or more non-transitory signal bearing physical media can bear the one or more instructions that when executed can direct performance of the operation o195. Furthermore, electronically-receiving-user-biological-status-information-from-electronically-involved-non-invasive-detection-electrolytes module m195 depicted in FIG. 37 as being included in the module m191, when executed and/or activated, can direct performance of and/or perform the operation o195. Illustratively, in one or more implementations, the operation o195 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving electrolytes (e.g. from electrolyte data of breath, saliva, urine, hair, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 96, the operation o191 can include operation o196 for electronically receiving user biological status information from electronically involved non-invasive detection including electronically receiving user biological status information from electronically involved non-invasive detection involving cellular sampling. Origination of a physically tangible component group can be accomplished through skilled in the art design choice selection including use of one or more components and/or subsystems explicitly and/or implicitly referred to herein for at least in part implementing execution of one or more instructions of the operation o196, for performance of the operation o196 by an electrical circuitry arrangement as activated thereto, and/or otherwise fulfillment of the operation o196. One or more non-transitory signal bearing physical media can bear the one or more instructions that when executed can direct performance of the operation o196. Furthermore, electronically-receiving-user-biological-status-information-from-electronically-involved-non-invasive-detection-cellular-sampling module m196 depicted in FIG. 37 as being included in the module m191, when executed and/or activated, can direct performance of and/or perform the operation o196. Illustratively, in one or more implementations, the operation o196 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving cellular sampling (e.g. from cellular sampling such as blood sampling, skin sampling, hair sampling, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 96, the operation o191 can include operation o197 for electronically receiving user biological status information from electronically involved non-invasive detection including electronically receiving user biological status information from electronically involved non-invasive detection involving tissue sampling. Origination of a physically tangible component group can be accomplished through skilled in the art design choice selection including use of one or more components and/or subsystems explicitly and/or implicitly referred to herein for at least in part implementing execution of one or more instructions of the operation o197, for performance of the operation o197 by an electrical circuitry arrangement as activated thereto, and/or otherwise fulfillment of the operation o197. One or more non-transitory signal bearing physical media can bear the one or more instructions that when executed can direct performance of the operation o197. Furthermore, electronically-receiving-user-biological-status-information-from-electronically-involved-non-invasive-detection-tissue-sampling module m197 depicted in FIG. 37 as being included in the module m191, when executed and/or activated, can direct performance of and/or perform the operation o197. Illustratively, in one or more implementations, the operation o197 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving tissue sampling (e.g. from tissue sampling of skin, hair, nails, tissue biopsy, etc. to a kiosk, personal, community, or other type vending, dispensing, or food fabricating machine located in a home, business, transportation facility, market, sports facility, office building, theater, school, hospital, park, restaurant, food court, etc.).

Figure 97:
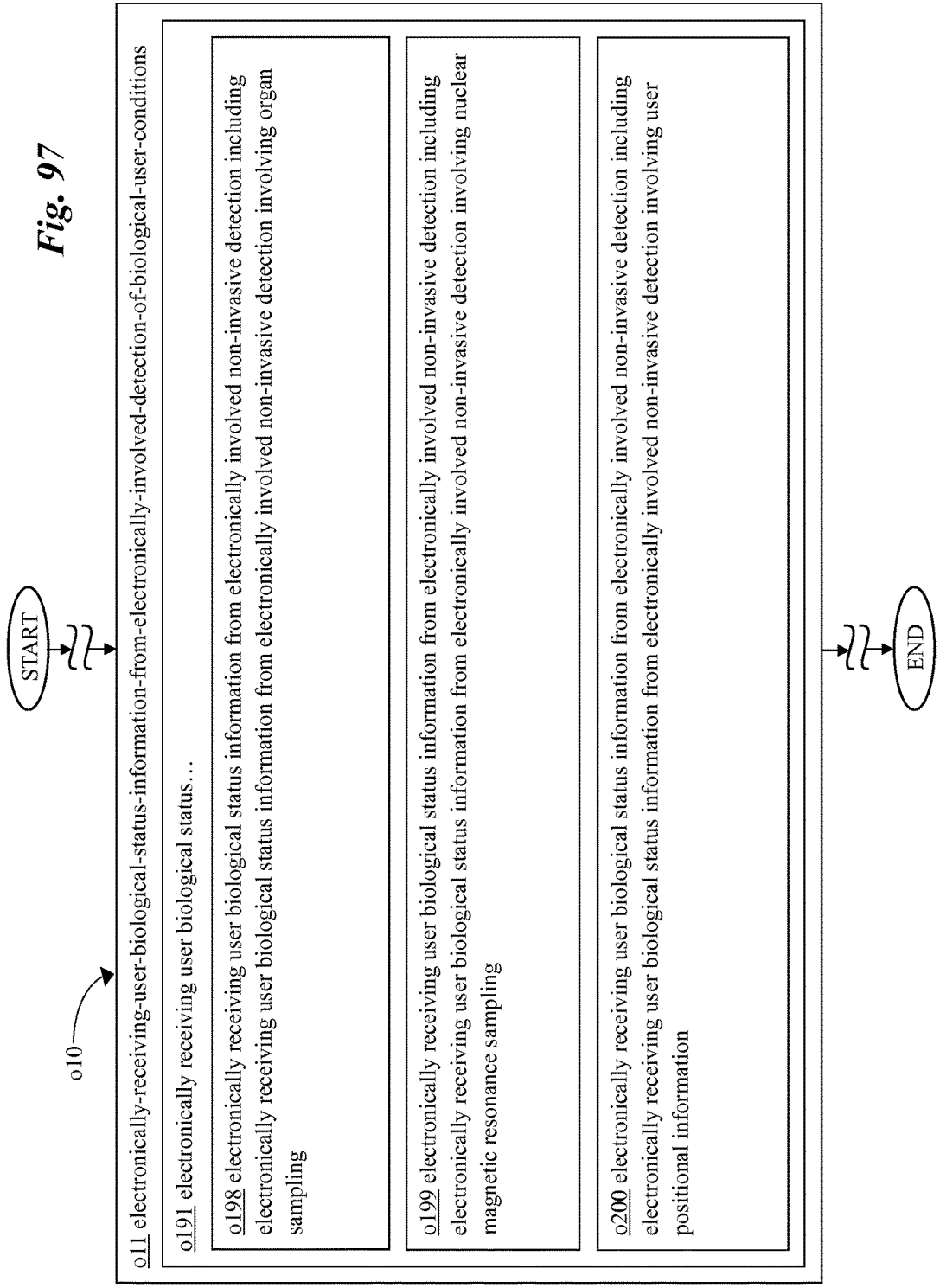

In one or more implementations, as shown in FIG. 97, the operation o191 can include operation o198 for electronically receiving user biological status information from electronically involved non-invasive detection including electronically receiving user biological status information from electronically involved non-invasive detection involving organ sampling. Origination of a physically tangible component group can be accomplished through skilled in the art design choice selection including use of one or more components and/or subsystems explicitly and/or implicitly referred to herein for at least in part implementing execution of one or more instructions of the operation o198, for performance of the operation o198 by an electrical circuitry arrangement as activated thereto, and/or otherwise fulfillment of the operation o198. One or more non-transitory signal bearing physical media can bear the one or more instructions that when executed can direct performance of the operation o198. Furthermore, electronically-receiving-user-biological-status-information-from-electronically-involved-non-invasive-detection-organ-sampling module m198 depicted in FIG. 38 as being included in the module m191, when executed and/or activated, can direct performance of and/or perform the operation o198. Illustratively, in one or more implementations, the operation o198 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving organ sampling (e.g. from organ sampling such as ultrasound, CAT scans, or NMRs of an organ, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 97, the operation o191 can include operation o199 for electronically receiving user biological status information from electronically involved non-invasive detection including electronically receiving user biological status information from electronically involved non-invasive detection involving nuclear magnetic resonance sampling. Origination of a physically tangible component group can be accomplished through skilled in the art design choice selection including use of one or more components and/or subsystems explicitly and/or implicitly referred to herein for at least in part implementing execution of one or more instructions of the operation o199, for performance of the operation o199 by an electrical circuitry arrangement as activated thereto, and/or otherwise fulfillment of the operation o199. One or more non-transitory signal bearing physical media can bear the one or more instructions that when executed can direct performance of the operation o199. Furthermore, electronically-receiving-user-biological-status-information-from-electronically-involved-non-invasive-detection-nuclear-magnetic-resonance-sampling module m199 depicted in FIG. 38 as being included in the module m191, when executed and/or activated, can direct performance of and/or perform the operation o199. Illustratively, in one or more implementations, the operation o199 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving nuclear magnetic resonance sampling (e.g. from nuclear magnetic resonance sampling of body portions such as head, trunk, chest cavity, whole body, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 97, the operation o191 can include operation o200 for electronically receiving user biological status information from electronically involved non-invasive detection including electronically receiving user biological status information from electronically involved non-invasive detection involving user positional information. Origination of a physically tangible component group can be accomplished through skilled in the art design choice selection including use of one or more components and/or subsystems explicitly and/or implicitly referred to herein for at least in part implementing execution of one or more instructions of the operation o200, for performance of the operation o200 by an electrical circuitry arrangement as activated thereto, and/or otherwise fulfillment of the operation o200. One or more non-transitory signal bearing physical media can bear the one or more instructions that when executed can direct performance of the operation o200. Furthermore, electronically-receiving-user-biological-status-information-from-electronically-involved-non-invasive-detection-user-positional-information-module m200 depicted in FIG. 38 as being included in the module m191, when executed and/or activated, can direct performance of and/or perform the operation o200. Illustratively, in one or more implementations, the operation o200 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving user positional information (e.g. from detection of user positional information such as from global position satellite (GPS) system data, fixed positional marker data such as through communication interaction with a fixed food dispensing station, communication interaction with others at known locations, communication interaction with an electronic personal device containing position data, etc. to a kiosk, personal, community, or other type vending, dispensing, or food fabricating machine located in a home, business, transportation facility, market, sports facility, office building, theater, school, hospital, park, restaurant, food court, etc.).

Figure 98:
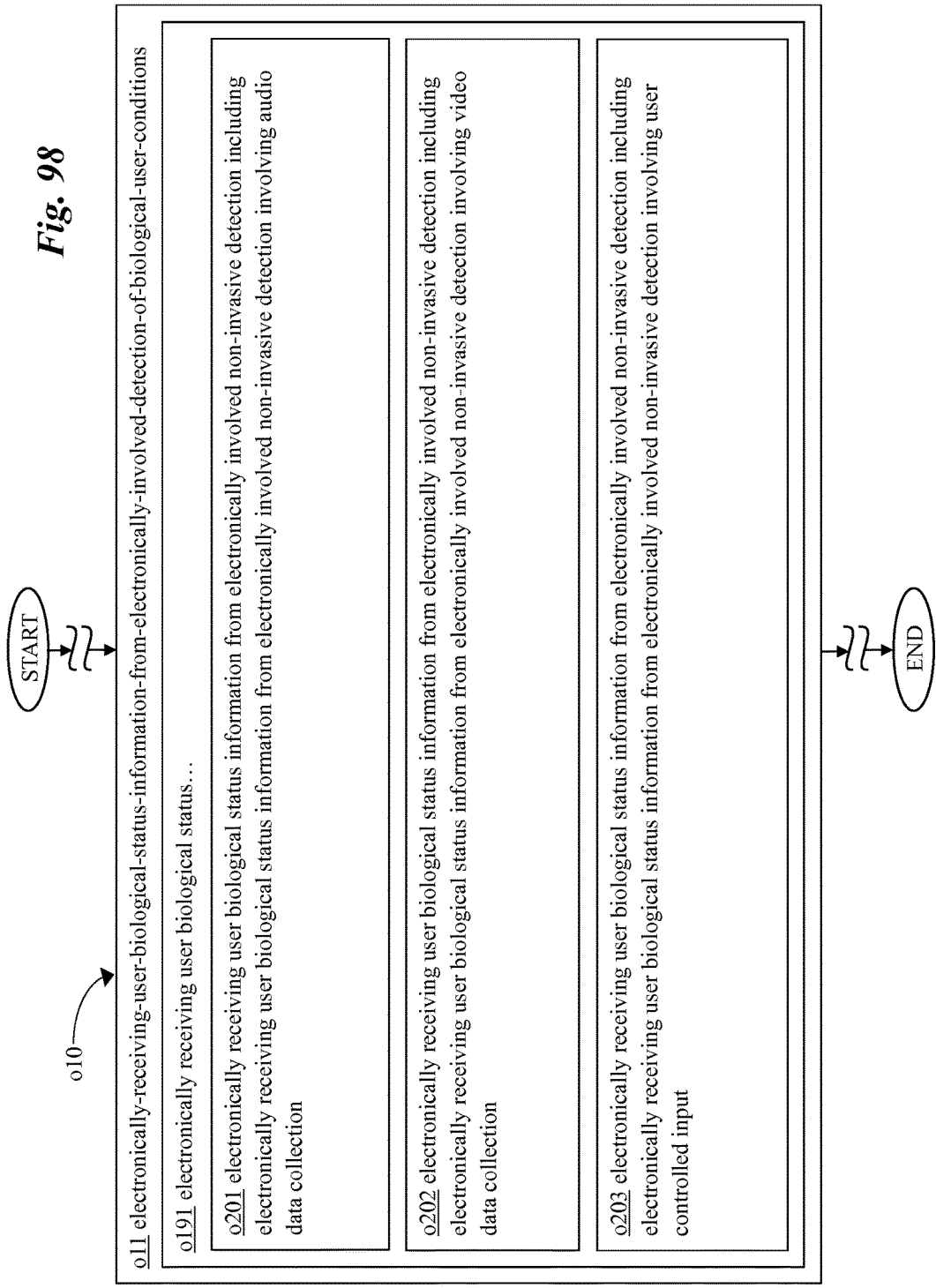

In one or more implementations, as shown in FIG. 98, the operation o191 can include operation o201 for electronically receiving user biological status information from electronically involved non-invasive detection including electronically receiving user biological status information from electronically involved non-invasive detection involving audio data collection. Origination of a physically tangible component group can be accomplished through skilled in the art design choice selection including use of one or more components and/or subsystems explicitly and/or implicitly referred to herein for at least in part implementing execution of one or more instructions of the operation o201, for performance of the operation o201 by an electrical circuitry arrangement as activated thereto, and/or otherwise fulfillment of the operation o201. One or more non-transitory signal bearing physical media can bear the one or more instructions that when executed can direct performance of the operation o201. Furthermore, electronically-receiving-user-biological-status-information-from-electronically-involved-non-invasive-detection-audio-data-collection module m201 depicted in FIG. 39 as being included in the module m191, when executed and/or activated, can direct performance of and/or perform the operation o201. Illustratively, in one or more implementations, the operation o201 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving audio data collection (e.g. from verbal comments by users, observers, etc. regarding health or disease status, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 98, the operation o191 can include operation o202 for electronically receiving user biological status information from electronically involved non-invasive detection including electronically receiving user biological status information from electronically involved non-invasive detection involving video data collection. Origination of a physically tangible component group can be accomplished through skilled in the art design choice selection including use of one or more components and/or subsystems explicitly and/or implicitly referred to herein for at least in part implementing execution of one or more instructions of the operation o202, for performance of the operation o202 by an electrical circuitry arrangement as activated thereto, and/or otherwise fulfillment of the operation o202. One or more non-transitory signal bearing physical media can bear the one or more instructions that when executed can direct performance of the operation o202. Furthermore, electronically-receiving-user-biological-status-information-from-electronically-involved-non-invasive-detection-video-data-collection module m202 depicted in FIG. 39 as being included in the module m191, when executed and/or activated, can direct performance of and/or perform the operation o202. Illustratively, in one or more implementations, the operation o202 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving video data collection (e.g. from detection through pattern recognition of video images, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 98, the operation o191 can include operation o203 for electronically receiving user biological status information from electronically involved non-invasive detection including electronically receiving user biological status information from electronically involved non-invasive detection involving user controlled input. Origination of a physically tangible component group can be accomplished through skilled in the art design choice selection including use of one or more components and/or subsystems explicitly and/or implicitly referred to herein for at least in part implementing execution of one or more instructions of the operation o203, for performance of the operation o203 by an electrical circuitry arrangement as activated thereto, and/or otherwise fulfillment of the operation o203. One or more non-transitory signal bearing physical media can bear the one or more instructions that when executed can direct performance of the operation o203. Furthermore, electronically-receiving-user-biological-status-information-from-electronically-involved-non-invasive-detection-user-controlled-input module m203 depicted in FIG. 39 as being included in the module m191, when executed and/or activated, can direct performance of and/or perform the operation o203. Illustratively, in one or more implementations, the operation o203 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving user controlled input (e.g. from user input through computer input devices such as keyboard, voice recognition, touch screen, mouse, etc. regarding health or disease status, etc. to a kiosk, personal, community, or other type vending, dispensing, or food fabricating machine located in a home, business, transportation facility, market, sports facility, office building, theater, school, hospital, park, restaurant, food court, etc.).

Figure 99:
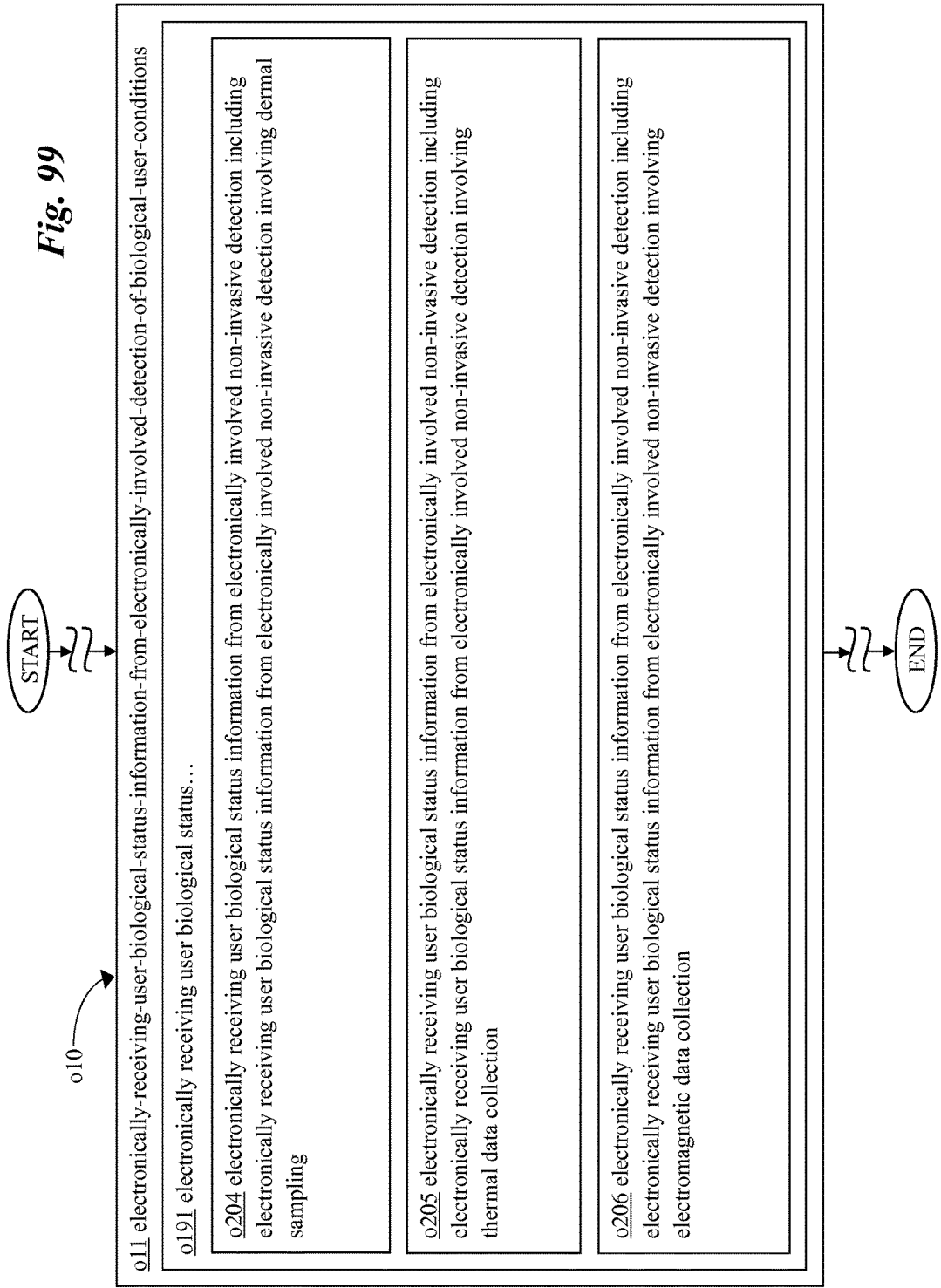

In one or more implementations, as shown in FIG. 99, the operation o191 can include operation o204 for electronically receiving user biological status information from electronically involved non-invasive detection including electronically receiving user biological status information from electronically involved non-invasive detection involving dermal sampling. Origination of a physically tangible component group can be accomplished through skilled in the art design choice selection including use of one or more components and/or subsystems explicitly and/or implicitly referred to herein for at least in part implementing execution of one or more instructions of the operation o204, for performance of the operation o204 by an electrical circuitry arrangement as activated thereto, and/or otherwise fulfillment of the operation o204. One or more non-transitory signal bearing physical media can bear the one or more instructions that when executed can direct performance of the operation o204. Furthermore, electronically-receiving-user-biological-status-information-from-electronically-involved-non-invasive-detection-dermal-sampling module m204 depicted in FIG. 40 as being included in the module m191, when executed and/or activated, can direct performance of and/or perform the operation o204. Illustratively, in one or more implementations, the operation o204 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving dermal sampling (e.g. from detection of user skin debris samples, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 99, the operation o191 can include operation o205 for electronically receiving user biological status information from electronically involved non-invasive detection including electronically receiving user biological status information from electronically involved non-invasive detection involving thermal data collection. Origination of a physically tangible component group can be accomplished through skilled in the art design choice selection including use of one or more components and/or subsystems explicitly and/or implicitly referred to herein for at least in part implementing execution of one or more instructions of the operation o205, for performance of the operation o205 by an electrical circuitry arrangement as activated thereto, and/or otherwise fulfillment of the operation o205. One or more non-transitory signal bearing physical media can bear the one or more instructions that when executed can direct performance of the operation o205. Furthermore, electronically-receiving-user-biological-status-information-from-electronically-involved-non-invasive-detection-thermal-data-collection module m205 depicted in FIG. 40 as being included in the module m191, when executed and/or activated, can direct performance of and/or perform the operation o205. Illustratively, in one or more implementations, the operation o205 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving thermal data collection (e.g. from forehead thermal scan, oral temperature, basal temperature, etc. collection regarding health or disease status, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 99, the operation o191 can include operation o206 for electronically receiving user biological status information from electronically involved non-invasive detection including electronically receiving user biological status information from electronically involved non-invasive detection involving electromagnetic data collection. Origination of a physically tangible component group can be accomplished through skilled in the art design choice selection including use of one or more components and/or subsystems explicitly and/or implicitly referred to herein for at least in part implementing execution of one or more instructions of the operation o206, for performance of the operation o206 by an electrical circuitry arrangement as activated thereto, and/or otherwise fulfillment of the operation o206. One or more non-transitory signal bearing physical media can bear the one or more instructions that when executed can direct performance of the operation o206. Furthermore, electronically-receiving-user-biological-status-information-from-electronically-involved-non-invasive-detection-electromagnetic-data-collection module m206 depicted in FIG. 40 as being included in the module m191, when executed and/or activated, can direct performance of and/or perform the operation o206. Illustratively, in one or more implementations, the operation o206 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving electromagnetic data collection (e.g. from detection with thermal infrared scans, x-ray scans, etc. to a kiosk, personal, community, or other type vending, dispensing, or food fabricating machine located in a home, business, transportation facility, market, sports facility, office building, theater, school, hospital, park, restaurant, food court, etc.).

Figure 100:
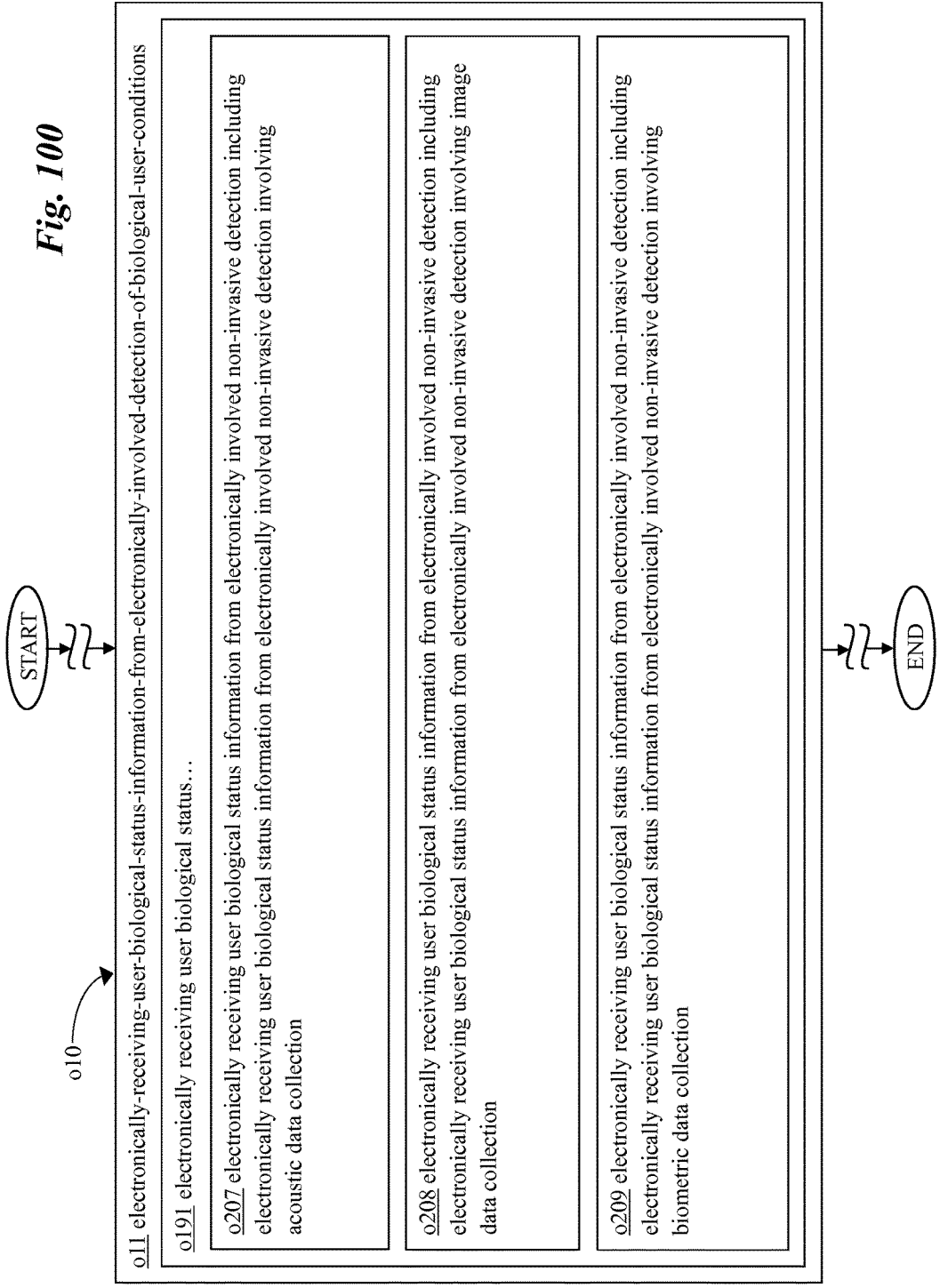

In one or more implementations, as shown in FIG. 100, the operation o191 can include operation o207 for electronically receiving user biological status information from electronically involved non-invasive detection including electronically receiving user biological status information from electronically involved non-invasive detection involving acoustic data collection. Origination of a physically tangible component group can be accomplished through skilled in the art design choice selection including use of one or more components and/or subsystems explicitly and/or implicitly referred to herein for at least in part implementing execution of one or more instructions of the operation o207, for performance of the operation o207 by an electrical circuitry arrangement as activated thereto, and/or otherwise fulfillment of the operation o207. One or more non-transitory signal bearing physical media can bear the one or more instructions that when executed can direct performance of the operation o207. Furthermore, electronically-receiving-user-biological-status-information-from-electronically-involved-non-invasive-detection-acoustic-data-collection module m207 depicted in FIG. 41 as being included in the module m191, when executed and/or activated, can direct performance of and/or perform the operation o207. Illustratively, in one or more implementations, the operation o207 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving acoustic data collection (e.g. from ultrasound images of various body portions, etc. regarding health or disease status, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 100, the operation o191 can include operation o208 for electronically receiving user biological status information from electronically involved non-invasive detection including electronically receiving user biological status information from electronically involved non-invasive detection involving image data collection. Origination of a physically tangible component group can be accomplished through skilled in the art design choice selection including use of one or more components and/or subsystems explicitly and/or implicitly referred to herein for at least in part implementing execution of one or more instructions of the operation o208, for performance of the operation o208 by an electrical circuitry arrangement as activated thereto, and/or otherwise fulfillment of the operation o208. One or more non-transitory signal bearing physical media can bear the one or more instructions that when executed can direct performance of the operation o208. Furthermore, electronically-receiving-user-biological-status-information-from-electronically-involved-non-invasive-detection-image-data-collection module m208 depicted in FIG. 41 as being included in the module m191, when executed and/or activated, can direct performance of and/or perform the operation o208. Illustratively, in one or more implementations, the operation o208 can be carried out, for example, by electronically receiving (e.g. swipes, scans, non-wireless, network direct device-todevice, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. radio frequency, WiFi, Bluetooth, packetized data, wireless protocols, infrared, electromagnetic, etc.) user biological status information (e.g. current, physiological, historical, functional, etc.) from electronically involved non-invasive detection (e.g. without insertion into body, cavity, etc. using external probes, sensors, devices, nanosensors such as biological, chemical, surgical, mechanical, electronic or other, etc.) involving image data collection (e.g. from detection of user image data of ultrasound scans, x-ray scans, thermal images, video images, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 100, the operation o191 can include operation o209 for electronically receiving user biological status information from electronically involved non-invasive detection including electronically receiving user biological status information from electronically involved non-invasive detection involving biometric data collection. Origination of a physically tangible component group can be accomplished through skilled in the art design choice selection including use of one or more components and/or subsystems explicitly and/or implicitly referred to herein for at least in part implementing execution of one or more instructions of the operation o209, for performance of the operation o209 by an electrical circuitry arrangement as activated thereto, and/or otherwise fulfillment of the operation o209. One or more non-transitory signal bearing physical media can bear the one or more instructions that when executed can direct performance of the operation o209. Furthermore, electronically-receiving-user-biological-status-information-from-electronically-involved-non-invasive-detection-biometric-data-collection module m209 depicted in FIG. 41 as being included in the module m191, when executed and/or activated, can direct performance of and/or perform the operation o209. Illustratively, in one or more implementations, the operation o209 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) user biological status information (e.g. quantified-self data, group, behavior life data, individual, functional, historical, physiological, current, etc.) from electronically involved non-invasive detection (e.g. nanosensors such as electronic, mechanical, surgical, chemical, biological, or other, devices, sensors, external probes, etc. without insertion into body, cavity, etc.) involving biometric data collection (e.g. from fingerprint, iris, voice, facial, or other biometric scans, etc. to a kiosk, personal, community, or other type vending, dispensing, or food fabricating machine located in a home, business, transportation facility, market, sports facility, office building, theater, school, hospital, park, restaurant, food court, etc.).

Figure 94:
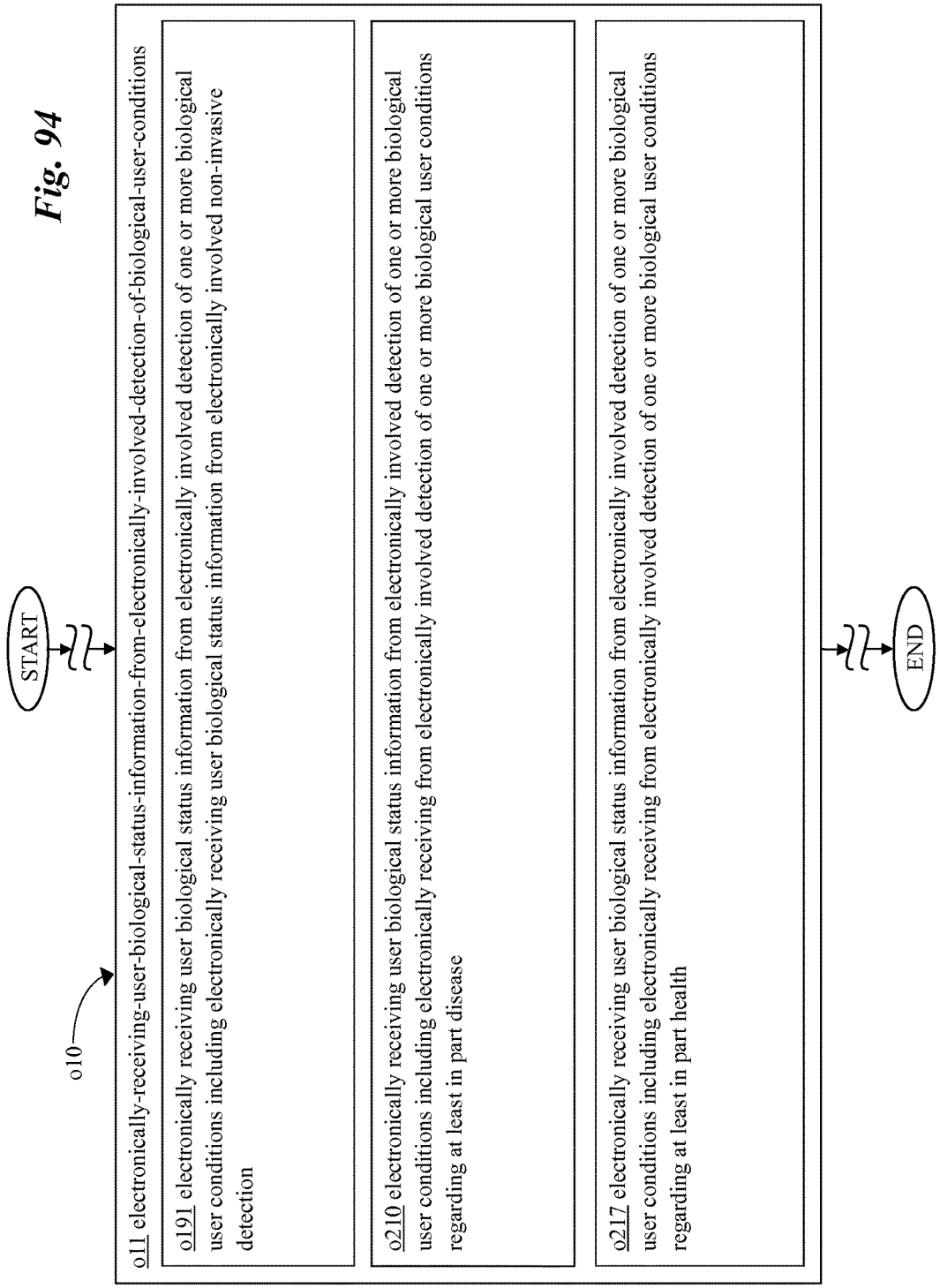

In one or more implementations, as shown in FIG. 94, the operation o11 can include operation o210 for electronically receiving user biological status information from electronically involved detection of one or more biological user conditions including electronically receiving from electronically involved detection of one or more biological user conditions regarding at least in part disease. Origination of a physically tangible component group can be accomplished through skilled in the art design choice selection including use of one or more components and/or subsystems explicitly and/or implicitly referred to herein for at least in part implementing execution of one or more instructions of the operation o210, for performance of the operation o210 by an electrical circuitry arrangement as activated thereto, and/or otherwise fulfillment of the operation o210. One or more non-transitory signal bearing physical media can bear the one or more instructions that when executed can direct performance of the operation o210. Furthermore, electronically-receiving-from-electronically-involved-detection-of-biological-user-conditions-regarding-disease module m210 depicted in FIG. 35 as being included in the module m11, when executed and/or activated, can direct performance of and/or perform the operation o210. Illustratively, in one or more implementations, the operation o210 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part disease (e.g. from detection of disease such as cancer, cardiovascular, chronic, acute, temporary, intermittent, contagious, epidemic, etc. to a kiosk, personal, community, or other type vending, dispensing, or food fabricating machine located in a home, business, transportation facility, market, sports facility, office building, theater, school, hospital, park, restaurant, food court, etc.).

Figure 101:
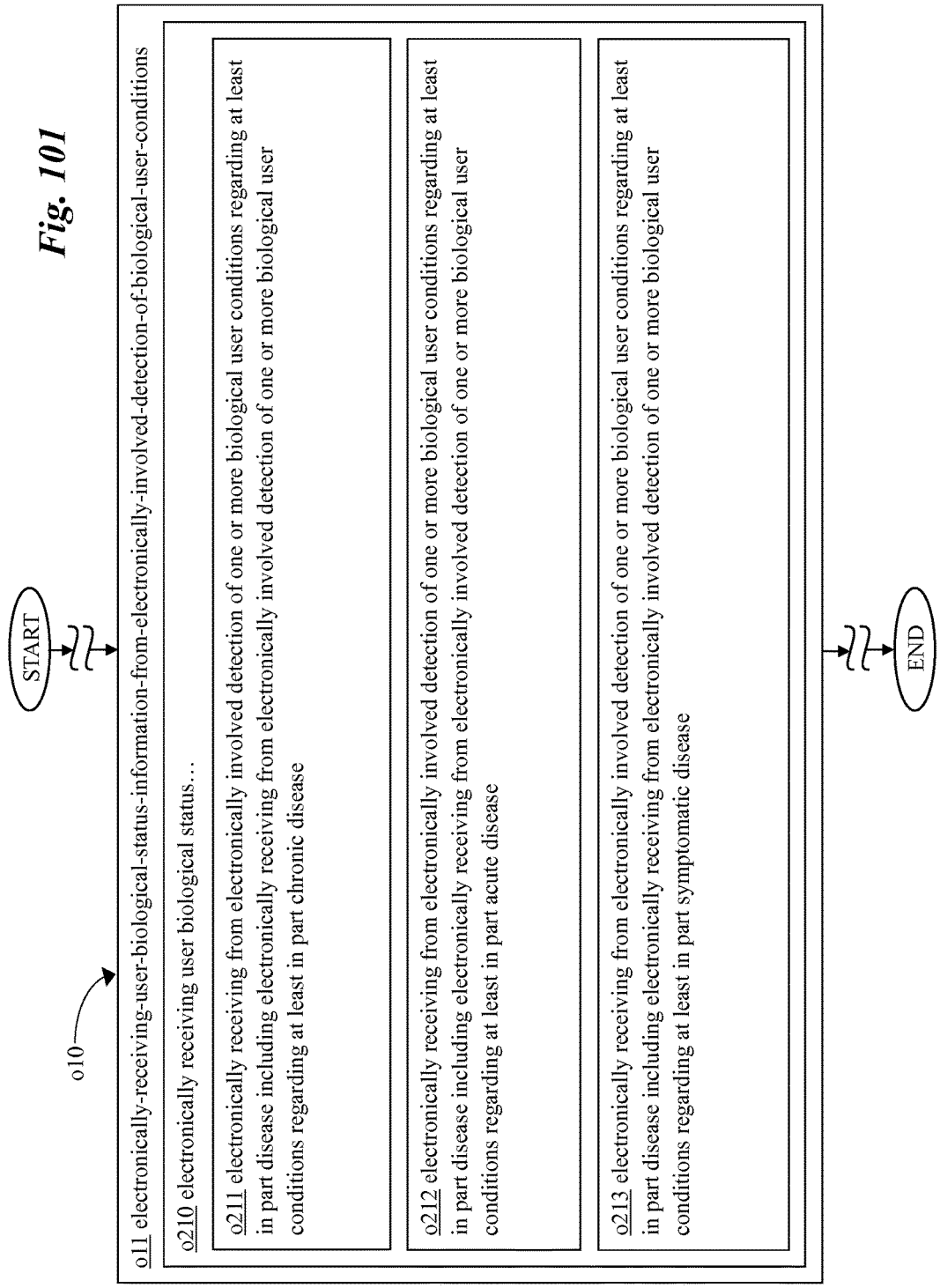

In one or more implementations, as shown in FIG. 101, the operation o210 can include operation o211 for electronically receiving from electronically involved detection of one or more biological user conditions regarding at least in part disease including electronically receiving from electronically involved detection of one or more biological user conditions regarding at least in part chronic disease. Origination of a physically tangible component group can be accomplished through skilled in the art design choice selection including use of one or more components and/or subsystems explicitly and/or implicitly referred to herein for at least in part implementing execution of one or more instructions of the operation o211, for performance of the operation o211 by an electrical circuitry arrangement as activated thereto, and/or otherwise fulfillment of the operation o211. One or more non-transitory signal bearing physical media can bear the one or more instructions that when executed can direct performance of the operation o211. Furthermore, electronically-receiving-from-electronically-involved-detection-of-biological-user-conditions-regarding-chronic-disease module m211 depicted in FIG. 42 as being included in the module m210, when executed and/or activated, can direct performance of and/or perform the operation o211. Illustratively, in one or more implementations, the operation o211 can be carried out, for example, by swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part chronic disease (e.g. data regarding cancer, cardiovascular disease, chronic obstructive pulmonary disorder, asthma, allergies, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 101, the operation o210 can include operation o212 for electronically receiving from electronically involved detection of one or more biological user conditions regarding at least in part disease including electronically receiving from electronically involved detection of one or more biological user conditions regarding at least in part acute disease. Origination of a physically tangible component group can be accomplished through skilled in the art design choice selection including use of one or more components and/or subsystems explicitly and/or implicitly referred to herein for at least in part implementing execution of one or more instructions of the operation o212, for performance of the operation o212 by an electrical circuitry arrangement as activated thereto, and/or otherwise fulfillment of the operation o212. One or more non-transitory signal bearing physical media can bear the one or more instructions that when executed can direct performance of the operation o212. Furthermore, electronically-receiving-from-electronically-involved-detection-of-biological-user-conditions-regarding-acute-disease module m212 depicted in FIG. 42 as being included in the module m210, when executed and/or activated, can direct performance of and/or perform the operation o212. Illustratively, in one or more implementations, the operation o212 can be carried out, for example, by electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part disease (e.g. from detection of disease such as cancer, cardiovascular, chronic, acute, temporary, intermittent, contagious, epidemic, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part acute disease (e.g. from detection of acute disease such as colds, influenza, other viral or bacterial related diseases, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 101, the operation o210 can include operation o213 for electronically receiving from electronically involved detection of one or more biological user conditions regarding at least in part disease including electronically receiving from electronically involved detection of one or more biological user conditions regarding at least in part symptomatic disease. Origination of a physically tangible component group can be accomplished through skilled in the art design choice selection including use of one or more components and/or subsystems explicitly and/or implicitly referred to herein for at least in part implementing execution of one or more instructions of the operation o213, for performance of the operation o213 by an electrical circuitry arrangement as activated thereto, and/or otherwise fulfillment of the operation o213. One or more non-transitory signal bearing physical media can bear the one or more instructions that when executed can direct performance of the operation o213. Furthermore, electronically-receiving-from-electronically-involved-detection-of-biological-user-conditions-regarding-symptomatic-disease module m213 depicted in FIG. 42 as being included in the module m210, when executed and/or activated, can direct performance of and/or perform the operation o213. Illustratively, in one or more implementations, the operation o213 can be carried out, for example, by swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part symptomatic disease (e.g. data regarding migraine headaches, joint pains, shortness of breath, etc. received at a kiosk, personal, community, or other type vending, dispensing, or food fabricating machine located in a home, business, transportation facility, market, sports facility, office building, theater, school, hospital, park, restaurant, food court, etc.).

Figure 102:
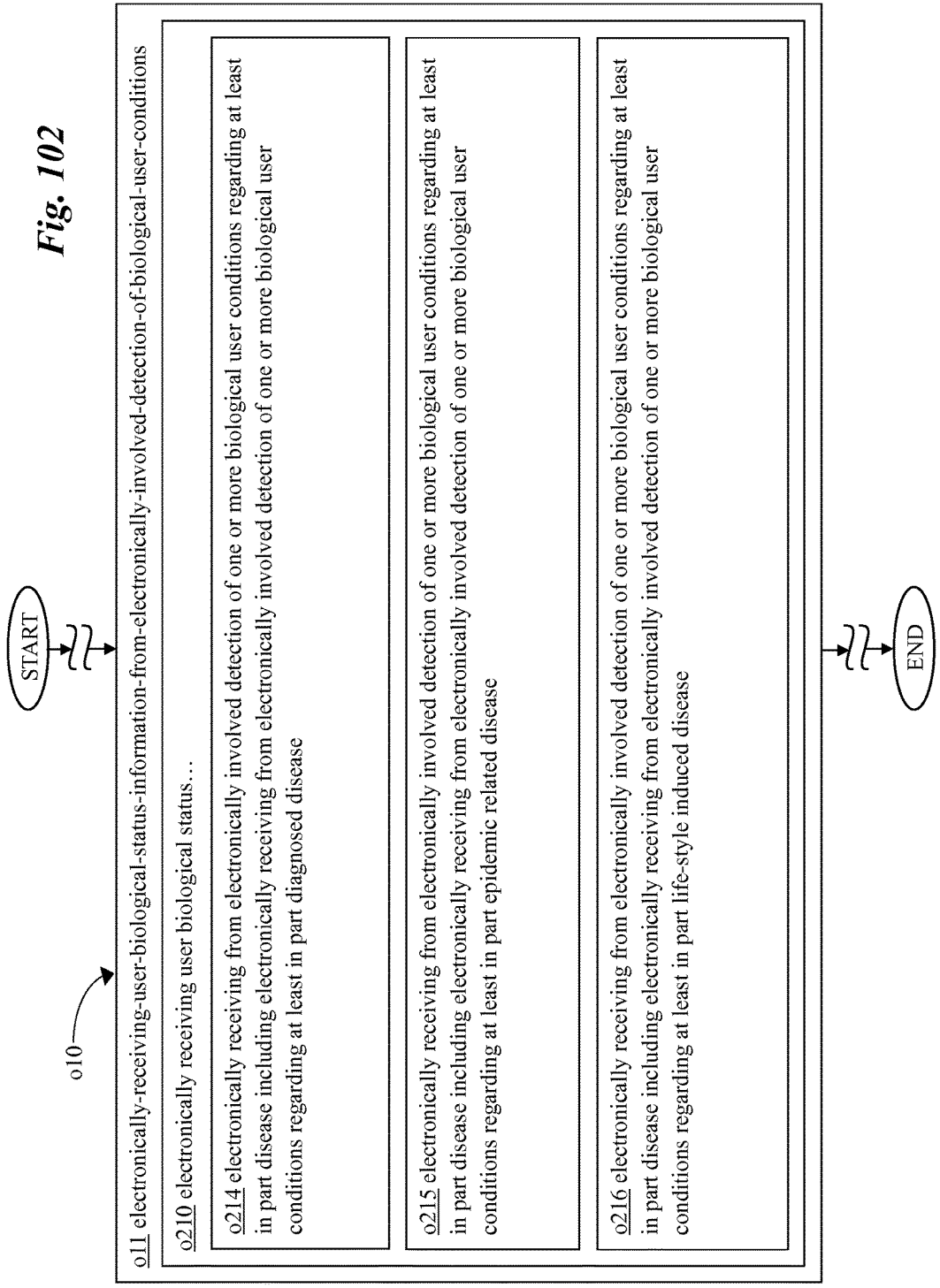

In one or more implementations, as shown in FIG. 102, the operation o210 can include operation o214 for electronically receiving from electronically involved detection of one or more biological user conditions regarding at least in part disease including electronically receiving from electronically involved detection of one or more biological user conditions regarding at least in part diagnosed disease. Origination of a physically tangible component group can be accomplished through skilled in the art design choice selection including use of one or more components and/or subsystems explicitly and/or implicitly referred to herein for at least in part implementing execution of one or more instructions of the operation o214, for performance of the operation o214 by an electrical circuitry arrangement as activated thereto, and/or otherwise fulfillment of the operation o214. One or more non-transitory signal bearing physical media can bear the one or more instructions that when executed can direct performance of the operation o214. Furthermore, electronically-receiving-from-electronically-involved-detection-of-biological-user-conditions-regarding-diagnosed-disease module m214 depicted in FIG. 43 as being included in the module m210, when executed and/or activated, can direct performance of and/or perform the operation o214. Illustratively, in one or more implementations, the operation o214 can be carried out, for example, by electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part disease (e.g. from detection of disease such as cancer, cardiovascular, chronic, acute, temporary, intermittent, contagious, epidemic, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part diagnosed disease (e.g. from detection of diagnosed disease such as cancer, heart disease, diabetes, hypothyroidism, chronic fatigue, influenza, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 102, the operation o210 can include operation o215 for electronically receiving from electronically involved detection of one or more biological user conditions regarding at least in part disease including electronically receiving from electronically involved detection of one or more biological user conditions regarding at least in part epidemic related disease. Origination of a physically tangible component group can be accomplished through skilled in the art design choice selection including use of one or more components and/or subsystems explicitly and/or implicitly referred to herein for at least in part implementing execution of one or more instructions of the operation o215, for performance of the operation o215 by an electrical circuitry arrangement as activated thereto, and/or otherwise fulfillment of the operation o215. One or more non-transitory signal bearing physical media can bear the one or more instructions that when executed can direct performance of the operation o215. Furthermore, electronically-receiving-from-electronically-involved-detection-of-biological-user-conditions-regarding-epidemic-related-disease module m215 depicted in FIG. 43 as being included in the module m210, when executed and/or activated, can direct performance of and/or perform the operation o215. Illustratively, in one or more implementations, the operation o215 can be carried out, for example, by electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part disease (e.g. from detection of disease such as cancer, cardiovascular, chronic, acute, temporary, intermittent, contagious, epidemic, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part epidemic related disease (e.g. data regarding influenza, strep throat, polio, common cold, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 102, the operation o210 can include operation o216 for electronically receiving from electronically involved detection of one or more biological user conditions regarding at least in part disease including electronically receiving from electronically involved detection of one or more biological user conditions regarding at least in part life-style induced disease. Origination of a physically tangible component group can be accomplished through skilled in the art design choice selection including use of one or more components and/or subsystems explicitly and/or implicitly referred to herein for at least in part implementing execution of one or more instructions of the operation o216, for performance of the operation o216 by an electrical circuitry arrangement as activated thereto, and/or otherwise fulfillment of the operation o216. One or more non-transitory signal bearing physical media can bear the one or more instructions that when executed can direct performance of the operation o216. Furthermore, electronically-receiving-from-electronically-involved-detection-of-biological-user-conditions-regarding-life-style-induced-disease module m216 depicted in FIG. 43 as being included in the module m210, when executed and/or activated, can direct performance of and/or perform the operation o216. Illustratively, in one or more implementations, the operation o216 can be carried out, for example, by electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part disease (e.g. from detection of disease such as cancer, cardiovascular, chronic, acute, temporary, intermittent, contagious, epidemic, etc. to a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part life-style induced disease (e.g. from detection of alcohol or drug induced intoxication, work induced enervation, immobility induced disease, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 94, the operation o11 can include operation o217 for electronically receiving user biological status information from electronically involved detection of one or more biological user conditions including electronically receiving from electronically involved detection of one or more biological user conditions regarding at least in part health. Origination of a physically tangible component group can be accomplished through skilled in the art design choice selection including use of one or more components and/or subsystems explicitly and/or implicitly referred to herein for at least in part implementing execution of one or more instructions of the operation o217, for performance of the operation o217 by an electrical circuitry arrangement as activated thereto, and/or otherwise fulfillment of the operation o217. One or more non-transitory signal bearing physical media can bear the one or more instructions that when executed can direct performance of the operation o217. Furthermore, electronically-receiving-from-electronically-involved-detection-of-biological-user-conditions-regarding-health module m217 depicted in FIG. 35 as being included in the module m11, when executed and/or activated, can direct performance of and/or perform the operation o217. Illustratively, in one or more implementations, the operation o217 can be carried out, for example, by electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, etc.) of one or more biological user conditions (e.g. disease, chronic, acute, symptomatic, diagnosed, epidemic, life-style, health, enhancement, reduction, augmentation, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part health (e.g. data regarding body weight management records, physical exercise records, fitness measurements such as waist measurement records, resting pulse, recovery rate data, etc. received at a kiosk, personal, community, or other type vending, dispensing, or food fabricating machine located in a home, business, transportation facility, market, sports facility, office building, theater, school, hospital, park, restaurant, food court, etc.).

Figure 103:
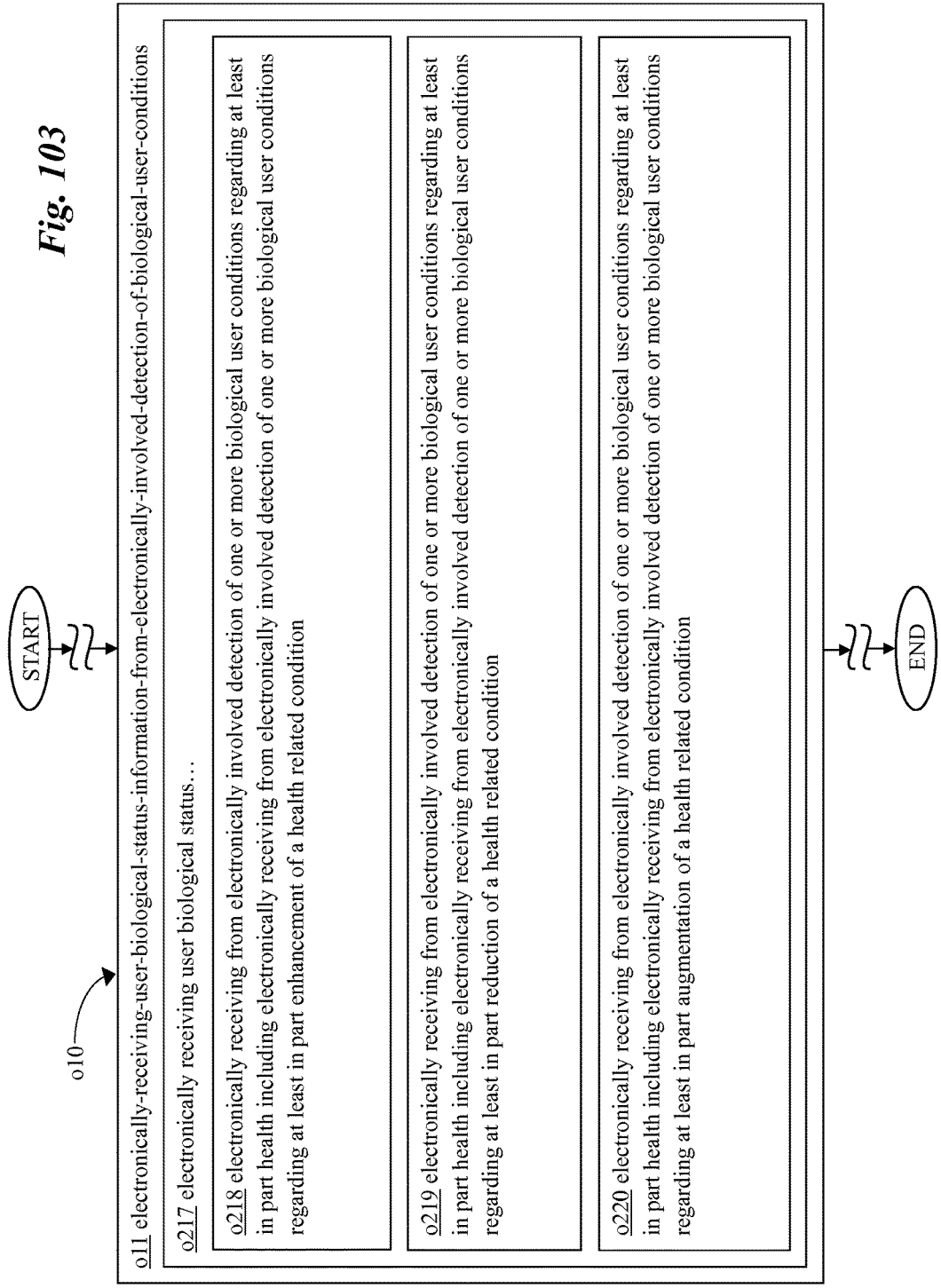

In one or more implementations, as shown in FIG. 103, the operation o217 can include operation o218 for electronically receiving from electronically involved detection of one or more biological user conditions regarding at least in part health including electronically receiving from electronically involved detection of one or more biological user conditions regarding at least in part enhancement of a health related condition. Origination of a physically tangible component group can be accomplished through skilled in the art design choice selection including use of one or more components and/or subsystems explicitly and/or implicitly referred to herein for at least in part implementing execution of one or more instructions of the operation o218, for performance of the operation o218 by an electrical circuitry arrangement as activated thereto, and/or otherwise fulfillment of the operation o218. One or more non-transitory signal bearing physical media can bear the one or more instructions that when executed can direct performance of the operation o218. Furthermore, electronically-receiving-from-electronically-involved-detection-of-biological-user-conditions-regarding-enhancement-of-a-health-related-condition module m218 depicted in FIG. 44 as being included in the module m217, when executed and/or activated, can direct performance of and/or perform the operation o218. Illustratively, in one or more implementations, the operation o218 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part health (e.g. data regarding body weight management records, physical exercise records, fitness measurements such as waist measurement records, resting pulse, recovery rate data, etc. received at a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part enhancement of a health related condition (e.g. from detection of user body weight, VO2 max, waist measurement, weight lifting ability, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 103, the operation o217 can include operation o219 for electronically receiving from electronically involved detection of one or more biological user conditions regarding at least in part health including electronically receiving from electronically involved detection of one or more biological user conditions regarding at least in part reduction of a health related condition. Origination of a physically tangible component group can be accomplished through skilled in the art design choice selection including use of one or more components and/or subsystems explicitly and/or implicitly referred to herein for at least in part implementing execution of one or more instructions of the operation o219, for performance of the operation o219 by an electrical circuitry arrangement as activated thereto, and/or otherwise fulfillment of the operation o219. One or more non-transitory signal bearing physical media can bear the one or more instructions that when executed can direct performance of the operation o219. Furthermore, electronically-receiving-from-electronically-involved-detection-of-biological-user-conditions-regarding-reduction-of-a-health-related-condition module m219 depicted in FIG. 44 as being included in the module m217, when executed and/or activated, can direct performance of and/or perform the operation o219. Illustratively, in one or more implementations, the operation o219 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part health (e.g. data regarding body weight management records, physical exercise records, fitness measurements such as waist measurement records, resting pulse, recovery rate data, etc. received at a kiosk, personal, community, or other type vending, dispensing, or food fabricating machine located in a home, business, transportation facility, market, sports facility, office building, theater, school, hospital, park, restaurant, food court, etc.) including electronically receiving (e.g. swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part reduction of a health related condition (e.g. data regarding reduction of swelling, joint pain, headaches, shortness of breath, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 103, the operation o217 can include operation o220 for electronically receiving from electronically involved detection of one or more biological user conditions regarding at least in part health including electronically receiving from electronically involved detection of one or more biological user conditions regarding at least in part augmentation of a health related condition. Origination of a physically tangible component group can be accomplished through skilled in the art design choice selection including use of one or more components and/or subsystems explicitly and/or implicitly referred to herein for at least in part implementing execution of one or more instructions of the operation o220, for performance of the operation o220 by an electrical circuitry arrangement as activated thereto, and/or otherwise fulfillment of the operation o220. One or more non-transitory signal bearing physical media can bear the one or more instructions that when executed can direct performance of the operation o220. Furthermore, electronically-receiving-from-electronically-involved-detection-of-biological-user-conditions-regarding-augmentation-of-a-health-related-condition module m220 depicted in FIG. 44 as being included in the module m217, when executed and/or activated, can direct performance of and/or perform the operation o220. Illustratively, in one or more implementations, the operation o220 can be carried out, for example, by electronically receiving (e.g. swipes, scans, non-wireless, network direct device-to-device, electromagnetic, infrared, wireless protocols, data packets, Bluetooth, WiFi, radio frequency, other transmission, transfer, etc.) from electronically involved detection (e.g. surgical, biological, electrical, chemical, electromechanical, nanosensor, sensor, device, non-invasive, invasive, other sensing, etc.) of one or more biological user conditions (e.g. disease, life-style, epidemic, diagnosed, symptomatic, enhancement, acute, reduction, chronic, augmentation, health, etc.) regarding at least in part health (e.g. data regarding body weight management records, physical exercise records, fitness measurements such as waist measurement records, resting pulse, recovery rate data, etc. received at a kiosk, personal, community, or other type vending, dispensing, or food fabricating machine located in a home, business, transportation facility, market, sports facility, office building, theater, school, hospital, park, restaurant, food court, etc.) including electronically receiving (e.g. radio frequency, WiFi, Bluetooth, packetized data, wireless protocols, infrared, electromagnetic, etc.) from electronically involved detection (e.g. invasive, non-invasive, device, sensor, nanosensor, electromechanical, chemical, electrical, biological, surgical, other sensing, etc.) of one or more biological user conditions (e.g. health, augmentation, chronic, reduction, acute, enhancement, symptomatic, diagnosed, epidemic, life-style, disease, etc.) regarding at least in part augmentation of a health related condition (e.g. from detection of progressive gains strength training, endurance exercise activity, etc. to a kiosk, personal, community, or other type vending, dispensing, or food fabricating machine located in a home, business, transportation facility, market, sports facility, office building, theater, school, hospital, park, restaurant, food court, etc.).

Figure 104:
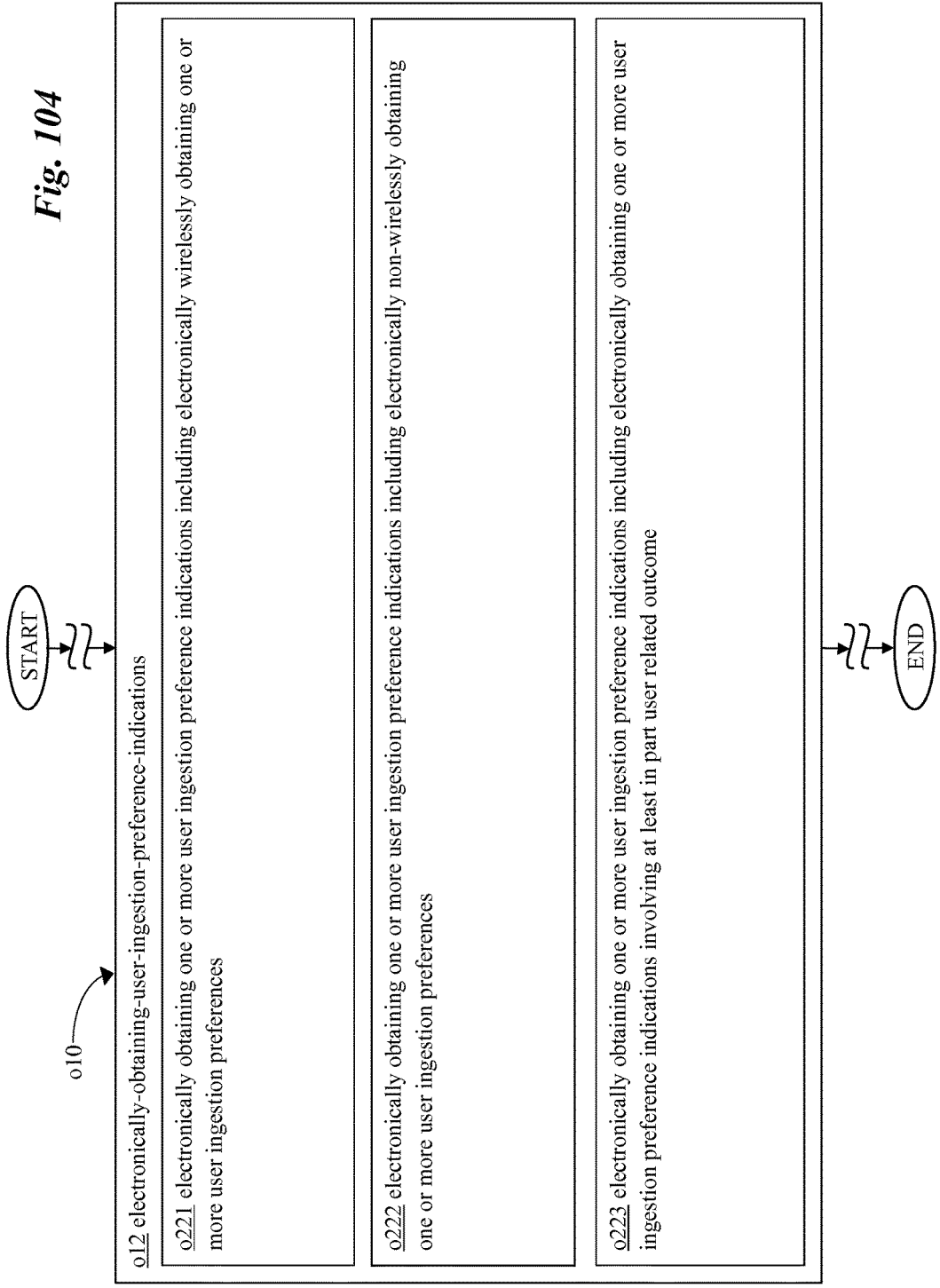

In one or more implementations, as shown in FIG. 104, the operation o12 can include operation o221 for electronically obtaining one or more user ingestion preference indications including electronically wirelessly obtaining one or more user ingestion preferences. Origination of a physically tangible component group can be accomplished through skilled in the art design choice selection including use of one or more components and/or subsystems explicitly and/or implicitly referred to herein for at least in part implementing execution of one or more instructions of the operation o221, for performance of the operation o221 by an electrical circuitry arrangement as activated thereto, and/or otherwise fulfillment of the operation o221. One or more non-transitory signal bearing physical media can bear the one or more instructions that when executed can direct performance of the operation o221. Furthermore, electronically-wirelessly-obtaining-user-ingestion-preferences module m221 depicted in FIG. 45 as being included in the module m12, when executed and/or activated, can direct performance of and/or perform the operation o221. Illustratively, in one or more implementations, the operation o221 can be carried out, for example, by electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically wirelessly obtaining (e.g. radio frequency, WiFi, Bluetooth, packetized data, wireless protocols, infrared, electromagnetic, other transmission, etc.) one or more user ingestion preferences (e.g. data regarding quantity of food eaten or drinks drunk, regarding level seasons used, amount or types of carbohydrates, fat, or proteins preferred, amount of caffeine preferred, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 104, the operation o12 can include operation o222 for electronically obtaining one or more user ingestion preference indications including electronically non-wirelessly obtaining one or more user ingestion preferences. Origination of a physically tangible component group can be accomplished through skilled in the art design choice selection including use of one or more components and/or subsystems explicitly and/or implicitly referred to herein for at least in part implementing execution of one or more instructions of the operation o222, for performance of the operation o222 by an electrical circuitry arrangement as activated thereto, and/or otherwise fulfillment of the operation o222. One or more non-transitory signal bearing physical media can bear the one or more instructions that when executed can direct performance of the operation o222. Furthermore, electronically-non-wirelessly-obtaining-user-ingestion-preferences module m222 depicted in FIG. 45 as being included in the module m12, when executed and/or activated, can direct performance of and/or perform the operation o222. Illustratively, in one or more implementations, the operation o222 can be carried out, for example, by electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically non-wirelessly obtaining (e.g. direct device-to-device, network, non-wireless, scans, swipes, other transfers, etc.) one or more user ingestion preferences (e.g. from detection of user ingestion preferences such as amount of food, food ethnicity, amount of time to eat, amount of time to wait, uniqueness of meal, etc. to a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 104, the operation o12 can include operation o223 for electronically obtaining one or more user ingestion preference indications including electronically obtaining one or more user ingestion preference indications involving at least in part user related outcome. Origination of a physically tangible component group can be accomplished through skilled in the art design choice selection including use of one or more components and/or subsystems explicitly and/or implicitly referred to herein for at least in part implementing execution of one or more instructions of the operation o223, for performance of the operation o223 by an electrical circuitry arrangement as activated thereto, and/or otherwise fulfillment of the operation o223. One or more non-transitory signal bearing physical media can bear the one or more instructions that when executed can direct performance of the operation o223. Furthermore, electronically-non-wirelessly-obtaining-user-ingestion-preference-indications-user-related-outcome module m223 depicted in FIG. 45 as being included in the module m12, when executed and/or activated, can direct performance of and/or perform the operation o223. Illustratively, in one or more implementations, the operation o223 can be carried out, for example, by electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.).

Figure 105:
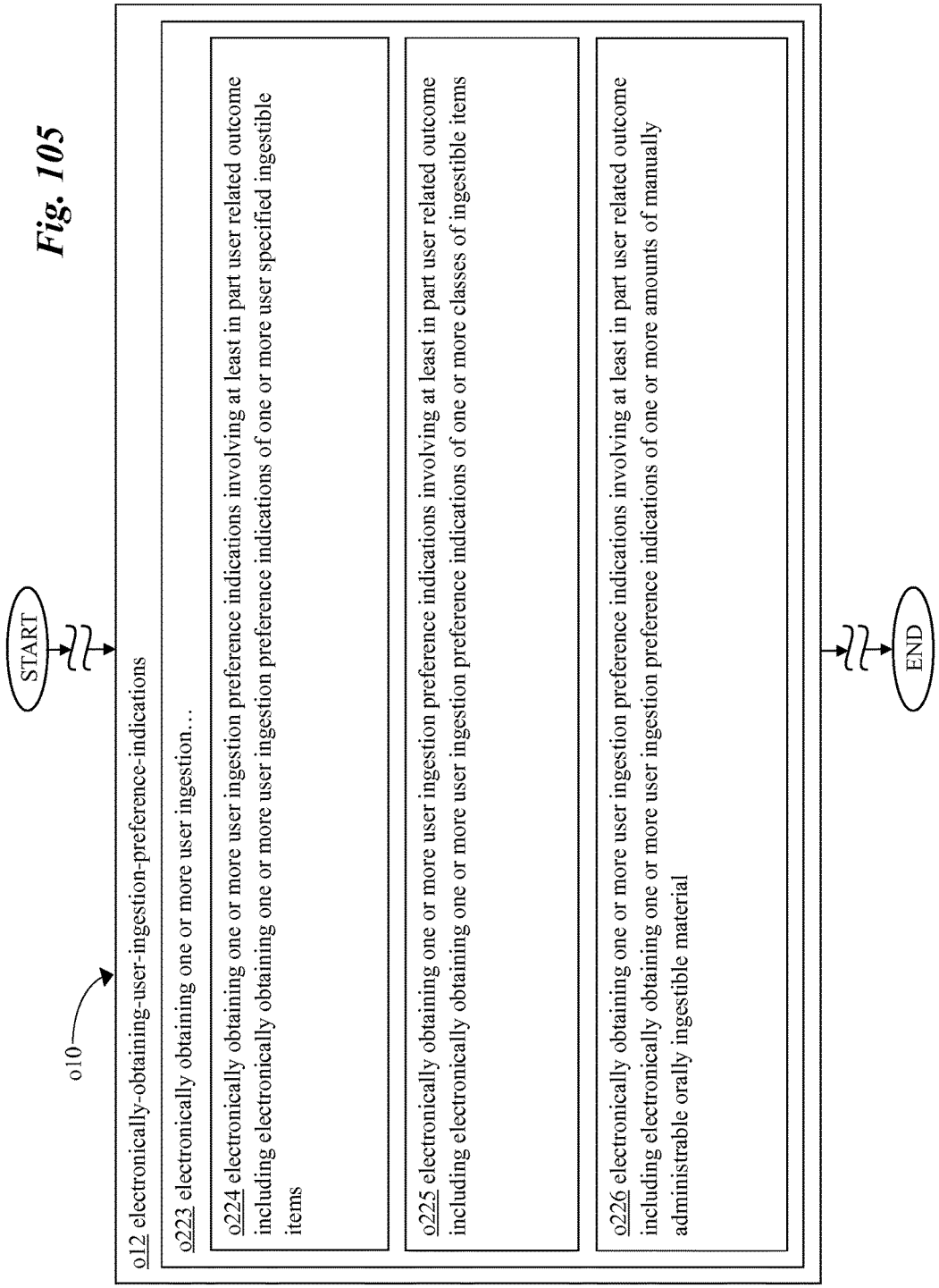

In one or more implementations, as shown in FIG. 105, the operation o223 can include operation o224 for electronically obtaining one or more user ingestion preference indications involving at least in part user related outcome including electronically obtaining one or more user ingestion preference indications of one or more user specified ingestible items. Origination of a physically tangible component group can be accomplished through skilled in the art design choice selection including use of one or more components and/or subsystems explicitly and/or implicitly referred to herein for at least in part implementing execution of one or more instructions of the operation o224, for performance of the operation o224 by an electrical circuitry arrangement as activated thereto, and/or otherwise fulfillment of the operation o224. One or more non-transitory signal bearing physical media can bear the one or more instructions that when executed can direct performance of the operation o224. Furthermore, electronically-non-wirelessly-obtaining-user-ingestion-preference-indications-of-user-specified-ingestible-items module m224 depicted in FIG. 46 as being included in the module m223, when executed and/or activated, can direct performance of and/or perform the operation o224. Illustratively, in one or more implementations, the operation o224 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) of one or more user specified ingestible items (e.g. indication regarding full course meal, sandwich, snack, drink, side-dish, main course, ethnic type, quantity, organic-based, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 105, the operation o223 can include operation o225 for electronically obtaining one or more user ingestion preference indications involving at least in part user related outcome including electronically obtaining one or more user ingestion preference indications of one or more classes of ingestible items. Origination of a physically tangible component group can be accomplished through skilled in the art design choice selection including use of one or more components and/or subsystems explicitly and/or implicitly referred to herein for at least in part implementing execution of one or more instructions of the operation o225, for performance of the operation o225 by an electrical circuitry arrangement as activated thereto, and/or otherwise fulfillment of the operation o225. One or more non-transitory signal bearing physical media can bear the one or more instructions that when executed can direct performance of the operation o225. Furthermore, electronically-non-wirelessly-obtaining-user-ingestion-preference-indications-of-classes-of-ingestible-items module m225 depicted in FIG. 46 as being included in the module m223, when executed and/or activated, can direct performance of and/or perform the operation o225. Illustratively, in one or more implementations, the operation o225 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) of one or more classes of ingestible items (e.g. data regarding quantity in calories or weight of how much fat, carbohydrates, sugars, or protein, preferred, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 105, the operation o223 can include operation o226 for electronically obtaining one or more user ingestion preference indications involving at least in part user related outcome including electronically obtaining one or more user ingestion preference indications of one or more amounts of manually administrable orally ingestible material. Origination of a physically tangible component group can be accomplished through skilled in the art design choice selection including use of one or more components and/or subsystems explicitly and/or implicitly referred to herein for at least in part implementing execution of one or more instructions of the operation o226, for performance of the operation o226 by an electrical circuitry arrangement as activated thereto, and/or otherwise fulfillment of the operation o226. One or more non-transitory signal bearing physical media can bear the one or more instructions that when executed can direct performance of the operation o226. Furthermore, electronically-non-wirelessly-obtaining-user-ingestion-preference-indications-of-amounts-of-manually-administrable-orally-ingestible-material module m226 depicted in FIG. 46 as being included in the module m223, when executed and/or activated, can direct performance of and/or perform the operation o226. Illustratively, in one or more implementations, the operation o226 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) of one or more amounts of manually administrable orally ingestible material (e.g. indication amount regarding full course meal, sandwich, snack, drink, side-dish, main course, ethnic type, quantity, organic-based, etc. received at a kiosk, personal, community, or other type vending, dispensing, or food fabricating machine located in a home, business, transportation facility, market, sports facility, office building, theater, school, hospital, park, restaurant, food court, etc.).

Figure 106:
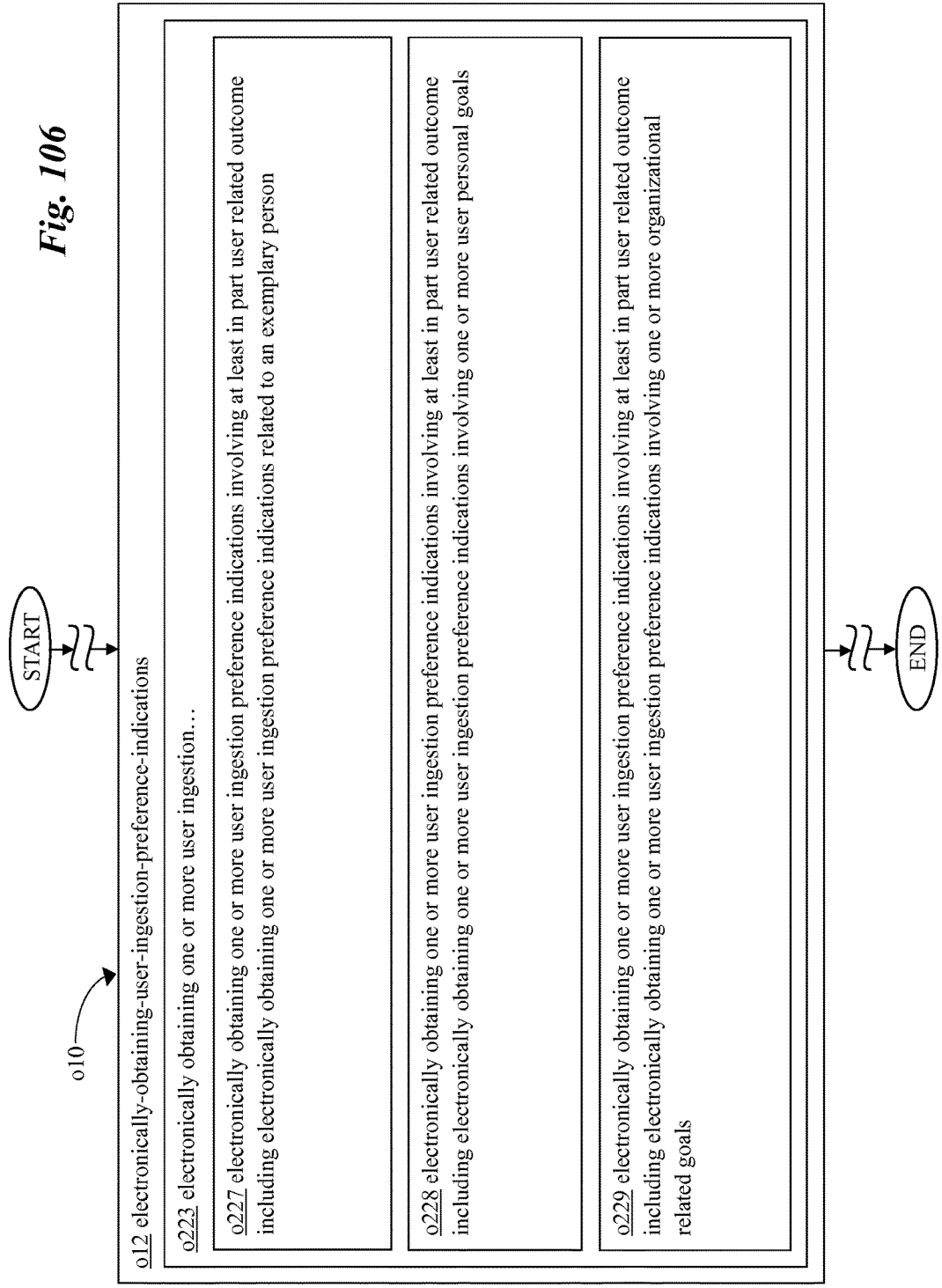

In one or more implementations, as shown in FIG. 106, the operation o223 can include operation o227 for electronically obtaining one or more user ingestion preference indications involving at least in part user related outcome including electronically obtaining one or more user ingestion preference indications related to an exemplary person. Origination of a physically tangible component group can be accomplished through skilled in the art design choice selection including use of one or more components and/or subsystems explicitly and/or implicitly referred to herein for at least in part implementing execution of one or more instructions of the operation o227, for performance of the operation o227 by an electrical circuitry arrangement as activated thereto, and/or otherwise fulfillment of the operation o227. One or more non-transitory signal bearing physical media can bear the one or more instructions that when executed can direct performance of the operation o227. Furthermore, electronically-non-wirelessly-obtaining-user-ingestion-preference-indications-of-selections-related-to-an-exemplary-person module m227 depicted in FIG. 47 as being included in the module m223, when executed and/or activated, can direct performance of and/or perform the operation o227. Illustratively, in one or more implementations, the operation o227 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) related to an exemplary person (e.g. indication that diet or food selection or drink selection of another person is to be used to guide fulfillment of selection for current customer, current patron, current user, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 106, the operation o223 can include operation o228 for electronically obtaining one or more user ingestion preference indications involving at least in part user related outcome including electronically obtaining one or more user ingestion preference indications involving one or more user personal goals. Origination of a physically tangible component group can be accomplished through skilled in the art design choice selection including use of one or more components and/or subsystems explicitly and/or implicitly referred to herein for at least in part implementing execution of one or more instructions of the operation o228, for performance of the operation o228 by an electrical circuitry arrangement as activated thereto, and/or otherwise fulfillment of the operation o228. One or more non-transitory signal bearing physical media can bear the one or more instructions that when executed can direct performance of the operation o228. Furthermore, electronically-non-wirelessly-obtaining-user-ingestion-preference-indications-user-personal-goals module m228 depicted in FIG. 47 as being included in the module m223, when executed and/or activated, can direct performance of and/or perform the operation o228. Illustratively, in one or more implementations, the operation o228 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) involving one or more user personal goals (e.g. indication regarding personal weight management goals, athletic fitness goals, work-related fitness goals, disease reduction goals concerning full course meal, sandwich, snack, drink, side-dish, main course, ethnic type, quantity, organic-based, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 106, the operation o223 can include operation o229 for electronically obtaining one or more user ingestion preference indications involving at least in part user related outcome including electronically obtaining one or more user ingestion preference indications involving one or more organizational related goals. Origination of a physically tangible component group can be accomplished through skilled in the art design choice selection including use of one or more components and/or subsystems explicitly and/or implicitly referred to herein for at least in part implementing execution of one or more instructions of the operation o229, for performance of the operation o229 by an electrical circuitry arrangement as activated thereto, and/or otherwise fulfillment of the operation o229. One or more non-transitory signal bearing physical media can bear the one or more instructions that when executed can direct performance of the operation o229. Furthermore, electronically-non-wirelessly-obtaining-user-ingestion-preference-indications-organizational-related-goals module m229 depicted in FIG. 47 as being included in the module m223, when executed and/or activated, can direct performance of and/or perform the operation o229. Illustratively, in one or more implementations, the operation o229 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving one or more organizational related goals (e.g. data regarding fitness goals of sports team, or company workforce, or school class, etc. received at a kiosk, personal, community, or other type vending, dispensing, or food fabricating machine located in a home, business, transportation facility, market, sports facility, office building, theater, school, hospital, park, restaurant, food court, etc.).

Figure 107:
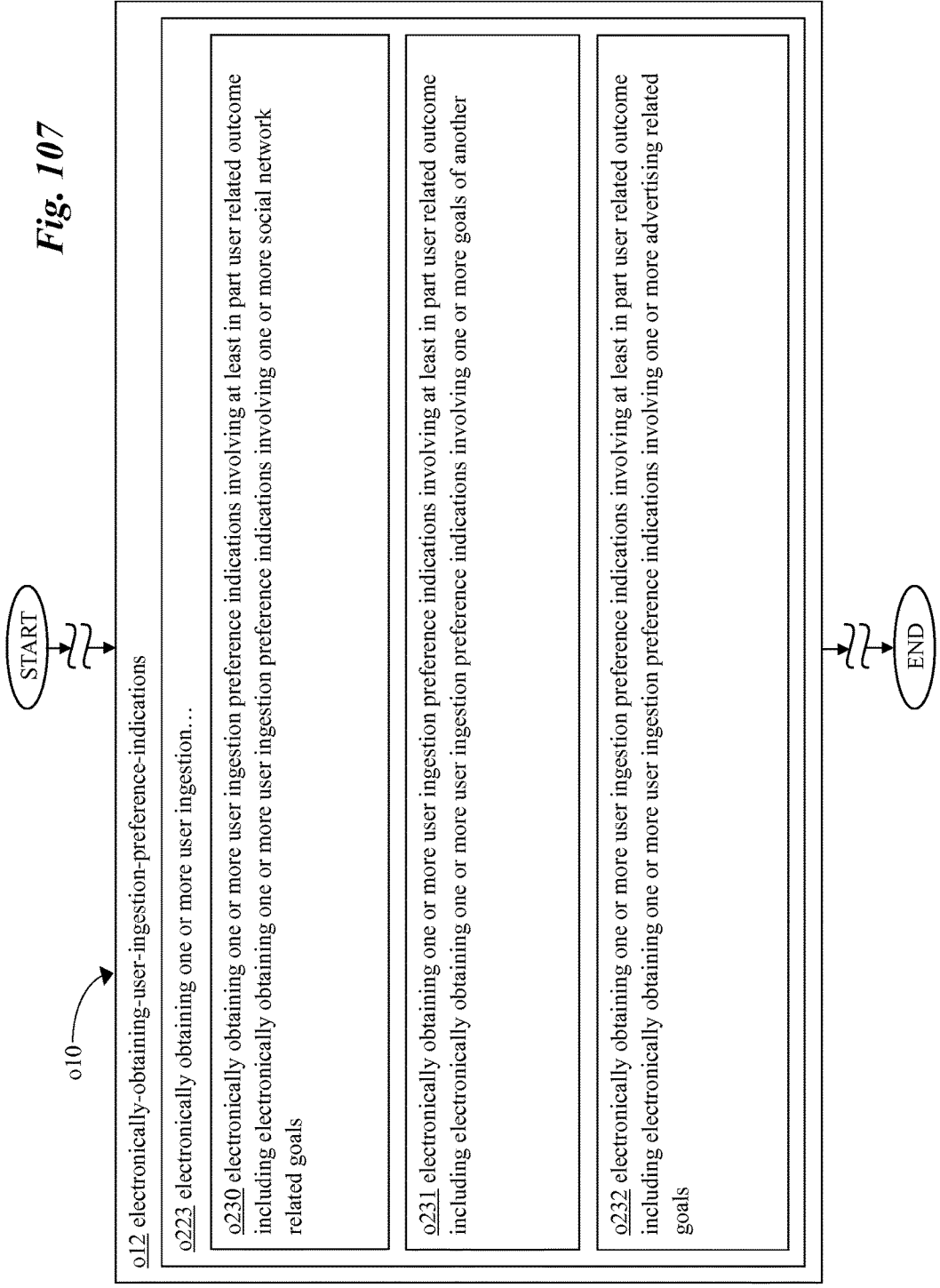

In one or more implementations, as shown in FIG. 107, the operation o223 can include operation o230 for electronically obtaining one or more user ingestion preference indications involving at least in part user related outcome including electronically obtaining one or more user ingestion preference indications involving one or more social network related goals. Origination of a physically tangible component group can be accomplished through skilled in the art design choice selection including use of one or more components and/or subsystems explicitly and/or implicitly referred to herein for at least in part implementing execution of one or more instructions of the operation o230, for performance of the operation o230 by an electrical circuitry arrangement as activated thereto, and/or otherwise fulfillment of the operation o230. One or more non-transitory signal bearing physical media can bear the one or more instructions that when executed can direct performance of the operation o230. Furthermore, electronically-non-wirelessly-obtaining-user-ingestion-preference-indications-social-network-related-goals module m230 depicted in FIG. 48 as being included in the module m223, when executed and/or activated, can direct performance of and/or perform the operation o230. Illustratively, in one or more implementations, the operation o230 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) involving one or more social network related goals (e.g. indication related to social network communication regarding weight management goals, athletic fitness goals, work-related fitness goals, disease reduction goals concerning full course meal, sandwich, snack, drink, side-dish, main course, ethnic type, quantity, organic-based, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 107, the operation o223 can include operation o231 for electronically obtaining one or more user ingestion preference indications involving at least in part user related outcome including electronically obtaining one or more user ingestion preference indications involving one or more goals of another. Origination of a physically tangible component group can be accomplished through skilled in the art design choice selection including use of one or more components and/or subsystems explicitly and/or implicitly referred to herein for at least in part implementing execution of one or more instructions of the operation o231, for performance of the operation o231 by an electrical circuitry arrangement as activated thereto, and/or otherwise fulfillment of the operation o231. One or more non-transitory signal bearing physical media can bear the one or more instructions that when executed can direct performance of the operation o231. Furthermore, electronically-non-wirelessly-obtaining-useringestion-preference-indications-goals-of-another module m231 depicted in FIG. 48 as being included in the module m223, when executed and/or activated, can direct performance of and/or perform the operation o231. Illustratively, in one or more implementations, the operation o231 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving one or more goals of another (e.g. data regarding fitness goals of parent, teacher, coach, tutor, government official, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 107, the operation o223 can include operation o232 for electronically obtaining one or more user ingestion preference indications involving at least in part user related outcome including electronically obtaining one or more user ingestion preference indications involving one or more advertising related goals. Origination of a physically tangible component group can be accomplished through skilled in the art design choice selection including use of one or more components and/or subsystems explicitly and/or implicitly referred to herein for at least in part implementing execution of one or more instructions of the operation o232, for performance of the operation o232 by an electrical circuitry arrangement as activated thereto, and/or otherwise fulfillment of the operation o232. One or more non-transitory signal bearing physical media can bear the one or more instructions that when executed can direct performance of the operation o232. Furthermore, electronically-non-wirelessly-obtaining-user-ingestion-preference-indications-advertising-related-goals module m232 depicted in FIG. 48 as being included in the module m223, when executed and/or activated, can direct performance of and/or perform the operation o232. Illustratively, in one or more implementations, the operation o232 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) involving at least in part user related outcome (e.g. data regarding goal to lose overall body weight, gain muscle weight, reach a personal athletic record, comply with certain dietary guidelines, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) involving one or more advertising related goals (e.g. indication related to advertising communication regarding weight management goals, athletic fitness goals, work-related fitness goals, disease reduction goals concerning full course meal, sandwich, snack, drink, side-dish, main course, ethnic type, quantity, organic-based, etc. received at a kiosk, personal, community, or other type vending, dispensing, or food fabricating machine located in a home, business, transportation facility, market, sports facility, office building, theater, school, hospital, park, restaurant, food court, etc.).

Figure 108:
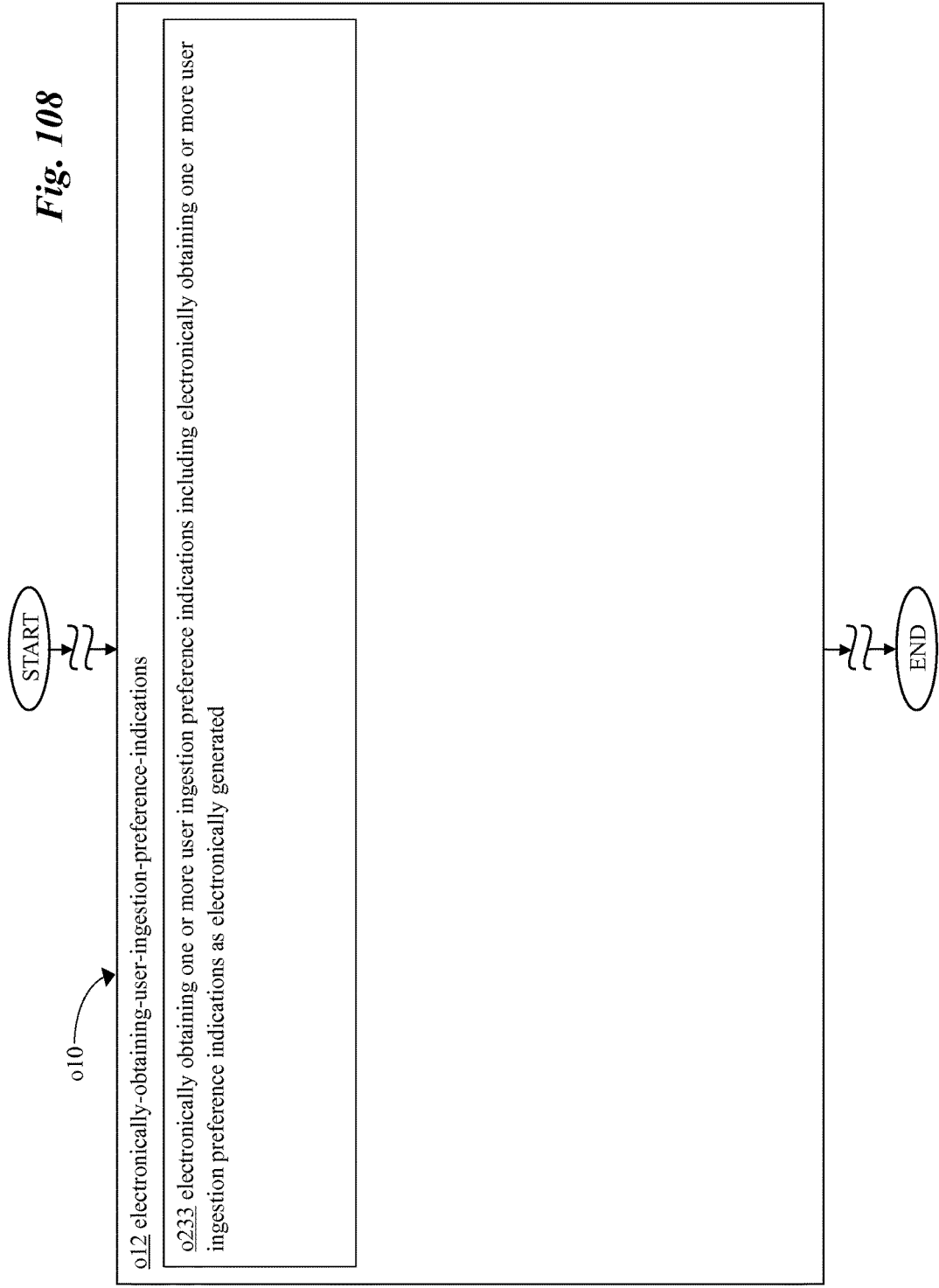

In one or more implementations, as shown in FIG. 108, the operation o12 can include operation o233 for electronically obtaining one or more user ingestion preference indications including electronically obtaining one or more user ingestion preference indications as electronically generated. Origination of a physically tangible component group can be accomplished through skilled in the art design choice selection including use of one or more components and/or subsystems explicitly and/or implicitly referred to herein for at least in part implementing execution of one or more instructions of the operation o233, for performance of the operation o233 by an electrical circuitry arrangement as activated thereto, and/or otherwise fulfillment of the operation o233. One or more non-transitory signal bearing physical media can bear the one or more instructions that when executed can direct performance of the operation o233. Furthermore, electronically-non-wirelessly-obtaining-user-ingestion-preference-indications-as-electronically-generated module m233 depicted in FIG. 49 as being included in the module m12, when executed and/or activated, can direct performance of and/or perform the operation o233. Illustratively, in one or more implementations, the operation o233 can be carried out, for example, by electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.).

Figure 109:
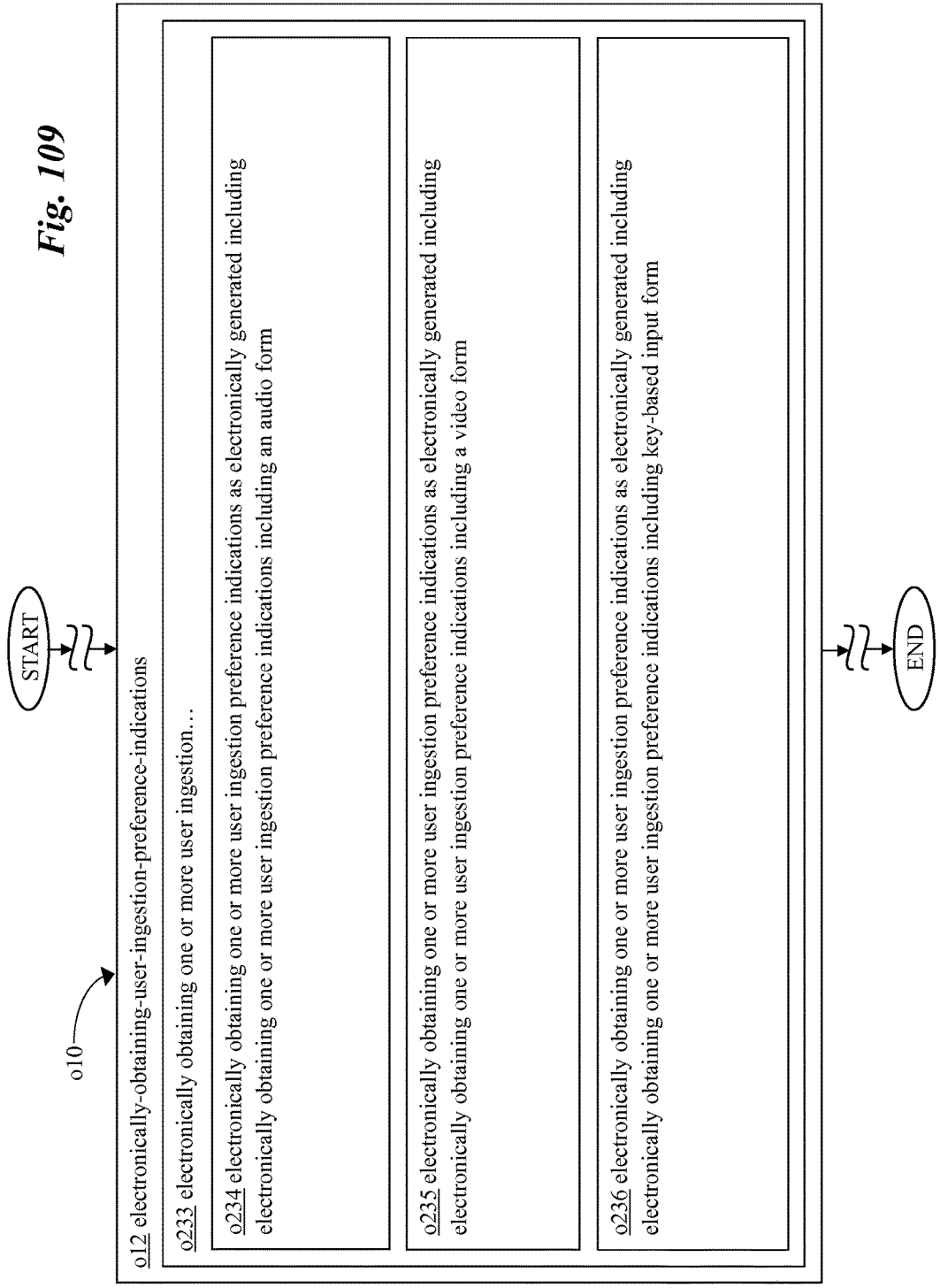

In one or more implementations, as shown in FIG. 109, the operation o233 can include operation o234 for electronically obtaining one or more user ingestion preference indications as electronically generated including electronically obtaining one or more user ingestion preference indications including an audio form. Origination of a physically tangible component group can be accomplished through skilled in the art design choice selection including use of one or more components and/or subsystems explicitly and/or implicitly referred to herein for at least in part implementing execution of one or more instructions of the operation o234, for performance of the operation o234 by an electrical circuitry arrangement as activated thereto, and/or otherwise fulfillment of the operation o234. One or more non-transitory signal bearing physical media can bear the one or more instructions that when executed can direct performance of the operation o234. Furthermore, electronically-non-wirelessly-obtaining-user-ingestion-preference-indications-including-an-audio-form module m234 depicted in FIG. 50 as being included in the module m233, when executed and/or activated, can direct performance of and/or perform the operation o234. Illustratively, in one or more implementations, the operation o234 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) including an audio form (e.g. indication expressed through verbal instruction announced by user or other, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 109, the operation o233 can include operation o235 for electronically obtaining one or more user ingestion preference indications as electronically generated including electronically obtaining one or more user ingestion preference indications including a video form. Origination of a physically tangible component group can be accomplished through skilled in the art design choice selection including use of one or more components and/or subsystems explicitly and/or implicitly referred to herein for at least in part implementing execution of one or more instructions of the operation o235, for performance of the operation o235 by an electrical circuitry arrangement as activated thereto, and/or otherwise fulfillment of the operation o235. One or more non-transitory signal bearing physical media can bear the one or more instructions that when executed can direct performance of the operation o235. Furthermore, electronically-non-wirelessly-obtaining-user-ingestion-preference-indications-including-a-video-form module m235 depicted in FIG. 50 as being included in the module m233, when executed and/or activated, can direct performance of and/or perform the operation o235. Illustratively, in one or more implementations, the operation o235 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) including a video form (e.g. indications as past video records of meals eaten, certain foods eaten, certain drinks drunk by user, patient, student, role model, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 109, the operation o233 can include operation o236 for electronically obtaining one or more user ingestion preference indications as electronically generated including electronically obtaining one or more user ingestion preference indications including key-based input form. Origination of a physically tangible component group can be accomplished through skilled in the art design choice selection including use of one or more components and/or subsystems explicitly and/or implicitly referred to herein for at least in part implementing execution of one or more instructions of the operation o236, for performance of the operation o236 by an electrical circuitry arrangement as activated thereto, and/or otherwise fulfillment of the operation o236. One or more non-transitory signal bearing physical media can bear the one or more instructions that when executed can direct performance of the operation o236. Furthermore, electronically-non-wirelessly-obtaining-user-ingestion-preference-indications-including-key-based-input-form module m236 depicted in FIG. 50 as being included in the module m233, when executed and/or activated, can direct performance of and/or perform the operation o236. Illustratively, in one or more implementations, the operation o236 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) including key-based input form (e.g. indication expressed through user or other interaction with computer keyboard, etc. received at a kiosk, personal, community, or other type vending, dispensing, or food fabricating machine located in a home, business, transportation facility, market, sports facility, office building, theater, school, hospital, park, restaurant, food court, etc.).

Figure 110:
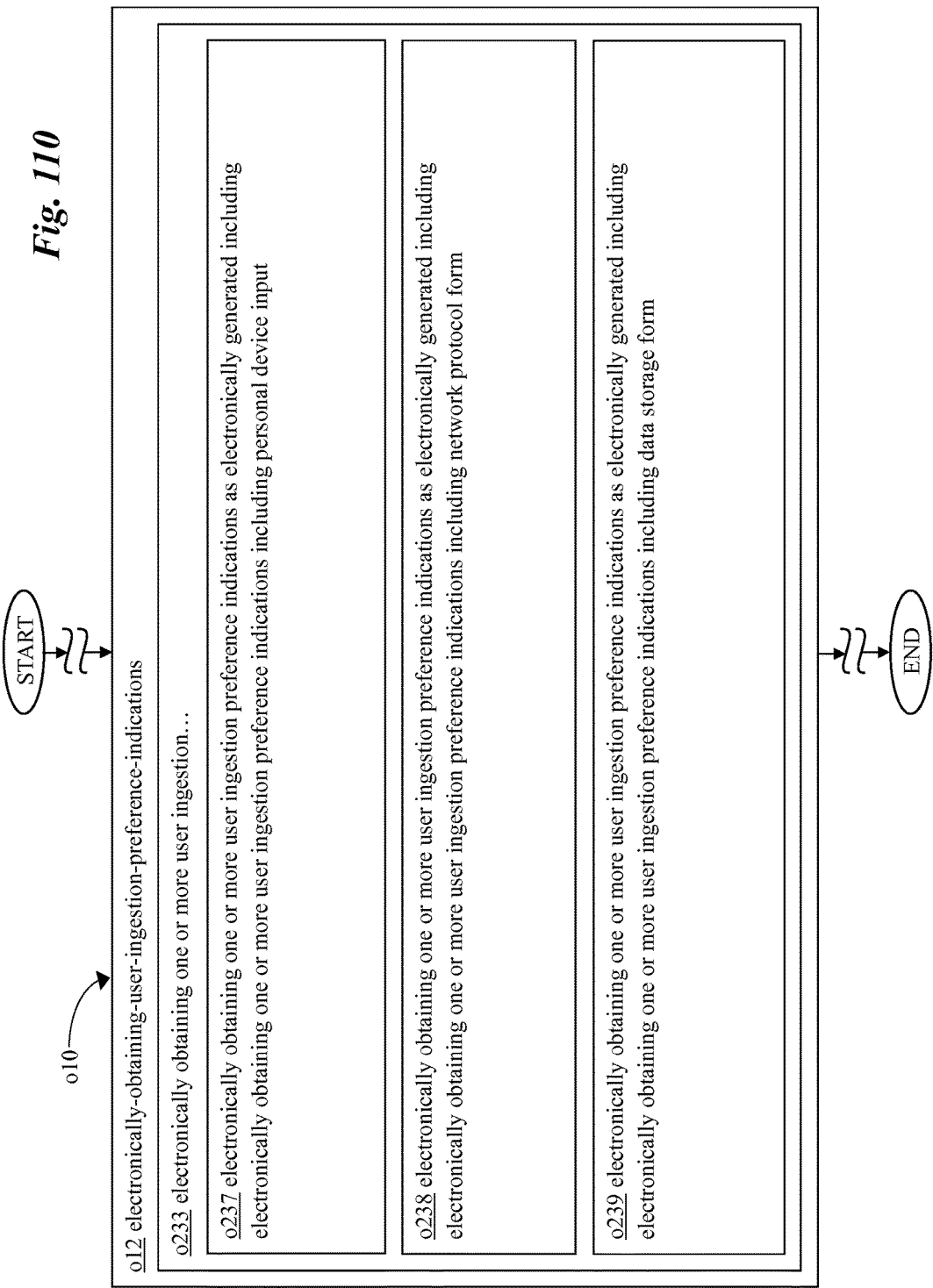

In one or more implementations, as shown in FIG. 110, the operation o233 can include operation o237 for electronically obtaining one or more user ingestion preference indications as electronically generated including electronically obtaining one or more user ingestion preference indications including personal device input. Origination of a physically tangible component group can be accomplished through skilled in the art design choice selection including use of one or more components and/or subsystems explicitly and/or implicitly referred to herein for at least in part implementing execution of one or more instructions of the operation o237, for performance of the operation o237 by an electrical circuitry arrangement as activated thereto, and/or otherwise fulfillment of the operation o237. One or more non-transitory signal bearing physical media can bear the one or more instructions that when executed can direct performance of the operation o237. Furthermore, electronically-non-wirelessly-obtaining-user-ingestion-preference-indications-including-personal-device-input module m237 depicted in FIG. 51 as being included in the module m233, when executed and/or activated, can direct performance of and/or perform the operation o237. Illustratively, in one or more implementations, the operation o237 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) including personal device input (e.g. indication as data collected, stored, modified, etc. on a smart phone, personal data assistant, tablet, phablet, laptop, smart watch, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 110, the operation o233 can include operation o238 for electronically obtaining one or more user ingestion preference indications as electronically generated including electronically obtaining one or more user ingestion preference indications including network protocol form. Origination of a physically tangible component group can be accomplished through skilled in the art design choice selection including use of one or more components and/or subsystems explicitly and/or implicitly referred to herein for at least in part implementing execution of one or more instructions of the operation o238, for performance of the operation o238 by an electrical circuitry arrangement as activated thereto, and/or otherwise fulfillment of the operation o238. One or more non-transitory signal bearing physical media can bear the one or more instructions that when executed can direct performance of the operation o238. Furthermore, electronically-non-wirelessly-obtaining-user-ingestion-preference-indications-including-network-protocol-form module m238 depicted in FIG. 51 as being included in the module m233, when executed and/or activated, can direct performance of and/or perform the operation o238. Illustratively, in one or more implementations, the operation o238 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. audio emission, video transmission, keyboard entry, personal device transfer, network protocol communication, data storage retrieval, social network output, exemplar input, etc.) including network protocol form (e.g. indication sent through communication network such as packet switched, Ethernet, internet, etc. received at a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 110, the operation o233 can include operation o239 for electronically obtaining one or more user ingestion preference indications as electronically generated including electronically obtaining one or more user ingestion preference indications including data storage form. Origination of a physically tangible component group can be accomplished through skilled in the art design choice selection including use of one or more components and/or subsystems explicitly and/or implicitly referred to herein for at least in part implementing execution of one or more instructions of the operation o239, for performance of the operation o239 by an electrical circuitry arrangement as activated thereto, and/or otherwise fulfillment of the operation o239. One or more non-transitory signal bearing physical media can bear the one or more instructions that when executed can direct performance of the operation o239. Furthermore, electronically-non-wirelessly-obtaining-user-ingestion-preference-indications-including-data-storage-form module m239 depicted in FIG. 51 as being included in the module m233, when executed and/or activated, can direct performance of and/or perform the operation o239. Illustratively, in one or more implementations, the operation o239 can be carried out, for example, by electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) as electronically generated (e.g. indications as generated by worn sensing device, by personal communication device, by remote network device, etc. received at a kiosk, personal, community, or other type vending, dispensing, or food fabricating machine located in a home, business, transportation facility, market, sports facility, office building, theater, school, hospital, park, restaurant, food court, etc.) including electronically obtaining (e.g. swipes, scans, non-wireless, network, direct device-to-device, other transfers, electromagnetic, infrared, protocols, wireless, packetized data, Bluetooth, WiFi, radio frequency, other transfers, etc.) one or more user ingestion preference indications (e.g. exemplar input, social network output, data storage retrieval, network protocol communication, personal device transfer, keyboard entry, video transmission, audio emission, etc.) including data storage form (e.g. indication as data stored on memory stick, server, network, cloud, etc. received at a kiosk, personal, community, or other type vending, dispensing, or food fabricating machine located in a home, business, transportation facility, market, sports facility, office building, theater, school, hospital, park, restaurant, food court, etc.).

Figure 111:
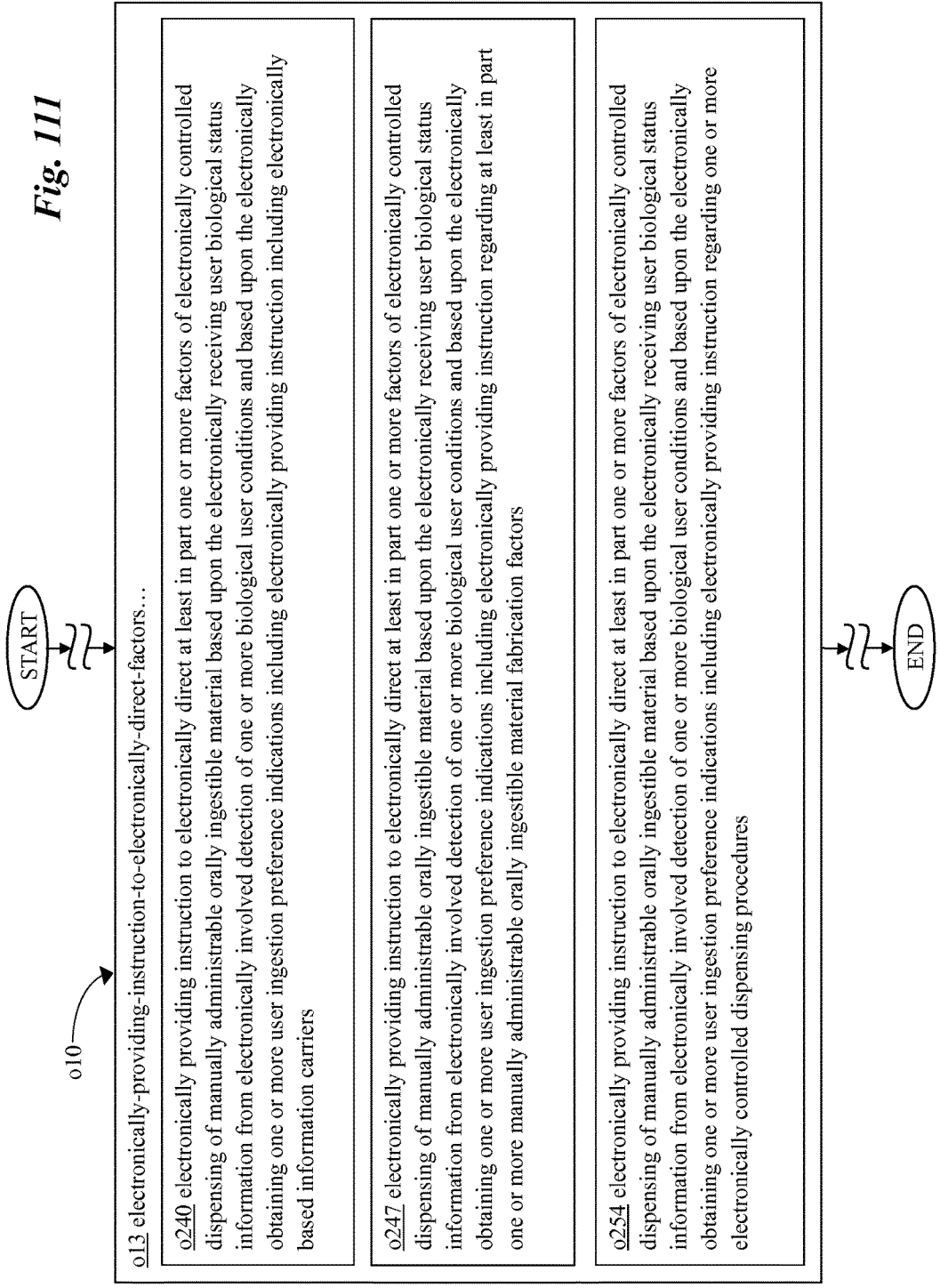

In one or more implementations, as shown in FIG. 111, the operation o13 can include operation o240 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications including electronically providing instruction including electronically based information carriers. Origination of a physically tangible component group can be accomplished through skilled in the art design choice selection including use of one or more components and/or subsystems explicitly and/or implicitly referred to herein for at least in part implementing execution of one or more instructions of the operation o240, for performance of the operation o240 by an electrical circuitry arrangement as activated thereto, and/or otherwise fulfillment of the operation o240. One or more non-transitory signal bearing physical media can bear the one or more instructions that when executed can direct performance of the operation o240. Furthermore, electronically-providing-instruction-including-electronically-based-information-carriers module m240 depicted in FIG. 52 as being included in the module m13, when executed and/or activated, can direct performance of and/or perform the operation o240. Illustratively, in one or more implementations, the operation o240 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.).

Figure 112:
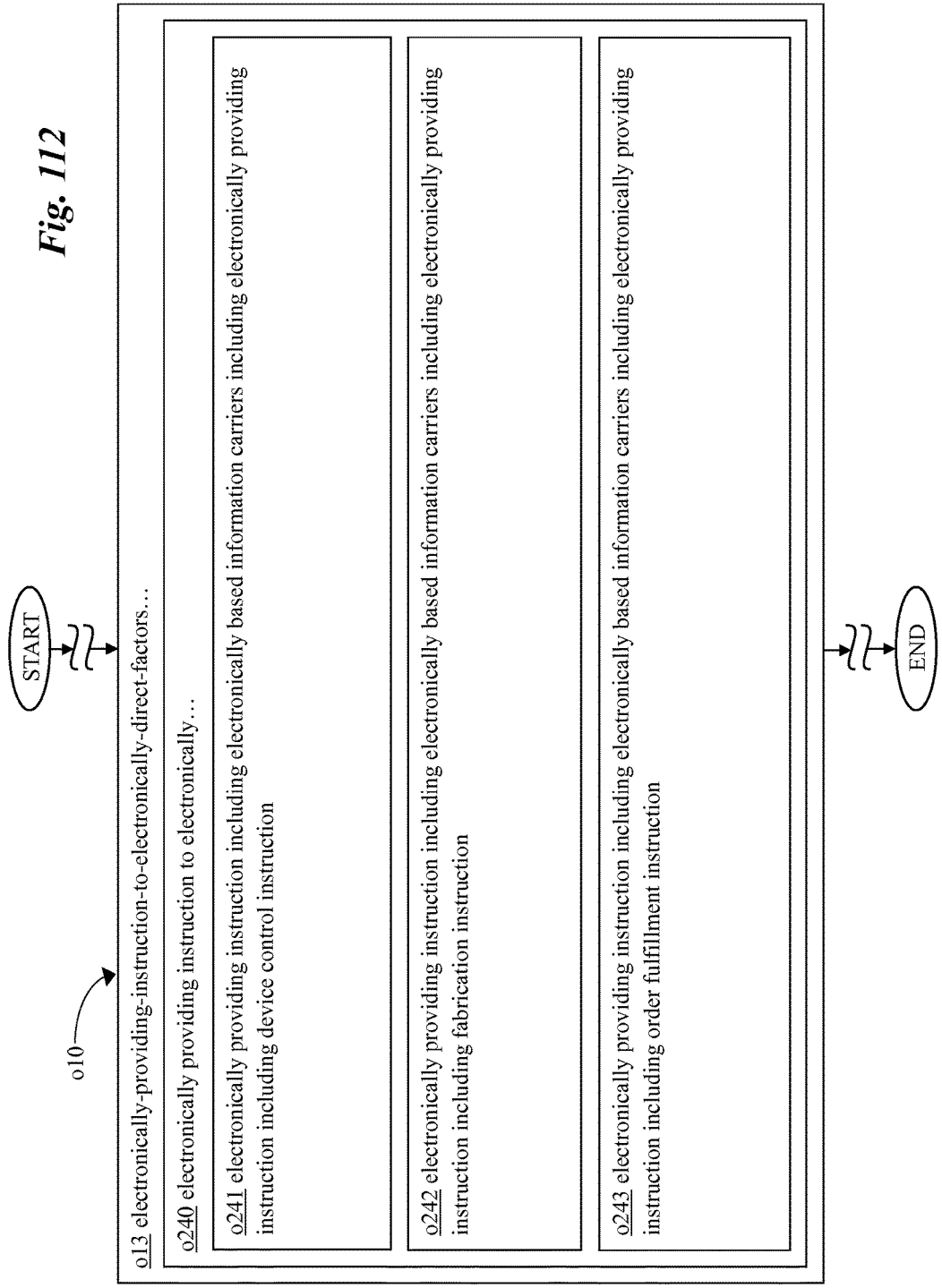

In one or more implementations, as shown in FIG. 112, the operation o240 can include operation o241 for electronically providing instruction including electronically based information carriers including electronically providing instruction including device control instruction. Origination of a physically tangible component group can be accomplished through skilled in the art design choice selection including use of one or more components and/or subsystems explicitly and/or implicitly referred to herein for at least in part implementing execution of one or more instructions of the operation o241, for performance of the operation o241 by an electrical circuitry arrangement as activated thereto, and/or otherwise fulfillment of the operation o241. One or more non-transitory signal bearing physical media can bear the one or more instructions that when executed can direct performance of the operation o241. Furthermore, electronically-providing-instruction-including-device-control-instruction module m241 depicted in FIG. 53 as being included in the module m240, when executed and/or activated, can direct performance of and/or perform the operation o241. Illustratively, in one or more implementations, the operation o241 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) including device control instruction (e.g. instruction as electromechanical device instruction, heating element instruction, food printing instruction, assembler instruction, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 112, the operation o240 can include operation o242 for electronically providing instruction including electronically based information carriers including electronically providing instruction including fabrication instruction. Origination of a physically tangible component group can be accomplished through skilled in the art design choice selection including use of one or more components and/or subsystems explicitly and/or implicitly referred to herein for at least in part implementing execution of one or more instructions of the operation o242, for performance of the operation o242 by an electrical circuitry arrangement as activated thereto, and/or otherwise fulfillment of the operation o242. One or more non-transitory signal bearing physical media can bear the one or more instructions that when executed can direct performance of the operation o242. Furthermore, electronically-providing-instruction-including-fabrication-instruction module m242 depicted in FIG. 53 as being included in the module m240, when executed and/or activated, can direct performance of and/or perform the operation o242. Illustratively, in one or more implementations, the operation o242 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including fabrication instruction (e.g. instruction as to food printing item selection, food printing component quantity selection, food printing shape instruction, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 112, the operation o240 can include operation o243 for electronically providing instruction including electronically based information carriers including electronically providing instruction including order fulfillment instruction. Origination of a physically tangible component group can be accomplished through skilled in the art design choice selection including use of one or more components and/or subsystems explicitly and/or implicitly referred to herein for at least in part implementing execution of one or more instructions of the operation o243, for performance of the operation o243 by an electrical circuitry arrangement as activated thereto, and/or otherwise fulfillment of the operation o243. One or more non-transitory signal bearing physical media can bear the one or more instructions that when executed can direct performance of the operation o243. Furthermore, electronically-providing-instruction-including-order-fulfillment-instruction module m243 depicted in FIG. 53 as being included in the module m240, when executed and/or activated, can direct performance of and/or perform the operation o243. Illustratively, in one or more implementations, the operation o243 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) including order fulfillment instruction (e.g. instruction as item selection, quantity selection, scheduling instruction, budgeting instruction, financial transaction instruction, etc. for a kiosk, personal, community, or other type vending, dispensing, or food fabricating machine located in a home, business, transportation facility, market, sports facility, office building, theater, school, hospital, park, restaurant, food court, etc.).

Figure 113:
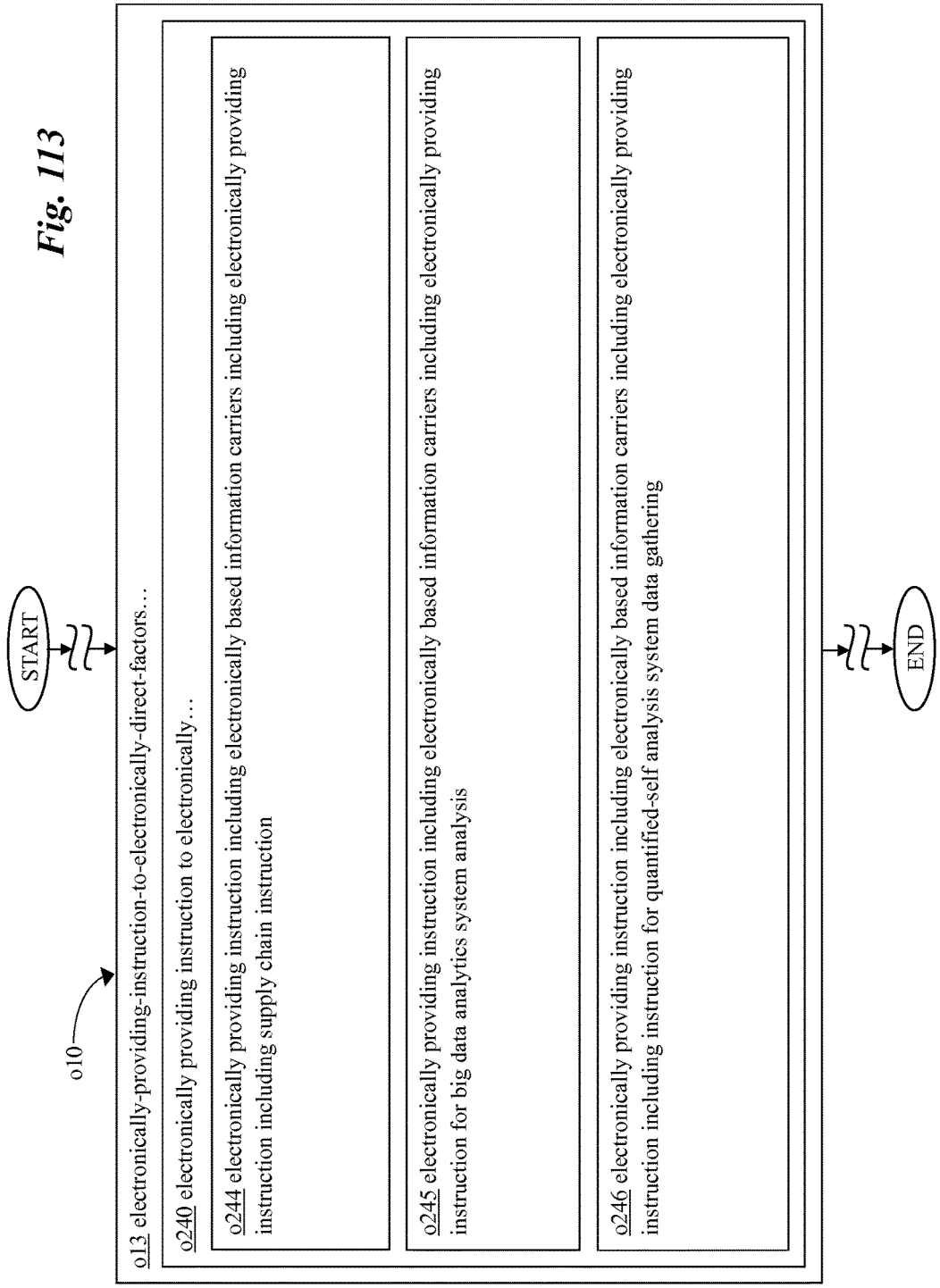

In one or more implementations, as shown in FIG. 113, the operation o240 can include operation o244 for electronically providing instruction including electronically based information carriers including electronically providing instruction including supply chain instruction. Origination of a physically tangible component group can be accomplished through skilled in the art design choice selection including use of one or more components and/or subsystems explicitly and/or implicitly referred to herein for at least in part implementing execution of one or more instructions of the operation o244, for performance of the operation o244 by an electrical circuitry arrangement as activated thereto, and/or otherwise fulfillment of the operation o244. One or more non-transitory signal bearing physical media can bear the one or more instructions that when executed can direct performance of the operation o244. Furthermore, electronically-providing-instruction-including-supply-chain-instruction module m244 depicted in FIG. 54 as being included in the module m240, when executed and/or activated, can direct performance of and/or perform the operation o244. Illustratively, in one or more implementations, the operation o244 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including supply chain instruction (e.g. instruction as to item resupply, quantity resupply, scheduling resupply, budgeting resupply, financial transaction resupply, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 113, the operation o240 can include operation o245 for electronically providing instruction including electronically based information carriers including electronically providing instruction for big data analytics system analysis. Origination of a physically tangible component group can be accomplished through skilled in the art design choice selection including use of one or more components and/or subsystems explicitly and/or implicitly referred to herein for at least in part implementing execution of one or more instructions of the operation o245, for performance of the operation o245 by an electrical circuitry arrangement as activated thereto, and/or otherwise fulfillment of the operation o245. One or more non-transitory signal bearing physical media can bear the one or more instructions that when executed can direct performance of the operation o245. Furthermore, electronically-providing-instruction-for-big-data-analytics-system-analysis module m245 depicted in FIG. 54 as being included in the module m240, when executed and/or activated, can direct performance of and/or perform the operation o245. Illustratively, in one or more implementations, the operation o245 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) for big data analytics system analysis (e.g. instruction as correlation studies, statistical analysis, pattern analysis, historical analysis etc. of collections of data for users, students, workers, civilians, customers, clients, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 113, the operation o240 can include operation o246 for electronically providing instruction including electronically based information carriers including electronically providing instruction including instruction for quantified-self analysis system data gathering. Origination of a physically tangible component group can be accomplished through skilled in the art design choice selection including use of one or more components and/or subsystems explicitly and/or implicitly referred to herein for at least in part implementing execution of one or more instructions of the operation o246, for performance of the operation o246 by an electrical circuitry arrangement as activated thereto, and/or otherwise fulfillment of the operation o246. One or more non-transitory signal bearing physical media can bear the one or more instructions that when executed can direct performance of the operation o246. Furthermore, electronically-providing-instruction-including-instruction-for-quantified-self-analysis-system-data-collection module m246 depicted in FIG. 54 as being included in the module m240, when executed and/or activated, can direct performance of and/or perform the operation o246. Illustratively, in one or more implementations, the operation o246 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including electronically based information carriers (e.g. indication sent through radio network, point-to-point broadcast network, packet network, etc. received at a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) including instruction (e.g. device control, fabrication, modular control, item order-based, remote control, supply chain, big data analytics, quantified-self based, etc.) for quantified-self analysis system data gathering (e.g. instruction as to when to collect data, type of data to collected, threshold used in data collection, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 111, the operation o13 can include operation o247 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications including electronically providing instruction regarding at least in part one or more manually administrable orally ingestible material fabrication factors. Origination of a physically tangible component group can be accomplished through skilled in the art design choice selection including use of one or more components and/or subsystems explicitly and/or implicitly referred to herein for at least in part implementing execution of one or more instructions of the operation o247, for performance of the operation o247 by an electrical circuitry arrangement as activated thereto, and/or otherwise fulfillment of the operation o247. One or more non-transitory signal bearing physical media can bear the one or more instructions that when executed can direct performance of the operation o247. Furthermore, electronically-providing-instruction-regarding-manually-administrable-orally-ingestible-material-fabrication-factors module m247 depicted in FIG. 52 as being included in the module m13, when executed and/or activated, can direct performance of and/or perform the operation o247. Illustratively, in one or more implementations, the operation o247 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.).

Figure 114:
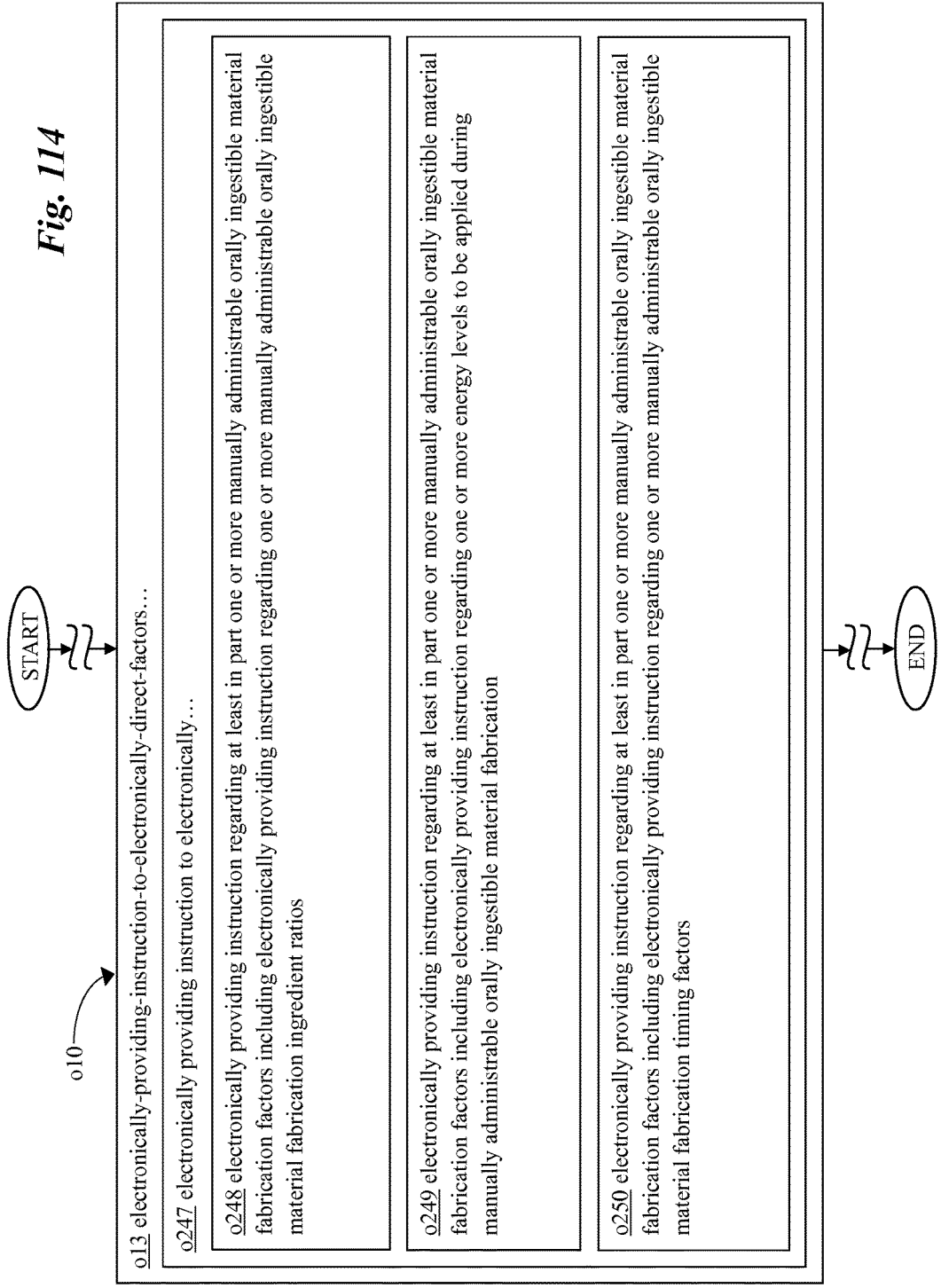

In one or more implementations, as shown in FIG. 114, the operation o247 can include operation o248 for electronically providing instruction regarding at least in part one or more manually administrable orally ingestible material fabrication factors including electronically providing instruction regarding one or more manually administrable orally ingestible material fabrication ingredient ratios. Origination of a physically tangible component group can be accomplished through skilled in the art design choice selection including use of one or more components and/or subsystems explicitly and/or implicitly referred to herein for at least in part implementing execution of one or more instructions of the operation o248, for performance of the operation o248 by an electrical circuitry arrangement as activated thereto, and/or otherwise fulfillment of the operation o248. One or more non-transitory signal bearing physical media can bear the one or more instructions that when executed can direct performance of the operation o248. Furthermore, electronically-providing-instruction-regarding-manually-administrable-orally-ingestible-material-fabrication-ingredient-ratios module m248 depicted in FIG. 55 as being included in the module m247, when executed and/or activated, can direct performance of and/or perform the operation o248. Illustratively, in one or more implementations, the operation o248 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material fabrication ingredient ratios (e.g. instruction as to carbohydrate-to-protein ratio, carbohydrate-to-fat ratio, fat-to-protein ratio, micronutrient ratios, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 114, the operation o247 can include operation o249 for electronically providing instruction regarding at least in part one or more manually administrable orally ingestible material fabrication factors including electronically providing instruction regarding one or more energy levels to be applied during manually administrable orally ingestible material fabrication. Origination of a physically tangible component group can be accomplished through skilled in the art design choice selection including use of one or more components and/or subsystems explicitly and/or implicitly referred to herein for at least in part implementing execution of one or more instructions of the operation o249, for performance of the operation o249 by an electrical circuitry arrangement as activated thereto, and/or otherwise fulfillment of the operation o249. One or more non-transitory signal bearing physical media can bear the one or more instructions that when executed can direct performance of the operation o249. Furthermore, electronically-providing-instruction-regarding-energy-levels-to-be-applied-during-manually-administrable-orally-ingestible-material-fabrication module m249 depicted in FIG. 55 as being included in the module m247, when executed and/or activated, can direct performance of and/or perform the operation o249. Illustratively, in one or more implementations, the operation o249 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more energy levels to be applied during manually administrable orally ingestible material fabrication (e.g. instruction as instruction for temperature to cook meal, for amount of microwave energy to apply to food item, for induction heating of cookware for ingestible material, for steaming of food items, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 114, the operation o247 can include operation o250 for electronically providing instruction regarding at least in part one or more manually administrable orally ingestible material fabrication factors including electronically providing instruction regarding one or more manually administrable orally ingestible material fabrication timing factors. Origination of a physically tangible component group can be accomplished through skilled in the art design choice selection including use of one or more components and/or subsystems explicitly and/or implicitly referred to herein for at least in part implementing execution of one or more instructions of the operation o250, for performance of the operation o250 by an electrical circuitry arrangement as activated thereto, and/or otherwise fulfillment of the operation o250. One or more non-transitory signal bearing physical media can bear the one or more instructions that when executed can direct performance of the operation o250. Furthermore, electronically-providing-instruction-regarding-manually-administrable-orally-ingestible-material-fabrication-timing-factors module m250 depicted in FIG. 55 as being included in the module m247, when executed and/or activated, can direct performance of and/or perform the operation o250. Illustratively, in one or more implementations, the operation o250 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material fabrication timing factors (e.g. instruction regarding timing as to when specified ingestible components are to fabricated relative to when other ingestible components are to be fabricated, timing as to when an ingestible product is to be completed, etc. for a kiosk, personal, community, or other type vending, dispensing, or food fabricating machine located in a home, business, transportation facility, market, sports facility, office building, theater, school, hospital, park, restaurant, food court, etc.).

Figure 115:
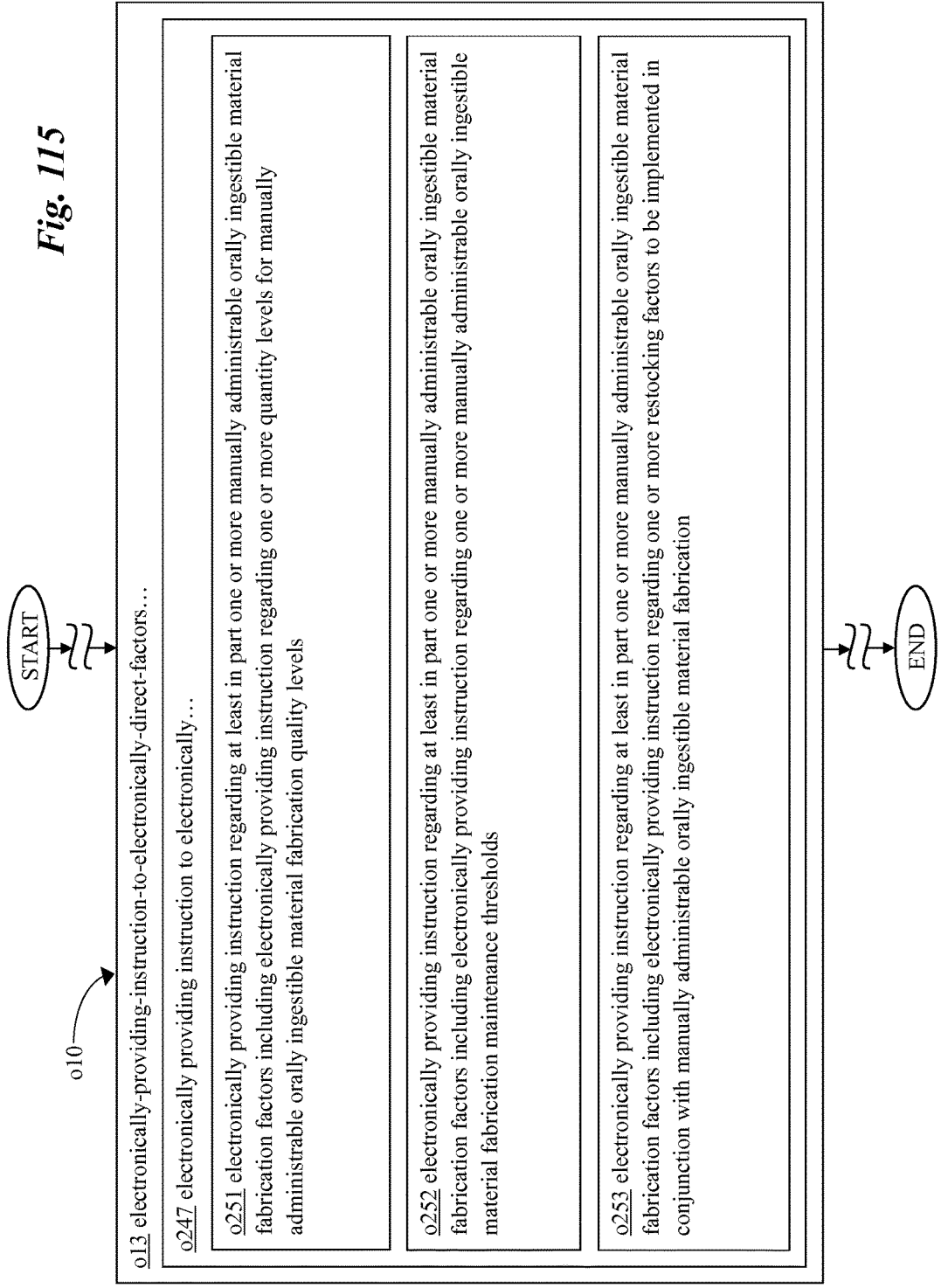

In one or more implementations, as shown in FIG. 115, the operation o247 can include operation o251 for electronically providing instruction regarding at least in part one or more manually administrable orally ingestible material fabrication factors including electronically providing instruction regarding one or more quantity levels for manually administrable orally ingestible material fabrication quality levels. Origination of a physically tangible component group can be accomplished through skilled in the art design choice selection including use of one or more components and/or subsystems explicitly and/or implicitly referred to herein for at least in part implementing execution of one or more instructions of the operation o251, for performance of the operation o251 by an electrical circuitry arrangement as activated thereto, and/or otherwise fulfillment of the operation o251. One or more non-transitory signal bearing physical media can bear the one or more instructions that when executed can direct performance of the operation o251. Furthermore, electronically-providing-instruction-regarding-manually-administrable-orally-ingestible-material-fabrication-quality-levels module m251 depicted in FIG. 56 as being included in the module m247, when executed and/or activated, can direct performance of and/or perform the operation o251. Illustratively, in one or more implementations, the operation o251 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more quantity levels for manually administrable orally ingestible material fabrication (e.g. instruction as instruction for amount of salt, sugar, fats, proteins, carbohydrates, etc. to use in preparation of food items for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 115, the operation o247 can include operation o252 for electronically providing instruction regarding at least in part one or more manually administrable orally ingestible material fabrication factors including electronically providing instruction regarding one or more manually administrable orally ingestible material fabrication maintenance thresholds. Origination of a physically tangible component group can be accomplished through skilled in the art design choice selection including use of one or more components and/or subsystems explicitly and/or implicitly referred to herein for at least in part implementing execution of one or more instructions of the operation o252, for performance of the operation o252 by an electrical circuitry arrangement as activated thereto, and/or otherwise fulfillment of the operation o252. One or more non-transitory signal bearing physical media can bear the one or more instructions that when executed can direct performance of the operation o252. Furthermore, electronically-providing-instruction-regarding-manually-administrable-orally-ingestible-material-fabrication-maintenance-thresholds module m252 depicted in FIG. 56 as being included in the module m247, when executed and/or activated, can direct performance of and/or perform the operation o252. Illustratively, in one or more implementations, the operation o252 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material fabrication maintenance thresholds (e.g. instruction as to when fabrication equipment is to be cleaned, repaired, restocked, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 115, the operation o247 can include operation o253 for electronically providing instruction regarding at least in part one or more manually administrable orally ingestible material fabrication factors including electronically providing instruction regarding one or more restocking factors to be implemented in conjunction with manually administrable orally ingestible material fabrication. Origination of a physically tangible component group can be accomplished through skilled in the art design choice selection including use of one or more components and/or subsystems explicitly and/or implicitly referred to herein for at least in part implementing execution of one or more instructions of the operation o253, for performance of the operation o253 by an electrical circuitry arrangement as activated thereto, and/or otherwise fulfillment of the operation o253. One or more non-transitory signal bearing physical media can bear the one or more instructions that when executed can direct performance of the operation o253. Furthermore, electronically-providing-instruction-regarding-restocking-factors-to-be-implemented-in-conjunction-with-manually-administrable-orally-ingestible-material-fabrication module m253 depicted in FIG. 56 as being included in the module m247, when executed and/or activated, can direct performance of and/or perform the operation o253. Illustratively, in one or more implementations, the operation o253 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding at least in part one or more manually administrable orally ingestible material fabrication factors (e.g. instruction as instruction for food printing, food item assembly, drink mixing, meal cooking, food item packaging, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more restocking factors to be implemented in conjunction with manually administrable orally ingestible material fabrication (e.g. instruction as instruction to be sent to supply chain for food items to restock inventory, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 111, the operation o13 can include operation o254 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications including electronically providing instruction regarding one or more electronically controlled dispensing procedures. Origination of a physically tangible component group can be accomplished through skilled in the art design choice selection including use of one or more components and/or subsystems explicitly and/or implicitly referred to herein for at least in part implementing execution of one or more instructions of the operation o254, for performance of the operation o254 by an electrical circuitry arrangement as activated thereto, and/or otherwise fulfillment of the operation o254. One or more non-transitory signal bearing physical media can bear the one or more instructions that when executed can direct performance of the operation o254. Furthermore, electronically-providing-instruction-regarding-electronically-controlled-dispensing-procedures module m254 depicted in FIG. 52 as being included in the module m13, when executed and/or activated, can direct performance of and/or perform the operation o254. Illustratively, in one or more implementations, the operation o254 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.).

Figure 116:
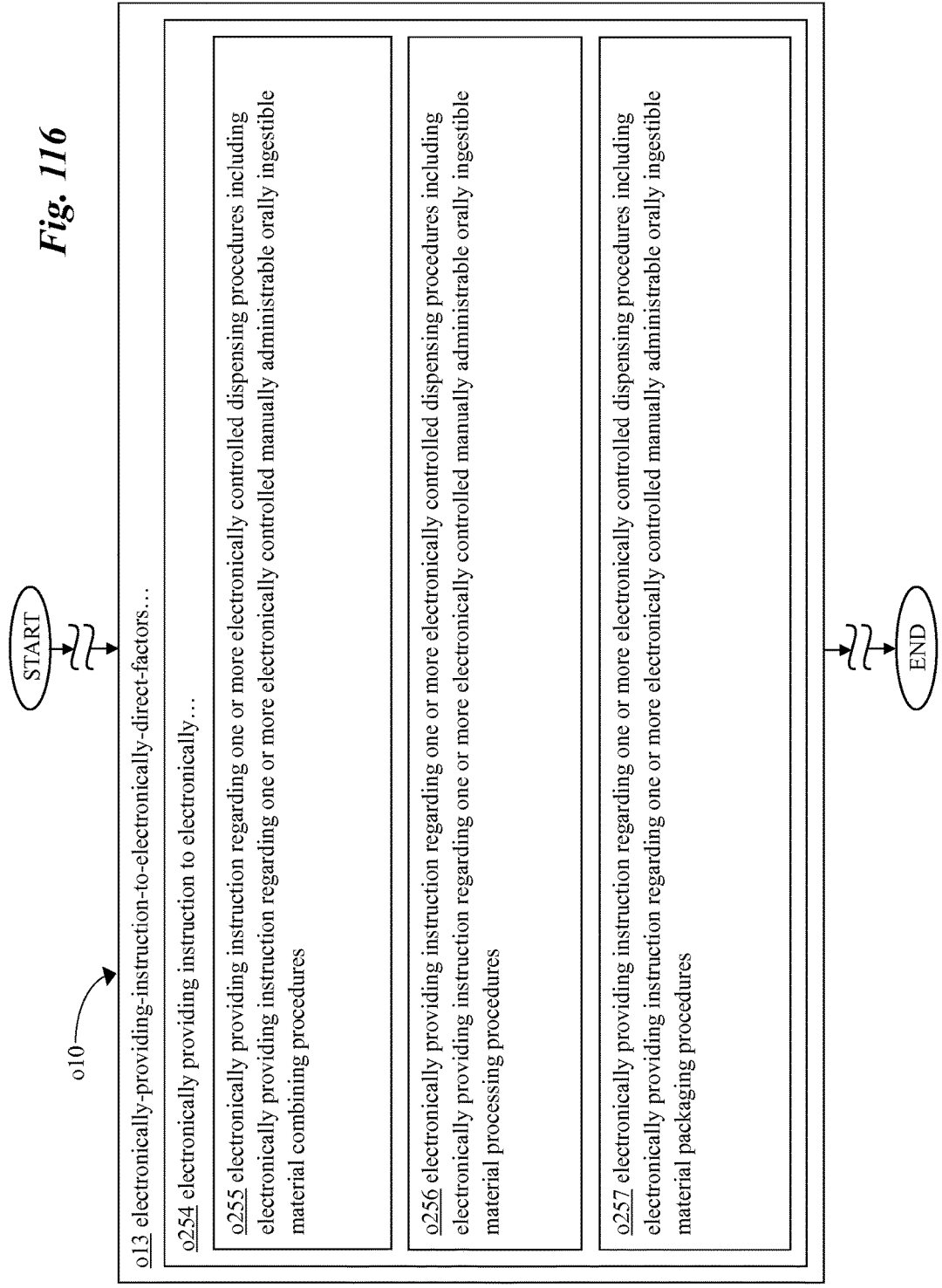

In one or more implementations, as shown in FIG. 116, the operation o254 can include operation o255 for electronically providing instruction regarding one or more electronically controlled dispensing procedures including electronically providing instruction regarding one or more electronically controlled manually administrable orally ingestible material combining procedures. Origination of a physically tangible component group can be accomplished through skilled in the art design choice selection including use of one or more components and/or subsystems explicitly and/or implicitly referred to herein for at least in part implementing execution of one or more instructions of the operation o255, for performance of the operation o255 by an electrical circuitry arrangement as activated thereto, and/or otherwise fulfillment of the operation o255. One or more non-transitory signal bearing physical media can bear the one or more instructions that when executed can direct performance of the operation o255. Furthermore, electronically-providing-instruction-regarding-electronically-controlled-manually-administrable-orally-ingestible-material-combining-procedures module m255 depicted in FIG. 57 as being included in the module m254, when executed and/or activated, can direct performance of and/or perform the operation o255. Illustratively, in one or more implementations, the operation o255 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more electronically controlled manually administrable orally ingestible material combining procedures (e.g. instruction as instruction regarding food combining rules as to ratios of what to mix concerning fruit, vegetable, meat, starch, oil, sugars, salt, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 116, the operation o254 can include operation o256 for electronically providing instruction regarding one or more electronically controlled dispensing procedures including electronically providing instruction regarding one or more electronically controlled manually administrable orally ingestible material processing procedures. Origination of a physically tangible component group can be accomplished through skilled in the art design choice selection including use of one or more components and/or subsystems explicitly and/or implicitly referred to herein for at least in part implementing execution of one or more instructions of the operation o256, for performance of the operation o256 by an electrical circuitry arrangement as activated thereto, and/or otherwise fulfillment of the operation o256. One or more non-transitory signal bearing physical media can bear the one or more instructions that when executed can direct performance of the operation o256. Furthermore, electronically-providing-instruction-regarding-electronically-controlled-manually-administrable-orally-ingestible-material-processing-procedures module m256 depicted in FIG. 57 as being included in the module m254, when executed and/or activated, can direct performance of and/or perform the operation o256. Illustratively, in one or more implementations, the operation o256 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled manually administrable orally ingestible material processing procedures (e.g. instruction as to ingestible material assembling, mixing, combining, extruding, printing, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 116, the operation o254 can include operation o257 for electronically providing instruction regarding one or more electronically controlled dispensing procedures including electronically providing instruction regarding one or more electronically controlled manually administrable orally ingestible material packaging procedures. Origination of a physically tangible component group can be accomplished through skilled in the art design choice selection including use of one or more components and/or subsystems explicitly and/or implicitly referred to herein for at least in part implementing execution of one or more instructions of the operation o257, for performance of the operation o257 by an electrical circuitry arrangement as activated thereto, and/or otherwise fulfillment of the operation o257. One or more non-transitory signal bearing physical media can bear the one or more instructions that when executed can direct performance of the operation o257. Furthermore, electronically-providing-instruction-regarding-electronically-controlled-manually-administrable-orally-ingestible-material-packaging-procedures module m257 depicted in FIG. 57 as being included in the module m254, when executed and/or activated, can direct performance of and/or perform the operation o257. Illustratively, in one or more implementations, the operation o257 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more electronically controlled manually administrable orally ingestible material packaging procedures (e.g. instruction as to size, internal dividers, thermal insulation capability, etc. for container to be used to package fabricated food items for a kiosk, personal, community, or other type vending, dispensing, or food fabricating machine located in a home, business, transportation facility, market, sports facility, office building, theater, school, hospital, park, restaurant, food court, etc.).

Figure 117:
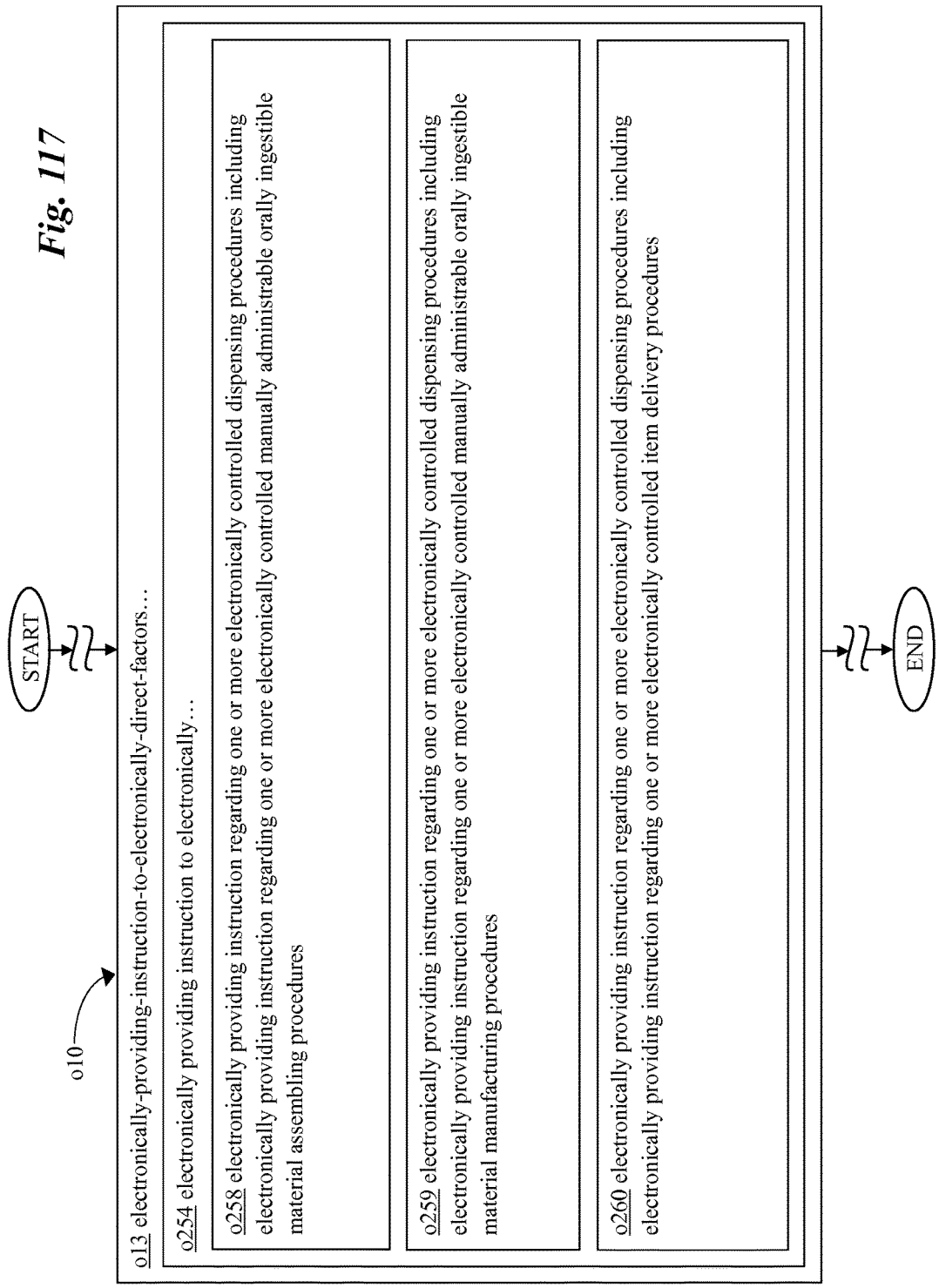

In one or more implementations, as shown in FIG. 117, the operation o254 can include operation o258 for electronically providing instruction regarding one or more electronically controlled dispensing procedures including electronically providing instruction regarding one or more electronically controlled manually administrable orally ingestible material assembling procedures. Origination of a physically tangible component group can be accomplished through skilled in the art design choice selection including use of one or more components and/or subsystems explicitly and/or implicitly referred to herein for at least in part implementing execution of one or more instructions of the operation o258, for performance of the operation o258 by an electrical circuitry arrangement as activated thereto, and/or otherwise fulfillment of the operation o258. One or more non-transitory signal bearing physical media can bear the one or more instructions that when executed can direct performance of the operation o258. Furthermore, electronically-providing-instruction-regarding-electronically-controlled-manually-administrable-orally-ingestible-material-assembling-procedures module m258 depicted in FIG. 58 as being included in the module m254, when executed and/or activated, can direct performance of and/or perform the operation o258. Illustratively, in one or more implementations, the operation o258 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled manually administrable orally ingestible material assembling procedures (e.g. instruction as to assembly order, timing, delivery schedule, etc. of ingestible material components, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 117, the operation o254 can include operation o259 for electronically providing instruction regarding one or more electronically controlled dispensing procedures including electronically providing instruction regarding one or more electronically controlled manually administrable orally ingestible material manufacturing procedures. Origination of a physically tangible component group can be accomplished through skilled in the art design choice selection including use of one or more components and/or subsystems explicitly and/or implicitly referred to herein for at least in part implementing execution of one or more instructions of the operation o259, for performance of the operation o259 by an electrical circuitry arrangement as activated thereto, and/or otherwise fulfillment of the operation o259. One or more non-transitory signal bearing physical media can bear the one or more instructions that when executed can direct performance of the operation o259. Furthermore, electronically-providing-instruction-regarding-electronically-controlled-manually-administrable-orally-ingestible-material-manufacturing-procedures module m259 depicted in FIG. 58 as being included in the module m254, when executed and/or activated, can direct performance of and/or perform the operation o259. Illustratively, in one or more implementations, the operation o259 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more electronically controlled manually administrable orally ingestible material manufacturing procedures (e.g. instruction as to service queue waiting times in fulfilling orders, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 117, the operation o254 can include operation o260 for electronically providing instruction regarding one or more electronically controlled dispensing procedures including electronically providing instruction regarding one or more electronically controlled item delivery procedures. Origination of a physically tangible component group can be accomplished through skilled in the art design choice selection including use of one or more components and/or subsystems explicitly and/or implicitly referred to herein for at least in part implementing execution of one or more instructions of the operation o260, for performance of the operation o260 by an electrical circuitry arrangement as activated thereto, and/or otherwise fulfillment of the operation o260. One or more non-transitory signal bearing physical media can bear the one or more instructions that when executed can direct performance of the operation o260. Furthermore, electronically-providing-instruction-regarding-electronically-controlled-item-delivery-procedures module m260 depicted in FIG. 58 as being included in the module m254, when executed and/or activated, can direct performance of and/or perform the operation o260. Illustratively, in one or more implementations, the operation o260 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled dispensing procedures (e.g. instruction as to sequence order of manufacturing components of an ingestible product, projected amount of ingestible material required for a specified time period for manufacturing, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more electronically controlled item delivery procedures (e.g. instruction as to delivery timing, routing, priorities involved, etc. for a kiosk, personal, community, or other type vending, dispensing, or food fabricating machine located in a home, business, transportation facility, market, sports facility, office building, theater, school, hospital, park, restaurant, food court, etc.).

Figure 118:
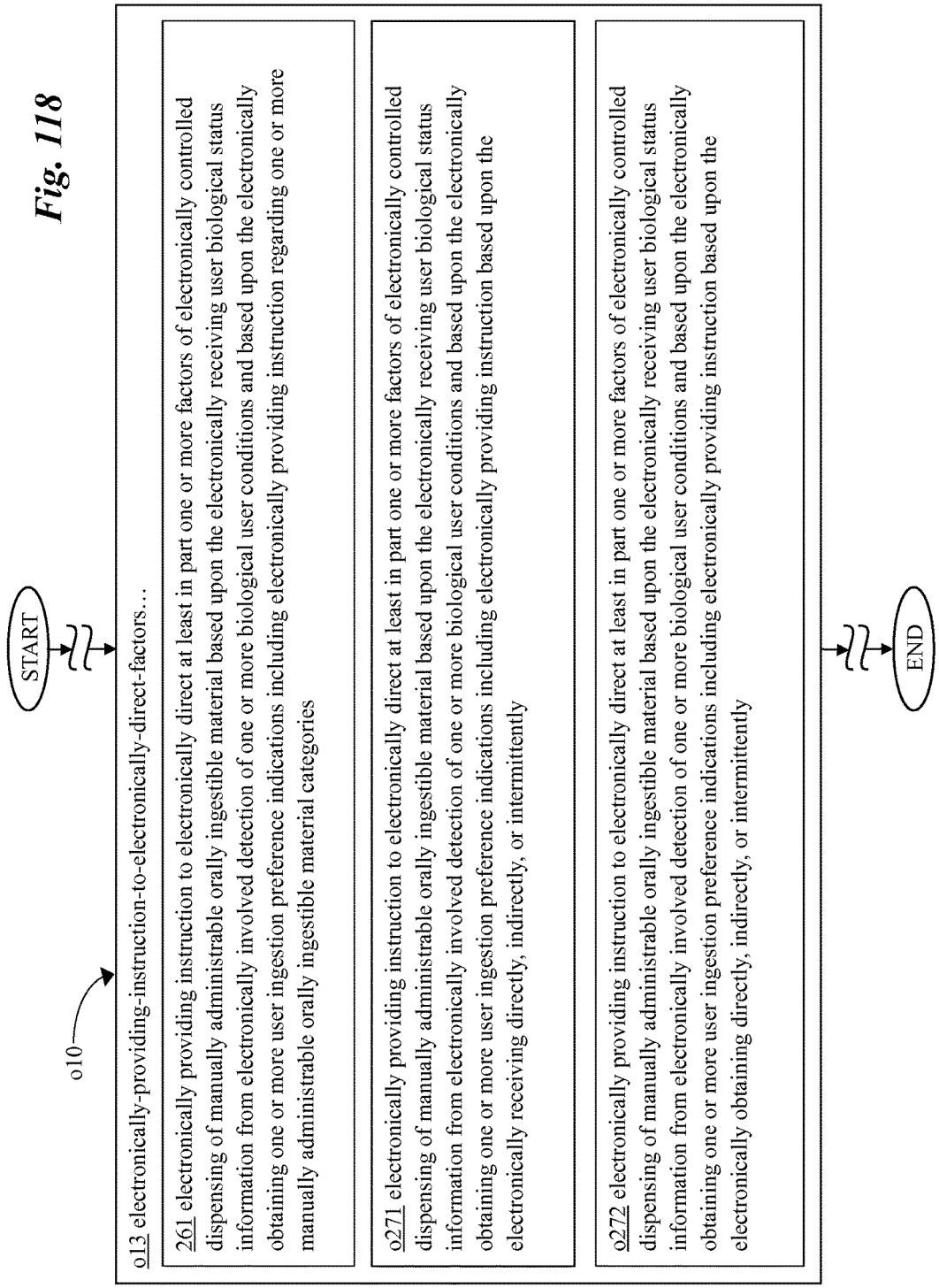

In one or more implementations, as shown in FIG. 118, the operation o13 can include operation o261 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications including electronically providing instruction regarding one or more manually administrable orally ingestible material categories. Origination of a physically tangible component group can be accomplished through skilled in the art design choice selection including use of one or more components and/or subsystems explicitly and/or implicitly referred to herein for at least in part implementing execution of one or more instructions of the operation o261, for performance of the operation o261 by an electrical circuitry arrangement as activated thereto, and/or otherwise fulfillment of the operation o261. One or more non-transitory signal bearing physical media can bear the one or more instructions that when executed can direct performance of the operation o261. Furthermore, electronically-providing-instruction-regarding-manually-administrable-orally-ingestible-material-categories module m261 depicted in FIG. 59 as being included in the module m13, when executed and/or activated, can direct performance of and/or perform the operation o261. Illustratively, in one or more implementations, the operation o261 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.).

Figure 119:
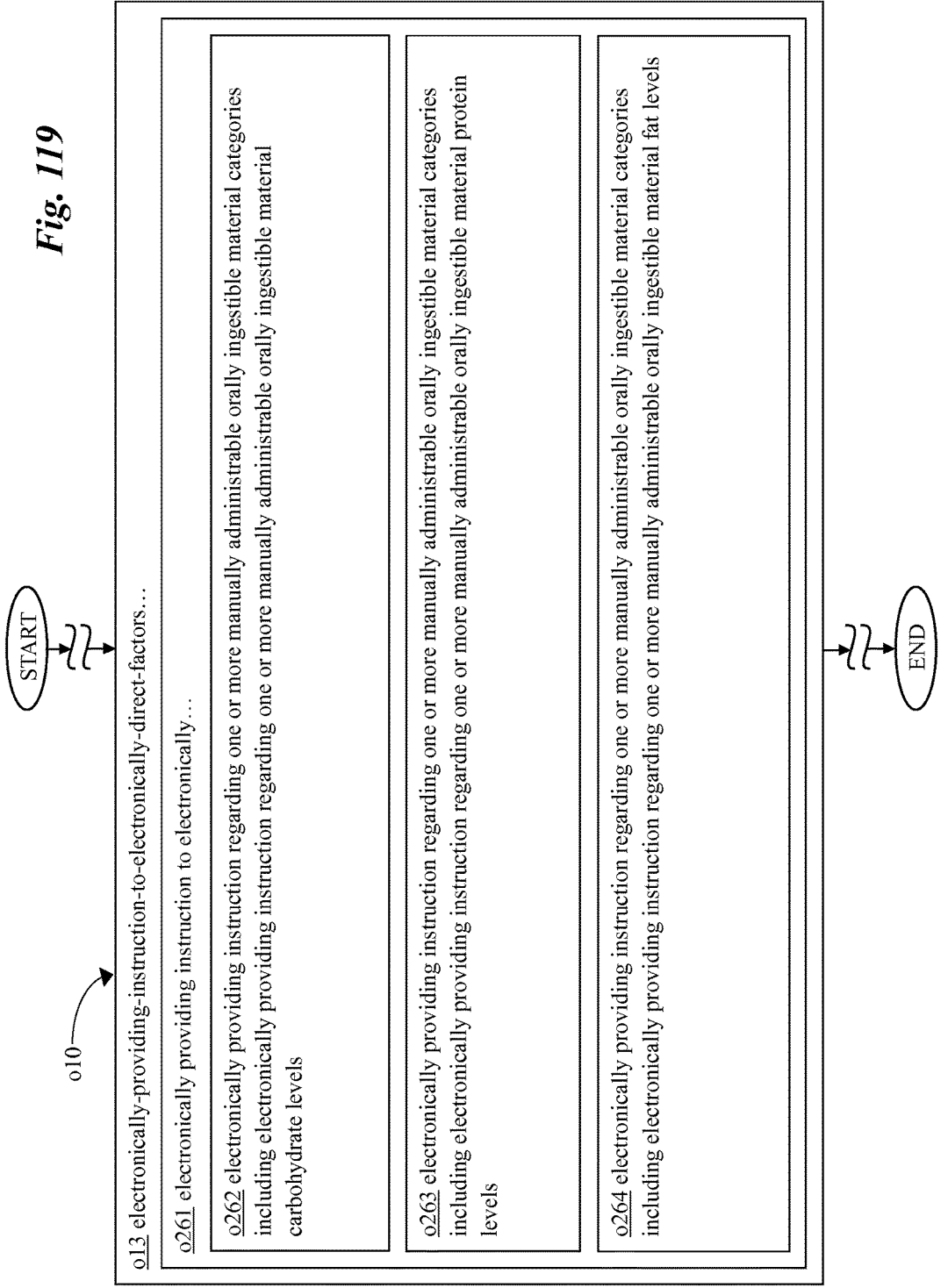

In one or more implementations, as shown in FIG. 119, the operation o261 can include operation o262 for electronically providing instruction regarding one or more manually administrable orally ingestible material categories including electronically providing instruction regarding one or more manually administrable orally ingestible material carbohydrate levels. Origination of a physically tangible component group can be accomplished through skilled in the art design choice selection including use of one or more components and/or subsystems explicitly and/or implicitly referred to herein for at least in part implementing execution of one or more instructions of the operation o262, for performance of the operation o262 by an electrical circuitry arrangement as activated thereto, and/or otherwise fulfillment of the operation o262. One or more non-transitory signal bearing physical media can bear the one or more instructions that when executed can direct performance of the operation o262. Furthermore, electronically-providing-instruction-regarding-carbohydrate-levels module m262 depicted in FIG. 60 as being included in the module m261, when executed and/or activated, can direct performance of and/or perform the operation o262. Illustratively, in one or more implementations, the operation o262 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material carbohydrate levels (e.g. instruction as to amounts used of dextrose, sucrose, fructose, high-fructose corn syrup, fiber, dextrin, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 119, the operation o261 can include operation o263 for electronically providing instruction regarding one or more manually administrable orally ingestible material categories including electronically providing instruction regarding one or more manually administrable orally ingestible material protein levels. Origination of a physically tangible component group can be accomplished through skilled in the art design choice selection including use of one or more components and/or subsystems explicitly and/or implicitly referred to herein for at least in part implementing execution of one or more instructions of the operation o263, for performance of the operation o263 by an electrical circuitry arrangement as activated thereto, and/or otherwise fulfillment of the operation o263. One or more non-transitory signal bearing physical media can bear the one or more instructions that when executed can direct performance of the operation o263. Furthermore, electronically-providing-instruction-regarding-protein-levels module m263 depicted in FIG. 60 as being included in the module m261, when executed and/or activated, can direct performance of and/or perform the operation o263. Illustratively, in one or more implementations, the operation o263 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more protein levels (e.g. instruction regarding protein quantity or quality of source relative to other food components for total meal, for particular food item, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 119, the operation o261 can include operation o264 for electronically providing instruction regarding one or more manually administrable orally ingestible material categories including electronically providing instruction regarding one or more manually administrable orally ingestible material fat levels. Origination of a physically tangible component group can be accomplished through skilled in the art design choice selection including use of one or more components and/or subsystems explicitly and/or implicitly referred to herein for at least in part implementing execution of one or more instructions of the operation o264, for performance of the operation o264 by an electrical circuitry arrangement as activated thereto, and/or otherwise fulfillment of the operation o264. One or more non-transitory signal bearing physical media can bear the one or more instructions that when executed can direct performance of the operation o264. Furthermore, electronically-providing-instruction-regarding-fat-levels module m264 depicted in FIG. 60 as being included in the module m261, when executed and/or activated, can direct performance of and/or perform the operation o264. Illustratively, in one or more implementations, the operation o264 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material fat levels (e.g. instruction as to amounts used of omega three fatty acids, omega six fatty acids, saturated fat, unsaturated fat, polyunsaturated fat, monounsaturated fat, etc. for a kiosk, personal, community, or other type vending, dispensing, or food fabricating machine located in a home, business, transportation facility, market, sports facility, office building, theater, school, hospital, park, restaurant, food court, etc.).

Figure 120:
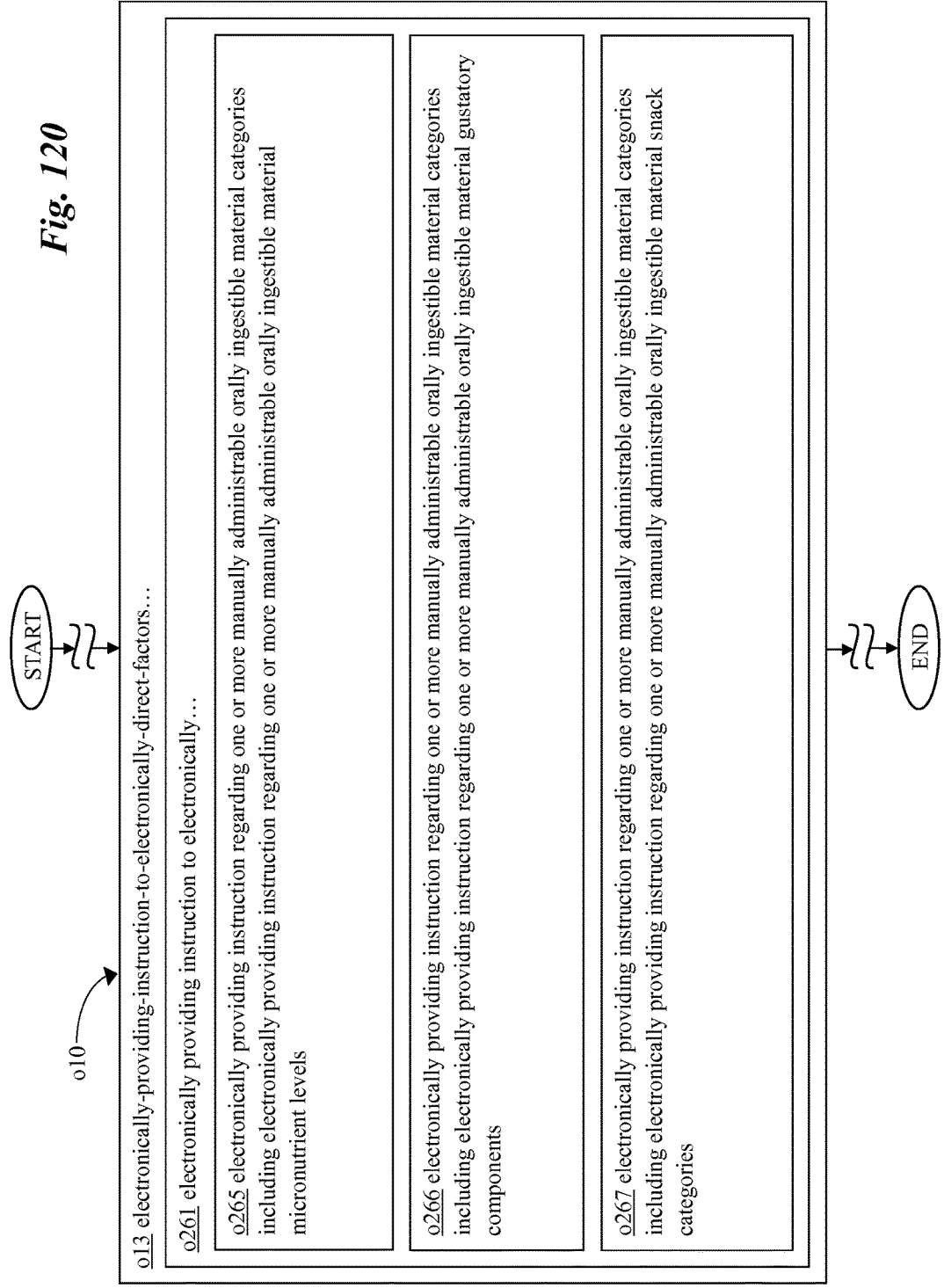

In one or more implementations, as shown in FIG. 120, the operation o261 can include operation o265 for electronically providing instruction regarding one or more manually administrable orally ingestible material categories including electronically providing instruction regarding one or more manually administrable orally ingestible material micronutrient levels. Origination of a physically tangible component group can be accomplished through skilled in the art design choice selection including use of one or more components and/or subsystems explicitly and/or implicitly referred to herein for at least in part implementing execution of one or more instructions of the operation o265, for performance of the operation o265 by an electrical circuitry arrangement as activated thereto, and/or otherwise fulfillment of the operation o265. One or more non-transitory signal bearing physical media can bear the one or more instructions that when executed can direct performance of the operation o265. Furthermore, electronically-providing-instruction-regarding-micronutrient-levels module m265 depicted in FIG. 61 as being included in the module m261, when executed and/or activated, can direct performance of and/or perform the operation o265. Illustratively, in one or more implementations, the operation o265 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material micronutrient levels (e.g. instruction regarding micronutrient quantity or quality or source relative to other food components for total meal, for particular food item, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 120, the operation o261 can include operation o266 for electronically providing instruction regarding one or more manually administrable orally ingestible material categories including electronically providing instruction regarding one or more manually administrable orally ingestible material gustatory components. Origination of a physically tangible component group can be accomplished through skilled in the art design choice selection including use of one or more components and/or subsystems explicitly and/or implicitly referred to herein for at least in part implementing execution of one or more instructions of the operation o266, for performance of the operation o266 by an electrical circuitry arrangement as activated thereto, and/or otherwise fulfillment of the operation o266. One or more non-transitory signal bearing physical media can bear the one or more instructions that when executed can direct performance of the operation o266. Furthermore, electronically-providing-instruction-regarding-gustatory-components module m266 depicted in FIG. 61 as being included in the module m261, when executed and/or activated, can direct performance of and/or perform the operation o266. Illustratively, in one or more implementations, the operation o266 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material gustatory components (e.g. instruction as to levels used of sweet tasting components, salty tasting components, sour tasting components, bitter tasting components, savory tasting components, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 120, the operation o261 can include operation o267 for electronically providing instruction regarding one or more manually administrable orally ingestible material categories including electronically providing instruction regarding one or more manually administrable orally ingestible material snack categories. Origination of a physically tangible component group can be accomplished through skilled in the art design choice selection including use of one or more components and/or subsystems explicitly and/or implicitly referred to herein for at least in part implementing execution of one or more instructions of the operation o267, for performance of the operation o267 by an electrical circuitry arrangement as activated thereto, and/or otherwise fulfillment of the operation o267. One or more non-transitory signal bearing physical media can bear the one or more instructions that when executed can direct performance of the operation o267. Furthermore, electronically-providing-instruction-regarding-snack-categories module m267 depicted in FIG. 61 as being included in the module m261, when executed and/or activated, can direct performance of and/or perform the operation o267. Illustratively, in one or more implementations, the operation o267 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material snack categories (e.g. instruction regarding hot snacks, cold snacks, individually packaged snacks, collection of snacks, prohibited ingredients, required ingredients, etc. for a kiosk, personal, community, or other type vending, dispensing, or food fabricating machine located in a home, business, transportation facility, market, sports facility, office building, theater, school, hospital, park, restaurant, food court, etc.).

Figure 121:
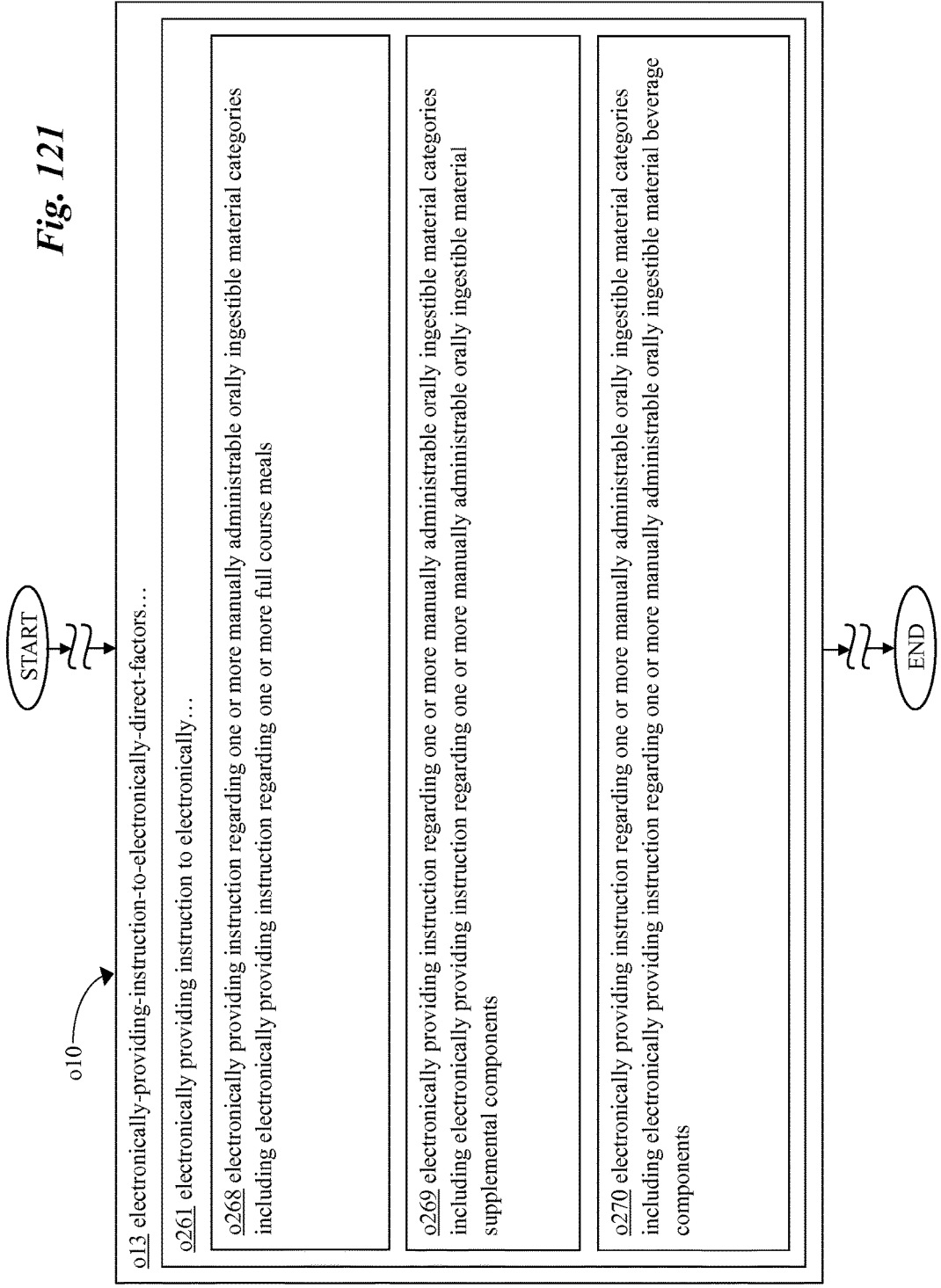

In one or more implementations, as shown in FIG. 121, the operation o261 can include operation o268 for electronically providing instruction regarding one or more manually administrable orally ingestible material categories including electronically providing instruction regarding one or more full course meals. Origination of a physically tangible component group can be accomplished through skilled in the art design choice selection including use of one or more components and/or subsystems explicitly and/or implicitly referred to herein for at least in part implementing execution of one or more instructions of the operation o268, for performance of the operation o268 by an electrical circuitry arrangement as activated thereto, and/or otherwise fulfillment of the operation o268. One or more non-transitory signal bearing physical media can bear the one or more instructions that when executed can direct performance of the operation o268. Furthermore, electronically-providing-instruction-regarding-full-course-meals module m268 depicted in FIG. 62 as being included in the module m261, when executed and/or activated, can direct performance of and/or perform the operation o268. Illustratively, in one or more implementations, the operation o268 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material full meals (e.g. instruction as to ethnic type of full meal to produce, portion size of full meal to produce, quality level of full meal to produce, non-organic components of full meal to produce, organic components of full meal to produce, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 121, the operation o261 can include operation o269 for electronically providing instruction regarding one or more manually administrable orally ingestible material categories including electronically providing instruction regarding one or more manually administrable orally ingestible material supplemental components. Origination of a physically tangible component group can be accomplished through skilled in the art design choice selection including use of one or more components and/or subsystems explicitly and/or implicitly referred to herein for at least in part implementing execution of one or more instructions of the operation o269, for performance of the operation o269 by an electrical circuitry arrangement as activated thereto, and/or otherwise fulfillment of the operation o269. One or more non-transitory signal bearing physical media can bear the one or more instructions that when executed can direct performance of the operation o269. Furthermore, electronically-providing-instruction-regarding-supplemental-components module m269 depicted in FIG. 62 as being included in the module m261, when executed and/or activated, can direct performance of and/or perform the operation o269. Illustratively, in one or more implementations, the operation o269 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material supplemental components (e.g. instruction regarding supplemental components such as thickeners, sweeteners, emulsifiers, preservatives, gelling agents, nutrient enhancers, taste enhancers, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 121, the operation o261 can include operation o270 for electronically providing instruction regarding one or more manually administrable orally ingestible material categories including electronically providing instruction regarding one or more manually administrable orally ingestible material beverage components. Origination of a physically tangible component group can be accomplished through skilled in the art design choice selection including use of one or more components and/or subsystems explicitly and/or implicitly referred to herein for at least in part implementing execution of one or more instructions of the operation o270, for performance of the operation o270 by an electrical circuitry arrangement as activated thereto, and/or otherwise fulfillment of the operation o270. One or more non-transitory signal bearing physical media can bear the one or more instructions that when executed can direct performance of the operation o270. Furthermore, electronically-providing-instruction-regarding-beverage-components module m270 depicted in FIG. 62 as being included in the module m261, when executed and/or activated, can direct performance of and/or perform the operation o270. Illustratively, in one or more implementations, the operation o270 can be carried out, for example, by electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) regarding one or more manually administrable orally ingestible material categories (e.g. instruction regarding handling and preparing categories such as full meals, quick snacks, drinks, side-orders, custom dishes, etc. for a kiosk, personal, community, or other type vending, dispensing, or food fabricating machine located in a home, business, transportation facility, market, sports facility, office building, theater, school, hospital, park, restaurant, food court, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) regarding one or more manually administrable orally ingestible material beverage components (e.g. instruction to as quantity or type to use of water, sugar, artificial sweetener, aeration, natural carbonation, artificial carbonation, phosphoric acid, fluoride, chlorine, alcohol, artificial or natural flavorings, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 118, the operation o13 can include operation o271 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications including electronically providing instruction based upon the electronically receiving directly, indirectly, or intermittently. Origination of a physically tangible component group can be accomplished through skilled in the art design choice selection including use of one or more components and/or subsystems explicitly and/or implicitly referred to herein for at least in part implementing execution of one or more instructions of the operation o271, for performance of the operation o271 by an electrical circuitry arrangement as activated thereto, and/or otherwise fulfillment of the operation o271. One or more non-transitory signal bearing physical media can bear the one or more instructions that when executed can direct performance of the operation o271. Furthermore, electronically-providing-instruction-based-upon-the-electronically-receiving-directly,-indirectly,-or-intermittently module m271 depicted in FIG. 59 as being included in the module m13, when executed and/or activated, can direct performance of and/or perform the operation o271. Illustratively, in one or more implementations, the operation o271 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically providing (e.g. internal component level, logic-based, packetized communication, protocol-based, signal levels, etc.) instruction (e.g. quantified-self based, big data analytics, supply chain, remote control, item order-based, modular control, fabrication, device control, etc.) based upon the electronically receiving directly, indirectly, or intermittently (e.g. receiving information directly, indirectly, or intermittently related to the electronically providing instruction, etc. for a kiosk, personal, community, or other type vending, dispensing, or food fabricating machine located in a home, business, transportation facility, market, sports facility, office building, theater, school, hospital, park, restaurant, food court, etc.).

In one or more implementations, as shown in FIG. 118, the operation o13 can include operation o272 for electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications including electronically providing instruction based upon the electronically obtaining directly, indirectly, or intermittently. Origination of a physically tangible component group can be accomplished through skilled in the art design choice selection including use of one or more components and/or subsystems explicitly and/or implicitly referred to herein for at least in part implementing execution of one or more instructions of the operation o272, for performance of the operation o272 by an electrical circuitry arrangement as activated thereto, and/or otherwise fulfillment of the operation o272. One or more non-transitory signal bearing physical media can bear the one or more instructions that when executed can direct performance of the operation o272. Furthermore, electronically-providing-instruction-based-upon-the-electronically-obtaining-directly,-indirectly,-or-intermittently module m272 depicted in FIG. 59 as being included in the module m13, when executed and/or activated, can direct performance of and/or perform the operation o272. Illustratively, in one or more implementations, the operation o272 can be carried out, for example, by electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) to electronically direct (e.g. adjust, modify, reduce, increase, select, exclude, stop, proceed, start, etc.) at least in part one or more factors (e.g. ingredient levels, re-stocking parameters, degree of applied energy, quality levels, timing parameters, quantity levels, etc.) of electronically controlled dispensing (e.g. combining, routing, processing, manufacturing, assembling, packaging, kiosk-based, delivering, selling, shipping, etc.) of manually administrable orally ingestible material (e.g. carbohydrate component, drink, protein component, supplement, fat component, full meal, micronutrient component, snack, gustatory component, sports bar, sports drink, confectionary, bakery good, sandwich, side order, main course, etc.) based upon (e.g. directly, indirectly, intermittently, etc.) the electronically receiving (e.g. radio frequency, WiFi, Bluetooth, packetized data, wireless protocols, infrared, electromagnetic, other transmission, direct device-to-device, network, non-wireless, scans, swipes, other transfers, etc.) user biological status information (e.g. current, physiological, historical, functional, individual, behavior life data, group, quantified-self data, etc.) from electronically involved detection (e.g. wearable, invasive, non-wearable, non-invasive, limb-based, trunk-based, head-based, etc.) of one or more biological user conditions (e.g. disease, chronic, acute, symptomatic, diagnosed, epidemic, life-style, health, enhancement, reduction, augmentation, etc.) and based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) one or more user ingestion preference indications (e.g. specific item, audio, item class, video, amount, key-based, selection by role model, from personal device, goal-based, network protocol, organizational, social network, data storage, advertising-based, cost-based, etc.) including electronically providing (e.g. signal levels, protocol-based, packetized communication, logic-based, internal component level, etc.) instruction (e.g. device control, fabrication, modular control, item order-based, remote control, supply chain, big data analytics, quantified-self based, etc.) based upon the electronically obtaining (e.g. radio frequency, WiFi, Bluetooth, packetized data, wireless protocols, infrared, electromagnetic, other transmission, direct device-to-device, network, non-wireless, scans, swipes, other transfers, etc.) directly, indirectly, or intermittently (e.g. receiving information directly, indirectly, or intermittently related to the electronically providing instruction, etc. for a kiosk, personal, community, or other type vending, dispensing, or food fabricating machine located in a home, business, transportation facility, market, sports facility, office building, theater, school, hospital, park, restaurant, food court, etc.).

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The one or more instructions discussed herein may be, for example, computer executable and/or logic-implemented instructions. In some implementations, signal-bearing medium as articles of manufacture may store the one or more instructions. In some implementations, the signal bearing medium may include a computer-readable medium. In some implementations, the signal-bearing medium may include a recordable medium. In some implementations, the signal-bearing medium may include a communication medium.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A computationally-implemented method comprising:
electronically controlling at least one analytics server device including at least:
electronically collecting at least one of user physiological status information or behavioral status information associated with at least one user including at least collecting at least one of image data or audio data indicative of dialogue with at least one individual associated with the at least one user that is electronically sensed in at least one life activity environment;
electronically obtaining one or more user ingestion preference indications associated with the at least one user;
electronically analyzing the collected at least one of user physiological status information or behavioral status information for determining at least one characteristic of the at least one user including at least electronically analyzing, by speech-based pattern recognition, the collected at least one of image data or audio data indicative of dialogue with at least one individual associated with the at least one user and extracting at least by word analysis at least one of one or more emotional, intellectual, or psychological characteristics of the at least one user;
electronically determining one or more instructions for electronically directing at least in part one or more factors of electronically controlled dispensing of manually administrable orally ingestible material including at least determining from the at least one characteristic at least one reaction of the at least one user to at least one food material and at least tuning at least one of macronutrient, micronutrient, or bacterial food content to the at least one of one or more one or more emotional, intellectual, or psychological characteristics of the at least one user; and
electronically transmitting the one or more instructions for electronically directing at least in part one or more factors of electronically controlled dispensing of manually administrable orally ingestible material to at least one food and nutrition fabrication device.

2. A computationally-implemented system, comprising:
at least one server device including one or more electronic devices including at least:
circuitry configured for electronically collecting at least one of user physiological status information or behavioral status information associated with at least one user including at least collecting at least one of image data or audio data indicative of dialogue with at least one individual associated with the at least one user that is electronically sensed in at least one life activity environment;
circuitry configured for electronically obtaining one or more user ingestion preference indications associated with the at least one user;
circuitry configured for electronically analyzing the collected at least one of user physiological status information or behavioral status information for determining at least one characteristic of the at least one user including at least circuitry configured for electronically analyzing, by speech-based pattern recognition, the collected at least one of image data or audio data indicative of dialogue with at least one individual associated with the at least one user and extracting at least by word analysis at least one of one or more emotional, intellectual, or psychological characteristics of the at least one user;
circuitry configured for electronically determining one or more instructions for electronically directing at least in part one or more factors of electronically controlled dispensing of manually administrable orally ingestible material including at least determining from the at least one characteristic at least one reaction of the at least one user to at least one food material and at least tuning at least one of macronutrient, micronutrient, or bacterial food content to the at least one of one or more one or more emotional, intellectual, or psychological characteristics of the at least one user; and circuitry configured for electronically transmitting the one or more instructions for electronically directing at least in part one or more factors of electronically controlled dispensing of manually administrable orally ingestible material to at least one food and nutrition fabrication device.

3. A computationally-implemented system comprising:

means for electronically controlling at least one analytics server device including at least:

means for electronically collecting at least one of user physiological status information or behavioral status information associated with at least one user including at least collecting at least one of image data or audio data indicative of dialogue with at least one individual associated with the at least one user that is electronically sensed in at least one life activity environment;

means for electronically obtaining one or more user ingestion preference indications associated with the at least one user;

means for electronically analyzing the collected at least one of user physiological status information or behavioral status information for determining at least one characteristic of the at least one user including at least means for electronically analyzing, by speech-based pattern recognition, the collected at least one of image data or audio data indicative of dialogue with at least one individual associated with the at least one user and extracting at least by word analysis at least one of one or more emotional, intellectual, or psychological characteristics of the at least one user;

means for electronically determining one or more instructions for electronically directing at least in part one or more factors of electronically controlled dispensing of manually administrable orally ingestible material including at least determining from the at least one characteristic at least one reaction of the at least one user to at least one food material and at least tuning at least one of macronutrient, micronutrient, or bacterial food content to the at least one of one or more one or more emotional, intellectual, or psychological characteristics of the at least one user; and means for electronically transmitting the one or more instructions for electronically directing at least in part one or more factors of electronically controlled dispensing of manually administrable orally ingestible material to at least one food and nutrition fabrication device.

4. The method of claim 1 wherein the electronically collecting at least one of user physiological status information or behavioral status information associated with at least one user includes:

receiving at least one of physiological status information or behavioral status information sensed by one or more non-wearable biological information data acquisition devices associated with the at least one user.

5. The method of claim 1 wherein the electronically collecting at least one of user physiological status information or behavioral status information associated with at least one user includes:

receiving at least one of physiological status information or behavioral status information sensed by at least one wearable biological information data acquisition device associated with the at least one user.

6. The method of claim 1 wherein the electronically collecting at least one of user physiological status information or behavioral status information associated with at least one user includes:

receiving at least one of physiological status information or behavioral status information entered by the at least one user via at least one user interface.

7. The method of claim 1 wherein the electronically collecting at least one of user physiological status information or behavioral status information associated with at least one user includes:

receiving at least physiological status information sensed by one or more biological information data acquisition devices associated with the at least one user, wherein the physiological status information includes at least information associated with at least one of molecular, chemical, analytes, electrolytes, cellular, tissue, organ, skeletal, muscular, immune, lymphatic, cardiovascular, urinary, digestive, respiratory, nervous, endocrine, reproductive, or integumentary.

8. The method of claim 1 wherein the electronically collecting at least one of user physiological status information or behavioral status information associated with at least one user includes:

receiving at least one of physiological status information or behavioral status information acquired by one or more biological information data acquisition devices associated with the at least one user, wherein the at least one of physiological status information or behavioral status information includes at least information associated with at least one of functional, sleeping, walking, running, sitting, posture, standing, squatting, lifting, speaking, listening, seeing, driving, eliminating, reacting, ambulating, thinking, location, electrical, past disease, present disease, potential disease, mechanical, structural, movement, sports, or recreation.

9. The method of claim 1 wherein the electronically collecting at least one of user physiological status information or behavioral status information associated with at least one user includes:

monitoring at least audio signals associated with home life dialogue among at least one of spouses, parents, children, relatives, visitors or guests.

10. The method of claim 1 wherein the electronically collecting at least one of user physiological status information or behavioral status information associated with at least one user includes:

monitoring at least audio signals associated with workplace dialogue including the at least one user.

11. The method of claim 1 wherein the electronically collecting at least one of user physiological status information or behavioral status information associated with at least one user includes:

monitoring at least audio signals associated with education-related dialogue including the at least one user.

12. The method of claim 1 wherein the electronically collecting at least one of user physiological status information or behavioral status information associated with at least one user includes:

monitoring at least audio signals associated with athletic-related dialogue including the at least one user.

13. The method of claim 1 wherein the electronically collecting at least one of user physiological status information or behavioral status information associated with at least one user includes:
   monitoring at least audio signals indicative of at least one of habits or traits associated with dialogue of the at least one user.

14. The method of claim 1 wherein the electronically collecting at least one of user physiological status information or behavioral status information associated with at least one user includes:
   monitoring at least brainwave patterns associated with dialogue of the at least one user.

15. The method of claim 1 wherein the electronically collecting at least one of user physiological status information or behavioral status information associated with at least one user includes:
   monitoring at least video signals associated with dialogue of the at least one user.

16. The method of claim 1 wherein the electronically collecting at least one of user physiological status information or behavioral status information associated with at least one user includes:
   monitoring at least location signals associated with dialogue of the at least one user.

17. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and extracting at least by word analysis at least one of one or more emotional, intellectual, psychological, or behavioral characteristics of the at least one user that is inconsistent with at least one normative standard associated with at least one profile associated with the at least one user.

18. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and extracting at least by word analysis at least one performance level associated with the at least one user.

19. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and measuring at least one of quality or quantity of performance of at least one activity of the at least one user.

20. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and determining by at least word analysis at least habit patterns associated with the at least one user.

21. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and determining at least by word analysis at least time spent in one or more activities associated with the at least one user including statistical analysis for determining at least one of rankings or assessments in comparison with at least one normative standard of the at least one user.

22. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and detecting at least by word analysis at least preferences associated with at least one of activities, habits, food choices, or associations including at least detecting one or more expressions by the at least one user indicative of one or more goals in terms of at least one of physical fitness, appearance, or mental acuity of the at least one user.

23. The method of claim 1 wherein the electronically analyzing the collected at least one of user physiological status information or behavioral status information for determining at least one characteristic of the at least one user includes:
   analyzing, by speech-based pattern recognition, the collected at least one of image data or audio data indicative of dialogue with at least one individual associated with the at least one user and determining at least by word analysis at least one of concentration levels, amount of involvement, degree of insight and expression, work capacity, interest level, level a distraction, ingenuity, or leadership of the at least one user.

24. The method of claim 1 wherein the electronically analyzing the collected at least one of user physiological status information or behavioral status information for determining at least one characteristic of the at least one user includes:
   analyzing, by speech-based pattern recognition for determining at least one of communication levels, cooperation levels, interest levels, or selfishness levels of the at least one user, the collected at least one of image data or audio data indicative of dialogue with at least one individual associated with the at least one user and extracting at least by word analysis at least one of one or more emotional, intellectual, or psychological characteristics of the at least one user.

25. The method of claim 1 wherein the electronically analyzing the collected at least one of user physiological status information or behavioral status information for determining at least one characteristic of the at least one user includes:
  analyzing, by speech-based pattern recognition, the collected at least one of image data or audio data indicative of dialogue with at least one individual associated with the at least one user and extracting at least by word analysis at least one of one or more emotional, intellectual, or psychological characteristics of the at least one user for detection of one or more emotionally-heated dialogue.

26. The method of claim 1 wherein the electronically analyzing the collected at least one of user physiological status information or behavioral status information for determining at least one characteristic of the at least one user includes:
  analyzing, by speech-based pattern recognition, the collected at least one of image data or audio data indicative of dialogue with at least one individual associated with the at least one user and extracting at least by word analysis at least one of one or more emotional, intellectual, or psychological characteristics of the at least one user for detection of at least one of stress level or health level.

27. The method of claim 1 wherein the electronically analyzing the collected at least one of user physiological status information or behavioral status information for determining at least one characteristic of the at least one user includes:
  analyzing, by speech-based pattern recognition, the collected at least one of image data or audio data indicative of dialogue with at least one individual associated with the at least one user and extracting at least by word analysis at least one of one or more emotional, intellectual, or psychological characteristics of the at least one user including at least tracking of at least one of task duration, output level, rest break profiles, or time expended in non-performance activity.

28. The method of claim 1 wherein the electronically analyzing the collected at least one of user physiological status information or behavioral status information for determining at least one characteristic of the at least one user includes:
  analyzing, by speech-based pattern recognition for determination of at least one of volume level, word choice, content of speech, signals of irritation, abrasive content, or method of expression of the at least one user, the collected at least one of image data or audio data indicative of dialogue with at least one individual associated with the at least one user and extracting at least by word analysis at least one of one or more emotional, intellectual, or psychological characteristics of the at least one user.

29. The method of claim 1 wherein the electronically analyzing the collected at least one of user physiological status information or behavioral status information for determining at least one characteristic of the at least one user includes:
  analyzing, by speech-based pattern recognition for determination of at least amount of eye contact through neurotypical metrics or neurotypical eye contacts of the at least one user, the collected at least one of image data or audio data indicative of dialogue with at least one individual associated with the at least one user and extracting at least by word analysis at least one of one or more emotional, intellectual, or psychological characteristics of the at least one user.

30. The method of claim 1 wherein the electronically analyzing the collected at least one of user physiological status information or behavioral status information for determining at least one characteristic of the at least one user includes:
  analyzing, by speech-based pattern recognition, the collected at least one of image data or audio data indicative of dialogue with at least one individual associated with the at least one user and determining at least by word analysis at least one measurement indicative of at least one of sleep quantity or sleep quality of the at least one user.

31. The method of claim 1 wherein the electronically analyzing the collected at least one of user physiological status information or behavioral status information for determining at least one characteristic of the at least one user includes:
  deriving at least one profile associated with reaction of a collection of individuals to the ingestion of the at least one food material at least from acquired physiological status information and at least one of one or more emotional, intellectual, psychological, or behavioral characteristics of the at least one user, wherein the collection of individuals includes the at least one user.

32. The method of claim 1 wherein the electronically analyzing the collected at least one of user physiological status information or behavioral status information for determining at least one characteristic of the at least one user includes:
  deriving at least one profile associated with reaction of a collection of individuals to the ingestion of the at least one food material at least from the acquired at least one of physiological status information or behavioral status information, and at least one of one or more emotional, intellectual, psychological, or behavioral characteristics of the at least one user, wherein the collection of individuals includes the at least one user and the collection of individuals is associated with at least one of a workplace environment, an educational environment, a home environment, or a social network environment.

33. The method of claim 1 wherein the electronically obtaining one or more user ingestion preference indications associated with the at least one user includes:
  at least one of:
    receiving one or more user ingestion preference indications entered by the at least one user via at least one user interface;
    receiving from the at least one user one or more user ingestion preference indications including at least collected information associated with food preferences including at least one of texture, color, taste, sweetness, sourness, or saltiness; or
    receiving from the at least one user at least one audio signal and detecting one or more user ingestion preference indications via at least one of word analysis or comment recognition.

34. The method of claim 1 wherein the electronically obtaining one or more user ingestion preference indications associated with the at least one user includes:
  detecting one or more user ingestion preference indications via at least one of word analysis or comment recognition of the monitored audio signals associated with dialogue of the at least one user.

35. The method of claim 1 wherein the electronically determining one or more instructions for electronically directing at least in part one or more factors of electronically controlled dispensing of manually administrable orally ingestible material includes:

electronically analyzing at least one of quality or quantity of athletic output sensed via at least one sensor associated with athletic equipment associated with the at least one user and at least tuning at least one of macronutrient, micronutrient, or bacterial food content to the at least one of quality or quantity of athletic output.

36. The method of claim 1 wherein the electronically determining one or more instructions for electronically directing at least in part one or more factors of electronically controlled dispensing of manually administrable orally ingestible material includes:

determining selection of at least one of quantity or types of sugars for preparing food material specified according to the one or more user ingestion preference indications including at least tuning at least one of macronutrient, micronutrient, or bacterial food content to at least one of ability to decrease adipose tissue, maintain energy levels, maintain endurance levels, maintain intellectual performance, or maintain work performance determined at least partly on at least profile associated with the at least one user.

37. The method of claim 1 wherein the electronically determining one or more instructions for electronically directing at least in part one or more factors of electronically controlled dispensing of manually administrable orally ingestible material includes:

determining selection of at least one of quantity or types of fats for preparing food material specified according to the one or more user ingestion preference indications including at least tuning at least one of macronutrient, micronutrient, or bacterial food content to at least one of ability to decrease adipose tissue, maintain energy levels, maintain endurance levels, maintain intellectual performance, or maintain work performance determined at least partly on at least one profile associated with the at least one user and the at least one of one or more emotional, intellectual, or psychological characteristics.

38. The method of claim 1 wherein the electronically determining one or more instructions for electronically directing at least in part one or more factors of electronically controlled dispensing of manually administrable orally ingestible material includes:

determining selection of at least one of quantity or types of contaminants for preparing food material specified according to the one or more user ingestion preference indications including at least tuning at least one of macronutrient, micronutrient, or bacterial food content to effects of at least one of mineral absorption or biochemical reactions associated with at least one of ability to decrease adipose tissue, maintain energy levels, maintain endurance levels, maintain intellectual performance, or maintain work performance determined at least partly on at least one profile associated with the at least one user and the at least one of one or more emotional, intellectual, or psychological characteristics.

39. The method of claim 1 wherein the electronically determining one or more instructions for electronically directing at least in part one or more factors of electronically controlled dispensing of manually administrable orally ingestible material includes:

determining selection of at least one of quantity or types of proteins for preparing food material specified according to the one or more user ingestion preference indications including at least tuning at least one of macronutrient, micronutrient, or bacterial food content to effects of at least one of absorbability or digestive efficacy associated with at least one of ability to decrease adipose tissue, maintain energy levels, maintain endurance levels, maintain intellectual performance, or maintain work performance determined at least partly on at least one profile associated with the at least one user and the at least one of one or more emotional, intellectual, or psychological characteristics.

40. The method of claim 1 wherein the electronically determining one or more instructions for electronically directing at least in part one or more factors of electronically controlled dispensing of manually administrable orally ingestible material includes:

determining at least processes for preparing food material including at least one of assembly, printing, sputtering, ablation, deposition, spraying, injection, mixing, combining, hydrating, dehydrating, applying energy, or removing energy specified according to the one or more user ingestion preference indications from at least one of quality or quantity of athletic output determined via at least one sensor associated with athletic equipment associated with the at least one user.

41. The method of claim 1 wherein the electronically determining one or more instructions for electronically directing at least in part one or more factors of electronically controlled dispensing of manually administrable orally ingestible material includes:

determining at least one of ingredients or processes for preparing food material including at least tuning at least one of macronutrient, micronutrient, or bacterial food content to at least indications in at least one of the physiological status information, the behavioral status information, or the dialogue with at least one individual associated with the at least one user of at least one of blood sugar levels, last time food or beverage was consumed, past or planned activity levels, or hormone levels.

42. The method of claim 1 wherein the electronically determining one or more instructions for electronically directing at least in part one or more factors of electronically controlled dispensing of manually administrable orally ingestible material includes:

determining at least one of ingredients or processes for preparing food material including at least tuning at least one of macronutrient, micronutrient, or bacterial food content to the dialogue with at least one individual associated with the at least one user indicative of at least one of stress levels, hunger levels, past activities, present activities, or expression of future activities of the at least one user.

43. The method of claim 1 wherein the electronically transmitting the one or more instructions for electronically directing at least in part one or more factors of electronically controlled dispensing of manually administrable orally ingestible material to at least one food and nutrition fabrication device includes:

electronically transmitting the one or more instructions for electronically directing at least in part one or more factors of electronically controlled dispensing of manually administrable orally ingestible material to at least one of a kiosk dispensing machine, a home food fabricator device, an airplane food fabrication device, or a restaurant food fabrication device.

\* \* \* \* \*